US011246592B2

(12) United States Patent
Shelton, IV et al.

(10) Patent No.: US 11,246,592 B2

(45) Date of Patent: Feb. 15, 2022

(54) SURGICAL INSTRUMENT COMPRISING AN ARTICULATION SYSTEM LOCKABLE TO A FRAME

(71) Applicant: Ethicon LLC, Guaynabo, PR (US)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 328 days.

(21) Appl. No.: 15/635,837

(22) Filed: Jun. 28, 2017

(65) Prior Publication Data

US 2019/0000472 A1 Jan. 3, 2019

(51) Int. Cl.

*A61B 17/072* (2006.01)
*A61B 17/29* (2006.01)

(Continued)

(52) U.S. Cl.

CPC ........ *A61B 17/07207* (2013.01); *A61B 17/29* (2013.01); *A61B 18/1442* (2013.01); *A61B 18/1445* (2013.01); *A61B 34/30* (2016.02); *A61B 2017/00017* (2013.01); *A61B 2017/00022* (2013.01); *A61B 2017/0046* (2013.01); *A61B 2017/00389* (2013.01); *A61B 2017/00393* (2013.01); *A61B 2017/00398* (2013.01);

(Continued)

(58) Field of Classification Search

CPC ...... A61B 17/07207; A61B 2017/2927; A61B 2017/00477; A61B 2017/00464; A61B 2017/2946; A61B 2017/0046; A61B 2017/07257; A61B 2017/07271; A61B 2017/07278; A61B 2017/2932; A61B 2017/2046; A61B 2017/00407; A61B 2017/2943

See application file for complete search history.

(56) References Cited

U.S. PATENT DOCUMENTS 66,052 A 6/1867 Smith
662,587 A 11/1900 Blake (Continued)

FOREIGN PATENT DOCUMENTS

AU 2012200594 A1 2/2012
AU 2012203035 A1 6/2012

(Continued)

OTHER PUBLICATIONS

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

(Continued)

*Primary Examiner* — Andrew M Tecco

(57) ABSTRACT

A surgical instrument comprising a shaft, an end effector rotatable relative to said shaft about an articulation joint, an articulation system configured to rotate the end effector, and an articulation lock. The articulation lock is configured to selectively couple the articulation system to a frame of the shaft. In various embodiments, the surgical instrument further comprises a lock plate movable within the shaft frame. In such embodiments, the articulation lock is configured to lock the articulation system to the lock plate.

20 Claims, 79 Drawing Sheets

14000
14316
14180
14182
14310
14422
14100
14184
14183
14182
14183
14422
14405
14406
14118
14404
14115
14424
14400
14403
14420
14426

(51) Int. Cl.
*A61B 18/14* (2006.01)
*A61B 34/30* (2016.01)
*A61B 17/00* (2006.01)
*A61B 18/00* (2006.01)
*A61B 90/00* (2016.01)

(52) U.S. Cl.
CPC .............. *A61B 2017/00407* (2013.01); *A61B 2017/00464* (2013.01); *A61B 2017/00473* (2013.01); *A61B 2017/00477* (2013.01); *A61B 2017/00734* (2013.01); *A61B 2017/00862* (2013.01); *A61B 2017/07214* (2013.01); *A61B 2017/07221* (2013.01); *A61B 2017/07228* (2013.01); *A61B 2017/07242* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *A61B 2017/2902* (2013.01); *A61B 2017/2903* (2013.01); *A61B 2017/2925* (2013.01); *A61B 2017/2927* (2013.01); *A61B 2017/2929* (2013.01); *A61B 2017/2932* (2013.01); *A61B 2017/2933* (2013.01); *A61B 2017/2939* (2013.01); *A61B 2017/2943* (2013.01); *A61B 2017/2946* (2013.01); *A61B 2018/0063* (2013.01); *A61B 2090/0801* (2016.02)

(56) References Cited

U.S. PATENT DOCUMENTS 670,748 A 3/1901 Weddeler
719,487 A 2/1903 Minor
804,229 A 11/1905 Hutchinson
951,393 A 3/1910 Hahn
1,075,556 A 10/1913 Fenoughty
1,188,721 A 6/1916 Bittner
1,306,107 A 6/1919 Elliott
1,314,601 A 9/1919 McCaskey
1,677,337 A 7/1928 Grove
1,794,907 A 3/1931 Kelly
1,849,427 A 3/1932 Hook
1,944,116 A 1/1934 Stratman
1,954,048 A 4/1934 Jeffrey et al.
2,028,635 A 1/1936 Wappler
2,037,727 A 4/1936 La Chapelle
2,132,295 A 10/1938 Hawkins
2,161,632 A 6/1939 Nattenheimer
D120,434 S 5/1940 Gold
2,211,117 A 8/1940 Hess
2,214,870 A 9/1940 West
2,224,882 A 12/1940 Peck
2,318,379 A 5/1943 Davis et al.
2,329,440 A 9/1943 La Place
2,377,581 A 6/1945 Shaffrey
2,406,389 A 8/1946 Royal Lee
2,441,096 A 5/1948 Happe
2,448,741 A 9/1948 Scott et al.
2,450,527 A 10/1948 Smith
2,491,872 A 12/1949 Neuman
2,507,872 A 5/1950 Unsinger
2,526,902 A 10/1950 Rublee
2,527,256 A 10/1950 Jackson
2,578,686 A 12/1951 Fish
2,638,901 A 5/1953 Sugarbaker
2,674,149 A 4/1954 Benson
2,701,489 A 2/1955 Osborn
2,711,461 A 6/1955 Happe
2,724,289 A 11/1955 Wight
2,742,955 A 4/1956 Dominguez
2,804,848 A 9/1957 O'Farrell et al.
2,808,482 A 10/1957 Zanichkowsky et al.
2,853,074 A 9/1958 Olson
2,856,192 A 10/1958 Schuster
2,887,004 A 5/1959 Stewart
2,957,353 A 10/1960 Lewis
2,959,974 A 11/1960 Emrick
3,026,744 A 3/1962 Rouse
3,032,769 A 5/1962 Palmer
3,060,972 A 10/1962 Sheldon
3,075,062 A 1/1963 Iaccarino
3,078,465 A 2/1963 Bobrov
3,079,606 A 3/1963 Bobrov et al.
3,080,564 A 3/1963 Stekopitov et al.
3,166,072 A 1/1965 Sullivan, Jr.
3,180,236 A 4/1965 Beckett
3,196,869 A 7/1965 Scholl
3,204,731 A 9/1965 Bent et al.
3,266,494 A 8/1966 Brownrigg et al.
3,269,630 A 8/1966 Fleischer
3,269,631 A 8/1966 Takaro
3,275,211 A 9/1966 Hirsch et al.
3,317,103 A 5/1967 Cullen et al.
3,317,105 A 5/1967 Astafjev et al.
3,357,296 A 12/1967 Lefever
3,359,978 A 12/1967 Smith, Jr.
3,377,893 A 4/1968 Shorb
3,480,193 A 11/1969 Ralston
3,490,675 A 1/1970 Green et al.
3,494,533 A 2/1970 Green et al.
3,499,591 A 3/1970 Green
3,503,396 A 3/1970 Pierie et al.
3,509,629 A 5/1970 Kidokoro
3,551,987 A 1/1971 Wilkinson
3,572,159 A 3/1971 Tschanz
3,583,393 A 6/1971 Takahashi
3,589,589 A 6/1971 Akopov
3,598,943 A 8/1971 Barrett
3,608,549 A 9/1971 Merrill
3,618,842 A 11/1971 Bryan
3,638,652 A 2/1972 Kelley
3,640,317 A 2/1972 Panfili
3,643,851 A 2/1972 Green et al.
3,650,453 A 3/1972 Smith, Jr.
3,661,339 A 5/1972 Shimizu
3,661,666 A 5/1972 Foster et al.
3,662,939 A 5/1972 Bryan
3,688,966 A 9/1972 Perkins et al.
3,695,646 A 10/1972 Mommsen
3,709,221 A 1/1973 Riely
3,717,294 A 2/1973 Green
3,724,237 A 4/1973 Wood
3,726,755 A 4/1973 Shannon
3,727,904 A 4/1973 Gabbey
3,734,207 A 5/1973 Fishbein
3,740,994 A 6/1973 De Carlo, Jr.
3,744,495 A 7/1973 Johnson
3,746,002 A 7/1973 Haller
3,747,603 A 7/1973 Adler
3,747,692 A 7/1973 Davidson
3,751,902 A 8/1973 Kingsbury et al.
3,752,161 A 8/1973 Bent
3,799,151 A 3/1974 Fukaumi et al.
3,808,452 A 4/1974 Hutchinson
3,815,476 A 6/1974 Green et al.
3,819,100 A 6/1974 Noiles et al.
3,821,919 A 7/1974 Knohl
3,826,978 A 7/1974 Kelly
3,836,171 A 9/1974 Hayashi et al.
3,837,555 A 9/1974 Green
3,841,474 A 10/1974 Maier
3,851,196 A 11/1974 Hinds
3,863,639 A 2/1975 Kleaveland
3,863,940 A 2/1975 Cummings
3,883,624 A 5/1975 McKenzie et al.
3,885,491 A 5/1975 Curtis
3,887,393 A 6/1975 La Rue, Jr.
3,892,228 A 7/1975 Mitsui
3,894,174 A 7/1975 Cartun
3,902,247 A 9/1975 Fleer et al.
3,940,844 A 3/1976 Colby et al.
3,944,163 A 3/1976 Hayashi et al.

(56) References Cited

U.S. PATENT DOCUMENTS

| | | | |
|---|---|---|---|
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |
| 4,100,820 | A | 7/1978 | Evett |
| 4,106,446 | A | 8/1978 | Yamada et al. |
| 4,106,620 | A | 8/1978 | Brimmer et al. |
| 4,108,211 | A | 8/1978 | Tanaka |
| 4,111,206 | A | 9/1978 | Vishnevsky et al. |
| 4,127,227 | A | 11/1978 | Green |
| 4,129,059 | A | 12/1978 | Van Eck |
| 4,132,146 | A | 1/1979 | Uhlig |
| 4,135,517 | A | 1/1979 | Reale |
| 4,154,122 | A | 5/1979 | Severin |
| 4,160,857 | A | 7/1979 | Nardella et al. |
| 4,169,990 | A | 10/1979 | Lerdman |
| 4,180,285 | A | 12/1979 | Reneau |
| 4,185,701 | A | 1/1980 | Boys |
| 4,190,042 | A | 2/1980 | Sinnreich |
| 4,198,734 | A | 4/1980 | Brumlik |
| 4,198,982 | A | 4/1980 | Fortner et al. |
| 4,203,444 | A | 5/1980 | Bonnell et al. |
| 4,207,898 | A | 6/1980 | Becht |
| 4,213,562 | A | 7/1980 | Garrett et al. |
| 4,226,242 | A | 10/1980 | Jarvik |
| 4,239,431 | A | 12/1980 | Davini |
| 4,241,861 | A | 12/1980 | Fleischer |
| 4,244,372 | A | 1/1981 | Kapitanov et al. |
| 4,250,436 | A | 2/1981 | Weissman |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,274,398 | A | 6/1981 | Scott, Jr. |
| 4,275,813 | A | 6/1981 | Noiles |
| 4,278,091 | A | 7/1981 | Borzone |
| 4,282,573 | A | 8/1981 | Imai et al. |
| 4,289,131 | A | 9/1981 | Mueller |
| 4,289,133 | A | 9/1981 | Rothfuss |
| 4,290,542 | A | 9/1981 | Fedotov et al. |
| D261,356 | S | 10/1981 | Robinson |
| 4,293,604 | A | 10/1981 | Campbell |
| 4,296,654 | A | 10/1981 | Mercer |
| 4,296,881 | A | 10/1981 | Lee |
| 4,304,236 | A | 12/1981 | Conta et al. |
| 4,305,539 | A | 12/1981 | Korolkov et al. |
| 4,312,363 | A | 1/1982 | Rothfuss et al. |
| 4,312,685 | A | 1/1982 | Riedl |
| 4,317,451 | A | 3/1982 | Cerwin et al. |
| 4,319,576 | A | 3/1982 | Rothfuss |
| 4,321,002 | A | 3/1982 | Froehlich |
| 4,321,746 | A | 3/1982 | Grinage |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,348,603 | A | 9/1982 | Huber |
| 4,349,028 | A | 9/1982 | Green |
| 4,350,151 | A | 9/1982 | Scott |
| 4,353,371 | A | 10/1982 | Cosman |
| 4,357,940 | A | 11/1982 | Muller |
| 4,361,057 | A | 11/1982 | Kochera |
| 4,366,544 | A | 12/1982 | Shima et al. |
| 4,369,013 | A | 1/1983 | Abildgaard et al. |
| 4,373,147 | A | 2/1983 | Carlson, Jr. |
| 4,376,380 | A | 3/1983 | Burgess |
| 4,379,457 | A | 4/1983 | Gravener et al. |
| 4,380,312 | A | 4/1983 | Landrus |
| 4,382,326 | A | 5/1983 | Rabuse |
| 4,383,634 | A | 5/1983 | Green |
| 4,389,963 | A | 6/1983 | Pearson |
| 4,393,728 | A | 7/1983 | Larson et al. |
| 4,394,613 | A | 7/1983 | Cole |
| 4,396,139 | A | 8/1983 | Hall et al. |
| 4,397,311 | A | 8/1983 | Kanshin et al. |
| 4,402,445 | A | 9/1983 | Green |
| 4,406,621 | A | 9/1983 | Bailey |
| 4,408,692 | A | 10/1983 | Sigel et al. |
| 4,409,057 | A | 10/1983 | Molenda et al. |
| 4,415,112 | A | 11/1983 | Green |
| 4,416,276 | A | 11/1983 | Newton et al. |
| 4,417,890 | A | 11/1983 | Dennehey et al. |
| 4,421,264 | A | 12/1983 | Arter et al. |
| 4,423,456 | A | 12/1983 | Zaidenweber |
| 4,425,915 | A | 1/1984 | Ivanov |
| 4,428,376 | A | 1/1984 | Mericle |
| 4,429,695 | A | 2/1984 | Green |
| 4,430,997 | A | 2/1984 | DiGiovanni et al. |
| 4,434,796 | A | 3/1984 | Karapetian et al. |
| 4,438,659 | A | 3/1984 | Desplats |
| 4,442,964 | A | 4/1984 | Becht |
| 4,448,194 | A | 5/1984 | DiGiovanni et al. |
| 4,451,743 | A | 5/1984 | Suzuki et al. |
| 4,452,376 | A | 6/1984 | Klieman et al. |
| 4,454,887 | A | 6/1984 | Kruger |
| 4,459,519 | A | 7/1984 | Erdman |
| 4,461,305 | A | 7/1984 | Cibley |
| 4,467,805 | A | 8/1984 | Fukuda |
| 4,468,597 | A | 8/1984 | Baumard et al. |
| 4,469,481 | A | 9/1984 | Kobayashi |
| 4,470,414 | A | 9/1984 | Imagawa et al. |
| 4,471,780 | A | 9/1984 | Menges et al. |
| 4,471,781 | A | 9/1984 | Di Giovanni et al. |
| 4,473,077 | A | 9/1984 | Noiles et al. |
| 4,475,679 | A | 10/1984 | Fleury, Jr. |
| 4,476,864 | A | 10/1984 | Tezel |
| 4,478,220 | A | 10/1984 | Di Giovanni et al. |
| 4,480,641 | A | 11/1984 | Failla et al. |
| 4,481,458 | A | 11/1984 | Lane |
| 4,483,562 | A | 11/1984 | Schoolman |
| 4,485,816 | A | 12/1984 | Krumme |
| 4,485,817 | A | 12/1984 | Swiggett |
| 4,486,928 | A | 12/1984 | Tucker et al. |
| 4,488,523 | A | 12/1984 | Shichman |
| 4,489,875 | A | 12/1984 | Crawford et al. |
| 4,493,983 | A | 1/1985 | Taggert |
| 4,494,057 | A | 1/1985 | Hotta |
| 4,499,895 | A | 2/1985 | Takayama |
| 4,500,024 | A | 2/1985 | DiGiovanni et al. |
| D278,081 | S | 3/1985 | Green |
| 4,503,842 | A | 3/1985 | Takayama |
| 4,505,272 | A | 3/1985 | Utyamyshev et al. |
| 4,505,273 | A | 3/1985 | Braun et al. |
| 4,505,414 | A | 3/1985 | Filipi |
| 4,506,671 | A | 3/1985 | Green |
| 4,512,038 | A | 4/1985 | Alexander et al. |
| 4,520,817 | A | 6/1985 | Green |
| 4,522,327 | A | 6/1985 | Korthoff et al. |
| 4,526,174 | A | 7/1985 | Froehlich |
| 4,527,724 | A | 7/1985 | Chow et al. |
| 4,530,357 | A | 7/1985 | Pawloski et al. |
| 4,530,453 | A | 7/1985 | Green |
| 4,531,522 | A | 7/1985 | Bedi et al. |
| 4,532,927 | A | 8/1985 | Miksza, Jr. |
| 4,540,202 | A | 9/1985 | Amphoux et al. |
| 4,548,202 | A | 10/1985 | Duncan |
| 4,556,058 | A | 12/1985 | Green |
| 4,560,915 | A | 12/1985 | Soultanian |
| 4,565,109 | A | 1/1986 | Tsay |
| 4,565,189 | A | 1/1986 | Mabuchi |
| 4,566,620 | A | 1/1986 | Green et al. |

(56) References Cited

U.S. PATENT DOCUMENTS 4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.
4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,869,414 A 9/1989 Green et al.
4,869,415 A 9/1989 Fox
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,679 A 4/1990 Averill et al.

(56) References Cited

U.S. PATENT DOCUMENTS 4,921,479 A 5/1990 Grayzel
4,925,082 A 5/1990 Kim
4,928,699 A 5/1990 Sasai
4,930,503 A 6/1990 Pruitt
4,930,674 A 6/1990 Barak
4,931,047 A 6/1990 Broadwin et al.
4,931,737 A 6/1990 Hishiki
4,932,960 A 6/1990 Green et al.
4,933,800 A 6/1990 Yang
4,933,843 A 6/1990 Scheller et al.
D309,350 S 7/1990 Sutherland et al.
4,938,408 A 7/1990 Bedi et al.
4,941,623 A 7/1990 Pruitt
4,943,182 A 7/1990 Hoblingre
4,944,443 A 7/1990 Oddsen et al.
4,946,067 A 8/1990 Kelsall
4,948,327 A 8/1990 Crupi, Jr.
4,949,707 A 8/1990 LeVahn et al.
4,951,860 A 8/1990 Peters et al.
4,951,861 A 8/1990 Schulze et al.
4,954,960 A 9/1990 Lo et al.
4,955,959 A 9/1990 Tompkins et al.
4,957,212 A 9/1990 Duck et al.
4,962,681 A 10/1990 Yang
4,962,877 A 10/1990 Hervas
4,964,559 A 10/1990 Deniega et al.
4,964,863 A 10/1990 Kanshin et al.
4,965,709 A 10/1990 Ngo
4,970,656 A 11/1990 Lo et al.
4,973,274 A 11/1990 Hirukawa
4,973,302 A 11/1990 Armour et al.
4,976,173 A 12/1990 Yang
4,978,049 A 12/1990 Green
4,978,333 A 12/1990 Broadwin et al.
4,979,952 A 12/1990 Kubota et al.
4,984,564 A 1/1991 Yuen
4,986,808 A 1/1991 Broadwin et al.
4,987,049 A 1/1991 Komamura et al.
4,988,334 A 1/1991 Hornlein et al.
4,995,877 A 2/1991 Ams et al.
4,995,959 A 2/1991 Metzner
4,996,975 A 3/1991 Nakamura
5,001,649 A 3/1991 Lo et al.
5,002,543 A 3/1991 Bradshaw et al.
5,002,553 A 3/1991 Shiber
5,005,754 A 4/1991 Van Overloop
5,009,661 A 4/1991 Michelson
5,012,411 A 4/1991 Policastro et al.
5,014,898 A 5/1991 Heidrich
5,014,899 A 5/1991 Presty et al.
5,015,227 A 5/1991 Broadwin et al.
5,018,515 A 5/1991 Gilman
5,018,657 A 5/1991 Pedlick et al.
5,024,652 A 6/1991 Dumenek et al.
5,024,671 A 6/1991 Tu et al.
5,025,559 A 6/1991 McCullough
5,027,834 A 7/1991 Pruitt
5,030,226 A 7/1991 Green et al.
5,031,814 A 7/1991 Tompkins et al.
5,033,552 A 7/1991 Hu
5,035,040 A 7/1991 Kerrigan et al.
5,037,018 A 8/1991 Matsuda et al.
5,038,109 A 8/1991 Goble et al.
5,038,247 A 8/1991 Kelley et al.
5,040,715 A 8/1991 Green et al.
5,042,707 A 8/1991 Taheri
5,056,953 A 10/1991 Marot et al.
5,060,658 A 10/1991 Dejter, Jr. et al.
5,061,269 A 10/1991 Muller
5,062,491 A 11/1991 Takeshima et al.
5,062,563 A 11/1991 Green et al.
5,065,929 A 11/1991 Schulze et al.
5,071,052 A 12/1991 Rodak et al.
5,071,430 A 12/1991 de Salis et al.
5,074,454 A 12/1991 Peters
5,077,506 A 12/1991 Krause
5,079,006 A 1/1992 Urquhart
5,080,556 A 1/1992 Carreno
5,083,695 A 1/1992 Foslien et al.
5,084,057 A 1/1992 Green et al.
5,088,979 A 2/1992 Filipi et al.
5,088,997 A 2/1992 Delahuerga et al.
5,089,606 A 2/1992 Cole et al.
5,094,247 A 3/1992 Hernandez et al.
5,098,004 A 3/1992 Kerrigan
5,098,360 A 3/1992 Hirota
5,100,042 A 3/1992 Gravener et al.
5,100,420 A 3/1992 Green et al.
5,104,025 A 4/1992 Main et al.
5,104,397 A 4/1992 Vasconcelos et al.
5,104,400 A 4/1992 Berguer et al.
5,106,008 A 4/1992 Tompkins et al.
5,108,368 A 4/1992 Hammerslag et al.
5,109,722 A 5/1992 Hufnagle et al.
5,111,987 A 5/1992 Moeinzadeh et al.
5,116,349 A 5/1992 Aranyi
D327,323 S 6/1992 Hunt
5,119,009 A 6/1992 McCaleb et al.
5,122,156 A 6/1992 Granger et al.
5,124,990 A 6/1992 Williamson
5,126,058 A 6/1992 Beckman
5,129,570 A 7/1992 Schulze et al.
5,137,198 A 8/1992 Nobis et al.
5,139,513 A 8/1992 Segato
5,141,144 A 8/1992 Foslien et al.
5,142,932 A 9/1992 Moya et al.
5,151,102 A 9/1992 Kamiyama et al.
5,155,941 A 10/1992 Takahashi et al.
5,156,315 A 10/1992 Green et al.
5,156,609 A 10/1992 Nakao et al.
5,156,614 A 10/1992 Green et al.
5,158,222 A 10/1992 Green et al.
5,158,567 A 10/1992 Green
D330,699 S 11/1992 Gill
5,163,598 A 11/1992 Peters et al.
5,168,605 A 12/1992 Bartlett
5,170,925 A 12/1992 Madden et al.
5,171,247 A 12/1992 Hughett et al.
5,171,249 A 12/1992 Stefanchik et al.
5,171,253 A 12/1992 Klieman
5,173,053 A 12/1992 Swanson et al.
5,173,133 A 12/1992 Morin et al.
5,176,677 A 1/1993 Wuchinich
5,176,688 A 1/1993 Narayan et al.
5,181,514 A 1/1993 Solomon et al.
5,187,422 A 2/1993 Izenbaard et al.
5,188,102 A 2/1993 Idemoto et al.
5,188,111 A 2/1993 Yates et al.
5,190,517 A 3/1993 Zieve et al.
5,190,544 A 3/1993 Chapman et al.
5,190,560 A 3/1993 Woods et al.
5,190,657 A 3/1993 Heagle et al.
5,192,288 A 3/1993 Thompson et al.
5,193,731 A 3/1993 Aranyi
5,195,505 A 3/1993 Josefsen
5,195,968 A 3/1993 Lundquist et al.
5,197,648 A 3/1993 Gingold
5,197,649 A 3/1993 Bessler et al.
5,197,966 A 3/1993 Sommerkamp
5,197,970 A 3/1993 Green et al.
5,200,280 A 4/1993 Karasa
5,201,750 A 4/1993 Hocherl et al.
5,205,459 A 4/1993 Brinkerhoff et al.
5,207,672 A 5/1993 Roth et al.
5,207,697 A 5/1993 Carusillo et al.
5,209,747 A 5/1993 Knoepfler
5,209,756 A 5/1993 Seedhom et al.
5,211,649 A 5/1993 Kohler et al.
5,211,655 A 5/1993 Hasson
5,217,457 A 6/1993 Delahuerga et al.
5,217,478 A 6/1993 Rexroth
5,219,111 A 6/1993 Bilotti et al.
5,220,269 A 6/1993 Chen et al.
5,221,036 A 6/1993 Takase

(56) References Cited

U.S. PATENT DOCUMENTS

| | | | |
|---|---|---|---|
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,576 | A | 5/1994 | Green et al. |
| 5,309,387 | A | 5/1994 | Mori |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller nee Degwitz et al. |
| 5,314,466 | A | 5/1994 | Stern et al. |
| 5,318,221 | A | 6/1994 | Green et al. |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,250 | A | 10/1994 | Christensen |
| 5,354,303 | A | 10/1994 | Spaeth et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |
| 5,368,015 | A | 11/1994 | Wilk |
| 5,368,592 | A | 11/1994 | Stern et al. |
| 5,369,565 | A | 11/1994 | Chen et al. |
| 5,370,645 | A | 12/1994 | Klicek et al. |
| 5,372,124 | A | 12/1994 | Takayama et al. |
| 5,372,596 | A | 12/1994 | Klicek et al. |
| 5,372,602 | A | 12/1994 | Burke |
| 5,374,277 | A | 12/1994 | Hassler |
| 5,375,588 | A | 12/1994 | Yoon |
| 5,376,095 | A | 12/1994 | Ortiz |
| 5,379,933 | A | 1/1995 | Green et al. |
| 5,381,649 | A | 1/1995 | Webb |
| 5,381,782 | A | 1/1995 | DeLaRama et al. |
| 5,381,943 | A | 1/1995 | Allen et al. |
| 5,382,247 | A | 1/1995 | Cimino et al. |
| 5,383,460 | A | 1/1995 | Jang et al. |
| 5,383,874 | A | 1/1995 | Jackson et al. |
| 5,383,880 | A | 1/1995 | Hooven |
| 5,383,881 | A | 1/1995 | Green et al. |
| 5,383,882 | A | 1/1995 | Buess et al. |

(56) References Cited

U.S. PATENT DOCUMENTS 5,383,888 A 1/1995 Zvenyatsky et al.
5,383,895 A 1/1995 Holmes et al.
5,388,568 A 2/1995 van der Heide
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,654 A 7/1995 Nic
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,354 A 12/1995 Tovey et al.
5,480,089 A 1/1996 Blewett
5,480,409 A 1/1996 Riza
5,482,197 A 1/1996 Green et al.
5,483,952 A 1/1996 Aranyi
5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,507,773 A 4/1996 Huitema et al.
5,509,596 A 4/1996 Green et al.
5,509,916 A 4/1996 Taylor
5,509,918 A 4/1996 Romano
5,511,564 A 4/1996 Wilk
5,514,129 A 5/1996 Smith

(56) References Cited

U.S. PATENT DOCUMENTS

| | | | |
|---|---|---|---|
| 5,514,149 | A | 5/1996 | Green et al. |
| 5,514,157 | A | 5/1996 | Nicholas et al. |
| 5,518,163 | A | 5/1996 | Hooven |
| 5,518,164 | A | 5/1996 | Hooven |
| 5,520,609 | A | 5/1996 | Moll et al. |
| 5,520,634 | A | 5/1996 | Fox et al. |
| 5,520,678 | A | 5/1996 | Heckele et al. |
| 5,520,700 | A | 5/1996 | Beyar et al. |
| 5,522,817 | A | 6/1996 | Sander et al. |
| 5,522,831 | A | 6/1996 | Sleister et al. |
| 5,527,264 | A | 6/1996 | Moll et al. |
| 5,527,320 | A | 6/1996 | Carruthers et al. |
| 5,529,235 | A | 6/1996 | Boiarski et al. |
| D372,086 | S | 7/1996 | Grasso et al. |
| 5,531,305 | A | 7/1996 | Roberts et al. |
| 5,531,744 | A | 7/1996 | Nardella et al. |
| 5,531,856 | A | 7/1996 | Moll et al. |
| 5,533,521 | A | 7/1996 | Granger |
| 5,533,581 | A | 7/1996 | Barth et al. |
| 5,533,661 | A | 7/1996 | Main et al. |
| 5,535,934 | A | 7/1996 | Boiarski et al. |
| 5,535,935 | A | 7/1996 | Vidal et al. |
| 5,535,937 | A | 7/1996 | Boiarski et al. |
| 5,540,375 | A | 7/1996 | Bolanos et al. |
| 5,540,705 | A | 7/1996 | Meade et al. |
| 5,541,376 | A | 7/1996 | Ladtkow et al. |
| 5,541,489 | A | 7/1996 | Dunstan |
| 5,542,594 | A | 8/1996 | McKean et al. |
| 5,542,945 | A | 8/1996 | Fritzsch |
| 5,542,949 | A | 8/1996 | Yoon |
| 5,543,119 | A | 8/1996 | Sutter et al. |
| 5,543,695 | A | 8/1996 | Culp et al. |
| 5,544,802 | A | 8/1996 | Crainich |
| 5,547,117 | A | 8/1996 | Hamblin et al. |
| 5,549,583 | A | 8/1996 | Sanford et al. |
| 5,549,621 | A | 8/1996 | Bessler et al. |
| 5,549,627 | A | 8/1996 | Kieturakis |
| 5,549,628 | A | 8/1996 | Cooper et al. |
| 5,549,637 | A | 8/1996 | Crainich |
| 5,551,622 | A | 9/1996 | Yoon |
| 5,553,624 | A | 9/1996 | Francese et al. |
| 5,553,675 | A | 9/1996 | Pitzen et al. |
| 5,553,765 | A | 9/1996 | Knodel et al. |
| 5,554,148 | A | 9/1996 | Aebischer et al. |
| 5,554,169 | A | 9/1996 | Green et al. |
| 5,556,020 | A | 9/1996 | Hou |
| 5,556,416 | A | 9/1996 | Clark et al. |
| 5,558,533 | A | 9/1996 | Hashizawa et al. |
| 5,558,665 | A | 9/1996 | Kieturakis |
| 5,558,671 | A | 9/1996 | Yates |
| 5,560,530 | A | 10/1996 | Bolanos et al. |
| 5,560,532 | A | 10/1996 | DeFonzo et al. |
| 5,561,881 | A | 10/1996 | Klinger et al. |
| 5,562,239 | A | 10/1996 | Boiarski et al. |
| 5,562,241 | A | 10/1996 | Knodel et al. |
| 5,562,682 | A | 10/1996 | Oberlin et al. |
| 5,562,690 | A | 10/1996 | Green et al. |
| 5,562,701 | A | 10/1996 | Huitema et al. |
| 5,562,702 | A | 10/1996 | Huitema et al. |
| 5,563,481 | A | 10/1996 | Krause |
| 5,564,615 | A | 10/1996 | Bishop et al. |
| 5,569,161 | A | 10/1996 | Ebling et al. |
| 5,569,270 | A | 10/1996 | Weng |
| 5,569,284 | A | 10/1996 | Young et al. |
| 5,571,090 | A | 11/1996 | Sherts |
| 5,571,100 | A | 11/1996 | Goble et al. |
| 5,571,116 | A | 11/1996 | Bolanos et al. |
| 5,571,285 | A | 11/1996 | Chow et al. |
| 5,571,488 | A | 11/1996 | Beerstecher et al. |
| 5,573,169 | A | 11/1996 | Green et al. |
| 5,573,543 | A | 11/1996 | Akopov et al. |
| 5,574,431 | A | 11/1996 | McKeown et al. |
| 5,575,054 | A | 11/1996 | Klinzing et al. |
| 5,575,789 | A | 11/1996 | Bell et al. |
| 5,575,799 | A | 11/1996 | Bolanos et al. |
| 5,575,803 | A | 11/1996 | Cooper et al. |
| 5,575,805 | A | 11/1996 | Li |
| 5,577,654 | A | 11/1996 | Bishop |
| 5,578,052 | A | 11/1996 | Koros et al. |
| 5,579,978 | A | 12/1996 | Green et al. |
| 5,580,067 | A | 12/1996 | Hamblin et al. |
| 5,582,611 | A | 12/1996 | Tsuruta et al. |
| 5,582,617 | A | 12/1996 | Klieman et al. |
| 5,582,907 | A | 12/1996 | Pall |
| 5,583,114 | A | 12/1996 | Barrows et al. |
| 5,584,425 | A | 12/1996 | Savage et al. |
| 5,586,711 | A | 12/1996 | Plyley et al. |
| 5,588,579 | A | 12/1996 | Schnut et al. |
| 5,588,580 | A | 12/1996 | Paul et al. |
| 5,588,581 | A | 12/1996 | Conlon et al. |
| 5,591,170 | A | 1/1997 | Spievack et al. |
| 5,591,187 | A | 1/1997 | Dekel |
| 5,597,107 | A | 1/1997 | Knodel et al. |
| 5,599,151 | A | 2/1997 | Daum et al. |
| 5,599,279 | A | 2/1997 | Slotman et al. |
| 5,599,344 | A | 2/1997 | Paterson |
| 5,599,350 | A | 2/1997 | Schulze et al. |
| 5,599,852 | A | 2/1997 | Scopelianos et al. |
| 5,601,224 | A | 2/1997 | Bishop et al. |
| 5,601,573 | A | 2/1997 | Fogelberg et al. |
| 5,601,604 | A | 2/1997 | Vincent |
| 5,602,449 | A | 2/1997 | Krause et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,607,095 | A | 3/1997 | Smith et al. |
| 5,607,433 | A | 3/1997 | Polla et al. |
| 5,607,436 | A | 3/1997 | Pratt et al. |
| 5,607,450 | A | 3/1997 | Zvenyatsky et al. |
| 5,607,474 | A | 3/1997 | Athanasiou et al. |
| 5,609,285 | A | 3/1997 | Grant et al. |
| 5,609,601 | A | 3/1997 | Kolesa et al. |
| 5,611,709 | A | 3/1997 | McAnulty |
| 5,613,499 | A | 3/1997 | Palmer et al. |
| 5,613,937 | A | 3/1997 | Garrison et al. |
| 5,613,966 | A | 3/1997 | Makower et al. |
| 5,614,887 | A | 3/1997 | Buchbinder |
| 5,615,820 | A | 4/1997 | Viola |
| 5,618,294 | A | 4/1997 | Aust et al. |
| 5,618,303 | A | 4/1997 | Marlow et al. |
| 5,618,307 | A | 4/1997 | Donlon et al. |
| 5,619,992 | A | 4/1997 | Guthrie et al. |
| 5,620,289 | A | 4/1997 | Curry |
| 5,620,326 | A | 4/1997 | Younker |
| 5,620,452 | A | 4/1997 | Yoon |
| 5,624,398 | A | 4/1997 | Smith et al. |
| 5,624,452 | A | 4/1997 | Yates |
| 5,626,587 | A | 5/1997 | Bishop et al. |
| 5,626,595 | A | 5/1997 | Sklar et al. |
| 5,626,979 | A | 5/1997 | Mitsui et al. |
| 5,628,446 | A | 5/1997 | Geiste et al. |
| 5,628,743 | A | 5/1997 | Cimino |
| 5,628,745 | A | 5/1997 | Bek |
| 5,630,539 | A | 5/1997 | Plyley et al. |
| 5,630,540 | A | 5/1997 | Blewett |
| 5,630,541 | A | 5/1997 | Williamson, IV et al. |
| 5,630,782 | A | 5/1997 | Adair |
| 5,631,973 | A | 5/1997 | Green |
| 5,632,432 | A | 5/1997 | Schulze et al. |
| 5,632,433 | A | 5/1997 | Grant et al. |
| 5,633,374 | A | 5/1997 | Humphrey et al. |
| 5,634,584 | A | 6/1997 | Okorocha et al. |
| 5,636,779 | A | 6/1997 | Palmer |
| 5,636,780 | A | 6/1997 | Green et al. |
| 5,638,582 | A | 6/1997 | Klatt et al. |
| 5,639,008 | A | 6/1997 | Gallagher et al. |
| D381,077 | S | 7/1997 | Hunt |
| 5,643,291 | A | 7/1997 | Pier et al. |
| 5,643,293 | A | 7/1997 | Kogasaka et al. |
| 5,643,294 | A | 7/1997 | Tovey et al. |
| 5,643,319 | A | 7/1997 | Green et al. |
| 5,645,209 | A | 7/1997 | Green et al. |
| 5,647,526 | A | 7/1997 | Green et al. |

(56) References Cited

U.S. PATENT DOCUMENTS 5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A * 10/1997 Schulze ........... A61B 17/07207 227/175.1
5,680,983 A 10/1997 Plyley et al.
5,681,341 A 10/1997 Lunsford et al.
5,683,349 A 11/1997 Makower et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.
5,735,874 A 4/1998 Measamer et al.
5,736,271 A 4/1998 Cisar et al.
5,738,474 A 4/1998 Blewett
5,738,629 A 4/1998 Moll et al.
5,738,648 A 4/1998 Lands et al.
5,741,271 A 4/1998 Nakao et al.
5,743,456 A 4/1998 Jones et al.
5,747,953 A 5/1998 Philipp
5,749,889 A 5/1998 Bacich et al.
5,749,893 A 5/1998 Vidal et al.
5,749,896 A 5/1998 Cook
5,749,968 A 5/1998 Melanson et al.
5,752,644 A 5/1998 Bolanos et al.
5,752,965 A 5/1998 Francis et al.
5,752,970 A 5/1998 Yoon
5,752,973 A 5/1998 Kieturakis
5,755,717 A 5/1998 Yates et al.
5,755,726 A 5/1998 Pratt et al.
5,758,814 A 6/1998 Gallagher et al.
5,762,255 A 6/1998 Chrisman et al.
5,762,256 A 6/1998 Mastri et al.
5,762,458 A 6/1998 Wang et al.
5,765,565 A 6/1998 Adair
5,766,188 A 6/1998 Igaki
5,766,205 A 6/1998 Zvenyatsky et al.
5,769,303 A 6/1998 Knodel et al.
5,769,640 A 6/1998 Jacobus et al.
5,769,748 A 6/1998 Eyerly et al.
5,769,791 A 6/1998 Benaron et al.
5,769,892 A 6/1998 Kingwell
5,772,099 A 6/1998 Gravener
5,772,379 A 6/1998 Evensen
5,772,578 A 6/1998 Heimberger et al.
5,772,659 A 6/1998 Becker et al.
5,773,991 A 6/1998 Chen
5,776,130 A 7/1998 Buysse et al.
5,778,939 A 7/1998 Hok-Yin
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,782,748 A 7/1998 Palmer et al.
5,782,749 A 7/1998 Riza

(56) References Cited

U.S. PATENT DOCUMENTS 5,782,859 A 7/1998 Nicholas et al.
5,784,934 A 7/1998 Izumisawa
5,785,232 A 7/1998 Vidal et al.
5,785,647 A 7/1998 Tompkins et al.
5,787,897 A 8/1998 Kieturakis
5,791,231 A 8/1998 Cohn et al.
5,792,135 A 8/1998 Madhani et al.
5,792,162 A 8/1998 Jolly et al.
5,792,165 A 8/1998 Klieman et al.
5,792,573 A 8/1998 Pitzen et al.
5,794,834 A 8/1998 Hamblin et al.
5,796,188 A 8/1998 Bays
5,797,536 A 8/1998 Smith et al.
5,797,537 A 8/1998 Oberlin et al.
5,797,538 A 8/1998 Heaton et al.
5,797,637 A 8/1998 Ervin
5,797,900 A 8/1998 Madhani et al.
5,797,906 A 8/1998 Rhum et al.
5,797,927 A 8/1998 Yoon
5,797,941 A 8/1998 Schulze et al.
5,797,959 A 8/1998 Castro et al.
5,799,857 A 9/1998 Robertson et al.
5,800,379 A 9/1998 Edwards
5,800,423 A 9/1998 Jensen
5,804,726 A 9/1998 Geib et al.
5,804,936 A 9/1998 Brodsky et al.
5,806,676 A 9/1998 Wasgien
5,807,241 A 9/1998 Heimberger
5,807,376 A 9/1998 Viola et al.
5,807,378 A 9/1998 Jensen et al.
5,807,393 A 9/1998 Williamson, IV et al.
5,809,441 A 9/1998 McKee
5,810,721 A 9/1998 Mueller et al.
5,810,811 A 9/1998 Yates et al.
5,810,846 A 9/1998 Virnich et al.
5,810,855 A 9/1998 Rayburn et al.
5,812,188 A 9/1998 Adair
5,813,813 A 9/1998 Daum et al.
5,814,055 A 9/1998 Knodel et al.
5,814,057 A 9/1998 Oi et al.
5,816,471 A 10/1998 Plyley et al.
5,817,084 A 10/1998 Jensen
5,817,091 A 10/1998 Nardella et al.
5,817,093 A 10/1998 Williamson, IV et al.
5,817,109 A 10/1998 McGarry et al.
5,817,119 A 10/1998 Klieman et al.
5,820,009 A 10/1998 Melling et al.
5,823,066 A 10/1998 Huitema et al.
5,824,333 A 10/1998 Scopelianos et al.
5,826,776 A 10/1998 Schulze et al.
5,827,271 A 10/1998 Buysse et al.
5,827,298 A 10/1998 Hart et al.
5,827,323 A 10/1998 Klieman et al.
5,829,662 A 11/1998 Allen et al.
5,830,598 A 11/1998 Patterson
5,833,690 A 11/1998 Yates et al.
5,833,695 A 11/1998 Yoon
5,833,696 A 11/1998 Whitfield et al.
5,836,503 A 11/1998 Ehrenfels et al.
5,836,960 A 11/1998 Kolesa et al.
5,839,369 A 11/1998 Chatterjee et al.
5,839,639 A 11/1998 Sauer et al.
5,841,284 A 11/1998 Takahashi
5,843,021 A 12/1998 Edwards et al.
5,843,096 A 12/1998 Igaki et al.
5,843,097 A 12/1998 Mayenberger et al.
5,843,122 A 12/1998 Riza
5,843,132 A 12/1998 Ilvento
5,843,169 A 12/1998 Taheri
5,846,254 A 12/1998 Schulze et al.
5,847,566 A 12/1998 Marritt et al.
5,849,011 A 12/1998 Jones et al.
5,849,020 A 12/1998 Long et al.
5,849,023 A 12/1998 Mericle
5,851,179 A 12/1998 Ritson et al.
5,851,212 A 12/1998 Zirps et al.
5,853,366 A 12/1998 Dowlatshahi
5,855,311 A 1/1999 Hamblin et al.
5,855,583 A 1/1999 Wang et al.
5,860,581 A 1/1999 Robertson et al.
5,860,975 A 1/1999 Goble et al.
5,865,361 A 2/1999 Milliman et al.
5,865,638 A 2/1999 Trafton
5,868,361 A 2/1999 Rinderer
5,868,760 A 2/1999 McGuckin, Jr.
5,868,790 A 2/1999 Vincent et al.
5,871,135 A 2/1999 Williamson, IV et al.
5,873,885 A 2/1999 Weidenbenner
5,876,401 A 3/1999 Schulze et al.
5,878,193 A 3/1999 Wang et al.
5,878,607 A 3/1999 Nunes et al.
5,878,937 A 3/1999 Green et al.
5,878,938 A 3/1999 Bittner et al.
5,881,777 A 3/1999 Bassi et al.
5,891,094 A 4/1999 Masterson et al.
5,891,160 A 4/1999 Williamson, IV et al.
5,891,558 A 4/1999 Bell et al.
5,893,506 A 4/1999 Powell
5,893,835 A 4/1999 Witt et al.
5,893,878 A 4/1999 Pierce
5,894,979 A 4/1999 Powell
5,897,552 A 4/1999 Edwards et al.
5,897,562 A 4/1999 Bolanos et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,907,664 A 5/1999 Wang et al.
5,908,402 A 6/1999 Blythe
5,908,427 A 6/1999 McKean et al.
5,909,062 A 6/1999 Krietzman
5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,924,864 A 7/1999 Loge et al.
5,928,137 A 7/1999 Green
5,928,256 A 7/1999 Riza
5,931,847 A 8/1999 Bittner et al.
5,931,853 A 8/1999 McEwen et al.
5,937,951 A 8/1999 Izuchukwu et al.
5,938,667 A 8/1999 Peyser et al.
5,941,442 A 8/1999 Geiste et al.
5,941,890 A 8/1999 Voegele et al.
5,944,172 A 8/1999 Hannula
5,944,715 A 8/1999 Goble et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,957,831 A 9/1999 Adair
5,964,394 A 10/1999 Robertson
5,964,774 A 10/1999 McKean et al.
5,966,126 A 10/1999 Szabo
5,971,916 A 10/1999 Koren
5,973,221 A 10/1999 Collyer et al.
D416,089 S 11/1999 Barton et al.

(56) References Cited

U.S. PATENT DOCUMENTS 5,976,122 A 11/1999 Madhani et al.
5,977,746 A 11/1999 Hershberger et al.
5,980,248 A 11/1999 Kusakabe et al.
5,984,949 A 11/1999 Levin
5,988,479 A 11/1999 Palmer
5,990,379 A 11/1999 Gregory
5,993,466 A 11/1999 Yoon
5,997,528 A 12/1999 Bisch et al.
5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,521 A 12/1999 Bidwell et al.
6,010,054 A 1/2000 Johnson et al.
6,010,513 A 1/2000 Tormala et al.
6,010,520 A 1/2000 Pattison
6,012,494 A 1/2000 Balazs
6,013,076 A 1/2000 Goble et al.
6,013,991 A 1/2000 Philipp
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,641 A 2/2000 Thompson
6,024,708 A 2/2000 Bales et al.
6,024,741 A 2/2000 Williamson, IV et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,032,849 A 3/2000 Mastri et al.
6,033,105 A 3/2000 Barker et al.
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
6,045,560 A 4/2000 McKean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,151 A 5/2000 Miyawaki et al.
6,068,627 A 5/2000 Orszulak et al.
6,071,233 A 6/2000 Ishikawa et al.
6,072,299 A 6/2000 Kurle et al.
6,074,386 A 6/2000 Goble et al.
6,074,401 A 6/2000 Gardiner et al.
6,075,441 A 6/2000 Maloney
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.
6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,090,123 A 7/2000 Culp et al.
6,093,186 A 7/2000 Goble
D429,252 S 8/2000 Haitani et al.
6,099,537 A 8/2000 Sugai et al.
6,099,551 A 8/2000 Gabbay
6,102,271 A 8/2000 Longo et al.
6,102,926 A 8/2000 Tartaglia et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,149,660 A 11/2000 Laufer et al.
6,151,323 A 11/2000 O'Connell et al.
6,152,935 A 11/2000 Kammerer et al.
6,155,473 A 12/2000 Tompkins et al.
6,156,056 A 12/2000 Kearns et al.
6,157,169 A 12/2000 Lee
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.

(56) References Cited

U.S. PATENT DOCUMENTS 6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,186,957 B1 2/2001 Milam
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.
6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.

(56) References Cited

U.S. PATENT DOCUMENTS 6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,189 B1 12/2002 Lang et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,506,399 B2 1/2003 Donovan
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.
6,535,764 B2 3/2003 Imran et al.
6,539,297 B2 3/2003 Weiberle et al.
D473,239 S 4/2003 Cockerill
6,539,816 B2 4/2003 Kogiso et al.
6,540,737 B2 4/2003 Bacher et al.
6,543,456 B1 4/2003 Freeman
6,545,384 B1 4/2003 Pelrine et al.
6,547,786 B1 4/2003 Goble
6,550,546 B2 4/2003 Thurler et al.
6,551,333 B2 4/2003 Kuhns et al.
6,554,861 B2 4/2003 Knox et al.
6,555,770 B2 4/2003 Kawase
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,578,751 B2 6/2003 Hartwick
6,582,364 B2 6/2003 Butler et al.
6,582,427 B1 6/2003 Goble et al.
6,582,441 B1 6/2003 He et al.
6,583,533 B2 6/2003 Pelrine et al.
6,585,144 B2 7/2003 Adams et al.
6,585,664 B2 7/2003 Burdorff et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,625,517 B1 9/2003 Bogdanov et al.
6,626,834 B2 9/2003 Dunne et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi
6,638,285 B2 10/2003 Gabbay
6,638,297 B1 10/2003 Huitema
RE38,335 E 11/2003 Aust et al.
6,641,528 B2 11/2003 Torii
6,644,532 B2 11/2003 Green et al.
6,645,201 B1 11/2003 Utley et al.

(56) References Cited

U.S. PATENT DOCUMENTS 6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.
6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,677,687 B2 1/2004 Ho et al.
6,679,269 B2 1/2004 Swanson
6,679,410 B2 1/2004 Wursch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman
6,695,774 B2 2/2004 Hale et al.
6,695,849 B2 2/2004 Michelson
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.
6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.

(56) References Cited

U.S. PATENT DOCUMENTS 6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,928,902 B1 8/2005 Eyssallenne
6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao

(56) References Cited

U.S. PATENT DOCUMENTS 7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,770 B1 7/2006 Smith
7,077,856 B2 7/2006 Whitman
7,080,769 B2 7/2006 Vresh et al.
7,081,114 B2 7/2006 Rashidi
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.
7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,161,036 B2 1/2007 Oikawa et al.
7,161,580 B2 1/2007 Bailey et al.
7,162,758 B2 1/2007 Skinner
7,163,563 B2 1/2007 Schwartz et al.
7,166,117 B2 1/2007 Hellenkamp
7,166,133 B2 1/2007 Evans et al.
7,168,604 B2 1/2007 Milliman et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella

(56) References Cited

U.S. PATENT DOCUMENTS 7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.
D541,418 S 4/2007 Schechter et al.
7,199,537 B2 4/2007 Okamura et al.
7,199,545 B2 4/2007 Oleynikov et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 4/2007 Frecker et al.
7,210,609 B2 5/2007 Leiboff et al.
7,211,081 B2 5/2007 Goble
7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.
7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,313,430 B2 12/2007 Urquhart et al.
7,314,473 B2 1/2008 Jinno et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.

(56) References Cited

U.S. PATENT DOCUMENTS 7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,424,965 B2 9/2008 Racenet et al.
7,427,607 B2 9/2008 Suzuki
D578,644 S 10/2008 Shumer et al.
7,430,772 B2 10/2008 Van Es
7,431,188 B1 10/2008 Marczyk
7,431,189 B2 10/2008 Shelton, IV et al.
7,431,230 B2 10/2008 McPherson et al.
7,431,694 B2 10/2008 Stefanchik et al.
7,431,730 B2 10/2008 Viola
7,434,715 B2 10/2008 Shelton, IV et al.
7,434,717 B2 10/2008 Shelton, IV et al.
7,435,249 B2 10/2008 Buysse et al.
7,438,209 B1 10/2008 Hess et al.
7,438,718 B2 10/2008 Milliman et al.
7,439,354 B2 10/2008 Lenges et al.
7,441,684 B2 10/2008 Shelton, IV et al.
7,441,685 B1 10/2008 Boudreaux
7,442,201 B2 10/2008 Pugsley et al.
7,443,547 B2 10/2008 Moreno et al.
7,446,131 B1 11/2008 Liu et al.
7,448,525 B2 11/2008 Shelton, IV et al.
7,450,010 B1 11/2008 Gravelle et al.
7,450,991 B2 11/2008 Smith et al.
7,451,904 B2 11/2008 Shelton, IV
7,455,208 B2 11/2008 Wales et al.
7,455,676 B2 11/2008 Holsten et al.
7,455,682 B2 11/2008 Viola
7,455,687 B2 11/2008 Saunders et al.
D582,934 S 12/2008 Byeon
7,461,767 B2 12/2008 Viola et al.
7,462,187 B2 12/2008 Johnston et al.
7,464,845 B2 12/2008 Chou
7,464,846 B2 12/2008 Shelton, IV et al.
7,464,847 B2 12/2008 Viola et al.
7,464,848 B2 12/2008 Green et al.
7,464,849 B2 12/2008 Shelton, IV et al.
7,467,740 B2 12/2008 Shelton, IV et al.
7,467,849 B2 12/2008 Silverbrook et al.
7,472,814 B2 1/2009 Mastri et al.
7,472,815 B2 1/2009 Shelton, IV et al.
7,472,816 B2 1/2009 Holsten et al.
7,473,221 B2 1/2009 Ewers et al.
7,473,253 B2 1/2009 Dycus et al.
7,473,263 B2 1/2009 Johnston et al.
7,476,237 B2 1/2009 Taniguchi et al.
7,479,147 B2 1/2009 Honeycutt et al.
7,479,608 B2 1/2009 Smith
7,481,347 B2 1/2009 Roy
7,481,348 B2 1/2009 Marczyk
7,481,349 B2 1/2009 Holsten et al.
7,481,824 B2 1/2009 Boudreaux et al.
7,485,124 B2 2/2009 Kuhns et al.
7,485,133 B2 2/2009 Cannon et al.
7,485,142 B2 2/2009 Milo
7,487,899 B2 2/2009 Shelton, IV et al.
7,489,055 B2 2/2009 Jeong et al.
7,490,749 B2 2/2009 Schall et al.
7,491,232 B2 2/2009 Bolduc et al.
7,492,261 B2 2/2009 Cambre et al.
7,494,039 B2 2/2009 Racenet et al.
7,494,460 B2 2/2009 Haarstad et al.
7,494,499 B2 2/2009 Nagase et al.
7,494,501 B2 2/2009 Ahlberg et al.
7,497,137 B2 3/2009 Tellenbach et al.
7,500,979 B2 3/2009 Hueil et al.
7,501,198 B2 3/2009 Barlev et al.
7,503,474 B2 3/2009 Hillstead et al.
7,506,790 B2 3/2009 Shelton, IV
7,506,791 B2 3/2009 Omaits et al.
7,507,202 B2 3/2009 Schoellhorn
7,510,107 B2 3/2009 Timm et al.
7,510,534 B2 3/2009 Burdorff et al.
7,510,566 B2 3/2009 Jacobs et al.
7,513,407 B1 4/2009 Chang
7,513,408 B2 4/2009 Shelton, IV et al.
7,517,356 B2 4/2009 Heinrich
7,524,320 B2 4/2009 Tierney et al.
7,527,632 B2 5/2009 Houghton et al.
7,530,984 B2 5/2009 Sonnenschein et al.
7,530,985 B2 5/2009 Takemoto et al.
7,533,906 B2 5/2009 Luettgen et al.
7,534,259 B2 5/2009 Lashinski et al.
7,540,867 B2 6/2009 Jinno et al.
7,540,872 B2 6/2009 Schechter et al.
7,542,807 B2 6/2009 Bertolero et al.
7,543,730 B1 6/2009 Marczyk
7,544,197 B2 6/2009 Kelsch et al.
7,546,939 B2 6/2009 Adams et al.
7,546,940 B2 6/2009 Milliman et al.
7,547,287 B2 6/2009 Boecker et al.
7,547,312 B2 6/2009 Bauman et al.
7,549,563 B2 6/2009 Mather et al.
7,549,564 B2 6/2009 Boudreaux
7,549,998 B2 6/2009 Braun
7,552,854 B2 6/2009 Wixey et al.
7,553,173 B2 6/2009 Kowalick
7,553,275 B2 6/2009 Padget et al.
7,554,343 B2 6/2009 Bromfield
7,556,185 B2 7/2009 Viola
7,556,186 B2 7/2009 Milliman
7,556,647 B2 7/2009 Drews et al.
7,559,449 B2 7/2009 Viola
7,559,450 B2 7/2009 Wales et al.
7,559,452 B2 7/2009 Wales et al.
7,559,937 B2 7/2009 de la Torre et al.
7,561,637 B2 7/2009 Jonsson et al.
7,562,910 B2 7/2009 Kertesz et al.
7,563,269 B2 7/2009 Hashiguchi
7,563,862 B2 7/2009 Sieg et al.
7,565,993 B2 7/2009 Milliman et al.
7,566,300 B2 7/2009 Devierre et al.

(56) References Cited

U.S. PATENT DOCUMENTS 7,567,045 B2 7/2009 Fristedt
7,568,603 B2 8/2009 Shelton, IV et al.
7,568,604 B2 8/2009 Ehrenfels et al.
7,568,619 B2 8/2009 Todd et al.
7,572,285 B2 8/2009 Frey et al.
7,575,144 B2 8/2009 Ortiz et al.
7,578,825 B2 8/2009 Huebner
D600,712 S 9/2009 LaManna et al.
7,583,063 B2 9/2009 Dooley
7,584,880 B2 9/2009 Racenet et al.
7,586,289 B2 9/2009 Andruk et al.
7,588,174 B2 9/2009 Holsten et al.
7,588,175 B2 9/2009 Timm et al.
7,588,176 B2 9/2009 Timm et al.
7,588,177 B2 9/2009 Racenet
7,591,783 B2 9/2009 Boulais et al.
7,591,818 B2 9/2009 Bertolero et al.
7,593,766 B2 9/2009 Faber et al.
7,595,642 B2 9/2009 Doyle
7,597,229 B2 10/2009 Boudreaux et al.
7,597,230 B2 10/2009 Racenet et al.
7,597,693 B2 10/2009 Garrison
7,597,699 B2 10/2009 Rogers
7,598,972 B2 10/2009 Tomita
7,600,663 B2 10/2009 Green
7,604,118 B2 10/2009 Iio et al.
7,604,150 B2 10/2009 Boudreaux
7,604,151 B2 10/2009 Hess et al.
7,604,668 B2 10/2009 Farnsworth et al.
7,605,826 B2 10/2009 Sauer
7,607,557 B2 10/2009 Shelton, IV et al.
7,608,091 B2 10/2009 Goldfarb et al.
D604,325 S 11/2009 Ebeling et al.
7,611,038 B2 11/2009 Racenet et al.
7,611,474 B2 11/2009 Hibner et al.
7,615,003 B2 11/2009 Stefanchik et al.
7,615,006 B2 11/2009 Abe
7,615,067 B2 11/2009 Lee et al.
7,617,961 B2 11/2009 Viola
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh, II et al.
7,670,334 B2 3/2010 Hueil et al.
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeller et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.

(56) References Cited

U.S. PATENT DOCUMENTS 7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,735,704 B2 6/2010 Bilotti
7,736,254 B2 6/2010 Schena
7,736,306 B2 6/2010 Brustad et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman
7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 10/2010 Hall et al.
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stotters et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.

(56) References Cited

U.S. PATENT DOCUMENTS 7,875,055 B2 1/2011 Cichocki, Jr.
7,879,063 B2 2/2011 Khosravi
7,879,070 B2 2/2011 Ortiz et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.
7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban, III et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag
7,976,563 B2 7/2011 Summerer
7,979,137 B2 7/2011 Tracey et al.
7,980,443 B2 7/2011 Scheib et al.
7,981,102 B2 7/2011 Patel et al.
7,981,132 B2 7/2011 Dubrul et al.
7,987,405 B2 7/2011 Turner et al.
7,988,015 B2 8/2011 Mason, II et al.
7,988,026 B2 8/2011 Knodel et al.
7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 9/2011 Marczyk et al.
8,011,553 B2 9/2011 Mastri et al.

(56) References Cited

U.S. PATENT DOCUMENTS 8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.
8,016,858 B2 9/2011 Whitman
8,016,881 B2 9/2011 Furst
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,882 B2 10/2011 Viola
8,028,883 B2 10/2011 Stope
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,438 B2 10/2011 Scirica
8,033,439 B2 10/2011 Racenet et al.
8,033,440 B2 10/2011 Wenchell et al.
8,033,442 B2 10/2011 Racenet et al.
8,034,077 B2 10/2011 Smith et al.
8,034,337 B2 10/2011 Simard
8,034,363 B2 10/2011 Li et al.
8,035,487 B2 10/2011 Malackowski
8,037,591 B2 10/2011 Spivey et al.
8,038,044 B2 10/2011 Viola
8,038,045 B2 10/2011 Bettuchi et al.
8,038,046 B2 10/2011 Smith et al.
8,038,686 B2 10/2011 Huitema et al.
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,503 B2 11/2011 Farnsworth et al.
8,052,636 B2 11/2011 Moll et al.
8,056,787 B2 11/2011 Boudreaux et al.
8,056,788 B2 11/2011 Mastri et al.
8,056,789 B1 11/2011 White et al.
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,236 B2 11/2011 Soltz
8,062,306 B2 11/2011 Nobis et al.
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,743 B2 12/2011 Kagan et al.
8,074,858 B2 12/2011 Marczyk
8,074,859 B2 12/2011 Kostrzewski
8,074,861 B2 12/2011 Ehrenfels et al.
8,075,476 B2 12/2011 Vargas
8,075,571 B2 12/2011 Vitali et al.
8,079,950 B2 12/2011 Stern et al.
8,079,989 B2 12/2011 Birk et al.
8,080,004 B2 12/2011 Downey et al.
8,083,118 B2 12/2011 Milliman et al.
8,083,119 B2 12/2011 Prommersberger
8,083,120 B2 12/2011 Shelton, IV et al.
8,084,001 B2 12/2011 Burns et al.
8,084,969 B2 12/2011 David et al.
8,085,013 B2 12/2011 Wei et al.
8,087,562 B1 1/2012 Manoux et al.
8,087,563 B2 1/2012 Milliman et al.
8,089,509 B2 1/2012 Chatenever et al.
8,091,753 B2 1/2012 Viola
8,091,756 B2 1/2012 Viola
8,092,443 B2 1/2012 Bischoff
8,092,932 B2 1/2012 Phillips et al.
8,093,572 B2 1/2012 Kuduvalli
8,096,458 B2 1/2012 Hessler
8,096,459 B2 1/2012 Ortiz et al.
8,097,017 B2 1/2012 Viola
8,100,310 B2 1/2012 Zemlok
8,100,824 B2 1/2012 Hegeman et al.
8,100,872 B2 1/2012 Patel
8,102,138 B2 1/2012 Sekine et al.
8,102,278 B2 1/2012 Deck et al.
8,105,320 B2 1/2012 Manzo
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,161,977 B2 4/2012 Shelton, IV et al.
8,162,138 B2 4/2012 Bettenhausen et al.
8,162,197 B2 4/2012 Mastri et al.

(56) References Cited

U.S. PATENT DOCUMENTS 8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho
8,172,120 B2 5/2012 Boyden et al.
8,172,122 B2 5/2012 Kasvikis et al.
8,172,124 B2 5/2012 Shelton, IV et al.
8,177,776 B2 5/2012 Humayun et al.
8,177,797 B2 5/2012 Shimoji et al.
8,179,705 B2 5/2012 Chapuis
8,180,458 B2 5/2012 Kane et al.
8,181,839 B2 5/2012 Beetel
8,181,840 B2 5/2012 Milliman
8,182,422 B2 5/2012 Bayer et al.
8,182,444 B2 5/2012 Uber, III et al.
8,183,807 B2 5/2012 Tsai et al.
8,186,555 B2 5/2012 Shelton, IV et al.
8,186,556 B2 5/2012 Viola
8,186,558 B2 5/2012 Sapienza
8,186,560 B2 5/2012 Hess et al.
8,190,238 B2 5/2012 Moll et al.
8,191,752 B2 6/2012 Scirica
8,192,350 B2 6/2012 Ortiz et al.
8,192,460 B2 6/2012 Orban, III et al.
8,192,651 B2 6/2012 Young et al.
8,193,129 B2 6/2012 Tagawa et al.
8,196,795 B2 6/2012 Moore et al.
8,196,796 B2 6/2012 Shelton, IV et al.
8,197,501 B2 6/2012 Shadeck et al.
8,197,502 B2 6/2012 Smith et al.
8,197,837 B2 6/2012 Jamiolkowski et al.
8,201,720 B2 6/2012 Hessler
8,201,721 B2 6/2012 Zemlok et al.
8,202,549 B2 6/2012 Stucky et al.
8,205,779 B2 6/2012 Ma et al.
8,205,780 B2 6/2012 Sorrentino et al.
8,205,781 B2 6/2012 Baxter, III et al.
8,207,863 B2 6/2012 Neubauer et al.
8,210,411 B2 7/2012 Yates et al.
8,210,414 B2 7/2012 Bettuchi et al.
8,210,415 B2 7/2012 Ward
8,210,416 B2 7/2012 Milliman et al.
8,210,721 B2 7/2012 Chen et al.
8,211,125 B2 7/2012 Spivey
8,214,019 B2 7/2012 Govari et al.
8,215,531 B2 7/2012 Shelton, IV et al.
8,215,532 B2 7/2012 Marczyk
8,215,533 B2 7/2012 Viola et al.
8,220,468 B2 7/2012 Cooper et al.
8,220,688 B2 7/2012 Laurent et al.
8,220,690 B2 7/2012 Hess et al.
8,221,402 B2 7/2012 Francischelli et al.
8,221,424 B2 7/2012 Cha
8,221,433 B2 7/2012 Lozier et al.
8,225,799 B2 7/2012 Bettuchi
8,225,979 B2 7/2012 Farascioni et al.
8,226,553 B2 7/2012 Shelton, IV et al.
8,226,635 B2 7/2012 Petrie et al.
8,226,675 B2 7/2012 Houser et al.
8,226,715 B2 7/2012 Hwang et al.
8,227,946 B2 7/2012 Kim
8,228,020 B2 7/2012 Shin et al.
8,228,048 B2 7/2012 Spencer
8,229,549 B2 7/2012 Whitman et al.
8,231,040 B2 7/2012 Zemlok et al.
8,231,042 B2 7/2012 Hessler et al.
8,231,043 B2 7/2012 Tarinelli et al.
8,235,272 B2 8/2012 Nicholas et al.
8,235,274 B2 8/2012 Cappola
8,236,010 B2 8/2012 Ortiz et al.
8,236,011 B2 8/2012 Harris et al.
8,236,020 B2 8/2012 Smith et al.
8,237,388 B2 8/2012 Jinno et al.
8,240,537 B2 8/2012 Marczyk
8,241,271 B2 8/2012 Millman et al.
8,241,284 B2 8/2012 Dycus et al.
8,241,308 B2 8/2012 Kortenbach et al.
8,241,322 B2 8/2012 Whitman et al.
8,245,594 B2 8/2012 Rogers et al.
8,245,898 B2 8/2012 Smith et al.
8,245,899 B2 8/2012 Swensgard et al.
8,245,900 B2 8/2012 Scirica
8,245,901 B2 8/2012 Stope
8,246,608 B2 8/2012 Omori et al.
8,246,637 B2 8/2012 Viola et al.
8,252,009 B2 8/2012 Weller et al.
8,256,654 B2 9/2012 Bettuchi et al.
8,256,655 B2 9/2012 Sniffin et al.
8,256,656 B2 9/2012 Milliman et al.
8,257,251 B2 9/2012 Shelton, IV et al.
8,257,356 B2 9/2012 Bleich et al.
8,257,386 B2 9/2012 Lee et al.
8,257,391 B2 9/2012 Orban, III et al.
8,257,634 B2 9/2012 Scirica
8,258,745 B2 9/2012 Smith et al.
8,261,958 B1 9/2012 Knodel
8,262,560 B2 9/2012 Whitman
8,262,655 B2 9/2012 Ghabrial et al.
8,266,232 B2 9/2012 Piper et al.
8,267,300 B2 9/2012 Boudreaux
8,267,849 B2 9/2012 Wazer et al.
8,267,924 B2 9/2012 Zemlok et al.
8,267,946 B2 9/2012 Whitfield et al.
8,267,951 B2 9/2012 Whayne et al.
8,268,344 B2 9/2012 Ma et al.
8,269,121 B2 9/2012 Smith
8,272,553 B2 9/2012 Mastri et al.
8,272,554 B2 9/2012 Whitman et al.
8,272,918 B2 9/2012 Lam
8,273,404 B2 9/2012 Dave et al.
8,276,594 B2 10/2012 Shah
8,276,801 B2 10/2012 Zemlok et al.
8,276,802 B2 10/2012 Kostrzewski
8,277,473 B2 10/2012 Sunaoshi et al.
8,281,446 B2 10/2012 Moskovich
8,281,973 B2 10/2012 Wenchell et al.
8,281,974 B2 10/2012 Hessler et al.
8,282,654 B2 10/2012 Ferrari et al.
8,285,367 B2 10/2012 Hyde et al.
8,286,723 B2 10/2012 Puzio et al.
8,286,845 B2 10/2012 Perry et al.
8,286,846 B2 10/2012 Smith et al.
8,286,847 B2 10/2012 Taylor
8,287,487 B2 10/2012 Estes
8,287,522 B2 10/2012 Moses et al.
8,287,561 B2 10/2012 Nunez et al.
8,288,984 B2 10/2012 Yang
8,289,403 B2 10/2012 Dobashi et al.
8,290,883 B2 10/2012 Takeuchi et al.
8,292,147 B2 10/2012 Viola
8,292,148 B2 10/2012 Viola
8,292,150 B2 10/2012 Bryant
8,292,151 B2 10/2012 Viola
8,292,152 B2 10/2012 Milliman et al.
8,292,155 B2 10/2012 Shelton, IV et al.
8,292,157 B2 10/2012 Smith et al.
8,292,158 B2 10/2012 Sapienza
8,292,801 B2 10/2012 Dejima et al.
8,292,888 B2 10/2012 Whitman
8,292,906 B2 10/2012 Taylor et al.
8,294,399 B2 10/2012 Suzuki et al.
8,298,161 B2 10/2012 Vargas
8,298,189 B2 10/2012 Fisher et al.
8,298,233 B2 10/2012 Mueller
8,298,677 B2 10/2012 Wiesner et al.
8,302,323 B2 11/2012 Fortier et al.
8,303,621 B2 11/2012 Miyamoto et al.
8,308,040 B2 11/2012 Huang et al.
8,308,041 B2 11/2012 Kostrzewski

(56) References Cited

U.S. PATENT DOCUMENTS 8,308,042 B2 11/2012 Aranyi
8,308,043 B2 11/2012 Bindra et al.
8,308,046 B2 11/2012 Prommersberger
8,308,659 B2 11/2012 Scheibe et al.
8,308,725 B2 11/2012 Bell et al.
8,310,188 B2 11/2012 Nakai
8,313,496 B2 11/2012 Sauer et al.
8,313,499 B2 11/2012 Magnusson et al.
8,313,509 B2 11/2012 Kostrzewski
8,317,070 B2 11/2012 Hueil et al.
8,317,071 B1 11/2012 Knodel
8,317,074 B2 11/2012 Ortiz et al.
8,317,437 B2 11/2012 Merkley et al.
8,317,744 B2 11/2012 Kirschenman
8,317,790 B2 11/2012 Bell et al.
8,319,002 B2 11/2012 Daniels et al.
D672,784 S 12/2012 Clanton et al.
8,322,455 B2 12/2012 Shelton, IV et al.
8,322,589 B2 12/2012 Boudreaux
8,322,590 B2 12/2012 Patel et al.
8,322,901 B2 12/2012 Michelotti
8,323,271 B2 12/2012 Humayun et al.
8,323,789 B2 12/2012 Rozhin et al.
8,324,585 B2 12/2012 McBroom et al.
8,327,514 B2 12/2012 Kim
8,328,061 B2 12/2012 Kasvikis
8,328,062 B2 12/2012 Viola
8,328,063 B2 12/2012 Milliman et al.
8,328,064 B2 12/2012 Racenet et al.
8,328,065 B2 12/2012 Shah
8,328,802 B2 12/2012 Deville et al.
8,328,823 B2 12/2012 Aranyi et al.
8,333,313 B2 12/2012 Boudreaux et al.
8,333,691 B2 12/2012 Schaaf
8,333,764 B2 12/2012 Francischelli et al.
8,333,779 B2 12/2012 Smith et al.
8,334,468 B2 12/2012 Palmer et al.
8,336,753 B2 12/2012 Olson et al.
8,336,754 B2 12/2012 Cappola et al.
8,342,377 B2 1/2013 Milliman et al.
8,342,378 B2 1/2013 Marczyk et al.
8,342,379 B2 1/2013 Whitman et al.
8,342,380 B2 1/2013 Viola
8,343,150 B2 1/2013 Artale
8,347,978 B2 1/2013 Forster et al.
8,348,118 B2 1/2013 Segura
8,348,123 B2 1/2013 Scirica et al.
8,348,124 B2 1/2013 Scirica
8,348,125 B2 1/2013 Viola et al.
8,348,126 B2 1/2013 Olson et al.
8,348,127 B2 1/2013 Marczyk
8,348,129 B2 1/2013 Bedi et al.
8,348,130 B2 1/2013 Shah et al.
8,348,131 B2 1/2013 Omaits et al.
8,348,837 B2 1/2013 Wenchell
8,348,959 B2 1/2013 Wolford et al.
8,348,972 B2 1/2013 Soltz et al.
8,349,987 B2 1/2013 Kapiamba et al.
8,352,004 B2 1/2013 Mannheimer et al.
8,353,437 B2 1/2013 Boudreaux
8,353,438 B2 1/2013 Baxter, III et al.
8,353,439 B2 1/2013 Baxter, III et al.
8,356,740 B1 1/2013 Knodel
8,357,144 B2 1/2013 Whitman et al.
8,357,158 B2 1/2013 McKenna et al.
8,357,161 B2 1/2013 Mueller
8,359,174 B2 1/2013 Nakashima et al.
8,360,296 B2 1/2013 Zingman
8,360,297 B2 1/2013 Shelton, IV et al.
8,360,298 B2 1/2013 Farascioni et al.
8,360,299 B2 1/2013 Zemlok et al.
8,361,501 B2 1/2013 DiTizio et al.
D676,866 S 2/2013 Chaudhri
8,365,972 B2 2/2013 Aranyi et al.
8,365,973 B1 2/2013 White et al.
8,365,975 B1 2/2013 Manoux et al.
8,365,976 B2 2/2013 Hess et al.
8,366,559 B2 2/2013 Papenfuss et al.
8,366,719 B2 2/2013 Markey et al.
8,366,787 B2 2/2013 Brown et al.
8,368,327 B2 2/2013 Benning et al.
8,369,056 B2 2/2013 Senriuchi et al.
8,371,393 B2 2/2013 Higuchi et al.
8,371,491 B2 2/2013 Huitema et al.
8,371,492 B2 2/2013 Aranyi et al.
8,371,493 B2 2/2013 Aranyi et al.
8,371,494 B2 2/2013 Racenet et al.
8,372,094 B2 2/2013 Bettuchi et al.
8,374,723 B2 2/2013 Zhao et al.
8,376,865 B2 2/2013 Forster et al.
8,377,029 B2 2/2013 Nagao et al.
8,377,044 B2 2/2013 Coe et al.
8,377,059 B2 2/2013 Deville et al.
8,381,828 B2 2/2013 Whitman et al.
8,382,773 B2 2/2013 Whitfield et al.
8,382,790 B2 2/2013 Uenohara et al.
D677,273 S 3/2013 Randall et al.
8,387,848 B2 3/2013 Johnson et al.
8,388,633 B2 3/2013 Rousseau et al.
8,389,588 B2 3/2013 Ringeisen et al.
8,393,513 B2 3/2013 Jankowski
8,393,514 B2 3/2013 Shelton, IV et al.
8,393,516 B2 3/2013 Kostrzewski
8,397,832 B2 3/2013 Blickle et al.
8,397,971 B2 3/2013 Yates et al.
8,397,972 B2 3/2013 Kostrzewski
8,397,973 B1 3/2013 Hausen
8,398,633 B2 3/2013 Mueller
8,398,669 B2 3/2013 Kim
8,398,673 B2 3/2013 Hinchliffe et al.
8,398,674 B2 3/2013 Prestel
8,400,108 B2 3/2013 Powell et al.
8,400,851 B2 3/2013 Byun
8,403,138 B2 3/2013 Weisshaupt et al.
8,403,195 B2 3/2013 Beardsley et al.
8,403,196 B2 3/2013 Beardsley et al.
8,403,198 B2 3/2013 Sorrentino et al.
8,403,832 B2 3/2013 Cunningham et al.
8,403,926 B2 3/2013 Nobis et al.
8,403,945 B2 3/2013 Whitfield et al.
8,403,946 B2 3/2013 Whitfield et al.
8,403,950 B2 3/2013 Palmer et al.
D680,646 S 4/2013 Hunt et al.
8,408,439 B2 4/2013 Huang et al.
8,408,442 B2 4/2013 Racenet et al.
8,409,079 B2 4/2013 Okamoto et al.
8,409,174 B2 4/2013 Omori
8,409,175 B2 4/2013 Lee et al.
8,409,211 B2 4/2013 Baroud
8,409,222 B2 4/2013 Whitfield et al.
8,409,223 B2 4/2013 Sorrentino et al.
8,411,500 B2 4/2013 Gapihan et al.
8,413,661 B2 4/2013 Rousseau et al.
8,413,870 B2 4/2013 Pastorelli et al.
8,413,871 B2 4/2013 Racenet et al.
8,413,872 B2 4/2013 Patel
8,414,469 B2 4/2013 Diolaiti
8,414,577 B2 4/2013 Boudreaux et al.
8,414,598 B2 4/2013 Brock et al.
8,418,073 B2 4/2013 Mohr et al.
8,418,906 B2 4/2013 Farascioni et al.
8,418,907 B2 4/2013 Johnson et al.
8,418,908 B1 4/2013 Beardsley
8,418,909 B2 4/2013 Kostrzewski
8,419,635 B2 4/2013 Shelton, IV et al.
8,419,717 B2 4/2013 Diolaiti et al.
8,419,747 B2 4/2013 Hinman et al.
8,419,754 B2 4/2013 Laby et al.
8,419,755 B2 4/2013 Deem et al.
8,423,182 B2 4/2013 Robinson et al.
8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.

(56) References Cited

U.S. PATENT DOCUMENTS 8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
8,435,257 B2 5/2013 Smith et al.
8,439,246 B1 5/2013 Knodel
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.
8,584,920 B2 11/2013 Hodgkinson
8,584,921 B2 11/2013 Scirica
8,585,583 B2 11/2013 Sakaguchi et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.

(56) References Cited

U.S. PATENT DOCUMENTS 8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.
8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer

(56) References Cited

U.S. PATENT DOCUMENTS 8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roβkamp et al.
8,869,913 B2 10/2014 Matthias et al.
8,870,050 B2 10/2014 Hodgkinson
8,870,867 B2 10/2014 Walberg et al.
8,870,912 B2 10/2014 Brisson et al.
8,875,971 B2 11/2014 Hall et al.
8,875,972 B2 11/2014 Weisenburgh, II et al.
8,876,857 B2 11/2014 Burbank
8,876,858 B2 11/2014 Braun
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.
8,899,464 B2 12/2014 Hueil et al.
8,899,465 B2 12/2014 Shelton, IV et al.
8,899,466 B2 12/2014 Baxter, III et al.
8,900,267 B2 12/2014 Woolfson et al.
8,905,287 B2 12/2014 Racenet et al.
8,905,977 B2 12/2014 Shelton et al.
8,910,846 B2 12/2014 Viola
8,910,847 B2 12/2014 Nalagatla et al.
8,911,426 B2 12/2014 Coppeta et al.
8,911,448 B2 12/2014 Stein
8,911,460 B2 12/2014 Neurohr et al.
8,911,471 B2 12/2014 Spivey et al.
8,912,746 B2 12/2014 Reid et al.
8,920,368 B2 12/2014 Sandhu et al.
8,920,433 B2 12/2014 Barrier et al.
8,920,435 B2 12/2014 Smith et al.
8,920,438 B2 12/2014 Aranyi et al.
8,920,443 B2 12/2014 Hiles et al.
8,920,444 B2 12/2014 Hiles et al.
8,922,163 B2 12/2014 Macdonald
8,925,782 B2 1/2015 Shelton, IV
8,925,783 B2 1/2015 Zemlok et al.
8,925,788 B2 1/2015 Hess et al.
8,926,506 B2 1/2015 Widenhouse et al.
8,926,598 B2 1/2015 Mollere et al.
8,931,576 B2 1/2015 Iwata
8,931,679 B2 1/2015 Kostrzewski
8,931,680 B2 1/2015 Milliman
8,931,682 B2 1/2015 Timm et al.
8,936,614 B2 1/2015 Allen, IV
8,939,343 B2 1/2015 Milliman et al.
8,939,344 B2 1/2015 Olson et al.
8,939,898 B2 1/2015 Omoto
8,944,069 B2 2/2015 Miller et al.
8,945,095 B2 2/2015 Blumenkranz et al.

(56) References Cited

U.S. PATENT DOCUMENTS 8,945,163 B2 2/2015 Voegele et al.
8,955,732 B2 2/2015 Zemlok et al.
8,956,342 B1 2/2015 Russo et al.
8,956,390 B2 2/2015 Shah et al.
8,958,860 B2 2/2015 Banerjee et al.
8,960,519 B2 2/2015 Whitman et al.
8,960,520 B2 2/2015 McCuen
8,960,521 B2 2/2015 Kostrzewski
8,961,191 B2 2/2015 Hanshew
8,961,504 B2 2/2015 Hoarau et al.
8,963,714 B2 2/2015 Medhal et al.
D725,674 S 3/2015 Jung et al.
8,967,443 B2 3/2015 McCuen
8,967,444 B2 3/2015 Beetel
8,967,446 B2 3/2015 Beardsley et al.
8,967,448 B2 3/2015 Carter et al.
8,968,276 B2 3/2015 Zemlok et al.
8,968,308 B2 3/2015 Horner et al.
8,968,312 B2 3/2015 Marczyk et al.
8,968,337 B2 3/2015 Whitfield et al.
8,968,340 B2 3/2015 Chowaniec et al.
8,968,355 B2 3/2015 Malkowski et al.
8,968,358 B2 3/2015 Reschke
8,970,507 B2 3/2015 Holbein et al.
8,973,803 B2 3/2015 Hall et al.
8,973,804 B2 3/2015 Hess et al.
8,973,805 B2 3/2015 Scirica et al.
8,974,440 B2 3/2015 Farritor et al.
8,974,542 B2 3/2015 Fujimoto et al.
8,974,932 B2 3/2015 McGahan et al.
8,978,954 B2 3/2015 Shelton, IV et al.
8,978,955 B2 3/2015 Aronhalt et al.
8,978,956 B2 3/2015 Schall et al.
8,979,843 B2 3/2015 Timm et al.
8,979,890 B2 3/2015 Boudreaux
8,982,195 B2 3/2015 Claus et al.
8,984,711 B2 3/2015 Ota et al.
8,985,240 B2 3/2015 Winnard
8,985,429 B2 3/2015 Balek et al.
8,986,302 B2 3/2015 Aldridge et al.
8,989,903 B2 3/2015 Weir et al.
8,991,676 B2 3/2015 Hess et al.
8,991,677 B2 3/2015 Moore et al.
8,991,678 B2 3/2015 Wellman et al.
8,992,042 B2 3/2015 Eichenholz
8,992,422 B2 3/2015 Spivey et al.
8,992,565 B2 3/2015 Brisson et al.
8,996,165 B2 3/2015 Wang et al.
8,998,058 B2 4/2015 Moore et al.
8,998,059 B2 4/2015 Smith et al.
8,998,060 B2 4/2015 Bruewer et al.
8,998,061 B2 4/2015 Williams et al.
8,998,939 B2 4/2015 Price et al.
9,000,720 B2 4/2015 Stulen et al.
9,002,518 B2 4/2015 Manzo et al.
9,004,339 B1 4/2015 Park
9,005,230 B2 4/2015 Yates et al.
9,005,238 B2 4/2015 DeSantis et al.
9,005,243 B2 4/2015 Stopek et al.
9,010,606 B2 4/2015 Aranyi et al.
9,010,608 B2 4/2015 Casasanta, Jr. et al.
9,010,611 B2 4/2015 Ross et al.
9,011,437 B2 4/2015 Woodruff et al.
9,011,439 B2 4/2015 Shalaby et al.
9,011,471 B2 4/2015 Timm et al.
9,014,856 B2 4/2015 Manzo et al.
9,016,539 B2 4/2015 Kostrzewski et al.
9,016,540 B2 4/2015 Whitman et al.
9,016,541 B2 4/2015 Viola et al.
9,016,542 B2 4/2015 Shelton, IV et al.
9,016,545 B2 4/2015 Aranyi et al.
9,017,331 B2 4/2015 Fox
9,017,355 B2 4/2015 Smith et al.
9,017,369 B2 4/2015 Renger et al.
9,017,371 B2 4/2015 Whitman et al.
9,017,849 B2 4/2015 Stulen et al.
9,017,851 B2 4/2015 Felder et al.
D729,274 S 5/2015 Clement et al.
9,021,684 B2 5/2015 Lenker et al.
9,023,014 B2 5/2015 Chowaniec et al.
9,023,069 B2 5/2015 Kasvikis et al.
9,023,071 B2 5/2015 Miller et al.
9,026,347 B2 5/2015 Gadh et al.
9,027,817 B2 5/2015 Milliman et al.
9,028,494 B2 5/2015 Shelton, IV et al.
9,028,495 B2 5/2015 Mueller et al.
9,028,510 B2 5/2015 Miyamoto et al.
9,028,511 B2 5/2015 Weller et al.
9,028,519 B2 5/2015 Yates et al.
9,030,166 B2 5/2015 Kano
9,030,169 B2 5/2015 Christensen et al.
9,033,203 B2 5/2015 Woodard, Jr. et al.
9,033,204 B2 5/2015 Shelton, IV et al.
9,034,505 B2 5/2015 Detry et al.
9,038,881 B1 5/2015 Schaller et al.
9,039,690 B2 5/2015 Kersten et al.
9,039,694 B2 5/2015 Ross et al.
9,039,720 B2 5/2015 Madan
9,040,062 B2 5/2015 Maeda et al.
9,043,027 B2 5/2015 Durant et al.
9,044,227 B2 6/2015 Shelton, IV et al.
9,044,228 B2 6/2015 Woodard, Jr. et al.
9,044,229 B2 6/2015 Scheib et al.
9,044,230 B2 6/2015 Morgan et al.
9,044,238 B2 6/2015 Orszulak
9,044,241 B2 6/2015 Barner et al.
9,044,261 B2 6/2015 Houser
9,044,281 B2 6/2015 Pool et al.
9,050,083 B2 6/2015 Yates et al.
9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,601 B2 7/2015 Moore et al.
9,084,602 B2 7/2015 Gleiman
9,086,875 B2 7/2015 Harrat et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,385 B2 8/2015 Shelton, IV et al.
9,101,475 B2 8/2015 Wei et al.

(56) References Cited

U.S. PATENT DOCUMENTS 9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,868 B2 8/2015 Felder et al.
9,113,873 B2 8/2015 Marczyk et al.
9,113,874 B2 8/2015 Shelton, IV et al.
9,113,876 B2 8/2015 Zemlok et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.
9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson

(56) References Cited

U.S. PATENT DOCUMENTS 9,283,045 B2 3/2016 Rhee et al.
9,283,054 B2 3/2016 Morgan et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.
9,364,220 B2 6/2016 Williams
9,364,226 B2 6/2016 Zemlok et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,669 B2 7/2016 Karkanias et al.
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
D767,624 S 9/2016 Lee et al.
9,433,411 B2 9/2016 Racenet et al.

(56) References Cited

U.S. PATENT DOCUMENTS 9,433,414 B2 9/2016 Chen et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Res et al.
9,451,958 B2 9/2016 Shelton, IV et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,040 B2 10/2016 Jeong et al.
9,463,260 B2 10/2016 Stope
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,523 B2 10/2016 Meade et al.
9,474,540 B2 10/2016 Stokes et al.
9,475,180 B2 10/2016 Eshleman et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,521,996 B2 12/2016 Armstrong
9,522,003 B2 12/2016 Weir et al.
9,522,014 B2 12/2016 Nishizawa et al.
9,522,029 B2 12/2016 Yates et al.
9,526,481 B2 12/2016 Storz et al.
9,526,499 B2 12/2016 Kostrzewski et al.
9,526,563 B2 12/2016 Twomey
9,526,564 B2 12/2016 Rusin
9,526,921 B2 12/2016 Kimball et al.
D776,683 S 1/2017 Gobinski et al.
D777,773 S 1/2017 Shi
9,532,783 B2 1/2017 Swayze et al.
9,539,060 B2 1/2017 Lightcap et al.
9,539,726 B2 1/2017 Simaan et al.
9,545,253 B2 1/2017 Worrell et al.
9,545,258 B2 1/2017 Smith et al.
9,549,732 B2 1/2017 Yates et al.
9,549,733 B2 1/2017 Knodel
9,549,735 B2 1/2017 Shelton, IV et al.
9,554,794 B2 1/2017 Baber et al.
9,554,796 B2 1/2017 Kostrzewski
9,554,803 B2 1/2017 Smith et al.
9,554,812 B2 1/2017 Inkpen et al.
9,559,624 B2 1/2017 Philipp
9,561,013 B2 2/2017 Tsuchiya
9,561,029 B2 2/2017 Scheib et al.
9,561,030 B2 2/2017 Zhang et al.
9,561,031 B2 2/2017 Heinrich et al.
9,561,032 B2 2/2017 Shelton, IV et al.
9,561,038 B2 2/2017 Shelton, IV et al.
9,561,045 B2 2/2017 Hinman et al.
9,566,061 B2 2/2017 Aronhalt et al.
9,566,062 B2 2/2017 Boudreaux
9,566,065 B2 2/2017 Knodel
9,566,067 B2 2/2017 Milliman et al.
9,572,574 B2 2/2017 Shelton, IV et al.
9,572,576 B2 2/2017 Hodgkinson et al.
9,572,577 B2 2/2017 Lloyd et al.
9,572,592 B2 2/2017 Price et al.
9,574,644 B2 2/2017 Parihar
9,579,088 B2 2/2017 Farritor et al.
9,579,143 B2 2/2017 Ullrich et al.
9,579,158 B2 2/2017 Brianza et al.
D780,803 S 3/2017 Gill et al.
D781,879 S 3/2017 Butcher et al.
D782,530 S 3/2017 Paek et al.
9,585,550 B2 3/2017 Abel et al.
9,585,657 B2 3/2017 Shelton, IV et al.
9,585,658 B2 3/2017 Shelton, IV
9,585,659 B2 3/2017 Viola et al.
9,585,660 B2 3/2017 Laurent et al.
9,585,662 B2 3/2017 Shelton, IV et al.
9,585,663 B2 3/2017 Shelton, IV et al.
9,585,672 B2 3/2017 Bastia
9,590,433 B2 3/2017 Li
9,592,050 B2 3/2017 Schmid et al.
9,592,052 B2 3/2017 Shelton, IV
9,592,053 B2 3/2017 Shelton, IV et al.
9,592,054 B2 3/2017 Schmid et al.
9,597,073 B2 3/2017 Sorrentino et al.
9,597,075 B2 3/2017 Shelton, IV et al.
9,597,078 B2 3/2017 Scirica et al.
9,597,080 B2 3/2017 Milliman et al.
9,597,104 B2 3/2017 Nicholas et al.
9,597,143 B2 3/2017 Madan et al.
9,603,595 B2 3/2017 Shelton, IV et al.
9,603,598 B2 3/2017 Shelton, IV et al.
9,603,599 B2 3/2017 Miller et al.
9,603,991 B2 3/2017 Shelton, IV et al.
D783,658 S 4/2017 Hurst et al.
9,610,068 B2 4/2017 Kappel et al.
9,610,079 B2 4/2017 Kamei et al.
9,610,080 B2 4/2017 Whitfield et al.
9,610,412 B2 4/2017 Zemlok et al.
9,614,258 B2 4/2017 Takahashi et al.
9,615,826 B2 4/2017 Shelton, IV et al.
9,622,745 B2 4/2017 Ingmanson et al.
9,622,746 B2 4/2017 Simms et al.
9,629,623 B2 4/2017 Lytle, IV et al.
9,629,626 B2 4/2017 Soltz et al.
9,629,627 B2 4/2017 Kostrzewski et al.
9,629,628 B2 4/2017 Aranyi
9,629,629 B2 4/2017 Leimbach et al.

(56) References Cited

U.S. PATENT DOCUMENTS 9,629,631 B2 4/2017 Nicholas et al.
9,629,632 B2 4/2017 Linder et al.
9,629,652 B2 4/2017 Mumaw et al.
9,629,814 B2 4/2017 Widenhouse et al.
D785,794 S 5/2017 Magno, Jr.
D786,280 S 5/2017 Ma
D786,896 S 5/2017 Kim et al.
D787,547 S 5/2017 Basargin et al.
D788,123 S 5/2017 Shan et al.
D788,140 S 5/2017 Hemsley et al.
9,636,091 B2 5/2017 Beardsley et al.
9,636,111 B2 5/2017 Wenchell
9,636,112 B2 5/2017 Penna et al.
9,636,113 B2 5/2017 Wenchell
9,636,850 B2 5/2017 Stopek (nee Prommersberger) et al.
9,641,122 B2 5/2017 Romanowich et al.
9,642,620 B2 5/2017 Baxter, III et al.
9,642,642 B2 5/2017 Lim
9,649,096 B2 5/2017 Sholev
9,649,110 B2 5/2017 Parihar et al.
9,649,111 B2 5/2017 Shelton, IV et al.
9,649,190 B2 5/2017 Mathies
9,655,613 B2 5/2017 Schaller
9,655,614 B2 5/2017 Swensgard et al.
9,655,615 B2 5/2017 Knodel et al.
9,655,616 B2 5/2017 Aranyi
9,655,624 B2 5/2017 Shelton, IV et al.
9,661,991 B2 5/2017 Glossop
9,662,108 B2 5/2017 Williams
9,662,110 B2 5/2017 Huang et al.
9,662,116 B2 5/2017 Smith et al.
9,662,131 B2 5/2017 Omori et al.
D788,792 S 6/2017 Alessandri et al.
D789,384 S 6/2017 Lin et al.
D790,570 S 6/2017 Butcher et al.
9,668,728 B2 6/2017 Williams et al.
9,668,729 B2 6/2017 Williams et al.
9,668,732 B2 6/2017 Patel et al.
9,668,733 B2 6/2017 Williams
9,668,734 B2 6/2017 Kostrzewski et al.
9,668,735 B2 6/2017 Beetel
9,675,344 B2 6/2017 Combrowski et al.
9,675,348 B2 6/2017 Smith et al.
9,675,351 B2 6/2017 Hodgkinson et al.
9,675,354 B2 6/2017 Weir et al.
9,675,355 B2 6/2017 Shelton, IV et al.
9,675,368 B2 6/2017 Guo et al.
9,675,372 B2 6/2017 Laurent et al.
9,675,375 B2 6/2017 Houser et al.
9,675,405 B2 6/2017 Trees et al.
9,675,819 B2 6/2017 Dunbar et al.
9,681,870 B2 6/2017 Baxter, III et al.
9,681,873 B2 6/2017 Smith et al.
9,681,884 B2 6/2017 Clem et al.
9,687,230 B2 6/2017 Leimbach et al.
9,687,231 B2 6/2017 Baxter, III et al.
9,687,232 B2 6/2017 Shelton, IV et al.
9,687,233 B2 6/2017 Fernandez et al.
9,687,236 B2 6/2017 Leimbach et al.
9,687,237 B2 6/2017 Schmid et al.
9,687,253 B2 6/2017 Detry et al.
9,689,466 B2 6/2017 Kanai et al.
9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,731,410 B2 8/2017 Hirabayashi et al.
9,733,663 B2 8/2017 Leimbach et al.
9,737,297 B2 8/2017 Racenet et al.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle

(56) References Cited

U.S. PATENT DOCUMENTS 9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.
9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,844,368 B2 12/2017 Boudreaux et al.
9,844,369 B2 12/2017 Huitema et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 * 1/2018 Fanelli ............ A61B 17/07207
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,552 B2 3/2018 Measamer et al.
9,907,553 B2 3/2018 Cole et al.
9,907,600 B2 3/2018 Stulen et al.
9,907,620 B2 3/2018 Shelton, IV et al.
9,913,641 B2 3/2018 Takemoto et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.

(56) References Cited

U.S. PATENT DOCUMENTS 9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.
9,993,258 B2 6/2018 Shelton, IV et al.
9,993,284 B2 6/2018 Boudreaux
9,999,408 B2 6/2018 Boudreaux et al.
9,999,423 B2 * 6/2018 Schuckmann ... A61B 17/07207
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
D822,206 S 7/2018 Shelton, IV et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,123 B2 7/2018 Williams et al.
10,022,125 B2 7/2018 (Prommersberger) Stopek et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 * 10/2018 Morgan ............... A61B 17/072
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,638 B2 10/2018 Viola et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter, III et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.

(56) References Cited

U.S. PATENT DOCUMENTS 10,123,798 B2 11/2018 Baxter, III et al.
10,124,493 B2 11/2018 Rothfuss et al.
10,130,352 B2 11/2018 Widenhouse et al.
10,130,359 B2 11/2018 Hess et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
D835,659 S 12/2018 Anzures et al.
D836,124 S 12/2018 Fan
10,143,474 B2 12/2018 Bucciaglia et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,163,065 B1 12/2018 Koski et al.
10,163,589 B2 12/2018 Zergiebel et al.
10,164,466 B2 12/2018 Calderoni
D837,244 S 1/2019 Kuo et al.
D837,245 S 1/2019 Kuo et al.
10,166,023 B2 1/2019 Vendely et al.
10,166,025 B2 1/2019 Leimbach et al.
10,166,026 B2 1/2019 Shelton, IV et al.
10,172,611 B2 1/2019 Shelton, IV et al.
10,172,615 B2 1/2019 Marczyk et al.
10,172,616 B2 1/2019 Murray et al.
10,172,617 B2 1/2019 Shelton, IV et al.
10,172,618 B2 1/2019 Shelton, IV et al.
10,172,619 B2 1/2019 Harris et al.
10,172,620 B2 1/2019 Harris et al.
10,172,636 B2 1/2019 Stulen et al.
10,172,669 B2 1/2019 Felder et al.
10,175,127 B2 1/2019 Collins et al.
10,178,992 B2 1/2019 Wise et al.
10,180,463 B2 1/2019 Beckman et al.
10,182,813 B2 1/2019 Leimbach et al.
10,182,815 B2 1/2019 Williams et al.
10,182,816 B2 1/2019 Shelton, IV et al.
10,182,818 B2 1/2019 Hensel et al.
10,182,819 B2 1/2019 Shelton, IV
10,182,868 B2 1/2019 Meier et al.
10,188,385 B2 * 1/2019 Kerr .................... A61B 17/068
10,188,393 B2 1/2019 Smith et al.
10,188,394 B2 1/2019 Shelton, IV et al.
10,190,888 B2 1/2019 Hryb et al.
D839,900 S 2/2019 Gan
D841,667 S 2/2019 Coren
10,194,801 B2 2/2019 Elhawary et al.
10,194,904 B2 2/2019 Viola et al.
10,194,907 B2 2/2019 Marczyk et al.
10,194,908 B2 2/2019 Duque et al.
10,194,910 B2 2/2019 Shelton, IV et al.
10,194,913 B2 2/2019 Nalagatla et al.
10,194,976 B2 2/2019 Boudreaux
10,194,992 B2 2/2019 Robinson
10,201,348 B2 2/2019 Scheib et al.
10,201,349 B2 2/2019 Leimbach et al.
10,201,363 B2 2/2019 Shelton, IV
10,201,364 B2 2/2019 Leimbach et al.
10,201,365 B2 2/2019 Boudreaux et al.
10,201,381 B2 2/2019 Zergiebel et al.
10,206,605 B2 2/2019 Shelton, IV et al.
10,206,676 B2 2/2019 Shelton, IV
10,206,677 B2 2/2019 Harris et al.
10,206,678 B2 2/2019 Shelton, IV et al.
10,206,748 B2 2/2019 Burbank
10,210,244 B1 2/2019 Branavan et al.
10,211,586 B2 2/2019 Adams et al.
10,213,198 B2 2/2019 Aronhalt et al.
10,213,201 B2 2/2019 Shelton, IV et al.
10,213,202 B2 2/2019 Flanagan et al.
10,213,203 B2 2/2019 Swayze et al.
10,213,204 B2 2/2019 Aranyi et al.
10,213,262 B2 2/2019 Shelton, IV et al.
D842,328 S 3/2019 Jian et al.
10,219,811 B2 3/2019 Haider et al.
10,219,832 B2 3/2019 Bagwell et al.
10,220,522 B2 3/2019 Rockrohr
10,226,239 B2 3/2019 Nicholas et al.
10,226,249 B2 3/2019 Jaworek et al.
10,226,250 B2 3/2019 Beckman et al.
10,226,251 B2 3/2019 Scheib et al.
10,226,274 B2 3/2019 Worrell et al.
10,231,634 B2 3/2019 Zand et al.
10,231,653 B2 3/2019 Bohm et al.
10,231,734 B2 3/2019 Thompson et al.
10,231,794 B2 3/2019 Shelton, IV et al.
10,238,385 B2 3/2019 Yates et al.
10,238,386 B2 3/2019 Overmyer et al.
10,238,387 B2 3/2019 Yates et al.
10,238,389 B2 3/2019 Yates et al.
10,238,390 B2 3/2019 Harris et al.
10,238,391 B2 3/2019 Leimbach et al.
D844,666 S 4/2019 Espeleta et al.
D844,667 S 4/2019 Espeleta et al.
D845,342 S 4/2019 Espeleta et al.
D847,199 S 4/2019 Whitmore
10,244,991 B2 4/2019 Shademan et al.
10,245,027 B2 4/2019 Shelton, IV et al.
10,245,028 B2 4/2019 Shelton, IV et al.
10,245,029 B2 4/2019 Hunter et al.
10,245,030 B2 4/2019 Hunter et al.
10,245,032 B2 4/2019 Shelton, IV
10,245,033 B2 4/2019 Overmyer et al.
10,245,034 B2 4/2019 Shelton, IV et al.
10,245,035 B2 4/2019 Swayze et al.
10,245,038 B2 4/2019 Hopkins et al.
10,245,058 B2 4/2019 Omori et al.
10,251,648 B2 4/2019 Harris et al.
10,251,649 B2 4/2019 Schellin et al.
10,251,725 B2 4/2019 Valentine et al.
10,258,322 B2 4/2019 Fanton et al.
10,258,330 B2 4/2019 Shelton, IV et al.
10,258,331 B2 4/2019 Shelton, IV et al.
10,258,332 B2 4/2019 Schmid et al.
10,258,333 B2 4/2019 Shelton, IV et al.
10,258,336 B2 4/2019 Baxter, III et al.
10,258,418 B2 4/2019 Shelton, IV et al.
10,264,797 B2 4/2019 Zhang et al.
10,265,065 B2 4/2019 Shelton, IV et al.
10,265,067 B2 4/2019 Yates et al.
10,265,068 B2 4/2019 Harris et al.
10,265,072 B2 4/2019 Shelton, IV et al.
10,265,073 B2 4/2019 Scheib et al.
10,265,074 B2 4/2019 Shelton, IV et al.
10,265,090 B2 4/2019 Ingmanson et al.
10,271,840 B2 4/2019 Sapre
10,271,844 B2 4/2019 Valentine et al.
10,271,845 B2 4/2019 Shelton, IV
10,271,846 B2 4/2019 Shelton, IV et al.
10,271,847 B2 4/2019 Racenet et al.
10,271,849 B2 4/2019 Vendely et al.
10,271,851 B2 4/2019 Shelton, IV et al.
D847,989 S 5/2019 Shelton, IV et al.
D848,473 S 5/2019 Zhu et al.
D849,046 S 5/2019 Kuo et al.
10,278,696 B2 5/2019 Gurumurthy et al.
10,278,697 B2 5/2019 Shelton, IV et al.

(56) References Cited

U.S. PATENT DOCUMENTS 10,278,702 B2 5/2019 Shelton, IV et al.
10,278,703 B2 5/2019 Nativ et al.
10,278,707 B2 5/2019 Thompson et al.
10,278,722 B2 5/2019 Shelton, IV et al.
10,278,780 B2 5/2019 Shelton, IV
10,285,694 B2 5/2019 Viola et al.
10,285,695 B2 5/2019 Jaworek et al.
10,285,699 B2 5/2019 Vendely et al.
10,285,700 B2 5/2019 Scheib
10,285,705 B2 5/2019 Shelton, IV et al.
10,292,701 B2 * 5/2019 Scheib ............. A61B 17/07292
10,292,704 B2 5/2019 Harris et al.
10,292,707 B2 5/2019 Shelton, IV et al.
10,293,100 B2 5/2019 Shelton, IV et al.
10,293,553 B2 5/2019 Racenet et al.
10,299,787 B2 5/2019 Shelton, IV
10,299,788 B2 5/2019 Heinrich et al.
10,299,789 B2 5/2019 Marczyk et al.
10,299,790 B2 5/2019 Beardsley
10,299,792 B2 5/2019 Huitema et al.
10,299,817 B2 5/2019 Shelton, IV et al.
10,299,818 B2 5/2019 Riva
10,299,878 B2 5/2019 Shelton, IV et al.
10,303,851 B2 5/2019 Nguyen et al.
D850,617 S 6/2019 Shelton, IV et al.
D851,676 S 6/2019 Foss et al.
D851,762 S 6/2019 Shelton, IV et al.
10,307,159 B2 6/2019 Harris et al.
10,307,160 B2 6/2019 Vendely et al.
10,307,161 B2 6/2019 Jankowski
10,307,163 B2 6/2019 Moore et al.
10,307,170 B2 6/2019 Parfett et al.
10,307,202 B2 6/2019 Smith et al.
10,314,559 B2 6/2019 Razzaque et al.
10,314,577 B2 6/2019 Laurent et al.
10,314,582 B2 6/2019 Shelton, IV et al.
10,314,584 B2 6/2019 Scirica et al.
10,314,587 B2 6/2019 Harris et al.
10,314,588 B2 6/2019 Turner et al.
10,314,589 B2 6/2019 Shelton, IV et al.
10,314,590 B2 6/2019 Shelton, IV et al.
10,315,566 B2 6/2019 Choi et al.
10,321,907 B2 6/2019 Shelton, IV et al.
10,321,909 B2 6/2019 Shelton, IV et al.
10,321,927 B2 6/2019 Hinman
10,327,743 B2 6/2019 St. Goar et al.
10,327,764 B2 6/2019 Harris et al.
10,327,765 B2 6/2019 Timm et al.
10,327,767 B2 6/2019 Shelton, IV et al.
10,327,769 B2 6/2019 Overmyer et al.
10,327,776 B2 6/2019 Harris et al.
10,327,777 B2 6/2019 Harris et al.
D854,032 S 7/2019 Jones et al.
D854,151 S 7/2019 Shelton, IV et al.
10,335,144 B2 7/2019 Shelton, IV et al.
10,335,145 B2 7/2019 Harris et al.
10,335,147 B2 7/2019 Rector et al.
10,335,148 B2 7/2019 Shelton, IV et al.
10,335,149 B2 7/2019 Baxter, III et al.
10,335,150 B2 7/2019 Shelton, IV
10,335,151 B2 7/2019 Shelton, IV et al.
10,337,148 B2 7/2019 Rouse et al.
10,342,533 B2 7/2019 Shelton, IV et al.
10,342,535 B2 7/2019 Scheib et al.
10,342,541 B2 7/2019 Shelton, IV et al.
10,342,543 B2 7/2019 Shelton, IV et al.
10,342,623 B2 7/2019 Huelman et al.
10,349,937 B2 7/2019 Williams
10,349,939 B2 7/2019 Shelton, IV et al.
10,349,941 B2 7/2019 Marczyk et al.
10,349,963 B2 7/2019 Fiksen et al.
10,350,016 B2 7/2019 Burbank et al.
10,357,246 B2 7/2019 Shelton, IV et al.
10,357,247 B2 7/2019 Shelton, IV et al.
10,357,248 B2 7/2019 Dalessandro et al.
10,357,252 B2 7/2019 Harris et al.
10,363,031 B2 7/2019 Alexander, III et al.
10,363,033 B2 7/2019 Timm et al.
10,363,036 B2 7/2019 Yates et al.
10,363,037 B2 7/2019 Aronhalt et al.
10,363,045 B2 7/2019 Whitfield et al.
D855,634 S 8/2019 Kim
D856,359 S 8/2019 Huang et al.
10,368,838 B2 8/2019 Williams et al.
10,368,861 B2 8/2019 Baxter, III et al.
10,368,863 B2 8/2019 Timm et al.
10,368,864 B2 8/2019 Harris et al.
10,368,865 B2 8/2019 Harris et al.
10,368,867 B2 8/2019 Harris et al.
10,368,892 B2 8/2019 Stulen et al.
10,376,262 B2 8/2019 Zemlok et al.
10,376,263 B2 8/2019 Morgan et al.
10,383,626 B2 8/2019 Soltz
10,383,628 B2 8/2019 Kang et al.
10,383,629 B2 8/2019 Ross et al.
10,383,630 B2 8/2019 Shelton, IV et al.
10,383,633 B2 8/2019 Shelton, IV et al.
10,383,634 B2 8/2019 Shelton, IV et al.
10,390,823 B2 8/2019 Shelton, IV et al.
10,390,825 B2 8/2019 Shelton, IV et al.
10,390,828 B2 8/2019 Vendely et al.
10,390,829 B2 8/2019 Eckert et al.
10,390,830 B2 8/2019 Schulz
10,390,841 B2 8/2019 Shelton, IV et al.
10,390,897 B2 8/2019 Kostrzewski
D860,219 S 9/2019 Rasmussen et al.
D861,035 S 9/2019 Park et al.
10,398,433 B2 9/2019 Boudreaux et al.
10,398,434 B2 9/2019 Shelton, IV et al.
10,398,436 B2 9/2019 Shelton, IV et al.
10,398,460 B2 9/2019 Overmyer
10,404,136 B2 9/2019 Oktavec et al.
10,405,854 B2 9/2019 Schmid et al.
10,405,857 B2 9/2019 Shelton, IV et al.
10,405,859 B2 9/2019 Harris et al.
10,405,863 B2 9/2019 Wise et al.
10,405,914 B2 9/2019 Manwaring et al.
10,405,932 B2 9/2019 Overmyer
10,405,937 B2 9/2019 Black et al.
10,413,291 B2 9/2019 Worthington et al.
10,413,293 B2 9/2019 Shelton, IV et al.
10,413,294 B2 9/2019 Shelton, IV et al.
10,413,297 B2 9/2019 Harris et al.
10,413,370 B2 9/2019 Yates et al.
10,413,373 B2 9/2019 Yates et al.
10,420,548 B2 9/2019 Whitman et al.
10,420,549 B2 9/2019 Yates et al.
10,420,550 B2 9/2019 Shelton, IV
10,420,552 B2 9/2019 Shelton, IV et al.
10,420,553 B2 9/2019 Shelton, IV et al.
10,420,554 B2 9/2019 Collings et al.
10,420,555 B2 9/2019 Shelton, IV et al.
10,420,558 B2 9/2019 Nalagatla et al.
10,420,559 B2 9/2019 Marczyk et al.
10,420,560 B2 9/2019 Shelton, IV et al.
10,420,561 B2 9/2019 Shelton, IV et al.
10,420,577 B2 9/2019 Chowaniec et al.
D861,707 S 10/2019 Yang
D862,518 S 10/2019 Niven et al.
D863,343 S 10/2019 Mazlish et al.
D864,388 S 10/2019 Barber
D865,174 S 10/2019 Auld et al.
10,426,463 B2 10/2019 Shelton, IV et al.
10,426,466 B2 10/2019 Contini et al.
10,426,467 B2 10/2019 Miller et al.
10,426,468 B2 10/2019 Contini et al.
10,426,469 B2 10/2019 Shelton, IV et al.
10,426,471 B2 10/2019 Shelton, IV et al.
10,426,476 B2 10/2019 Harris et al.
10,426,477 B2 10/2019 Harris et al.
10,426,478 B2 10/2019 Shelton, IV et al.
10,426,481 B2 10/2019 Aronhalt et al.
10,426,555 B2 10/2019 Crowley et al.
10,433,837 B2 10/2019 Worthington et al.

(56) References Cited

U.S. PATENT DOCUMENTS 10,433,839 B2 10/2019 Scheib et al.
10,433,840 B2 10/2019 Shelton, IV et al.
10,433,844 B2 10/2019 Shelton, IV et al.
10,433,845 B2 10/2019 Baxter, III et al.
10,433,846 B2 10/2019 Vendely et al.
10,433,849 B2 10/2019 Shelton, IV et al.
10,433,918 B2 10/2019 Shelton, IV et al.
10,441,279 B2 10/2019 Shelton, IV et al.
10,441,280 B2 10/2019 Timm et al.
10,441,281 B2 10/2019 Shelton, IV et al.
10,441,285 B2 10/2019 Shelton, IV et al.
10,441,286 B2 10/2019 Shelton, IV et al.
10,441,345 B2 10/2019 Aldridge et al.
10,441,369 B2 10/2019 Shelton, IV et al.
10,448,948 B2 10/2019 Shelton, IV et al.
10,448,950 B2 10/2019 Shelton, IV et al.
10,448,952 B2 10/2019 Shelton, IV et al.
10,456,122 B2 10/2019 Koltz et al.
10,456,132 B2 10/2019 Gettinger et al.
10,456,133 B2 10/2019 Yates et al.
10,456,137 B2 10/2019 Vendely et al.
10,456,140 B2 10/2019 Shelton, IV et al.
D865,796 S 11/2019 Xu et al.
10,463,367 B2 11/2019 Kostrzewski et al.
10,463,369 B2 11/2019 Shelton, IV et al.
10,463,370 B2 11/2019 Yates et al.
10,463,371 B2 11/2019 Kostrzewski
10,463,372 B2 11/2019 Shelton, IV et al.
10,463,373 B2 11/2019 Mozdzierz et al.
10,463,382 B2 11/2019 Ingmanson et al.
10,463,383 B2 11/2019 Shelton, IV et al.
10,463,384 B2 11/2019 Shelton, IV et al.
10,470,762 B2 11/2019 Leimbach et al.
10,470,763 B2 11/2019 Yates et al.
10,470,764 B2 11/2019 Baxter, III et al.
10,470,767 B2 11/2019 Gleiman et al.
10,470,768 B2 11/2019 Harris et al.
10,470,769 B2 11/2019 Shelton, IV et al.
10,471,282 B2 11/2019 Kirk et al.
10,471,576 B2 11/2019 Totsu
10,471,607 B2 11/2019 Butt et al.
10,478,185 B2 11/2019 Nicholas
10,478,187 B2 11/2019 Shelton, IV et al.
10,478,207 B2 * 11/2019 Lathrop ................ A61B 34/71
D869,655 S 12/2019 Shelton, IV et al.
D870,742 S 12/2019 Cornell
10,492,785 B2 * 12/2019 Overmyer ........ A61B 17/07207
10,499,917 B2 12/2019 Scheib et al.
10,508,720 B2 12/2019 Nicholas
10,517,592 B2 12/2019 Shelton, IV et al.
10,537,351 B2 1/2020 Shelton, IV et al.
10,542,976 B2 1/2020 Calderoni et al.
10,542,985 B2 1/2020 Zhan et al.
10,548,593 B2 2/2020 Shelton, IV et al.
10,561,419 B2 2/2020 Beardsley
10,561,474 B2 2/2020 Adams et al.
D879,808 S 3/2020 Harris et al.
D879,809 S 3/2020 Harris et al.
10,595,887 B2 3/2020 Shelton, IV et al.
10,595,929 B2 3/2020 Boudreaux et al.
10,603,041 B2 3/2020 Miller et al.
10,610,236 B2 4/2020 Baril
10,610,346 B2 4/2020 Schwartz
10,624,709 B2 4/2020 Remm
10,625,062 B2 4/2020 Matlock et al.
10,631,858 B2 4/2020 Burbank
10,631,860 B2 4/2020 Bakos et al.
D888,953 S 6/2020 Baxter, III et al.
10,695,081 B2 6/2020 Shelton, IV et al.
D890,784 S 7/2020 Shelton, IV et al.
10,702,266 B2 7/2020 Parihar et al.
10,722,233 B2 7/2020 Wellman
10,736,616 B2 8/2020 Scheib et al.
10,743,930 B2 8/2020 Nagtegaal
10,751,048 B2 8/2020 Whitman et al.
10,765,442 B2 9/2020 Strobl
10,772,628 B2 9/2020 Chen et al.
10,772,630 B2 9/2020 Wixey
10,772,651 B2 9/2020 Shelton, IV et al.
10,779,821 B2 9/2020 Harris et al.
10,786,248 B2 9/2020 Rousseau et al.
10,799,306 B2 10/2020 Robinson et al.
10,806,451 B2 10/2020 Harris et al.
10,813,683 B2 10/2020 Baxter, III et al.
10,842,357 B2 11/2020 Moskowitz et al.
10,842,473 B2 11/2020 Scheib et al.
10,842,492 B2 11/2020 Shelton, IV et al.
D906,355 S 12/2020 Messerly et al.
10,849,621 B2 12/2020 Whitfield et al.
10,849,623 B2 12/2020 Dunki-Jacobs et al.
10,849,697 B2 12/2020 Yates et al.
10,856,870 B2 12/2020 Harris et al.
10,874,392 B2 12/2020 Scirica et al.
10,874,393 B2 12/2020 Satti, III et al.
D907,647 S 1/2021 Siebel et al.
D907,648 S 1/2021 Siebel et al.
D908,216 S 1/2021 Messerly et al.
10,892,899 B2 1/2021 Shelton, IV et al.
D910,847 S 2/2021 Shelton, IV et al.
10,905,415 B2 2/2021 DiNardo et al.
10,912,559 B2 2/2021 Harris et al.
10,912,562 B2 2/2021 Dunki-Jacobs et al.
D914,878 S 3/2021 Shelton, IV et al.
10,932,804 B2 3/2021 Scheib et al.
10,932,806 B2 3/2021 Shelton, IV et al.
10,932,872 B2 3/2021 Shelton, IV et al.
10,944,728 B2 3/2021 Wiener et al.
10,952,708 B2 3/2021 Scheib et al.
10,952,728 B2 3/2021 Shelton, IV et al.
10,959,744 B2 3/2021 Shelton, IV et al.
D917,500 S 4/2021 Siebel et al.
10,966,717 B2 4/2021 Shah et al.
10,966,791 B2 4/2021 Harris et al.
10,973,515 B2 4/2021 Harris et al.
10,973,517 B2 4/2021 Wixey
10,973,520 B2 4/2021 Shelton, IV et al.
10,980,535 B2 4/2021 Yates et al.
10,980,560 B2 4/2021 Shelton, IV et al.
10,987,178 B2 4/2021 Shelton, IV et al.
2001/0000531 A1 4/2001 Casscells et al.
2001/0025183 A1 9/2001 Shahidi
2001/0025184 A1 9/2001 Messerly
2001/0034530 A1 10/2001 Malackowski et al.
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0029032 A1 3/2002 Arkin
2002/0029036 A1 3/2002 Goble et al.
2002/0042620 A1 4/2002 Julian et al.
2002/0087048 A1 7/2002 Brock et al.
2002/0091374 A1 7/2002 Cooper
2002/0095175 A1 7/2002 Brock et al.
2002/0103494 A1 8/2002 Pacey
2002/0111624 A1 8/2002 Witt et al.
2002/0116063 A1 8/2002 Giannetti et al.
2002/0117534 A1 8/2002 Green et al.
2002/0127265 A1 9/2002 Bowman et al.
2002/0128633 A1 9/2002 Brock et al.
2002/0134811 A1 9/2002 Napier et al.
2002/0135474 A1 9/2002 Sylliassen
2002/0143340 A1 10/2002 Kaneko
2002/0151770 A1 10/2002 Noll et al.
2002/0158593 A1 10/2002 Henderson et al.
2002/0177848 A1 11/2002 Truckai et al.
2002/0185514 A1 12/2002 Adams et al.
2002/0188170 A1 12/2002 Santamore et al.
2002/0188287 A1 12/2002 Zvuloni et al.
2003/0009193 A1 1/2003 Corsaro
2003/0011245 A1 1/2003 Fiebig
2003/0012805 A1 1/2003 Chen et al.
2003/0040670 A1 2/2003 Govari
2003/0045835 A1 3/2003 Anderson et al.
2003/0047230 A1 3/2003 Kim

(56) References Cited

U.S. PATENT DOCUMENTS

| | | | |
|---|---|---|---|
| 2003/0066858 | A1 | 4/2003 | Holgersson |
| 2003/0078647 | A1 | 4/2003 | Vallana et al. |
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0094356 | A1 | 5/2003 | Waldron |
| 2003/0096158 | A1 | 5/2003 | Takano et al. |
| 2003/0114851 | A1 | 6/2003 | Truckai et al. |
| 2003/0121586 | A1 | 7/2003 | Mitra et al. |
| 2003/0139741 | A1 | 7/2003 | Goble et al. |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0163085 | A1 | 8/2003 | Tanner et al. |
| 2003/0164172 | A1 | 9/2003 | Chumas et al. |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216732 | A1 | 11/2003 | Truckai et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092992 | A1 | 5/2004 | Adams et al. |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0232201 | A1 | 11/2004 | Wenchell et al. |
| 2004/0236352 | A1 | 11/2004 | Wang et al. |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0260315 | A1 | 12/2004 | Dell et al. |
| 2004/0267310 | A1 | 12/2004 | Racenet et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0032511 | A1 | 2/2005 | Malone et al. |
| 2005/0033352 | A1 | 2/2005 | Zepf et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0070929 | A1 | 3/2005 | Dalessandro et al. |
| 2005/0075561 | A1 | 4/2005 | Golden |
| 2005/0080342 | A1 | 4/2005 | Gilreath et al. |
| 2005/0085693 | A1 | 4/2005 | Belson et al. |
| 2005/0090817 | A1 | 4/2005 | Phan |
| 2005/0096683 | A1 | 5/2005 | Ellins et al. |
| 2005/0116673 | A1 | 6/2005 | Carl et al. |
| 2005/0124855 | A1 | 6/2005 | Jaffe et al. |
| 2005/0125897 | A1 | 6/2005 | Wyslucha et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0203550 | A1 | 9/2005 | Laufer et al. |
| 2005/0209614 | A1 | 9/2005 | Fenter et al. |
| 2005/0216055 | A1 | 9/2005 | Scirica et al. |
| 2005/0222587 | A1 | 10/2005 | Jinno et al. |
| 2005/0222611 | A1 | 10/2005 | Weitkamp |
| 2005/0222616 | A1 | 10/2005 | Rethy et al. |
| 2005/0222665 | A1 | 10/2005 | Aranyi |
| 2005/0228224 | A1 | 10/2005 | Okada et al. |
| 2005/0228446 | A1 | 10/2005 | Mooradian et al. |
| 2005/0230453 | A1 | 10/2005 | Viola |
| 2005/0240178 | A1 | 10/2005 | Morley et al. |
| 2005/0245965 | A1 | 11/2005 | Orban, III et al. |
| 2005/0246881 | A1 | 11/2005 | Kelly et al. |
| 2005/0251063 | A1 | 11/2005 | Basude |
| 2005/0256452 | A1 | 11/2005 | DeMarchi et al. |
| 2005/0261676 | A1 | 11/2005 | Hall et al. |
| 2005/0263563 | A1 | 12/2005 | Racenet et al. |
| 2005/0267455 | A1 | 12/2005 | Eggers et al. |
| 2005/0274034 | A1 | 12/2005 | Hayashida et al. |
| 2005/0283188 | A1 | 12/2005 | Loshakove et al. |
| 2005/0283226 | A1 | 12/2005 | Haverkost |
| 2006/0008787 | A1 | 1/2006 | Hayman et al. |
| 2006/0015009 | A1 | 1/2006 | Jaffe et al. |
| 2006/0020258 | A1 | 1/2006 | Strauss et al. |

(56) References Cited

U.S. PATENT DOCUMENTS

2006/0020336 A1 1/2006 Liddicoat
2006/0025812 A1 2/2006 Shelton
2006/0041188 A1 2/2006 Dirusso et al.
2006/0047275 A1 3/2006 Goble
2006/0049229 A1 3/2006 Milliman et al.
2006/0052824 A1 3/2006 Ransick et al.
2006/0052825 A1 3/2006 Ransick et al.
2006/0064086 A1 3/2006 Odom
2006/0079735 A1 4/2006 Martone et al.
2006/0079874 A1 4/2006 Faller et al.
2006/0079879 A1 4/2006 Faller et al.
2006/0086032 A1 4/2006 Valencic et al.
2006/0087746 A1 4/2006 Lipow
2006/0089535 A1 4/2006 Raz et al.
2006/0097699 A1 5/2006 Kamenoff
2006/0100643 A1 5/2006 Laufer et al.
2006/0100649 A1 5/2006 Hart
2006/0106369 A1 5/2006 Desai et al.
2006/0111711 A1 5/2006 Goble
2006/0111723 A1 5/2006 Chapolini et al.
2006/0116634 A1 6/2006 Shachar
2006/0142772 A1 6/2006 Ralph et al.
2006/0144898 A1 7/2006 Bilotti et al.
2006/0154546 A1 7/2006 Murphy et al.
2006/0161050 A1 7/2006 Butler et al.
2006/0161185 A1 7/2006 Saadat et al.
2006/0167471 A1 7/2006 Phillips
2006/0173290 A1 8/2006 Lavallee et al.
2006/0173470 A1 8/2006 Oray et al.
2006/0176031 A1 8/2006 Forman et al.
2006/0176242 A1 8/2006 Jaramaz et al.
2006/0178556 A1 8/2006 Hasser et al.
2006/0180633 A1 8/2006 Emmons
2006/0180634 A1 8/2006 Shelton et al.
2006/0185682 A1 8/2006 Marczyk
2006/0199999 A1 9/2006 Ikeda et al.
2006/0201989 A1 9/2006 Ojeda
2006/0206100 A1 9/2006 Eskridge et al.
2006/0217729 A1 9/2006 Eskridge et al.
2006/0235368 A1 10/2006 Oz
2006/0241666 A1 10/2006 Briggs et al.
2006/0244460 A1 11/2006 Weaver
2006/0252981 A1 11/2006 Matsuda et al.
2006/0252990 A1 11/2006 Kubach
2006/0252993 A1 11/2006 Freed et al.
2006/0258904 A1 11/2006 Stefanchik et al.
2006/0259073 A1 11/2006 Miyamoto et al.
2006/0261763 A1 11/2006 Iott et al.
2006/0263444 A1 11/2006 Ming et al.
2006/0264831 A1 11/2006 Skwarek et al.
2006/0264929 A1 11/2006 Goble et al.
2006/0271042 A1 11/2006 Latterell et al.
2006/0271102 A1 11/2006 Bosshard et al.
2006/0282064 A1 12/2006 Shimizu et al.
2006/0284730 A1 12/2006 Schmid et al.
2006/0287576 A1 12/2006 Tsuji et al.
2006/0289602 A1 12/2006 Wales et al.
2006/0291981 A1 12/2006 Viola et al.
2007/0009570 A1 1/2007 Kim et al.
2007/0010702 A1 1/2007 Wang et al.
2007/0010838 A1 1/2007 Shelton et al.
2007/0016235 A1 1/2007 Tanaka et al.
2007/0018958 A1 1/2007 Tavakoli et al.
2007/0026039 A1 2/2007 Drumheller et al.
2007/0026040 A1 2/2007 Crawley et al.
2007/0027468 A1 2/2007 Wales et al.
2007/0027551 A1 2/2007 Farnsworth et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0155010 A1 7/2007 Farnsworth et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0194079 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0208359 A1 9/2007 Hoffman
2007/0208375 A1 9/2007 Nishizawa et al.
2007/0213750 A1 9/2007 Weadock
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0260132 A1 11/2007 Sterling
2007/0262592 A1 11/2007 Hwang et al.
2007/0270660 A1 11/2007 Caylor et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0003196 A1 1/2008 Jonn et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0071328 A1 3/2008 Haubrich et al.
2008/0077158 A1 3/2008 Haider et al.
2008/0078802 A1 4/2008 Hess et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0108443 A1 5/2008 Jinno et al.
2008/0114250 A1 5/2008 Urbano et al.
2008/0125634 A1 5/2008 Ryan et al.

(56) References Cited

U.S. PATENT DOCUMENTS

2008/0125749 A1 5/2008 Olson
2008/0128469 A1 6/2008 Dalessandro et al.
2008/0129253 A1 6/2008 Shiue et al.
2008/0135600 A1 6/2008 Hiranuma et al.
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0234709 A1 9/2008 Houser
2008/0242939 A1 10/2008 Johnston
2008/0243088 A1 10/2008 Evans
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255663 A1 10/2008 Akpek et al.
2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296346 A1 12/2008 Shelton, IV et al.
2008/0297287 A1 12/2008 Shachar et al.
2008/0298784 A1 12/2008 Kastner
2008/0308602 A1 12/2008 Timm et al.
2008/0308603 A1 12/2008 Shelton et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0012534 A1 1/2009 Madhani et al.
2009/0015195 A1 1/2009 Loth-Krausser
2009/0020958 A1 1/2009 Soul
2009/0048583 A1 2/2009 Williams et al.
2009/0048589 A1 2/2009 Takashino et al.
2009/0076506 A1 3/2009 Baker
2009/0078736 A1 3/2009 Van Lue
2009/0081313 A1 3/2009 Aghion et al.
2009/0088659 A1 4/2009 Graham et al.
2009/0090763 A1 4/2009 Zemlok et al.
2009/0092651 A1 4/2009 Shah et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0118762 A1 5/2009 Crainch et al.
2009/0119011 A1 5/2009 Kondo et al.
2009/0131819 A1 5/2009 Ritchie et al.
2009/0132400 A1 5/2009 Conway
2009/0143855 A1 6/2009 Weber et al.
2009/0149871 A9 6/2009 Kagan et al.
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0198272 A1 8/2009 Kerver et al.
2009/0204108 A1 8/2009 Steffen
2009/0204109 A1 8/2009 Grove et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0221993 A1 9/2009 Sohi et al.
2009/0227834 A1 9/2009 Nakamoto et al.
2009/0234273 A1 9/2009 Intoccia et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248100 A1 10/2009 Vaisnys et al.
2009/0253959 A1 10/2009 Yoshie et al.
2009/0255974 A1 10/2009 Viola
2009/0261141 A1 10/2009 Stratton et al.
2009/0262078 A1 10/2009 Pizzi
2009/0270895 A1 10/2009 Churchill et al.
2009/0278406 A1 11/2009 Hoffman
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0325859 A1 12/2009 Ameer et al.
2010/0005035 A1 1/2010 Carpenter et al.
2010/0012703 A1 1/2010 Calabrese et al.
2010/0015104 A1 1/2010 Fraser et al.
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0030239 A1 2/2010 Viola et al.
2010/0032179 A1 2/2010 Hanspers et al.
2010/0036370 A1 2/2010 Mirel et al.
2010/0051668 A1 3/2010 Milliman et al.
2010/0057118 A1 3/2010 Dietz et al.
2010/0065604 A1 3/2010 Weng
2010/0069942 A1 3/2010 Shelton, IV
2010/0076483 A1 3/2010 Imuta
2010/0076489 A1 3/2010 Stopek et al.
2010/0081883 A1 4/2010 Murray et al.
2010/0094340 A1 4/2010 Stopek et al.
2010/0100123 A1 4/2010 Bennett
2010/0100124 A1 4/2010 Calabrese et al.
2010/0116519 A1 5/2010 Gareis
2010/0122339 A1 5/2010 Boccacci
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0179022 A1 7/2010 Shirokoshi
2010/0180711 A1 7/2010 Kilibarda et al.
2010/0191262 A1 7/2010 Harris et al.
2010/0191292 A1 7/2010 DeMeo et al.
2010/0193566 A1 8/2010 Scheib et al.
2010/0204717 A1 8/2010 Knodel
2010/0204721 A1 8/2010 Young et al.
2010/0217281 A1 8/2010 Matsuoka et al.
2010/0222901 A1 9/2010 Swayze et al.
2010/0228250 A1 9/2010 Brogna
2010/0234687 A1 9/2010 Azarbarzin et al.
2010/0241137 A1 9/2010 Doyle et al.
2010/0245102 A1 9/2010 Yokoi
2010/0249497 A1 9/2010 Peine et al.

(56) References Cited

U.S. PATENT DOCUMENTS

2010/0249947 A1 9/2010 Lesh et al.
2010/0256675 A1 10/2010 Romans
2010/0258327 A1 10/2010 Esenwein et al.
2010/0267662 A1 10/2010 Fielder et al.
2010/0274160 A1 10/2010 Yachi et al.
2010/0292540 A1 11/2010 Hess et al.
2010/0298636 A1 11/2010 Castro et al.
2010/0301097 A1 12/2010 Scirica et al.
2010/0310623 A1 12/2010 Laurencin et al.
2010/0312261 A1 12/2010 Suzuki et al.
2010/0318085 A1 12/2010 Austin et al.
2010/0331856 A1 12/2010 Carlson et al.
2011/0006101 A1 1/2011 Hall et al.
2011/0009694 A1 1/2011 Schultz et al.
2011/0011916 A1 1/2011 Levine
2011/0016960 A1 1/2011 Debrailly
2011/0021871 A1 1/2011 Berkelaar
2011/0022032 A1 1/2011 Zemlok et al.
2011/0024477 A1 2/2011 Hall
2011/0024478 A1 2/2011 Shelton, IV
2011/0025311 A1 2/2011 Chauvin et al.
2011/0029270 A1 2/2011 Mueglitz
2011/0036891 A1 2/2011 Zemlok et al.
2011/0046667 A1 2/2011 Culligan et al.
2011/0052660 A1 3/2011 Yang et al.
2011/0056717 A1 3/2011 Herisse
2011/0060363 A1 3/2011 Hess et al.
2011/0066156 A1 3/2011 McGahan et al.
2011/0082538 A1 4/2011 Dahlgren et al.
2011/0087276 A1 4/2011 Bedi et al.
2011/0088921 A1 4/2011 Forgues et al.
2011/0091515 A1 4/2011 Zilberman et al.
2011/0095064 A1 4/2011 Taylor et al.
2011/0101069 A1 5/2011 Bombard et al.
2011/0101794 A1 5/2011 Schroeder et al.
2011/0112517 A1 5/2011 Peine et al.
2011/0112530 A1 5/2011 Keller
2011/0114697 A1 5/2011 Baxter, III et al.
2011/0121049 A1 5/2011 Malinouskas et al.
2011/0125149 A1 5/2011 El-Galley et al.
2011/0125176 A1 5/2011 Yates et al.
2011/0127945 A1 6/2011 Yoneda
2011/0129706 A1 6/2011 Takahashi et al.
2011/0144764 A1 6/2011 Bagga et al.
2011/0147433 A1 6/2011 Shelton, IV et al.
2011/0160725 A1 6/2011 Kabaya et al.
2011/0163146 A1 7/2011 Ortiz et al.
2011/0172495 A1 7/2011 Armstrong
2011/0174861 A1 7/2011 Shelton, IV et al.
2011/0192882 A1 8/2011 Hess et al.
2011/0199225 A1 8/2011 Touchberry et al.
2011/0218400 A1 9/2011 Ma et al.
2011/0218550 A1 9/2011 Ma
2011/0220381 A1 9/2011 Friese et al.
2011/0225105 A1 9/2011 Scholer et al.
2011/0230713 A1 9/2011 Kleemann et al.
2011/0238044 A1 9/2011 Main et al.
2011/0241597 A1 10/2011 Zhu et al.
2011/0256266 A1 10/2011 Orme et al.
2011/0271186 A1 11/2011 Owens
2011/0275901 A1 11/2011 Shelton, IV
2011/0276083 A1 11/2011 Shelton, IV et al.
2011/0278343 A1 11/2011 Knodel et al.
2011/0279268 A1 11/2011 Konishi et al.
2011/0290856 A1 12/2011 Shelton, IV et al.
2011/0290858 A1 12/2011 Whitman et al.
2011/0293690 A1 12/2011 Griffin et al.
2011/0295295 A1 12/2011 Shelton, IV et al.
2011/0313894 A1 12/2011 Dye et al.
2011/0315413 A1 12/2011 Fisher et al.
2012/0004636 A1 1/2012 Lo
2012/0007442 A1 1/2012 Rhodes et al.
2012/0016239 A1 1/2012 Barthe et al.
2012/0016413 A1 1/2012 Timm et al.
2012/0016467 A1 1/2012 Chen et al.
2012/0029272 A1 2/2012 Shelton, IV et al.
2012/0033360 A1 2/2012 Hsu
2012/0059286 A1 3/2012 Hastings et al.
2012/0064483 A1 3/2012 Lint et al.
2012/0074200 A1 3/2012 Schmid et al.
2012/0078244 A1 3/2012 Worrell et al.
2012/0080336 A1 4/2012 Shelton, IV et al.
2012/0080344 A1 4/2012 Shelton, IV
2012/0080478 A1 4/2012 Morgan et al.
2012/0080498 A1 4/2012 Shelton, IV et al.
2012/0086276 A1 4/2012 Sawyers
2012/0095458 A1 4/2012 Cybulski et al.
2012/0109186 A1 5/2012 Parrott et al.
2012/0116261 A1 5/2012 Mumaw et al.
2012/0116262 A1 5/2012 Houser et al.
2012/0116265 A1 5/2012 Houser et al.
2012/0116266 A1 5/2012 Houser et al.
2012/0116381 A1 5/2012 Houser et al.
2012/0118595 A1 5/2012 Pellenc
2012/0123463 A1 5/2012 Jacobs
2012/0125792 A1 5/2012 Cassivi
2012/0130217 A1 5/2012 Kauphusman et al.
2012/0132286 A1 5/2012 Lim et al.
2012/0171539 A1 7/2012 Rejman et al.
2012/0175398 A1 7/2012 Sandborn et al.
2012/0190964 A1 7/2012 Hyde et al.
2012/0197272 A1 8/2012 Oray et al.
2012/0211542 A1 8/2012 Racenet
2012/0220990 A1 8/2012 Mckenzie et al.
2012/0234895 A1 9/2012 O'Connor et al.
2012/0234897 A1 9/2012 Shelton, IV et al.
2012/0239068 A1 9/2012 Morris et al.
2012/0248169 A1 10/2012 Widenhouse et al.
2012/0251861 A1 10/2012 Liang et al.
2012/0253328 A1 10/2012 Cunningham et al.
2012/0271327 A1 10/2012 West et al.
2012/0283707 A1 11/2012 Giordano et al.
2012/0289811 A1 11/2012 Viola et al.
2012/0289979 A1 11/2012 Eskaros et al.
2012/0292367 A1 11/2012 Morgan et al.
2012/0296342 A1 11/2012 Haglund Wendelschafer
2012/0298719 A1 11/2012 Shelton, IV et al.
2012/0298722 A1 11/2012 Hess et al.
2012/0301498 A1 11/2012 Altreuter et al.
2012/0303002 A1 11/2012 Chowaniec et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0057162 A1 3/2013 Pollischansky
2013/0068816 A1 3/2013 Mandakolathur Vasudevan et al.
2013/0087597 A1 4/2013 Shelton, IV et al.
2013/0090534 A1 4/2013 Burns et al.
2013/0096568 A1 4/2013 Justis
2013/0098970 A1 4/2013 Racenet et al.
2013/0105552 A1 5/2013 Weir et al.
2013/0106352 A1 5/2013 Nagamine
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153641 A1 6/2013 Shelton, IV et al.
2013/0158390 A1 6/2013 Tan et al.
2013/0162198 A1 6/2013 Yokota et al.
2013/0169217 A1 7/2013 Watanabe et al.
2013/0172878 A1 7/2013 Smith
2013/0175317 A1 7/2013 Yates et al.
2013/0211244 A1 8/2013 Nathaniel

(56) References Cited

U.S. PATENT DOCUMENTS

2013/0214025 A1 8/2013 Zemlok et al.
2013/0215449 A1 8/2013 Yamasaki
2013/0233906 A1 9/2013 Hess et al.
2013/0238021 A1 9/2013 Gross et al.
2013/0248578 A1 9/2013 Arteaga Gonzalez
2013/0253480 A1 9/2013 Kimball et al.
2013/0256373 A1 10/2013 Schmid et al.
2013/0256380 A1 10/2013 Schmid et al.
2013/0267978 A1 10/2013 Trissel
2013/0270322 A1 10/2013 Scheib et al.
2013/0277410 A1 10/2013 Fernandez et al.
2013/0306704 A1 11/2013 Balbierz et al.
2013/0317753 A1 11/2013 Kamen et al.
2013/0324982 A1 12/2013 Smith et al.
2013/0327552 A1 12/2013 Lovelass et al.
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0012289 A1 1/2014 Snow et al.
2014/0012299 A1 1/2014 Stoddard et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0048580 A1 2/2014 Merchant et al.
2014/0081176 A1 3/2014 Hassan
2014/0094681 A1 4/2014 Valentine et al.
2014/0100558 A1 4/2014 Schmitz et al.
2014/0107640 A1 4/2014 Yates et al.
2014/0110456 A1 4/2014 Taylor
2014/0115229 A1 4/2014 Kothamasu et al.
2014/0131418 A1 5/2014 Kostrzewski
2014/0135832 A1 5/2014 Park et al.
2014/0151433 A1 6/2014 Shelton, IV et al.
2014/0158747 A1 6/2014 Measamer et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0188091 A1 7/2014 Vidal et al.
2014/0188159 A1 7/2014 Steege
2014/0207124 A1 7/2014 Aldridge et al.
2014/0207125 A1 7/2014 Applegate et al.
2014/0209658 A1 7/2014 Skalla et al.
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch, Jr. et al.
2014/0249573 A1 9/2014 Arav
2014/0252061 A1 9/2014 Estrella et al.
2014/0263541 A1 9/2014 Leimbach et al.
2014/0263552 A1 9/2014 Hall et al.
2014/0263558 A1 9/2014 Hausen et al.
2014/0276730 A1 9/2014 Boudreaux et al.
2014/0284371 A1 9/2014 Morgan et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0367445 A1 12/2014 Ingmanson et al.
2014/0374130 A1 12/2014 Nakamura et al.
2014/0378950 A1 12/2014 Chiu
2015/0002089 A1 1/2015 Rejman et al.
2015/0008248 A1 1/2015 Giordano et al.
2015/0025549 A1 1/2015 Kilroy et al.
2015/0038961 A1 2/2015 Clark et al.
2015/0053737 A1 2/2015 Leimbach et al.
2015/0053742 A1 2/2015 Shelton, IV et al.
2015/0053743 A1 2/2015 Yates et al.
2015/0053746 A1 2/2015 Shelton, IV et al.
2015/0053748 A1 2/2015 Yates et al.
2015/0060518 A1 3/2015 Shelton, IV et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0076212 A1 3/2015 Shelton, IV
2015/0080868 A1 3/2015 Kerr
2015/0082624 A1 3/2015 Craig et al.
2015/0083781 A1 3/2015 Giordano et al.
2015/0083782 A1 3/2015 Scheib et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090761 A1 4/2015 Giordano et al.
2015/0090762 A1 4/2015 Giordano et al.
2015/0122870 A1 5/2015 Zemlok et al.
2015/0127021 A1 5/2015 Harris et al.
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196296 A1 7/2015 Swayze et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0209045 A1 7/2015 Hodgkinson et al.
2015/0222212 A1 8/2015 Iwata
2015/0223868 A1 8/2015 Brandt et al.
2015/0230697 A1 8/2015 Phee et al.
2015/0231409 A1 8/2015 Racenet et al.
2015/0238118 A1 8/2015 Legassey et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297228 A1 10/2015 Huitema et al.
2015/0297229 A1 10/2015 Schellin et al.
2015/0297233 A1 10/2015 Huitema et al.
2015/0297234 A1 10/2015 Schellin et al.
2015/0302539 A1 10/2015 Mazar et al.
2015/0303417 A1 10/2015 Koeder et al.
2015/0313594 A1 11/2015 Shelton, IV et al.
2015/0324317 A1 11/2015 Collins et al.

(56) References Cited

U.S. PATENT DOCUMENTS

2015/0327864 A1 11/2015 Hodgkinson et al.
2015/0336249 A1 11/2015 Iwata et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374369 A1 12/2015 Yates et al.
2015/0374371 A1 12/2015 Richard et al.
2015/0374372 A1 12/2015 Zergiebel et al.
2015/0374378 A1 12/2015 Giordano et al.
2016/0000430 A1 1/2016 Ming et al.
2016/0000431 A1 1/2016 Giordano et al.
2016/0000437 A1 1/2016 Giordano et al.
2016/0000438 A1 1/2016 Swayze et al.
2016/0000442 A1 1/2016 Shelton, IV
2016/0000452 A1 1/2016 Yates et al.
2016/0000453 A1 1/2016 Yates et al.
2016/0023342 A1 1/2016 Koenig et al.
2016/0030042 A1 2/2016 Heinrich et al.
2016/0051316 A1 2/2016 Boudreaux
2016/0058443 A1 3/2016 Yates et al.
2016/0066815 A1 3/2016 Mei et al.
2016/0066913 A1 3/2016 Swayze et al.
2016/0069449 A1 3/2016 Kanai et al.
2016/0074040 A1 3/2016 Widenhouse et al.
2016/0074103 A1 3/2016 Sartor
2016/0082161 A1 3/2016 Zilberman et al.
2016/0089137 A1 3/2016 Hess et al.
2016/0089198 A1 3/2016 Arya et al.
2016/0095585 A1 4/2016 Zergiebel et al.
2016/0106431 A1 4/2016 Shelton, IV et al.
2016/0113653 A1 4/2016 Zingman
2016/0120544 A1 5/2016 Shelton, IV et al.
2016/0120545 A1 5/2016 Shelton, IV et al.
2016/0120594 A1 5/2016 Privitera
2016/0135835 A1 5/2016 Onuma
2016/0135895 A1 5/2016 Faasse et al.
2016/0139666 A1 5/2016 Rubin et al.
2016/0166248 A1 6/2016 Deville et al.
2016/0166256 A1 6/2016 Baxter, III et al.
2016/0174974 A1 6/2016 Schmid et al.
2016/0174978 A1* 6/2016 Overmyer ........ A61B 17/07207 227/178.1
2016/0183939 A1 6/2016 Shelton, IV et al.
2016/0183943 A1 6/2016 Shelton, IV
2016/0183944 A1 6/2016 Swensgard et al.
2016/0192916 A1 7/2016 Shelton, IV et al.
2016/0192917 A1 7/2016 Shelton, IV et al.
2016/0192918 A1 7/2016 Shelton, IV et al.
2016/0192960 A1 7/2016 Bueno et al.
2016/0192977 A1 7/2016 Manwaring et al.
2016/0199063 A1 7/2016 Mandakolathur Vasudevan et al.
2016/0199089 A1 7/2016 Hess et al.
2016/0199956 A1 7/2016 Shelton, IV et al.
2016/0206310 A1 7/2016 Shelton, IV
2016/0206314 A1 7/2016 Scheib et al.
2016/0235404 A1 8/2016 Shelton, IV
2016/0235409 A1 8/2016 Shelton, IV et al.
2016/0235467 A1 8/2016 Godara et al.
2016/0235494 A1 8/2016 Shelton, IV et al.
2016/0242782 A1 8/2016 Shelton, IV et al.
2016/0242783 A1 8/2016 Shelton, IV et al.
2016/0249910 A1 9/2016 Shelton, IV et al.
2016/0249922 A1 9/2016 Morgan et al.
2016/0256071 A1 9/2016 Shelton, IV et al.
2016/0256154 A1 9/2016 Shelton, IV et al.
2016/0256159 A1 9/2016 Pinjala et al.
2016/0256160 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262746 A1 9/2016 Shelton, IV et al.
2016/0262921 A1 9/2016 Balbierz et al.
2016/0270780 A1 9/2016 Hall et al.
2016/0278765 A1 9/2016 Shelton, IV et al.
2016/0278771 A1 9/2016 Shelton, IV et al.
2016/0287265 A1 10/2016 Macdonald et al.
2016/0287279 A1 10/2016 Bovay et al.
2016/0310143 A1 10/2016 Bettuchi
2016/0314716 A1 10/2016 Grubbs
2016/0314717 A1 10/2016 Grubbs
2016/0345976 A1 12/2016 Gonzalez et al.
2016/0346034 A1 12/2016 Arya et al.
2016/0354088 A1 12/2016 Cabrera et al.
2016/0367122 A1 12/2016 Ichimura et al.
2016/0374672 A1 12/2016 Bear et al.
2016/0374675 A1 12/2016 Shelton, IV et al.
2016/0374678 A1 12/2016 Becerra et al.
2017/0000553 A1 1/2017 Wiener et al.
2017/0007236 A1 1/2017 Shelton, IV et al.
2017/0007237 A1 1/2017 Yates et al.
2017/0007243 A1 1/2017 Shelton, IV et al.
2017/0007244 A1 1/2017 Shelton, IV et al.
2017/0007245 A1 1/2017 Shelton, IV et al.
2017/0007247 A1 1/2017 Shelton, IV et al.
2017/0007248 A1 1/2017 Shelton, IV et al.
2017/0007249 A1 1/2017 Shelton, IV et al.
2017/0007250 A1 1/2017 Shelton, IV et al.
2017/0007347 A1 1/2017 Jaworek et al.
2017/0014125 A1 1/2017 Shelton, IV et al.
2017/0027572 A1 2/2017 Nalagatla et al.
2017/0027573 A1 2/2017 Nalagatla et al.
2017/0049444 A1 2/2017 Schellin et al.
2017/0049447 A1 2/2017 Barton et al.
2017/0049448 A1 2/2017 Widenhouse et al.
2017/0055819 A1 3/2017 Hansen et al.
2017/0055986 A1 3/2017 Harris et al.
2017/0055999 A1 3/2017 Baxter, III et al.
2017/0056000 A1 3/2017 Nalagatla et al.
2017/0056002 A1 3/2017 Nalagatla et al.
2017/0056005 A1 3/2017 Shelton, IV et al.
2017/0066054 A1 3/2017 Birky
2017/0079642 A1 3/2017 Overmyer et al.
2017/0086827 A1 3/2017 Vendely et al.
2017/0086829 A1 3/2017 Vendely et al.
2017/0086830 A1 3/2017 Yates et al.
2017/0086831 A1 3/2017 Shelton, IV et al.
2017/0086832 A1 3/2017 Harris et al.
2017/0086836 A1 3/2017 Harris et al.
2017/0086838 A1 3/2017 Harris et al.
2017/0086842 A1 3/2017 Shelton, IV et al.
2017/0086843 A1 3/2017 Vendely et al.
2017/0086844 A1 3/2017 Vendely et al.
2017/0086930 A1 3/2017 Thompson et al.
2017/0105733 A1 4/2017 Scheib et al.
2017/0119388 A1 5/2017 Kostrzewski
2017/0119390 A1 5/2017 Schellin et al.
2017/0119397 A1 5/2017 Harris et al.
2017/0143335 A1 5/2017 Gupta et al.
2017/0150965 A1 6/2017 Williams
2017/0172382 A1 6/2017 Nir et al.
2017/0172550 A1 6/2017 Mukherjee et al.
2017/0172662 A1 6/2017 Panescu et al.
2017/0172672 A1 6/2017 Bailey et al.
2017/0182195 A1 6/2017 Wagner
2017/0182211 A1 6/2017 Raxworthy et al.
2017/0196558 A1 7/2017 Morgan et al.
2017/0196561 A1 7/2017 Shelton, IV et al.
2017/0196562 A1 7/2017 Shelton, IV et al.
2017/0196637 A1 7/2017 Shelton, IV et al.
2017/0196648 A1 7/2017 Ward et al.
2017/0196649 A1 7/2017 Yates et al.
2017/0202571 A1 7/2017 Shelton, IV et al.
2017/0202596 A1 7/2017 Shelton, IV et al.
2017/0202770 A1 7/2017 Friedrich et al.
2017/0209145 A1 7/2017 Swayze et al.
2017/0209146 A1 7/2017 Yates et al.
2017/0209226 A1 7/2017 Overmyer et al.
2017/0215881 A1 8/2017 Shelton, IV et al.
2017/0215943 A1 8/2017 Allen, IV
2017/0224331 A1 8/2017 Worthington et al.
2017/0224332 A1 8/2017 Hunter et al.
2017/0224334 A1 8/2017 Worthington et al.
2017/0224335 A1 8/2017 Weaner et al.

(56) References Cited

U.S. PATENT DOCUMENTS

2017/0224339 A1 8/2017 Huang et al.
2017/0231627 A1 8/2017 Shelton, IV et al.
2017/0231628 A1 8/2017 Shelton, IV et al.
2017/0231629 A1 8/2017 Stopek et al.
2017/0238928 A1 8/2017 Morgan et al.
2017/0238929 A1 8/2017 Yates et al.
2017/0238962 A1 8/2017 Hansen et al.
2017/0245854 A1 8/2017 Zemlok et al.
2017/0245952 A1 8/2017 Shelton, IV et al.
2017/0249431 A1 8/2017 Shelton, IV et al.
2017/0255799 A1 9/2017 Zhao et al.
2017/0258469 A1 9/2017 Shelton, IV et al.
2017/0262110 A1 9/2017 Polishchuk et al.
2017/0265774 A1 9/2017 Johnson et al.
2017/0265856 A1 9/2017 Shelton, IV et al.
2017/0281155 A1 10/2017 Shelton, IV et al.
2017/0281164 A1 10/2017 Harris et al.
2017/0281166 A1 10/2017 Morgan et al.
2017/0281167 A1 10/2017 Shelton, IV et al.
2017/0281169 A1 10/2017 Harris et al.
2017/0281171 A1 10/2017 Shelton, IV et al.
2017/0281173 A1 10/2017 Shelton, IV et al.
2017/0281174 A1 10/2017 Harris et al.
2017/0281183 A1 10/2017 Miller et al.
2017/0281184 A1 10/2017 Shelton, IV et al.
2017/0281185 A1 10/2017 Miller et al.
2017/0281186 A1 10/2017 Shelton, IV et al.
2017/0281187 A1 10/2017 Shelton, IV et al.
2017/0281189 A1 10/2017 Nalagatla et al.
2017/0290584 A1 10/2017 Jasemian et al.
2017/0290585 A1 10/2017 Shelton, IV et al.
2017/0296169 A1 10/2017 Yates et al.
2017/0296170 A1 10/2017 Shelton, IV et al.
2017/0296173 A1 10/2017 Shelton, IV et al.
2017/0296177 A1 10/2017 Harris et al.
2017/0296179 A1 10/2017 Shelton, IV et al.
2017/0296185 A1 10/2017 Swensgard et al.
2017/0296213 A1 10/2017 Swensgard et al.
2017/0311944 A1 11/2017 Morgan et al.
2017/0311949 A1 11/2017 Shelton, IV
2017/0312041 A1 11/2017 Giordano et al.
2017/0312042 A1 11/2017 Giordano et al.
2017/0319201 A1 11/2017 Morgan et al.
2017/0319207 A1 11/2017 Shelton, IV et al.
2017/0319209 A1 11/2017 Morgan et al.
2017/0325813 A1 11/2017 Aranyi et al.
2017/0333034 A1 11/2017 Morgan et al.
2017/0333035 A1 11/2017 Morgan et al.
2017/0333070 A1 11/2017 Laurent et al.
2017/0348010 A1 12/2017 Chiang
2017/0348043 A1 12/2017 Wang et al.
2017/0354413 A1 12/2017 Chen et al.
2017/0354415 A1 12/2017 Casasanta, Jr. et al.
2017/0358052 A1 12/2017 Yuan
2017/0360439 A1 12/2017 Chen et al.
2017/0360441 A1 12/2017 Sgroi
2017/0360442 A1 12/2017 Shelton, IV et al.
2017/0364183 A1 12/2017 Xiao
2017/0367695 A1 12/2017 Shelton, IV et al.
2017/0367696 A1 12/2017 Shelton, IV et al.
2017/0367697 A1 12/2017 Shelton, IV et al.
2017/0367698 A1 12/2017 Shelton, IV et al.
2017/0367699 A1 12/2017 Shelton, IV et al.
2017/0367700 A1 12/2017 Leimbach et al.
2017/0367991 A1 12/2017 Widenhouse et al.
2018/0000483 A1 1/2018 Leimbach et al.
2018/0000545 A1 1/2018 Giordano et al.
2018/0008270 A1 1/2018 Moore et al.
2018/0008271 A1 1/2018 Moore et al.
2018/0008356 A1 1/2018 Giordano et al.
2018/0008357 A1 1/2018 Giordano et al.
2018/0028184 A1 2/2018 Shelton, IV et al.
2018/0028185 A1 2/2018 Shelton, IV et al.
2018/0042611 A1 2/2018 Swayze et al.
2018/0049819 A1 2/2018 Harris et al.
2018/0049824 A1 2/2018 Harris et al.
2018/0049883 A1 2/2018 Moskowitz et al.
2018/0055513 A1 3/2018 Shelton, IV et al.
2018/0055524 A1 3/2018 Shelton, IV et al.
2018/0055525 A1 3/2018 Shelton, IV et al.
2018/0055526 A1 3/2018 Shelton, IV et al.
2018/0064437 A1 3/2018 Yates et al.
2018/0064440 A1 3/2018 Shelton, IV et al.
2018/0064441 A1 3/2018 Shelton, IV et al.
2018/0064442 A1 3/2018 Shelton, IV et al.
2018/0064443 A1 3/2018 Shelton, IV et al.
2018/0070939 A1 3/2018 Giordano et al.
2018/0070942 A1 3/2018 Shelton, IV et al.
2018/0078248 A1 3/2018 Swayze et al.
2018/0078268 A1 3/2018 Messerly et al.
2018/0085116 A1 3/2018 Yates et al.
2018/0085117 A1 3/2018 Shelton, IV et al.
2018/0092710 A1 4/2018 Bosisio et al.
2018/0103953 A1 4/2018 Shelton, IV et al.
2018/0103955 A1 4/2018 Shelton, IV et al.
2018/0110516 A1 4/2018 Baxter, III et al.
2018/0110518 A1 4/2018 Overmyer et al.
2018/0110519 A1 4/2018 Lytle, IV et al.
2018/0110520 A1 4/2018 Shelton, IV et al.
2018/0110521 A1 4/2018 Shelton, IV et al.
2018/0110522 A1 4/2018 Shelton, IV et al.
2018/0110523 A1 4/2018 Shelton, IV
2018/0110574 A1 4/2018 Shelton, IV et al.
2018/0110575 A1 4/2018 Shelton, IV et al.
2018/0114591 A1 4/2018 Pribanic et al.
2018/0116658 A1 5/2018 Aronhalt, IV et al.
2018/0116662 A1 5/2018 Shelton, IV et al.
2018/0116665 A1 5/2018 Hall et al.
2018/0125481 A1 5/2018 Yates et al.
2018/0125484 A1 5/2018 Kostrzewski
2018/0125487 A1 5/2018 Beardsley
2018/0125488 A1 5/2018 Morgan et al.
2018/0125489 A1 5/2018 Leimbach et al.
2018/0125590 A1 5/2018 Giordano et al.
2018/0125594 A1 5/2018 Beardsley
2018/0126504 A1 5/2018 Shelton, IV et al.
2018/0132845 A1 5/2018 Schmid et al.
2018/0132849 A1 5/2018 Miller et al.
2018/0132850 A1 5/2018 Leimbach et al.
2018/0132851 A1 5/2018 Hall et al.
2018/0132926 A1 5/2018 Asher et al.
2018/0132952 A1 5/2018 Spivey et al.
2018/0133856 A1 5/2018 Shelton, IV et al.
2018/0140299 A1 5/2018 Weaner et al.
2018/0140368 A1 5/2018 Shelton, IV et al.
2018/0146960 A1 5/2018 Shelton, IV et al.
2018/0150153 A1 5/2018 Yoon et al.
2018/0153542 A1 6/2018 Shelton, IV et al.
2018/0161034 A1 6/2018 Scheib et al.
2018/0168575 A1 6/2018 Simms et al.
2018/0168576 A1 6/2018 Hunter et al.
2018/0168577 A1 6/2018 Aronhalt et al.
2018/0168578 A1 6/2018 Aronhalt et al.
2018/0168579 A1 6/2018 Aronhalt et al.
2018/0168580 A1 6/2018 Hunter et al.
2018/0168581 A1 6/2018 Hunter et al.
2018/0168582 A1 6/2018 Swayze et al.
2018/0168583 A1 6/2018 Hunter et al.
2018/0168584 A1 6/2018 Harris et al.
2018/0168585 A1 6/2018 Shelton, IV et al.
2018/0168586 A1 6/2018 Shelton, IV et al.
2018/0168589 A1 6/2018 Swayze et al.
2018/0168590 A1 6/2018 Overmyer et al.
2018/0168591 A1 6/2018 Swayze et al.
2018/0168592 A1 6/2018 Overmyer et al.
2018/0168593 A1 6/2018 Overmyer et al.
2018/0168594 A1 6/2018 Shelton, IV et al.
2018/0168595 A1 6/2018 Overmyer et al.
2018/0168596 A1 6/2018 Beckman et al.
2018/0168597 A1 6/2018 Fanelli et al.
2018/0168598 A1 6/2018 Shelton, IV et al.
2018/0168599 A1 6/2018 Bakos et al.
2018/0168600 A1 6/2018 Shelton, IV et al.
2018/0168601 A1 6/2018 Bakos et al.

(56) References Cited

U.S. PATENT DOCUMENTS

2018/0168602 A1 6/2018 Bakos et al.
2018/0168603 A1 6/2018 Morgan et al.
2018/0168604 A1 6/2018 Shelton, IV et al.
2018/0168605 A1 6/2018 Baber et al.
2018/0168606 A1 6/2018 Shelton, IV et al.
2018/0168607 A1 6/2018 Shelton, IV et al.
2018/0168608 A1 6/2018 Shelton, IV et al.
2018/0168609 A1 6/2018 Fanelli et al.
2018/0168610 A1 6/2018 Shelton, IV et al.
2018/0168611 A1 6/2018 Shelton, IV et al.
2018/0168613 A1 6/2018 Shelton, IV et al.
2018/0168614 A1 6/2018 Shelton, IV et al.
2018/0168615 A1 6/2018 Shelton, IV et al.
2018/0168616 A1 6/2018 Shelton, IV et al.
2018/0168617 A1 6/2018 Shelton, IV et al.
2018/0168618 A1 6/2018 Scott et al.
2018/0168619 A1 6/2018 Scott et al.
2018/0168620 A1 6/2018 Huang et al.
2018/0168621 A1 6/2018 Shelton, IV et al.
2018/0168623 A1 6/2018 Simms et al.
2018/0168624 A1 6/2018 Shelton, IV et al.
2018/0168625 A1 6/2018 Posada et al.
2018/0168626 A1 6/2018 Shelton, IV et al.
2018/0168627 A1 6/2018 Weaner et al.
2018/0168628 A1 6/2018 Hunter et al.
2018/0168629 A1 6/2018 Shelton, IV et al.
2018/0168630 A1 6/2018 Shelton, IV et al.
2018/0168631 A1 6/2018 Harris et al.
2018/0168632 A1 6/2018 Harris et al.
2018/0168633 A1 6/2018 Shelton, IV et al.
2018/0168634 A1 6/2018 Harris et al.
2018/0168635 A1 6/2018 Shelton, IV et al.
2018/0168636 A1 6/2018 Shelton, IV et al.
2018/0168637 A1 6/2018 Harris et al.
2018/0168638 A1 6/2018 Harris et al.
2018/0168639 A1 6/2018 Shelton, IV et al.
2018/0168640 A1 6/2018 Shelton, IV et al.
2018/0168641 A1 6/2018 Harris et al.
2018/0168642 A1 6/2018 Shelton, IV et al.
2018/0168643 A1 6/2018 Shelton, IV et al.
2018/0168644 A1 6/2018 Shelton, IV et al.
2018/0168645 A1 6/2018 Shelton, IV et al.
2018/0168646 A1 6/2018 Shelton, IV et al.
2018/0168647 A1 6/2018 Shelton, IV et al.
2018/0168648 A1 6/2018 Shelton, IV et al.
2018/0168649 A1 6/2018 Shelton, IV et al.
2018/0168650 A1 6/2018 Shelton, IV et al.
2018/0168651 A1 6/2018 Shelton, IV et al.
2018/0168715 A1 6/2018 Strobl
2018/0168754 A1 6/2018 Overmyer
2018/0199940 A1 7/2018 Zergiebel et al.
2018/0206843 A1 7/2018 Yates et al.
2018/0206906 A1 7/2018 Moua et al.
2018/0214147 A1 8/2018 Merchant et al.
2018/0221046 A1 8/2018 Demmy et al.
2018/0221050 A1 8/2018 Kostrzewski et al.
2018/0228490 A1 8/2018 Richard et al.
2018/0235609 A1 8/2018 Harris et al.
2018/0242962 A1 8/2018 Walen et al.
2018/0250001 A1 9/2018 Aronhalt et al.
2018/0250020 A1 9/2018 Carusillo
2018/0250086 A1 9/2018 Grubbs
2018/0271520 A1 9/2018 Shelton, IV et al.
2018/0271604 A1 9/2018 Grout et al.
2018/0273597 A1 9/2018 Stimson
2018/0280020 A1 10/2018 Hess et al.
2018/0286274 A1 10/2018 Kamiguchi et al.
2018/0289369 A1 10/2018 Shelton, IV et al.
2018/0289371 A1 10/2018 Wang et al.
2018/0296211 A1 10/2018 Timm et al.
2018/0296215 A1 10/2018 Baxter, III et al.
2018/0296216 A1 10/2018 Shelton, IV et al.
2018/0296217 A1 10/2018 Moore et al.
2018/0303481 A1 10/2018 Shelton, IV et al.
2018/0303482 A1 10/2018 Shelton, IV et al.
2018/0310931 A1 11/2018 Hall et al.
2018/0311002 A1 11/2018 Giordano et al.
2018/0317907 A1 11/2018 Kostrzewski
2018/0317916 A1 11/2018 Wixey
2018/0317917 A1 11/2018 Huang et al.
2018/0317918 A1 11/2018 Shelton, IV
2018/0317919 A1 11/2018 Shelton, IV et al.
2018/0325528 A1 11/2018 Windolf et al.
2018/0333155 A1 11/2018 Hall et al.
2018/0333169 A1 11/2018 Leimbach et al.
2018/0344319 A1 12/2018 Shelton, IV et al.
2018/0353170 A1 12/2018 Overmyer et al.
2018/0353176 A1 12/2018 Shelton, IV et al.
2018/0353177 A1 12/2018 Shelton, IV et al.
2018/0353178 A1 12/2018 Shelton, IV et al.
2018/0353179 A1 12/2018 Shelton, IV et al.
2018/0360443 A1 12/2018 Shelton, IV et al.
2018/0360445 A1 12/2018 Shelton, IV et al.
2018/0360446 A1 12/2018 Shelton, IV et al.
2018/0360447 A1 12/2018 Shelton, IV et al.
2018/0360448 A1 12/2018 Harris et al.
2018/0360449 A1 12/2018 Shelton, IV et al.
2018/0360450 A1 12/2018 Shelton, IV et al.
2018/0360452 A1 12/2018 Shelton, IV et al.
2018/0360454 A1 12/2018 Shelton, IV et al.
2018/0360455 A1 12/2018 Shelton, IV et al.
2018/0360456 A1 12/2018 Shelton, IV et al.
2018/0360471 A1 12/2018 Parfett et al.
2018/0360472 A1 12/2018 Harris et al.
2018/0360473 A1 12/2018 Shelton, IV et al.
2018/0360549 A1 12/2018 Hares et al.
2018/0368822 A1 12/2018 Shelton, IV et al.
2018/0368833 A1 12/2018 Shelton, IV et al.
2018/0368837 A1 12/2018 Morgan et al.
2018/0368838 A1 12/2018 Shelton, IV et al.
2018/0368839 A1 12/2018 Shelton, IV et al.
2018/0368840 A1 12/2018 Shelton, IV et al.
2018/0368841 A1 12/2018 Shelton, IV et al.
2018/0368842 A1 12/2018 Shelton, IV et al.
2018/0368843 A1 12/2018 Shelton, IV et al.
2018/0368844 A1 12/2018 Bakos et al.
2018/0368845 A1 12/2018 Bakos et al.
2018/0368846 A1 12/2018 Shelton, IV et al.
2018/0368847 A1 12/2018 Shelton, IV et al.
2019/0000446 A1 1/2019 Shelton, IV et al.
2019/0000448 A1 1/2019 Shelton, IV et al.
2019/0000450 A1 1/2019 Shelton, IV et al.
2019/0000454 A1 1/2019 Swayze et al.
2019/0000456 A1 1/2019 Shelton, IV et al.
2019/0000457 A1 1/2019 Shelton, IV et al.
2019/0000458 A1 1/2019 Shelton, IV et al.
2019/0000459 A1 1/2019 Shelton, IV et al.
2019/0000460 A1 1/2019 Shelton, IV et al.
2019/0000461 A1 1/2019 Shelton, IV et al.
2019/0000462 A1 1/2019 Shelton, IV et al.
2019/0000463 A1 1/2019 Shelton, IV et al.
2019/0000464 A1 1/2019 Shelton, IV et al.
2019/0000465 A1 1/2019 Shelton, IV et al.
2019/0000466 A1 1/2019 Shelton, IV et al.
2019/0000467 A1 1/2019 Shelton, IV et al.
2019/0000468 A1 1/2019 Adams et al.
2019/0000469 A1 1/2019 Shelton, IV et al.
2019/0000470 A1 1/2019 Yates et al.
2019/0000471 A1 1/2019 Shelton, IV et al.
2019/0000473 A1 1/2019 Shelton, IV et al.
2019/0000474 A1 1/2019 Shelton, IV et al.
2019/0000475 A1 1/2019 Shelton, IV et al.
2019/0000476 A1 1/2019 Shelton, IV et al.
2019/0000477 A1 1/2019 Shelton, IV et al.
2019/0000478 A1 1/2019 Messerly et al.
2019/0000479 A1 1/2019 Harris et al.
2019/0000481 A1 1/2019 Harris et al.
2019/0000525 A1 1/2019 Messerly et al.
2019/0000528 A1 1/2019 Yates et al.
2019/0000530 A1 1/2019 Yates et al.
2019/0000531 A1 1/2019 Messerly et al.
2019/0000534 A1 1/2019 Messerly et al.
2019/0000538 A1 1/2019 Widenhouse et al.
2019/0000555 A1 1/2019 Schings et al.

(56) References Cited

U.S. PATENT DOCUMENTS

2019/0000565 A1 1/2019 Shelton, IV et al.
2019/0003292 A1 1/2019 Balan et al.
2019/0008509 A1 1/2019 Shelton, IV et al.
2019/0008511 A1 1/2019 Kerr et al.
2019/0015096 A1 1/2019 Shelton, IV et al.
2019/0015102 A1 1/2019 Baber et al.
2019/0015165 A1 1/2019 Giordano et al.
2019/0029675 A1 1/2019 Yates et al.
2019/0029676 A1 1/2019 Yates et al.
2019/0029677 A1 1/2019 Yates et al.
2019/0029678 A1 1/2019 Shelton, IV et al.
2019/0029681 A1 1/2019 Swayze et al.
2019/0029682 A1 1/2019 Huitema et al.
2019/0029701 A1 1/2019 Shelton, IV et al.
2019/0033955 A1 1/2019 Leimbach et al.
2019/0038279 A1 2/2019 Shelton, IV et al.
2019/0038281 A1 2/2019 Shelton, IV et al.
2019/0038282 A1 2/2019 Shelton, IV et al.
2019/0038283 A1 2/2019 Shelton, IV et al.
2019/0038292 A1 2/2019 Zhang
2019/0038371 A1 2/2019 Wixey et al.
2019/0046181 A1 2/2019 McCuen
2019/0046187 A1 2/2019 Yates et al.
2019/0059886 A1 2/2019 Shelton, IV et al.
2019/0076143 A1 3/2019 Smith
2019/0090870 A1 3/2019 Shelton, IV et al.
2019/0090871 A1 3/2019 Shelton, IV et al.
2019/0091183 A1 3/2019 Tomat et al.
2019/0099177 A1 4/2019 Yates et al.
2019/0099178 A1 4/2019 Leimbach et al.
2019/0099179 A1 4/2019 Leimbach et al.
2019/0099180 A1 4/2019 Leimbach et al.
2019/0099181 A1 4/2019 Shelton, IV et al.
2019/0099182 A1 4/2019 Bakos et al.
2019/0099183 A1 4/2019 Leimbach et al.
2019/0099184 A1 4/2019 Setser et al.
2019/0099224 A1 4/2019 Leimbach et al.
2019/0099229 A1 4/2019 Spivey et al.
2019/0102930 A1 4/2019 Leimbach et al.
2019/0104919 A1 4/2019 Shelton, IV et al.
2019/0105035 A1 4/2019 Shelton, IV et al.
2019/0105036 A1 4/2019 Morgan et al.
2019/0105037 A1 4/2019 Morgan et al.
2019/0105038 A1 4/2019 Schmid et al.
2019/0105039 A1 4/2019 Morgan et al.
2019/0105043 A1 4/2019 Jaworek et al.
2019/0105044 A1 4/2019 Shelton, IV et al.
2019/0105049 A1 4/2019 Moore et al.
2019/0110791 A1 4/2019 Shelton, IV et al.
2019/0110792 A1 4/2019 Shelton, IV et al.
2019/0110793 A1 4/2019 Parihar et al.
2019/0117216 A1 4/2019 Overmyer et al.
2019/0117217 A1 4/2019 Overmyer et al.
2019/0117222 A1 4/2019 Shelton, IV et al.
2019/0117224 A1 4/2019 Setser et al.
2019/0117225 A1 4/2019 Moore et al.
2019/0125320 A1 5/2019 Shelton, IV et al.
2019/0125321 A1 5/2019 Shelton, IV et al.
2019/0125324 A1 5/2019 Scheib et al.
2019/0125335 A1 5/2019 Shelton, IV et al.
2019/0125336 A1 5/2019 Deck et al.
2019/0125338 A1 5/2019 Shelton, IV et al.
2019/0125339 A1 5/2019 Shelton, IV et al.
2019/0125343 A1 5/2019 Wise et al.
2019/0125344 A1 5/2019 DiNardo et al.
2019/0125345 A1 5/2019 Baber et al.
2019/0125347 A1 5/2019 Stokes et al.
2019/0125348 A1 5/2019 Shelton, IV et al.
2019/0125352 A1 5/2019 Shelton, IV et al.
2019/0125353 A1 5/2019 Shelton, IV et al.
2019/0125354 A1 5/2019 Deck et al.
2019/0125355 A1 5/2019 Shelton, IV et al.
2019/0125356 A1 5/2019 Shelton, IV et al.
2019/0125357 A1 5/2019 Shelton, IV et al.
2019/0125358 A1 5/2019 Shelton, IV et al.
2019/0125359 A1 5/2019 Shelton, IV et al.
2019/0125360 A1 5/2019 Shelton, IV et al.
2019/0125361 A1 5/2019 Shelton, IV et al.
2019/0125365 A1 5/2019 Parfett et al.
2019/0125377 A1 5/2019 Shelton, IV
2019/0125378 A1 5/2019 Shelton, IV et al.
2019/0125379 A1 5/2019 Shelton, IV et al.
2019/0125380 A1 5/2019 Hunter et al.
2019/0125384 A1 5/2019 Scheib et al.
2019/0125387 A1 5/2019 Parihar et al.
2019/0125388 A1 5/2019 Shelton, IV et al.
2019/0125389 A1 5/2019 Shelton, IV et al.
2019/0125430 A1 5/2019 Shelton, IV et al.
2019/0125431 A1 5/2019 Shelton, IV et al.
2019/0125432 A1 5/2019 Shelton, IV et al.
2019/0125454 A1 5/2019 Stokes et al.
2019/0125455 A1 5/2019 Shelton, IV et al.
2019/0125456 A1 5/2019 Shelton, IV et al.
2019/0125457 A1 5/2019 Parihar et al.
2019/0125458 A1 5/2019 Shelton, IV et al.
2019/0125459 A1 5/2019 Shelton, IV et al.
2019/0125475 A1 5/2019 Wise et al.
2019/0125476 A1 5/2019 Shelton, IV et al.
2019/0133422 A1 5/2019 Nakamura
2019/0133585 A1 5/2019 Smith et al.
2019/0142421 A1 5/2019 Shelton, IV
2019/0150925 A1 5/2019 Marczyk et al.
2019/0159778 A1 5/2019 Shelton, IV et al.
2019/0183490 A1 6/2019 Shelton, IV et al.
2019/0183491 A1 6/2019 Shelton, IV et al.
2019/0183492 A1 6/2019 Shelton, IV et al.
2019/0183493 A1 6/2019 Shelton, IV et al.
2019/0183494 A1 6/2019 Shelton, IV et al.
2019/0183495 A1 6/2019 Shelton, IV et al.
2019/0183496 A1 6/2019 Shelton, IV et al.
2019/0183497 A1 6/2019 Shelton, IV et al.
2019/0183498 A1 6/2019 Shelton, IV et al.
2019/0183499 A1 6/2019 Shelton, IV et al.
2019/0183500 A1 6/2019 Shelton, IV et al.
2019/0183501 A1 6/2019 Shelton, IV et al.
2019/0183502 A1 6/2019 Shelton, IV et al.
2019/0183503 A1 6/2019 Shelton, IV et al.
2019/0183504 A1 6/2019 Shelton, IV et al.
2019/0183505 A1 6/2019 Vendely et al.
2019/0183592 A1 6/2019 Shelton, IV et al.
2019/0183594 A1 6/2019 Shelton, IV et al.
2019/0183597 A1 6/2019 Shelton, IV et al.
2019/0192137 A1 6/2019 Shelton, IV et al.
2019/0192138 A1 6/2019 Shelton, IV et al.
2019/0192141 A1 6/2019 Shelton, IV et al.
2019/0192144 A1 6/2019 Parfett et al.
2019/0192145 A1 6/2019 Shelton, IV et al.
2019/0192146 A1 6/2019 Widenhouse et al.
2019/0192147 A1 6/2019 Shelton, IV et al.
2019/0192148 A1 6/2019 Shelton, IV et al.
2019/0192149 A1 6/2019 Shelton, IV et al.
2019/0192150 A1 6/2019 Widenhouse et al.
2019/0192151 A1 6/2019 Shelton, IV et al.
2019/0192152 A1 6/2019 Morgan et al.
2019/0192153 A1 6/2019 Shelton, IV et al.
2019/0192154 A1 6/2019 Shelton, IV et al.
2019/0192155 A1 6/2019 Shelton, IV et al.
2019/0192156 A1 6/2019 Simms et al.
2019/0192157 A1 6/2019 Scott et al.
2019/0192158 A1 6/2019 Scott et al.
2019/0192159 A1 6/2019 Simms et al.
2019/0192227 A1 6/2019 Shelton, IV et al.
2019/0192235 A1 6/2019 Harris et al.
2019/0192236 A1 6/2019 Shelton, IV et al.
2019/0200844 A1 7/2019 Shelton, IV et al.
2019/0200863 A1 7/2019 Shelton, IV et al.
2019/0200895 A1 7/2019 Shelton, IV et al.
2019/0200905 A1 7/2019 Shelton, IV et al.
2019/0200906 A1 7/2019 Shelton, IV et al.
2019/0200977 A1 7/2019 Shelton, IV et al.
2019/0200981 A1 7/2019 Harris et al.
2019/0200991 A1 7/2019 Moore et al.
2019/0200992 A1 7/2019 Moore et al.
2019/0200993 A1 7/2019 Moore et al.

(56) References Cited

U.S. PATENT DOCUMENTS

2019/0200994 A1 7/2019 Moore et al.
2019/0200998 A1 7/2019 Shelton, IV et al.
2019/0201023 A1 7/2019 Shelton, IV et al.
2019/0201024 A1 7/2019 Shelton, IV et al.
2019/0201025 A1 7/2019 Shelton, IV et al.
2019/0201026 A1 7/2019 Shelton, IV et al.
2019/0201027 A1 7/2019 Shelton, IV et al.
2019/0201028 A1 7/2019 Shelton, IV et al.
2019/0201029 A1 7/2019 Shelton, IV et al.
2019/0201030 A1 7/2019 Shelton, IV et al.
2019/0201033 A1 7/2019 Yates et al.
2019/0201034 A1 7/2019 Shelton, IV et al.
2019/0201045 A1 7/2019 Yates et al.
2019/0201046 A1 7/2019 Shelton, IV et al.
2019/0201047 A1 7/2019 Yates et al.
2019/0201104 A1 7/2019 Shelton, IV et al.
2019/0201105 A1 7/2019 Shelton, IV et al.
2019/0201111 A1 7/2019 Shelton, IV et al.
2019/0201112 A1 7/2019 Wiener et al.
2019/0201113 A1 7/2019 Shelton, IV et al.
2019/0201114 A1 7/2019 Shelton, IV et al.
2019/0201115 A1 7/2019 Shelton, IV et al.
2019/0201116 A1 7/2019 Shelton, IV et al.
2019/0201118 A1 7/2019 Shelton, IV et al.
2019/0201120 A1 7/2019 Shelton, IV et al.
2019/0201135 A1 7/2019 Shelton, IV et al.
2019/0201136 A1 7/2019 Shelton, IV et al.
2019/0201137 A1 7/2019 Shelton, IV et al.
2019/0201138 A1 7/2019 Yates et al.
2019/0201139 A1 7/2019 Shelton, IV et al.
2019/0201140 A1 7/2019 Yates et al.
2019/0201141 A1 7/2019 Shelton, IV et al.
2019/0201142 A1 7/2019 Shelton, IV et al.
2019/0201145 A1 7/2019 Shelton, IV et al.
2019/0201594 A1 7/2019 Shelton, IV et al.
2019/0205001 A1 7/2019 Messerly et al.
2019/0205566 A1 7/2019 Shelton, IV et al.
2019/0205567 A1 7/2019 Shelton, IV et al.
2019/0206003 A1 7/2019 Harris et al.
2019/0206004 A1 7/2019 Shelton, IV et al.
2019/0206050 A1 7/2019 Yates et al.
2019/0206551 A1 7/2019 Yates et al.
2019/0206555 A1 7/2019 Morgan et al.
2019/0206561 A1 7/2019 Shelton, IV et al.
2019/0206562 A1 7/2019 Shelton, IV et al.
2019/0206563 A1 7/2019 Shelton, IV et al.
2019/0206564 A1 7/2019 Shelton, IV et al.
2019/0206565 A1 7/2019 Shelton, IV
2019/0206569 A1 7/2019 Shelton, IV et al.
2019/0208641 A1 7/2019 Yates et al.
2019/0209164 A1 7/2019 Timm et al.
2019/0209165 A1 7/2019 Timm et al.
2019/0209171 A1 7/2019 Shelton, IV et al.
2019/0209172 A1 7/2019 Shelton, IV et al.
2019/0209247 A1 7/2019 Giordano et al.
2019/0209248 A1 7/2019 Giordano et al.
2019/0209249 A1 7/2019 Giordano et al.
2019/0209250 A1 7/2019 Giordano et al.
2019/0216558 A1 7/2019 Giordano et al.
2019/0223865 A1 7/2019 Shelton, IV et al.
2019/0223871 A1 7/2019 Moore et al.
2019/0261984 A1 8/2019 Nelson et al.
2019/0261991 A1 8/2019 Beckman et al.
2019/0267403 A1 8/2019 Li et al.
2019/0269400 A1 9/2019 Mandakolathur Vasudevan et al.
2019/0269402 A1 9/2019 Murray et al.
2019/0269403 A1 9/2019 Baxter, III et al.
2019/0269407 A1 9/2019 Swensgard et al.
2019/0269428 A1 9/2019 Allen et al.
2019/0274677 A1 9/2019 Shelton, IV
2019/0274678 A1 9/2019 Shelton, IV
2019/0274679 A1 9/2019 Shelton, IV
2019/0274680 A1 9/2019 Shelton, IV
2019/0274685 A1 9/2019 Olson et al.
2019/0290263 A1 9/2019 Morgan et al.
2019/0290264 A1 9/2019 Morgan et al.
2019/0290265 A1 9/2019 Shelton, IV et al.
2019/0290266 A1 9/2019 Scheib et al.
2019/0290267 A1 9/2019 Baxter, III et al.
2019/0290274 A1 9/2019 Shelton, IV
2019/0290281 A1 9/2019 Aronhalt et al.
2019/0290297 A1 9/2019 Haider et al.
2019/0298340 A1 10/2019 Shelton, IV et al.
2019/0298341 A1 10/2019 Shelton, IV et al.
2019/0298342 A1 10/2019 Shelton, IV et al.
2019/0298343 A1 10/2019 Shelton, IV et al.
2019/0298346 A1 10/2019 Shelton, IV et al.
2019/0298347 A1 10/2019 Shelton, IV et al.
2019/0298348 A1 10/2019 Harris et al.
2019/0298350 A1 10/2019 Shelton, IV et al.
2019/0298352 A1 10/2019 Shelton, IV et al.
2019/0298353 A1 10/2019 Shelton, IV et al.
2019/0298354 A1 10/2019 Shelton, IV et al.
2019/0298355 A1 10/2019 Shelton, IV et al.
2019/0298356 A1 10/2019 Shelton, IV et al.
2019/0298357 A1 10/2019 Shelton, IV et al.
2019/0298360 A1 10/2019 Shelton, IV et al.
2019/0298361 A1 10/2019 Shelton, IV et al.
2019/0298362 A1 10/2019 Shelton, IV et al.
2019/0307452 A1 10/2019 Shelton, IV et al.
2019/0307453 A1 10/2019 Shelton, IV et al.
2019/0307454 A1 10/2019 Shelton, IV et al.
2019/0307455 A1 10/2019 Shelton, IV et al.
2019/0307456 A1 10/2019 Shelton, IV et al.
2019/0307476 A1 10/2019 Shelton, IV et al.
2019/0307477 A1 10/2019 Shelton, IV et al.
2019/0307478 A1 10/2019 Shelton, IV et al.
2019/0307479 A1 10/2019 Shelton, IV et al.
2019/0314016 A1 10/2019 Huitema et al.
2019/0314017 A1 10/2019 Huitema et al.
2019/0314018 A1 10/2019 Huitema et al.
2019/0321039 A1 10/2019 Harris et al.
2019/0321040 A1 10/2019 Shelton, IV
2019/0321041 A1 10/2019 Shelton, IV
2019/0328386 A1 10/2019 Harris et al.
2019/0328387 A1 10/2019 Overmyer et al.
2019/0328390 A1 10/2019 Harris et al.
2019/0336128 A1 11/2019 Harris et al.
2019/0343514 A1 11/2019 Shelton, IV et al.
2019/0343515 A1 11/2019 Morgan et al.
2019/0343518 A1 11/2019 Shelton, IV
2019/0343525 A1 11/2019 Shelton, IV et al.
2019/0350581 A1 11/2019 Baxter, III et al.
2019/0350582 A1 11/2019 Shelton, IV et al.
2019/0357909 A1 11/2019 Huitema et al.
2019/0365384 A1 12/2019 Baxter, III et al.
2019/0374224 A1 12/2019 Huitema et al.
2020/0000461 A1 1/2020 Yates et al.
2020/0000468 A1 1/2020 Shelton, IV et al.
2020/0000469 A1 1/2020 Shelton, IV et al.
2020/0000471 A1 1/2020 Shelton, IV et al.
2020/0000531 A1 1/2020 Giordano et al.
2020/0008800 A1 1/2020 Shelton, IV et al.
2020/0008802 A1 1/2020 Aronhalt et al.
2020/0008809 A1 1/2020 Shelton, IV et al.
2020/0015819 A1 1/2020 Shelton, IV et al.
2020/0022702 A1 1/2020 Shelton, IV et al.
2020/0029964 A1 1/2020 Overmyer et al.
2020/0030050 A1 1/2020 Shelton, IV et al.
2020/0038016 A1 2/2020 Shelton, IV et al.
2020/0038018 A1 2/2020 Shelton, IV et al.
2020/0038020 A1 2/2020 Yates et al.
2020/0046348 A1 2/2020 Shelton, IV et al.
2020/0046893 A1 2/2020 Shelton, IV et al.
2020/0054320 A1 2/2020 Harris et al.
2020/0054321 A1 2/2020 Harris et al.
2020/0054322 A1 2/2020 Harris et al.
2020/0054323 A1 2/2020 Harris et al.
2020/0054324 A1 2/2020 Shelton, IV et al.
2020/0054326 A1 2/2020 Harris et al.
2020/0054328 A1 2/2020 Harris et al.
2020/0054330 A1 2/2020 Harris et al.
2020/0054332 A1 2/2020 Shelton, IV et al.
2020/0054333 A1 2/2020 Shelton, IV et al.

(56) References Cited

U.S. PATENT DOCUMENTS

| | | | |
|---|---|---|---|
| 2020/0054334 | A1 | 2/2020 | Shelton, IV et al. |
| 2020/0054355 | A1 | 2/2020 | Laurent et al. |
| 2020/0060680 | A1 | 2/2020 | Shelton, IV et al. |
| 2020/0060681 | A1 | 2/2020 | Shelton, IV et al. |
| 2020/0060713 | A1 | 2/2020 | Leimbach et al. |
| 2020/0077994 | A1 | 3/2020 | Shelton, IV et al. |
| 2020/0078015 | A1 | 3/2020 | Miller et al. |
| 2020/0078016 | A1 | 3/2020 | Swayze et al. |
| 2020/0085427 | A1 | 3/2020 | Giordano et al. |
| 2020/0085431 | A1 | 3/2020 | Swayze et al. |
| 2020/0085435 | A1 | 3/2020 | Shelton, IV et al. |
| 2020/0085436 | A1 | 3/2020 | Beckman et al. |
| 2020/0085518 | A1 | 3/2020 | Giordano et al. |
| 2020/0093484 | A1 | 3/2020 | Shelton, IV et al. |
| 2020/0093485 | A1 | 3/2020 | Shelton, IV et al. |
| 2020/0093487 | A1 | 3/2020 | Baber et al. |
| 2020/0093488 | A1 | 3/2020 | Baber et al. |
| 2020/0093506 | A1 | 3/2020 | Leimbach et al. |
| 2020/0093550 | A1 | 3/2020 | Spivey et al. |
| 2020/0100699 | A1 | 4/2020 | Shelton, IV et al. |
| 2020/0100783 | A1 | 4/2020 | Yates et al. |
| 2020/0100787 | A1 | 4/2020 | Shelton, IV et al. |
| 2020/0107829 | A1 | 4/2020 | Shelton, IV et al. |
| 2020/0138434 | A1 | 5/2020 | Miller et al. |
| 2020/0138435 | A1 | 5/2020 | Shelton, IV et al. |
| 2020/0138436 | A1 | 5/2020 | Yates et al. |
| 2020/0138437 | A1 | 5/2020 | Vendely et al. |
| 2020/0138534 | A1 | 5/2020 | Garcia Kilroy et al. |
| 2020/0146678 | A1 | 5/2020 | Leimbach et al. |
| 2020/0146741 | A1 | 5/2020 | Long et al. |
| 2020/0155151 | A1 | 5/2020 | Overmyer et al. |
| 2020/0155155 | A1 | 5/2020 | Shelton, IV et al. |
| 2020/0178958 | A1 | 6/2020 | Overmyer et al. |
| 2020/0178960 | A1 | 6/2020 | Overmyer et al. |
| 2020/0187943 | A1 | 6/2020 | Shelton, IV et al. |
| 2020/0214706 | A1 | 7/2020 | Vendely et al. |
| 2020/0214731 | A1 | 7/2020 | Shelton, IV et al. |
| 2020/0222047 | A1 | 7/2020 | Shelton, IV et al. |
| 2020/0229812 | A1 | 7/2020 | Parihar et al. |
| 2020/0229816 | A1 | 7/2020 | Bakos et al. |
| 2020/0237371 | A1 | 7/2020 | Huitema et al. |
| 2020/0246001 | A1 | 8/2020 | Ming et al. |
| 2020/0253605 | A1 | 8/2020 | Swayze et al. |
| 2020/0261075 | A1 | 8/2020 | Boudreaux et al. |
| 2020/0261086 | A1 | 8/2020 | Zeiner et al. |
| 2020/0261106 | A1 | 8/2020 | Hess et al. |
| 2020/0268377 | A1 | 8/2020 | Schmid et al. |
| 2020/0268394 | A1 | 8/2020 | Parfett et al. |
| 2020/0275926 | A1 | 9/2020 | Shelton, IV et al. |
| 2020/0275927 | A1 | 9/2020 | Shelton, IV et al. |
| 2020/0275928 | A1 | 9/2020 | Shelton, IV et al. |
| 2020/0275930 | A1 | 9/2020 | Harris et al. |
| 2020/0281585 | A1 | 9/2020 | Timm et al. |
| 2020/0281587 | A1 | 9/2020 | Schmid et al. |
| 2020/0281590 | A1 | 9/2020 | Shelton, IV et al. |
| 2020/0289112 | A1 | 9/2020 | Whitfield et al. |
| 2020/0297340 | A1 | 9/2020 | Hess et al. |
| 2020/0297341 | A1 | 9/2020 | Yates et al. |
| 2020/0297346 | A1 | 9/2020 | Shelton, IV et al. |
| 2020/0297438 | A1 | 9/2020 | Shelton, IV et al. |
| 2020/0305862 | A1 | 10/2020 | Yates et al. |
| 2020/0305863 | A1 | 10/2020 | Yates et al. |
| 2020/0305864 | A1 | 10/2020 | Yates et al. |
| 2020/0305865 | A1 | 10/2020 | Shelton, IV |
| 2020/0305868 | A1 | 10/2020 | Shelton, IV |
| 2020/0305869 | A1 | 10/2020 | Shelton, IV |
| 2020/0305870 | A1 | 10/2020 | Shelton, IV |
| 2020/0305871 | A1 | 10/2020 | Shelton, IV et al. |
| 2020/0305874 | A1 | 10/2020 | Huitema et al. |
| 2020/0315612 | A1 | 10/2020 | Shelton, IV et al. |
| 2020/0315616 | A1 | 10/2020 | Yates et al. |
| 2020/0315625 | A1 | 10/2020 | Hall et al. |
| 2020/0315983 | A1 | 10/2020 | Widenhouse et al. |
| 2020/0323526 | A1 | 10/2020 | Huang et al. |
| 2020/0330092 | A1 | 10/2020 | Shelton, IV et al. |
| 2020/0330093 | A1 | 10/2020 | Shelton, IV et al. |
| 2020/0330094 | A1 | 10/2020 | Baxter, III et al. |
| 2020/0330096 | A1 | 10/2020 | Shelton, IV et al. |
| 2020/0337693 | A1 | 10/2020 | Shelton, IV et al. |
| 2020/0337702 | A1 | 10/2020 | Shelton, IV et al. |
| 2020/0337703 | A1 | 10/2020 | Shelton, IV et al. |
| 2020/0337791 | A1 | 10/2020 | Shelton, IV et al. |
| 2020/0345346 | A1 | 11/2020 | Shelton, IV et al. |
| 2020/0345349 | A1 | 11/2020 | Kimball et al. |
| 2020/0345352 | A1 | 11/2020 | Shelton, IV et al. |
| 2020/0345353 | A1 | 11/2020 | Leimbach et al. |
| 2020/0345354 | A1 | 11/2020 | Leimbach et al. |
| 2020/0345355 | A1 | 11/2020 | Baxter, III et al. |
| 2020/0345356 | A1 | 11/2020 | Leimbach et al. |
| 2020/0345357 | A1 | 11/2020 | Leimbach et al. |
| 2020/0345358 | A1 | 11/2020 | Jenkins |
| 2020/0345359 | A1 | 11/2020 | Baxter, III et al. |
| 2020/0345360 | A1 | 11/2020 | Leimbach et al. |
| 2020/0345446 | A1 | 11/2020 | Kimball et al. |
| 2020/0352562 | A1 | 11/2020 | Timm et al. |
| 2020/0367885 | A1 | 11/2020 | Yates et al. |
| 2020/0367886 | A1 | 11/2020 | Shelton, IV et al. |
| 2020/0375585 | A1 | 12/2020 | Swayze et al. |
| 2020/0375592 | A1 | 12/2020 | Hall et al. |
| 2020/0375593 | A1 | 12/2020 | Hunter et al. |
| 2020/0375597 | A1 | 12/2020 | Shelton, IV et al. |
| 2020/0390444 | A1 | 12/2020 | Harris et al. |
| 2020/0397433 | A1 | 12/2020 | Lytle, IV et al. |
| 2020/0397434 | A1 | 12/2020 | Overmyer et al. |
| 2020/0405290 | A1 | 12/2020 | Shelton, IV et al. |
| 2020/0405291 | A1 | 12/2020 | Shelton, IV et al. |
| 2020/0405292 | A1 | 12/2020 | Shelton, IV et al. |
| 2020/0405293 | A1 | 12/2020 | Shelton, IV et al. |
| 2020/0405294 | A1 | 12/2020 | Shelton, IV |
| 2020/0405295 | A1 | 12/2020 | Shelton, IV et al. |
| 2020/0405296 | A1 | 12/2020 | Shelton, IV et al. |
| 2020/0405297 | A1 | 12/2020 | Shelton, IV et al. |
| 2020/0405301 | A1 | 12/2020 | Shelton, IV et al. |
| 2020/0405302 | A1 | 12/2020 | Shelton, IV et al. |
| 2020/0405303 | A1 | 12/2020 | Shelton, IV |
| 2020/0405305 | A1 | 12/2020 | Shelton, IV et al. |
| 2020/0405306 | A1 | 12/2020 | Shelton, IV et al. |
| 2020/0405307 | A1 | 12/2020 | Shelton, IV et al. |
| 2020/0405308 | A1 | 12/2020 | Shelton, IV |
| 2020/0405309 | A1 | 12/2020 | Shelton, IV et al. |
| 2020/0405311 | A1 | 12/2020 | Shelton, IV et al. |
| 2020/0405312 | A1 | 12/2020 | Shelton, IV et al. |
| 2020/0405313 | A1 | 12/2020 | Shelton, IV |
| 2020/0405314 | A1 | 12/2020 | Shelton, IV et al. |
| 2020/0405316 | A1 | 12/2020 | Shelton, IV et al. |
| 2020/0405341 | A1 | 12/2020 | Hess et al. |
| 2020/0405409 | A1 | 12/2020 | Shelton, IV et al. |
| 2020/0405410 | A1 | 12/2020 | Shelton, IV |
| 2020/0405416 | A1 | 12/2020 | Shelton, IV et al. |
| 2020/0405422 | A1 | 12/2020 | Shelton, IV et al. |
| 2020/0405436 | A1 | 12/2020 | Shelton, IV et al. |
| 2020/0405437 | A1 | 12/2020 | Shelton, IV et al. |
| 2020/0405438 | A1 | 12/2020 | Shelton, IV et al. |
| 2020/0405439 | A1 | 12/2020 | Shelton, IV et al. |
| 2020/0405440 | A1 | 12/2020 | Shelton, IV et al. |
| 2020/0405441 | A1 | 12/2020 | Shelton, IV et al. |
| 2020/0410177 | A1 | 12/2020 | Shelton, IV |
| 2020/0410180 | A1 | 12/2020 | Shelton, IV et al. |
| 2021/0000466 | A1 | 1/2021 | Leimbach et al. |
| 2021/0000467 | A1 | 1/2021 | Shelton, IV et al. |
| 2021/0000470 | A1 | 1/2021 | Leimbach et al. |
| 2021/0015480 | A1 | 1/2021 | Shelton, IV et al. |
| 2021/0022741 | A1 | 1/2021 | Baxter, III et al. |
| 2021/0030416 | A1 | 2/2021 | Shelton, IV et al. |
| 2021/0045742 | A1 | 2/2021 | Shelton, IV et al. |
| 2021/0052271 | A1 | 2/2021 | Harris et al. |
| 2021/0059661 | A1 | 3/2021 | Schmid et al. |
| 2021/0059662 | A1 | 3/2021 | Shelton, IV |
| 2021/0059664 | A1 | 3/2021 | Hensel et al. |
| 2021/0059666 | A1 | 3/2021 | Schmid et al. |
| 2021/0059669 | A1 | 3/2021 | Yates et al. |
| 2021/0059670 | A1 | 3/2021 | Overmyer et al. |
| 2021/0059671 | A1 | 3/2021 | Shelton, IV et al. |
| 2021/0059672 | A1 | 3/2021 | Giordano et al. |

(56) References Cited

U.S. PATENT DOCUMENTS

| | | | |
|---|---|---|---|
| 2021/0059673 | A1 | 3/2021 | Shelton, IV et al. |
| 2021/0068817 | A1 | 3/2021 | Shelton, IV et al. |
| 2021/0068818 | A1 | 3/2021 | Overmyer et al. |
| 2021/0068820 | A1 | 3/2021 | Parihar et al. |
| 2021/0068830 | A1 | 3/2021 | Baber et al. |
| 2021/0068831 | A1 | 3/2021 | Baber et al. |
| 2021/0068832 | A1 | 3/2021 | Yates et al. |
| 2021/0068835 | A1 | 3/2021 | Shelton, IV et al. |
| 2021/0077092 | A1 | 3/2021 | Parihar et al. |
| 2021/0077099 | A1 | 3/2021 | Shelton, IV et al. |
| 2021/0077100 | A1 | 3/2021 | Shelton, IV et al. |
| 2021/0085313 | A1 | 3/2021 | Morgan et al. |
| 2021/0085314 | A1 | 3/2021 | Schmid et al. |
| 2021/0085315 | A1 | 3/2021 | Aronhalt et al. |
| 2021/0085316 | A1 | 3/2021 | Harris et al. |
| 2021/0085317 | A1 | 3/2021 | Miller et al. |
| 2021/0085318 | A1 | 3/2021 | Swayze et al. |
| 2021/0085319 | A1 | 3/2021 | Swayze et al. |
| 2021/0085320 | A1 | 3/2021 | Leimbach et al. |
| 2021/0085321 | A1 | 3/2021 | Shelton, IV et al. |
| 2021/0085325 | A1 | 3/2021 | Shelton, IV et al. |
| 2021/0085326 | A1 | 3/2021 | Vendely et al. |
| 2021/0093321 | A1 | 4/2021 | Auld et al. |
| 2021/0093323 | A1 | 4/2021 | Scirica et al. |
| 2021/0100541 | A1 | 4/2021 | Shelton, IV et al. |
| 2021/0100550 | A1 | 4/2021 | Shelton, IV et al. |
| 2021/0100982 | A1 | 4/2021 | Laby et al. |
| 2021/0106333 | A1 | 4/2021 | Shelton, IV et al. |
| 2021/0107031 | A1 | 4/2021 | Bales, Jr. et al. |
| 2021/0121175 | A1 | 4/2021 | Yates et al. |
| 2021/0128146 | A1 | 5/2021 | Shelton, IV et al. |
| 2021/0137522 | A1 | 5/2021 | Shelton, IV et al. |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101378791 | A | 3/2009 |
| CN | 101507635 | A | 8/2009 |
| CN | 101522120 | A | 9/2009 |
| CN | 101669833 | A | 3/2010 |
| CN | 101721236 | A | 6/2010 |
| CN | 101828940 | A | 9/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247183 | A | 11/2011 |
| CN | 101779977 | B | 12/2011 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 103648410 | B | 10/2016 |
| CN | 106344091 | A | 1/2017 |
| CN | 104349800 | B | 11/2017 |
| CN | 107635483 | A | 1/2018 |
| DE | 273689 | C | 5/1914 |
| DE | 1775926 | A | 1/1972 |
| DE | 0000756 | A1 | 2/1979 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0122046 | A1 | 10/1984 |
| EP | 0129442 | B1 | 11/1987 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |

(56) References Cited

FOREIGN PATENT DOCUMENTS

| | | | | |
|---|---|---|---|---|
| EP | 0669104 | A1 | 8/1995 | |
| EP | 0705571 | A1 | 4/1996 | |
| EP | 0528478 | B1 | 5/1996 | |
| EP | 0770355 | A1 | 5/1997 | |
| EP | 0625335 | B1 | 11/1997 | |
| EP | 0879742 | A1 | 11/1998 | |
| EP | 0650701 | B1 | 3/1999 | |
| EP | 0923907 | A1 | 6/1999 | |
| EP | 0484677 | B2 | 7/2000 | |
| EP | 1034747 | A1 | 9/2000 | |
| EP | 1034748 | A1 | 9/2000 | |
| EP | 0726632 | B1 | 10/2000 | |
| EP | 1053719 | A1 | 11/2000 | |
| EP | 1055399 | A1 | 11/2000 | |
| EP | 1055400 | A1 | 11/2000 | |
| EP | 1064882 | A1 | 1/2001 | |
| EP | 1080694 | A1 | 3/2001 | |
| EP | 1090592 | A1 | 5/2001 | |
| EP | 1095627 | A1 | 5/2001 | |
| EP | 0806914 | B1 | 9/2001 | |
| EP | 1234587 | A1 | 8/2002 | |
| EP | 1284120 | A1 | 2/2003 | |
| EP | 0717967 | B1 | 5/2003 | |
| EP | 0869742 | B1 | 5/2003 | |
| EP | 1374788 | A1 | 1/2004 | |
| EP | 1407719 | A2 | 4/2004 | |
| EP | 0996378 | B1 | 6/2004 | |
| EP | 1558161 | A1 | 8/2005 | |
| EP | 1157666 | B1 | 9/2005 | |
| EP | 0880338 | B1 | 10/2005 | |
| EP | 1158917 | B1 | 11/2005 | |
| EP | 1344498 | B1 | 11/2005 | |
| EP | 1330989 | B1 | 12/2005 | |
| EP | 1632191 | A2 | 3/2006 | |
| EP | 1082944 | B1 | 5/2006 | |
| EP | 1253866 | B1 | 7/2006 | |
| EP | 1723914 | A1 | 11/2006 | |
| EP | 1285633 | B1 | 12/2006 | |
| EP | 1011494 | B1 | 1/2007 | |
| EP | 1767163 | A1 | 3/2007 | |
| EP | 1837041 | A1 | 9/2007 | |
| EP | 0922435 | B1 | 10/2007 | |
| EP | 1599146 | B1 | 10/2007 | |
| EP | 1330201 | B1 | 6/2008 | |
| EP | 2039302 | A2 | 3/2009 | |
| EP | 1719461 | B1 | 6/2009 | |
| EP | 2116196 | A2 | 11/2009 | |
| EP | 1769754 | B1 | 6/2010 | |
| EP | 1627605 | B1 | 12/2010 | |
| EP | 2316345 | A1 | 5/2011 | |
| EP | 1962711 | B1 | 2/2012 | |
| EP | 2486862 | A2 | 8/2012 | |
| EP | 2486868 | A2 | 8/2012 | |
| EP | 2517638 | A1 | 10/2012 | |
| EP | 2606812 | A1 | 6/2013 | |
| EP | 2649948 | A1 | 10/2013 | |
| EP | 2649949 | A1 | 10/2013 | |
| EP | 2668910 | A2 | 12/2013 | |
| EP | 2687164 | A2 | 1/2014 | |
| EP | 2713902 | A1 | 4/2014 | |
| EP | 2743042 | A2 * | 6/2014 | ............. A61B 17/29 |
| EP | 2764827 | A2 | 8/2014 | |
| EP | 2777524 | A2 | 9/2014 | |
| EP | 2789299 | A1 | 10/2014 | |
| EP | 2842500 | A1 | 3/2015 | |
| EP | 2853220 | A1 | 4/2015 | |
| EP | 2298220 | B1 | 6/2016 | |
| EP | 2510891 | B1 | 6/2016 | |
| EP | 3031404 | A1 | 6/2016 | |
| EP | 3047806 | A1 | 7/2016 | |
| EP | 3078334 | A1 | 10/2016 | |
| EP | 2364651 | B1 | 11/2016 | |
| EP | 2747235 | B1 | 11/2016 | |
| EP | 3095399 | A2 | 11/2016 | |
| EP | 3120781 | A2 | 1/2017 | |
| EP | 3135225 | A2 | 3/2017 | |
| EP | 2789299 | B1 | 5/2017 | |
| EP | 3225190 | A2 | 10/2017 | |
| EP | 3326548 | A1 | 5/2018 | |
| EP | 3363378 | A1 | 8/2018 | |
| EP | 3275378 | B1 | 7/2019 | |
| FR | 459743 | A | 11/1913 | |
| FR | 999646 | A | 2/1952 | |
| FR | 1112936 | A | 3/1956 | |
| FR | 2598905 | A1 | 11/1987 | |
| FR | 2689749 | B1 | 7/1994 | |
| FR | 2765794 | A1 | 1/1999 | |
| FR | 2815842 | A1 | 5/2002 | |
| GB | 939929 | A | 10/1963 | |
| GB | 1210522 | A | 10/1970 | |
| GB | 121759 | A | 12/1970 | |
| GB | 1339394 | A | 12/1973 | |
| GB | 2024012 | A | 1/1980 | |
| GB | 2109241 | A | 6/1983 | |
| GB | 2090534 | B | 6/1984 | |
| GB | 930100110 | A | 11/1993 | |
| GB | 2272159 | A | 5/1994 | |
| GB | 2336214 | A | 10/1999 | |
| GB | 2509523 | A | 7/2014 | |
| JP | S4711908 | Y1 | 5/1972 | |
| JP | S5033988 | U | 4/1975 | |
| JP | S5367286 | A | 6/1978 | |
| JP | S56112235 | A | 9/1981 | |
| JP | S60113007 | A | 6/1985 | |
| JP | S62170011 | U | 10/1987 | |
| JP | S63270040 | A | 11/1988 | |
| JP | S63318824 | A | 12/1988 | |
| JP | H0129503 | B2 | 6/1989 | |
| JP | H02106189 | A | 4/1990 | |
| JP | H0378514 | U | 8/1991 | |
| JP | H0385009 | U | 8/1991 | |
| JP | H04215747 | A | 8/1992 | |
| JP | H04131860 | U | 12/1992 | |
| JP | H0584252 | A | 4/1993 | |
| JP | H05123325 | A | 5/1993 | |
| JP | H05226945 | A | 9/1993 | |
| JP | H0630945 | A | 2/1994 | |
| JP | H06237937 | A | 8/1994 | |
| JP | H06327684 | A | 11/1994 | |
| JP | H079622 | U | 2/1995 | |
| JP | H07124166 | A | 5/1995 | |
| JP | H07163573 | A | 6/1995 | |
| JP | H07255735 | A | 10/1995 | |
| JP | H07285089 | A | 10/1995 | |
| JP | H0833642 | A | 2/1996 | |
| JP | H08164141 | A | 6/1996 | |
| JP | H08182684 | A | 7/1996 | |
| JP | H08507708 | A | 8/1996 | |
| JP | H08229050 | A | 9/1996 | |
| JP | H08289895 | A | 11/1996 | |
| JP | H09-323068 | A | 12/1997 | |
| JP | H10118090 | A | 5/1998 | |
| JP | H10-200699 | A | 7/1998 | |
| JP | H10296660 | A | 11/1998 | |
| JP | 2000014632 | A | 1/2000 | |
| JP | 2000033071 | A | 2/2000 | |
| JP | 2000112002 | A | 4/2000 | |
| JP | 2000166932 | A | 6/2000 | |
| JP | 2000171730 | A | 6/2000 | |
| JP | 2000210299 | A | 8/2000 | |
| JP | 2000271141 | A | 10/2000 | |
| JP | 2000287987 | A | 10/2000 | |
| JP | 2000325303 | A | 11/2000 | |
| JP | 2001-69758 | A | 3/2001 | |
| JP | 2001087272 | A | 4/2001 | |
| JP | 2001208655 | A | 8/2001 | |
| JP | 2001514541 | A | 9/2001 | |
| JP | 2001276091 | A | 10/2001 | |
| JP | 2002051974 | A | 2/2002 | |
| JP | 2002054903 | A | 2/2002 | |
| JP | 2002085415 | A | 3/2002 | |
| JP | 2002143078 | A | 5/2002 | |
| JP | 2002153481 | A | 5/2002 | |
| JP | 2002528161 | A | 9/2002 | |

(56) References Cited

FOREIGN PATENT DOCUMENTS

| | | | |
|---|---|---|---|
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2006187649 | A | 7/2008 |
| JP | 2008154804 | A | 7/2008 |
| JP | 2008220032 | A | 9/2008 |
| JP | 2009507526 | A | 2/2009 |
| JP | 200990113 | A | 4/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | D1432094 | | 12/2011 |
| JP | 2012115542 | A | 6/2012 |
| JP | 2012143283 | A | 8/2012 |
| JP | 2012145767 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541983 | A | 11/2013 |
| JP | 2013541997 | A | 11/2013 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016512057 | A | 4/2016 |
| JP | 2016530949 | A | 10/2016 |
| JP | 1601498 | S | 4/2018 |
| KR | 20100110134 | A | 10/2010 |
| KR | 20110003229 | A | 1/2011 |
| KR | 300631507 | | 3/2012 |
| KR | 300747646 | | 6/2014 |
| RU | 1814161 | C | 5/1993 |
| RU | 2008830 | C1 | 3/1994 |
| RU | 2052979 | C1 | 1/1996 |
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| SU | 1814161 | A1 | 5/1993 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A2 | 5/2000 |
| WO | WO-0053112 | A2 | 9/2000 |
| WO | WO-0024448 | A2 | 10/2000 |
| WO | WO-0057796 | A1 | 10/2000 |
| WO | WO-010572 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |

(56) References Cited

FOREIGN PATENT DOCUMENTS

| | | | |
|---|---|---|---|
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-20071370304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-201108672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2019036490 | A1 | 2/2019 |

OTHER PUBLICATIONS

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

B.R. Coolman, DVM, MS et al., "Comparison of Skin Staples With Sutures for Anastomosis of the Small Intestine in Dogs," Abstract; http://www.blackwellsynergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Disclosed Anonymously, "Motor-Driven Surgical Stapler Improvements," Research Disclosure Database No. 526041, Published: Feb. 2008.

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Solorio et al., "Gelatin Microspheres Crosslinked with Genipin for Local Delivery of Growth Factors," J. Tissue Eng. Regen. Med. (2010), 4(7): pp. 514-523.

Pitt et al., "Attachment of Hyaluronan to Metallic Surfaces," J. Biomed. Mater. Res. 68A: pp. 95-106, 2004.

Covidien iDrive™ Ultra in Service Reference Card, "iDrive™ Ultra Powered Stapling Device," (4 pages).

Covidien iDrive™ Ultra Powered Stapling System ibrochure, "The Power of iDrive™ Ultra Powered Stapling System and Tri-Staple™ Technology," (23 pages).

Covidien "iDrive™ Ultra Powered Stapling System, A Guide for Surgeons," (6 pages).

Covidien "iDrive™ Ultra Powered Stapling System, Cleaning and Sterilization Guide," (2 pages).

"Indian Standard: Automotive Vehicles—Brakes and Braking Systems (IS 11852-1:2001)", Mar. 1, 2001.

Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.

Covidien Brochure "iDrive™ Ultra Powered Stapling System," (6 pages).

Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

Data Sheet of LM4F230H5QR, 2007.

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

http://ninpgan.net/publications/51-100/89.pdf; 2004, Ning Pan, On Uniqueness of Fibrous Materials, Design & Nature II. Eds: Colins, M. and Brebbia, C. Wit Press, Boston, 493-504.

Seils et al., Covidien Summary: Clinical Study "UCONN Biodynamics: Final Report on Results," (2 pages).

Byrne et al., "Molecular Imprinting Within Hydrogels," Advanced Drug Delivery Reviews, 54 (2002) pp. 149-161.

Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.

Chen et al., "Elastomeric Biomaterials for Tissue Engineering," Progress in Polymer Science 38 (2013), pp. 584-671.

Matsuda, "Thermodynamics of Formation of Porous Polymeric Membrane from Solutions," Polymer Journal, vol. 23, No. 5, pp. 435-444 (1991).

Covidien Brochure, "Endo GIA™ Black Reload with Tri-Staple™ Technology," (2012), 2 pages.

(56) References Cited

OTHER PUBLICATIONS

"Biomedical Coatings," Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3—Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3—Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al., Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7(2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
"Foot and Ankle: Core Knowledge in Orthopaedics"; by DiGiovanni MD, Elsevier; left columm, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
"Tutorial overview of inductively coupled RFID Systems," UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applicatipns," Research Article, Nov. 14, 2011, pp. 1-12, vol. 2012, Article ID 879294, Hindawi Publishing Corporation.
"Pushing Pixels (GIF)", published on dribble.com, 2013.
"Sodium stearate C18H35NaO2", Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry—II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power

(56) References Cited

OTHER PUBLICATIONS

Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

* cited by examiner 27040
27020
27050
27022
27054
27000
27052

27040
27042
27020
27022
27058
27050
27054
27000
27010
27002
27044
27052
27056

27000
27020
27040
27050
27054
27010
27052
27012

27040
27050
27044
27054
27022
27000
27010
27052
27002

SURGICAL INSTRUMENT COMPRISING AN ARTICULATION SYSTEM LOCKABLE TO A FRAME

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 100 is a cross-sectional view of a trocar seal system prior to the insertion of an end effector there through;

FIG. 101 is a cross-sectional view of the trocar seal system of FIG. 100 illustrating the end effector depicted in FIG. 100 being inserted there through;

FIG. 102 is a cross-sectional view of the trocar seal system of FIG. 100 illustrating the insertion of the end effector depicted in FIG. 100 there through;

FIG. 103 is a cross-sectional view of the trocar seal system of FIG. 100 illustrating an end effector comprising the shortened staple cartridge of FIG. 85 and a shortened anvil with a protective tip being inserted there through;

FIG. 104 is a cross-sectional view of a trocar seal system of FIG. 100 prior to an end effector comprising the elongate cartridge of FIG. 86 and a shortened anvil with a sharp tip being inserted there through;

FIG. 105 is a cross-sectional view of the trocar seal system of FIG. 100 illustrating the end effector depicted in FIG. 104 being inserted there through; and FIG. 106 is a cross-sectional view of the trocar seal system of FIG. 100 illustrating the end effector depicted in FIG. 104 being inserted there through.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
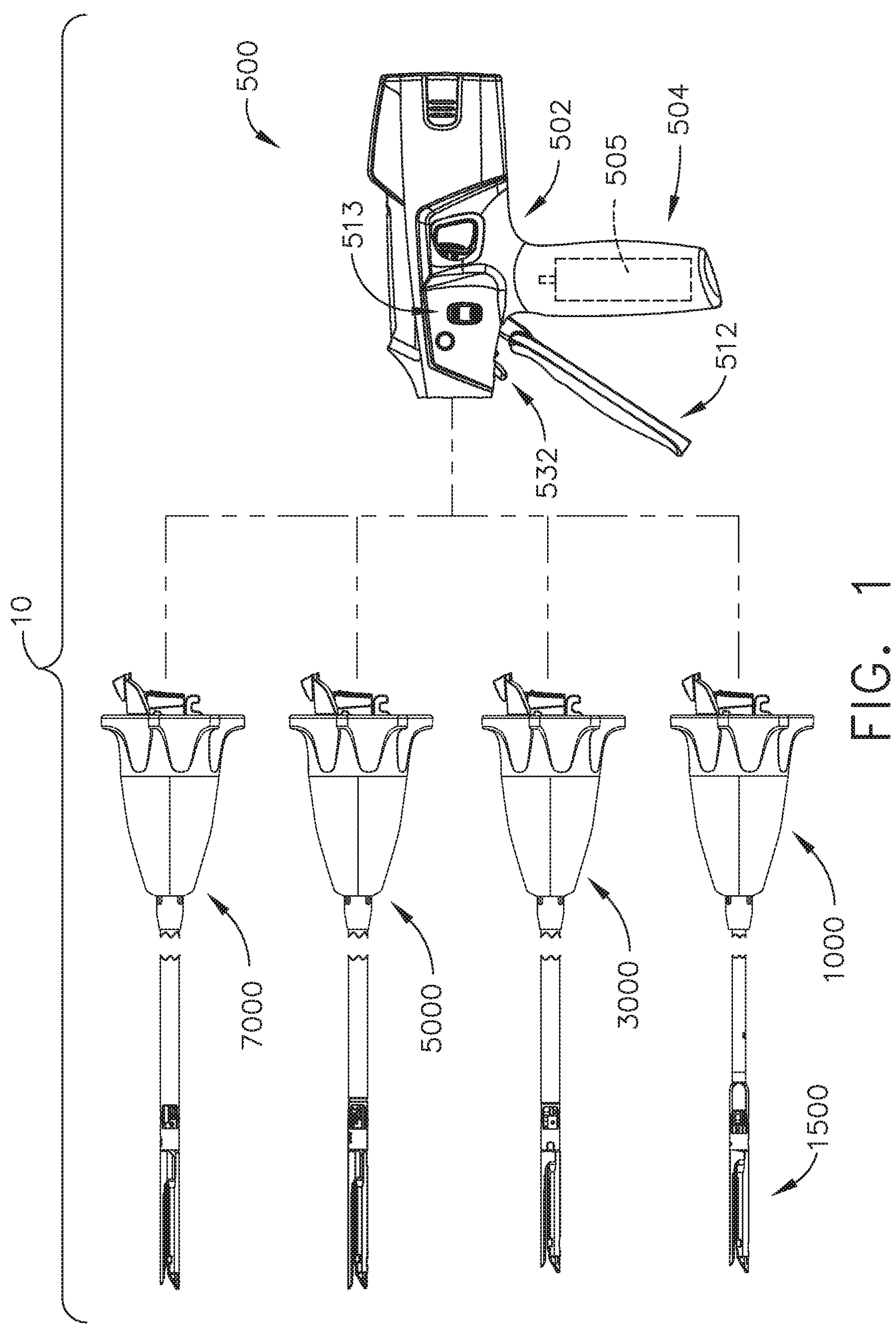
FIG. 1 is a side elevational view of a surgical system comprising a handle assembly and multiple interchangeable surgical tool assemblies that may be used therewith.

Applicant of the present application owns the following U.S. Patent Applications that were filed on Jun. 28, 2017 and which are each herein incorporated by reference in their respective entireties:

U.S. patent application Ser. No. 15/635,693, entitled SURGICAL INSTRUMENT COMPRISING AN OFFSET ARTICULATION JOINT, now U.S. Pat. No. 11,058,424;

U.S. patent application Ser. No. 15/635,729, entitled SURGICAL INSTRUMENT COMPRISING AN ARTICULATION SYSTEM RATIO, now U.S. Pat. No. 11,000,279;

U.S. patent application Ser. No. 15/635,785, entitled SURGICAL INSTRUMENT COMPRISING AN ARTICULATION SYSTEM RATIO, now U.S. Pat. No. 11,083,455;

U.S. patent application Ser. No. 15/635,808, entitled SURGICAL INSTRUMENT COMPRISING FIRING MEMBER SUPPORTS, now U.S. Patent Application Publication No. 2019/0000471;

U.S. patent application Ser. No. 15/635,941, entitled SURGICAL INSTRUMENT COMPRISING AN ARTICULATION SYSTEM LOCKABLE BY A CLOSURE SYSTEM, now U.S. Pat. No. 10,779,824;

U.S. patent application Ser. No. 15/636,029, entitled SURGICAL INSTRUMENT COMPRISING A SHAFT INCLUDING A HOUSING ARRANGEMENT, now U.S. Patent Application Publication No. 2019/0000477;

U.S. patent application Ser. No. 15/635,958, entitled SURGICAL INSTRUMENT COMPRISING SELECTIVELY ACTUATABLE ROTATABLE COUPLERS; now U.S. Patent Application Publication No. 2019/0000474;

U.S. patent application Ser. No. 15/635,981 entitled SURGICAL STAPLING INSTRUMENTS COMPRISING SHORTENED STAPLE CARTRIDGE NOSES, now U.S. Patent Application Publication No. 2019/0000475;

U.S. patent application Ser. No. 15/636,009, entitled SURGICAL INSTRUMENT COMPRISING A SHAFT INCLUDING A CLOSURE TUBE PROFILE, now U.S. Patent Application Publication No. 2019/0000476;

U.S. patent application Ser. No. 15/635,663, entitled METHOD FOR ARTICULATING A SURGICAL INSTRUMENT, now U.S. Pat. No. 10,765,427;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS, now U.S. Pat. No. 11,020,114;

U.S. patent application Ser. No. 15/635,549, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING, now U.S. Pat. No. 10,588,633;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS, now U.S. Patent Application Publication No. 2019/0000459;

U.S. patent application Ser. No. 15/635,578, entitled SURGICAL END EFFECTORS WITH IMPROVED JAW APERTURE ARRANGEMENTS, now U.S. Pat. No. 10,786,253;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT, now U.S. Patent Application Publication No. 2019/0000461;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW, now U.S. Patent Application Publication No. 2019/0000462;

U.S. patent application Ser. No. 15/635,621 entitled SURGICAL INSTRUMENT WITH POSITIVE JAW OPENING FEATURES, now U.S. Pat. No. 10,758,232;

U.S. patent application Ser. No. 15/635,631, entitled SURGICAL INSTRUMENT WITH AXIALLY MOVABLE CLOSURE MEMBER, now U.S. Pat. No. 10,639,037;

U.S. patent application Ser. No. 15/635,521, entitled SURGICAL INSTRUMENT LOCKOUT ARRANGEMENT, now U.S. Pat. No. 10,695,057;

U.S. Design patent application Ser. No. 29/609,087, entitled STAPLE FORMING ANVIL, now U.S. Pat. No. D851,762;

U.S. Design patent application Ser. No. 29/609,083 entitled SURGICAL INSTRUMENT SHAFT, now U.S. Pat. No. D854,151; and U.S. Design patent application Ser. No. 29/609,093, entitled SURGICAL FASTENER CARTRIDGE, now U.S. Pat. No. D869,655.

Applicant of the present application owns the following U.S. Patent Applications that were filed on Jun. 27, 2017 and which are each herein incorporated by reference in their respective entireties:

U.S. patent application Ser. No. 15/634,035, entitled SURGICAL ANVIL ARRANGEMENTS, now U.S. Pat. No. 10,772,629;

U.S. patent application Ser. No. 15/634,046, entitled SURGICAL ANVIL ARRANGEMENTS, now U.S. Pat. No. 10,993,716;

U.S. patent application Ser. No. 15/634,054, entitled SURGICAL ANVIL ARRANGEMENTS, now U.S. Pat. No. 10,856,869;

U.S. patent application Ser. No. 15/634,068 entitled SURGICAL FIRING MEMBER ARRANGEMENTS, now U.S. Patent Application Publication No. 2018/0368843;

U.S. patent application Ser. No. 15/634,076, entitled STAPLE FORMING POCKET ARRANGEMENTS, now U.S. Patent Application Publication No. 2018/0368844;

U.S. patent application Ser. No. 15/634,090, entitled STAPLE FORMING POCKET ARRANGEMENTS, now U.S. Pat. No. 11,090,049;

U.S. patent application Ser. No. 15/634,099, entitled SURGICAL END EFFECTORS AND ANVILS, now U.S. Pat. No. 11,141,154; and U.S. patent application Ser. No. 15/634,117 entitled ARTICULATION SYSTEMS FOR SURGICAL INSTRUMENTS, now U.S. Pat. No. 10,631,859.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES;

U.S. patent application Ser. No. 15/386,240, entitled SURGICAL END EFFECTORS AND ADAPTABLE FIRING MEMBERS THEREFOR;

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TISSUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT;

U.S. patent application Ser. No. 15/385,947, entitled STAPLE CARTRIDGES AND ARRANGEMENTS OF STAPLES AND STAPLE CAVITIES THEREIN;

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,904, entitled STAPLE FIRING MEMBER COMPRISING A MISSING CARTRIDGE AND/OR SPENT CARTRIDGE LOCKOUT;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE;

U.S. patent application Ser. No. 15/385,909, entitled FIRING ASSEMBLY COMPRISING A MULTIPLE FAILED-STATE FUSE;

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLE/FASTENERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLE/FASTENERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLE/FASTENERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,906, entitled FIRING MEMBER PIN CONFIGURATIONS;

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15/386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES;

U.S. patent application Ser. No. 15/386,236, entitled CONNECTION PORTIONS FOR DEPOSABLE LOADING UNITS FOR SURGICAL STAPLING INSTRUMENTS;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CON-

FIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT;

U.S. patent application Ser. No. 15/385,895, entitled SHAFT ASSEMBLY COMPRISING FIRST AND SECOND ARTICULATION LOCKOUTS;

U.S. patent application Ser. No. 15/385,916, entitled SURGICAL STAPLING SYSTEMS;

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE/FASTENER CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design Patent Application Serial No. 29/569,218, entitled SURGICAL FASTENER;

U.S. Design Patent Application Serial No. 29/569,227, entitled SURGICAL FASTENER;

U.S. Design Patent Application Serial No. 29/569,259, entitled SURGICAL FASTENER CARTRIDGE; and U.S. Design Patent Application Serial No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLE/FASTENERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Patent Application Publication No. 2016/0367256;

U.S. patent application Ser. No. 14/742,941, entitled SURGICAL END EFFECTORS WITH DUAL CAM ACTUATED JAW CLOSING FEATURES, now U.S. Patent Application Publication No. 2016/0367248;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Patent Application Publication No. 2016/0367245.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Patent Application Publication No. 2016/0256184;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Patent Application Publication No. 2016/0256153;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Patent Application Publication No. 2016/0256187;

U.S. patent application Ser. No. 14/640,817, entitled INTERACTIVE FEEDBACK SYSTEM FOR POWERED SURGICAL INSTRUMENTS, now U.S. Patent Application Publication No. 2016/0256186;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Patent Application Publication No. 2016/0256155;

U.S. patent application Ser. No. 14/640,837, entitled SMART SENSORS WITH LOCAL SIGNAL PROCESSING, now U.S. Patent Application Publication No. 2016/0256163;

U.S. patent application Ser. No. 14/640,765, entitled SYSTEM FOR DETECTING THE MIS-INSERTION OF A STAPLE CARTRIDGE INTO A SURGICAL STAPLE/FASTENER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Patent Application Publication No. 2016/0256162; and U.S. patent application Ser. No. 14/640,780, entitled SURGICAL INSTRUMENT COMPRISING A LOCKABLE BATTERY HOUSING, now U.S. Patent Application Publication No. 2016/0256161.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Patent Application Publication No. 2016/0249919;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Patent Application Publication No. 2016/0249915;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Patent Application Publication No. 2016/0249918;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Patent Application Publication No. 2016/0249908;

U.S. patent application Ser. No. 14/633,548, entitled POWER ADAPTER FOR A SURGICAL INSTRUMENT, now U.S. Patent Application Publication No. 2016/0249909;

U.S. patent application Ser. No. 14/633,526, entitled ADAPTABLE SURGICAL INSTRUMENT HANDLE, now U.S. Patent Application Publication No. 2016/0249945;

U.S. patent application Ser. No. 14/633,541, entitled MODULAR STAPLING ASSEMBLY, now U.S. Patent Application Publication No. 2016/0249927; and U.S. patent application Ser. No. 14/633,562, entitled SURGICAL APPARATUS CONFIGURED TO TRACK AN END-OF-LIFE PARAMETER, now U.S. Patent Application Publication No. 2016/0249917.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Patent Application Publication No. 2016/0174977;

U.S. patent application Ser. No. 14/574,483, entitled SURGICAL INSTRUMENT ASSEMBLY COMPRISING LOCKABLE SYSTEMS, now U.S. Patent Application Publication No. 2016/0174969;

U.S. patent application Ser. No. 14/575,139, entitled DRIVE ARRANGEMENTS FOR ARTICULATABLE SURGICAL INSTRUMENTS, now U.S. Patent Application Publication No. 2016/0174978;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Patent Application Publication No. 2016/0174976;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Patent Application Publication No. 2016/0174972;

U.S. patent application Ser. No. 14/575,143, entitled SURGICAL INSTRUMENTS WITH IMPROVED CLOSURE ARRANGEMENTS, now U.S. Patent Application Publication No. 2016/0174983;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Patent Application Publication No. 2016/0174975;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Patent Application Publication No. 2016/0174973;

U.S. patent application Ser. No. 14/574,493, entitled SURGICAL INSTRUMENT ASSEMBLY COMPRISING A FLEXIBLE ARTICULATION SYSTEM, now U.S. Patent Application Publication No. 2016/0174970; and U.S. patent application Ser. No. 14/574,500, entitled SURGICAL INSTRUMENT ASSEMBLY COMPRISING A LOCKABLE ARTICULATION SYSTEM, now U.S. Patent Application Publication No. 2016/0174971.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Patent Application Publication No. 2014/0246471;

U.S. patent application Ser. No. 13/782,323, entitled ROTARY POWERED ARTICULATION JOINTS FOR SURGICAL INSTRUMENTS, now U.S. Patent Application Publication No. 2014/0246472;

U.S. patent application Ser. No. 13/782,338, entitled THUMBWHEEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Patent Application Publication No. 2014/0263542;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Patent Application Publication No. 2014/0263564;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Patent Application Publication No. 2014/0263538;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Patent Application Publication No. 2014/0277017.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, now U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Patent Application Publication No. 2016/0066912;

U.S. patent application Ser. No. 14/479,119, entitled ADJUNCT WITH INTEGRATED SENSORS TO QUANTIFY TISSUE COMPRESSION, now U.S. Patent Application Publication No. 2016/0066914;

U.S. patent application Ser. No. 14/478,908, entitled MONITORING DEVICE DEGRADATION BASED ON COMPONENT EVALUATION, now U.S. Patent Application Publication No. 2016/0066910;

U.S. patent application Ser. No. 14/478,895, entitled MULTIPLE SENSORS WITH ONE SENSOR AFFECTING A SECOND SENSOR'S OUTPUT OR INTERPRETATION, now U.S. Patent Application Publication No. 2016/0066909;

U.S. patent application Ser. No. 14/479,110, entitled POLARITY OF HALL MAGNET TO DETECT MISLOADED CARTRIDGE, now U.S. Patent Application Publication No. 2016/0066915;

U.S. patent application Ser. No. 14/479,098, entitled SMART CARTRIDGE WAKE UP OPERATION AND DATA RETENTION, now U.S. Patent Application Publication No. 2016/0066911;

U.S. patent application Ser. No. 14/479,115, entitled MULTIPLE MOTOR CONTROL FOR POWERED MEDICAL DEVICE, now U.S. Patent Application Publication No. 2016/0066916; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Patent Application Publication No. 2014/0305987;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Patent Application Publication No. 2014/0305988;

U.S. patent application Ser. No. 14/248,588, entitled POWERED LINEAR SURGICAL STAPLE/FASTENER, now U.S. Patent Application Publication No. 2014/0309666;

U.S. patent application Ser. No. 14/248,591, entitled TRANSMISSION ARRANGEMENT FOR A SURGICAL INSTRUMENT, now U.S. Patent Application Publication No. 2014/0305991;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Patent Application Publication No. 2014/0305994;

U.S. patent application Ser. No. 14/248,587, entitled POWERED SURGICAL STAPLE/FASTENER, now U.S. Patent Application Publication No. 2014/0309665;

U.S. patent application Ser. No. 14/248,586, entitled DRIVE SYSTEM DECOUPLING ARRANGEMENT FOR A SURGICAL INSTRUMENT, now U.S. Patent Application Publication No. 2014/0305990; and U.S. patent application Ser. No. 14/248,607, entitled MODULAR MOTOR DRIVEN SURGICAL INSTRUMENTS WITH STATUS INDICATION ARRANGEMENTS, now U.S. Patent Application Publication No. 2014/0305992.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIG. 1 depicts a motor-driven surgical system 10 that may be used to perform a variety of different surgical procedures. As can be seen in FIG. 1, one example of the surgical system 10 includes four interchangeable surgical tool assemblies 1000, 3000, 5000, and 7000 that are each adapted for interchangeable use with a handle assembly 500. Each interchangeable surgical tool assembly 1000, 3000, 5000, and 7000 may be designed for use in connection with the performance of one or more specific surgical procedures. In another surgical system embodiment, one or more of the interchangeable surgical tool assemblies 1000, 3000, 5000, and 7000 may also be effectively employed with a tool drive assembly of a robotically controlled or automated surgical system. For example, the surgical tool assemblies disclosed herein may be employed with various robotic systems, instruments, components and methods such as, but not limited to, those disclosed in U.S. Pat. No. 9,072,535, entitled SURGICAL STAPLING INSTRUMENTS WITH ROTATABLE STAPLE DEPLOYMENT ARRANGEMENTS, which is hereby incorporated by reference herein in its entirety.

Figure 2:
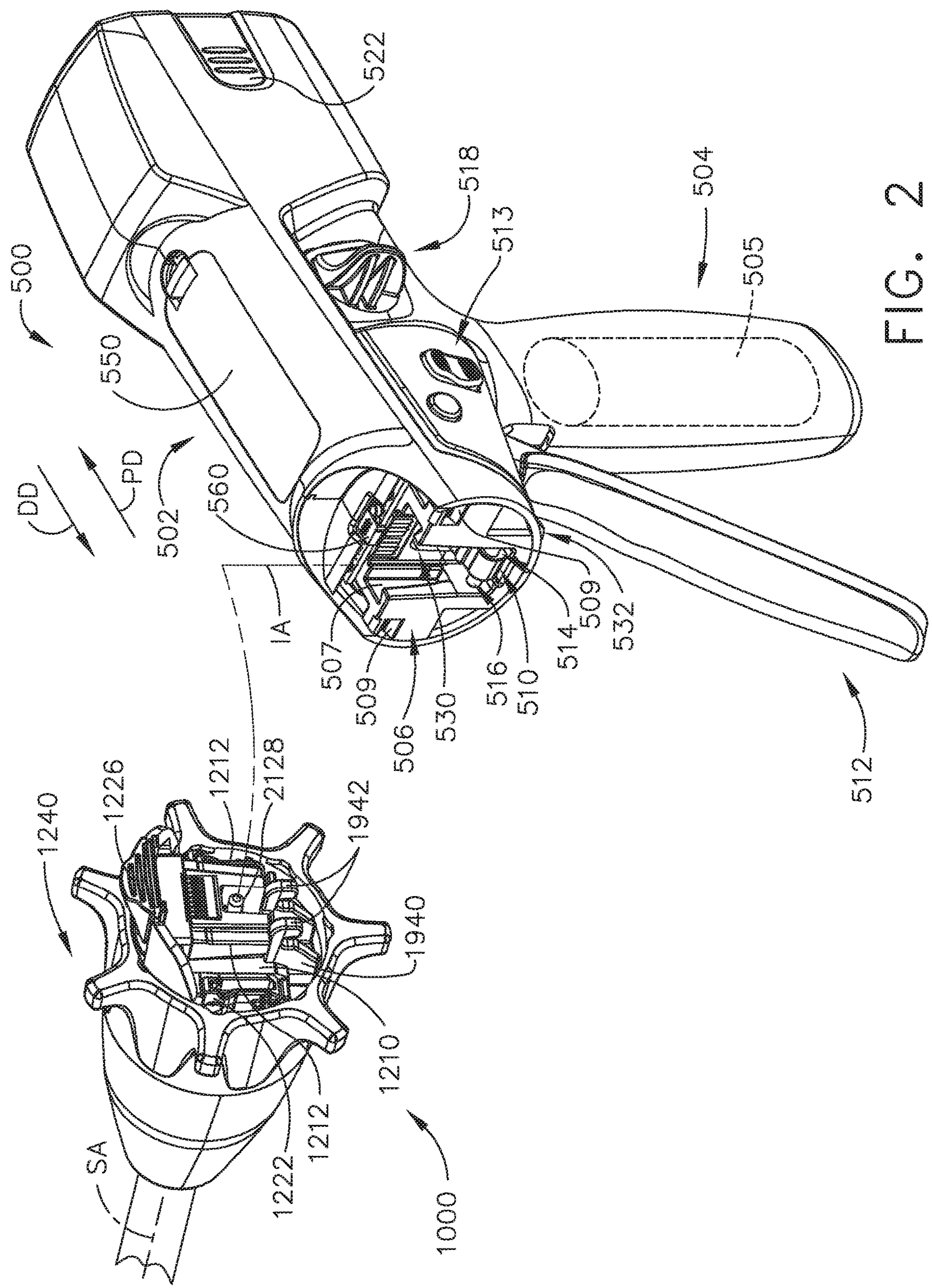
FIG. 2 is an exploded assembly view of portions of the handle assembly and one of the interchangeable surgical tool assemblies depicted in FIG. 1.

FIG. 2 illustrates attachment of an interchangeable surgical tool assembly 1000 to the handle assembly 500. It will be understood that any of the other interchangeable tool assemblies 3000, 5000, and 7000 may be coupled to the handle assembly 500 in a similar manner. The attachment arrangement and process depicted in FIG. 2 may also be employed in connection with attachment of any of the interchangeable surgical tool assemblies 1000, 3000, 5000 and 7000 to a tool drive portion or tool drive housing of a robotic system. The handle assembly 500 may comprise a handle housing 502 that includes a pistol grip portion 504 that can be gripped and manipulated by the clinician. As will be briefly discussed below, the handle assembly 500 operably supports a plurality of drive systems 510, 530 that are configured to generate and apply various control motions to corresponding portions of the interchangeable surgical tool assembly 1000, 3000, 5000, and/or 7000 that is operably attached thereto.

As can be seen in FIG. 2, the handle assembly 500 may further include a handle frame 506 that operably supports the plurality of drive systems. For example, the handle frame 506 can operably support a "first" or closure drive system, generally designated as 510, which may be employed to apply closing and opening motions to the interchangeable surgical tool assembly 1000, 3000, 5000, and 7000 that is operably attached or coupled to the handle assembly 500. In at least one form, the closure drive system 510 may include an actuator in the form of a closure trigger 512 that is pivotally supported by the handle frame 506. Such an arrangement enables the closure trigger 512 to be manipulated by a clinician such that, when the clinician grips the pistol grip portion 504 of the handle assembly 500, the closure trigger 512 may be easily pivoted from a starting or "unactuated" position to an "actuated" position and more particularly to a fully compressed or fully actuated position. In various forms, the closure drive system 510 further includes a closure linkage assembly 514 that is pivotally coupled to the closure trigger 512 or otherwise operably interfaces therewith. As will be discussed in further detail below, in the illustrated example, the closure linkage assembly 514 includes a transverse attachment pin 516 that facilitates attachment to a corresponding drive system on the surgical tool assembly. In use, to actuate the closure drive system 510, the clinician depresses the closure trigger 512 towards the pistol grip portion 504. As described in further detail in U.S. patent application Ser. No. 14/226,142, entitled SURGICAL INSTRUMENT COMPRISING A SENSOR SYSTEM, now U.S. Patent Application Publication No. 2015/0272575, which is hereby incorporated by reference in its entirety herein, the closure drive system 510 is configured to lock the closure trigger 512 into the fully depressed or fully actuated position when the clinician fully depresses the closure trigger 512 to attain the full closure stroke. When the clinician desires to unlock the closure trigger 512 to permit the closure trigger 512 to be biased to the unactuated position, the clinician activates a closure release button assembly 518 which enables the closure trigger to return to its unactuated position. The closure release button assembly 518 may also be configured to interact with various sensors that communicate with a microprocessor 560 in the handle assembly 500 for tracking the position of the closure trigger 512. Further details concerning the configuration and operation of the closure release button assembly 518 may be found in U.S. Patent Application Publication No. 2015/0272575.

In at least one form, the handle assembly 500 and the handle frame 506 may operably support another drive system referred to herein as a firing drive system 530 that is configured to apply firing motions to corresponding portions of the interchangeable surgical tool assembly that is attached thereto. As was described in detail in U.S. Patent Application Publication No. 2015/0272575, the firing drive system 530 may employ an electric motor 505 that is located in the pistol grip portion 504 of the handle assembly 500. In various forms, the motor 505 may be a DC brushed driving motor having a maximum speed of approximately 25,000 RPM, for example. In other arrangements, the motor 505 may include a brushless motor, a cordless motor, a synchronous motor, a stepper motor, or any other suitable electric motor. The motor 505 may be powered by a power source 522 that in one form may comprise a removable power pack. The power pack may support a plurality of Lithium Ion ("LI") or other suitable batteries therein. A number of batteries connected in series may be used as the power source 522 for the surgical system 10. In addition, the power source 522 may be replaceable and/or rechargeable.

The electric motor 505 is configured to axially drive a longitudinally movable drive member in a distal and proximal directions depending upon the polarity of the voltage applied to the motor. For example, when the motor is driven in one rotary direction, the longitudinally movable drive member will be axially driven in a distal direction "DD". When the motor 505 is driven in the opposite rotary direction, the longitudinally movable drive member will be axially driven in a proximal direction "PD". The handle assembly 500 can include a switch 513 which can be configured to reverse the polarity applied to the electric motor 505 by the power source 522 or otherwise control the motor 505. The handle assembly 500 can also include a sensor or sensors that are configured to detect the position of the drive member and/or the direction in which the drive member is being moved. Actuation of the motor 505 can be controlled by a firing trigger 532 (FIG. 1) that is pivotally supported on the handle assembly 500. The firing trigger 532 may be pivoted between an unactuated position and an actuated position. The firing trigger 532 may be biased into the unactuated position by a spring or other biasing arrangement such that, when the clinician releases the firing trigger 532, the firing trigger 532 may be pivoted or otherwise returned to the unactuated position by the spring or biasing arrangement. In at least one form, the firing trigger 532 can be positioned "outboard" of the closure trigger 512 as was discussed above. As discussed in U.S. Patent Application Publication No. 2015/0272575, the handle assembly 500 may be equipped with a firing trigger safety button to prevent the inadvertent actuation of the firing trigger 532. When the closure trigger 512 is in the unactuated position, the safety button is contained in the handle assembly 500 where the clinician cannot readily access it and move it between a safety position preventing actuation of the firing trigger 532 and a firing position wherein the firing trigger 532 may be fired. As the clinician depresses the closure trigger 512, the safety button and the firing trigger 532 pivot downwardly where they can then be manipulated by the clinician.

In at least one form, the longitudinally movable drive member may have a rack of teeth formed thereon for meshing engagement with a corresponding drive gear arrangement that interfaces with the motor. Further details regarding those features may be found in U.S. Patent Application Publication No. 2015/0272575. In at least one form, the handle assembly 500 also includes a manually-actuatable "bailout" assembly that is configured to enable the clinician to manually retract the longitudinally movable drive member should the motor 505 become disabled. The bailout assembly may include a lever or bailout handle assembly that is stored within the handle assembly 500 under a releasable door 550. See FIG. 2. The lever may be configured to be manually pivoted into ratcheting engagement with the teeth in the drive member. Thus, the clinician can manually retract the drive member by using the bailout handle assembly to ratchet the drive member in the proximal direction "PD". U.S. Pat. No. 8,608,045, entitled POWERED SURGICAL CUTTING AND STAPLING APPARATUS WITH MANUALLY RETRACTABLE FIRING SYSTEM, the entire disclosure of which is hereby incorporated by reference herein, discloses bailout arrangements and other components, arrangements and systems that may also be employed with any one of the various interchangeable surgical tool assemblies disclosed herein.

Figure 3:
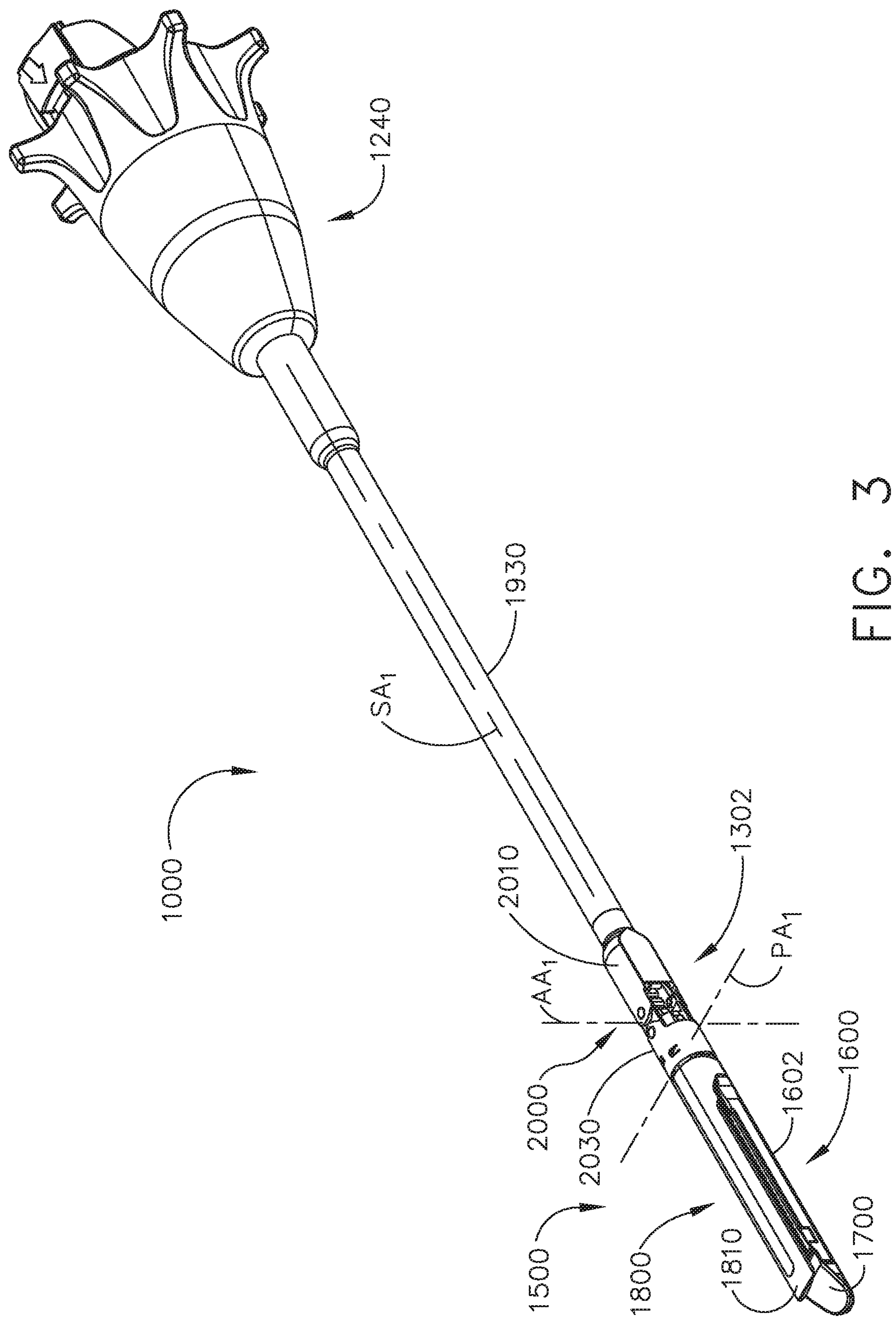
FIG. 3 is a perspective view of one of the interchangeable surgical tool assemblies depicted in FIG. 1.
Figure 4:
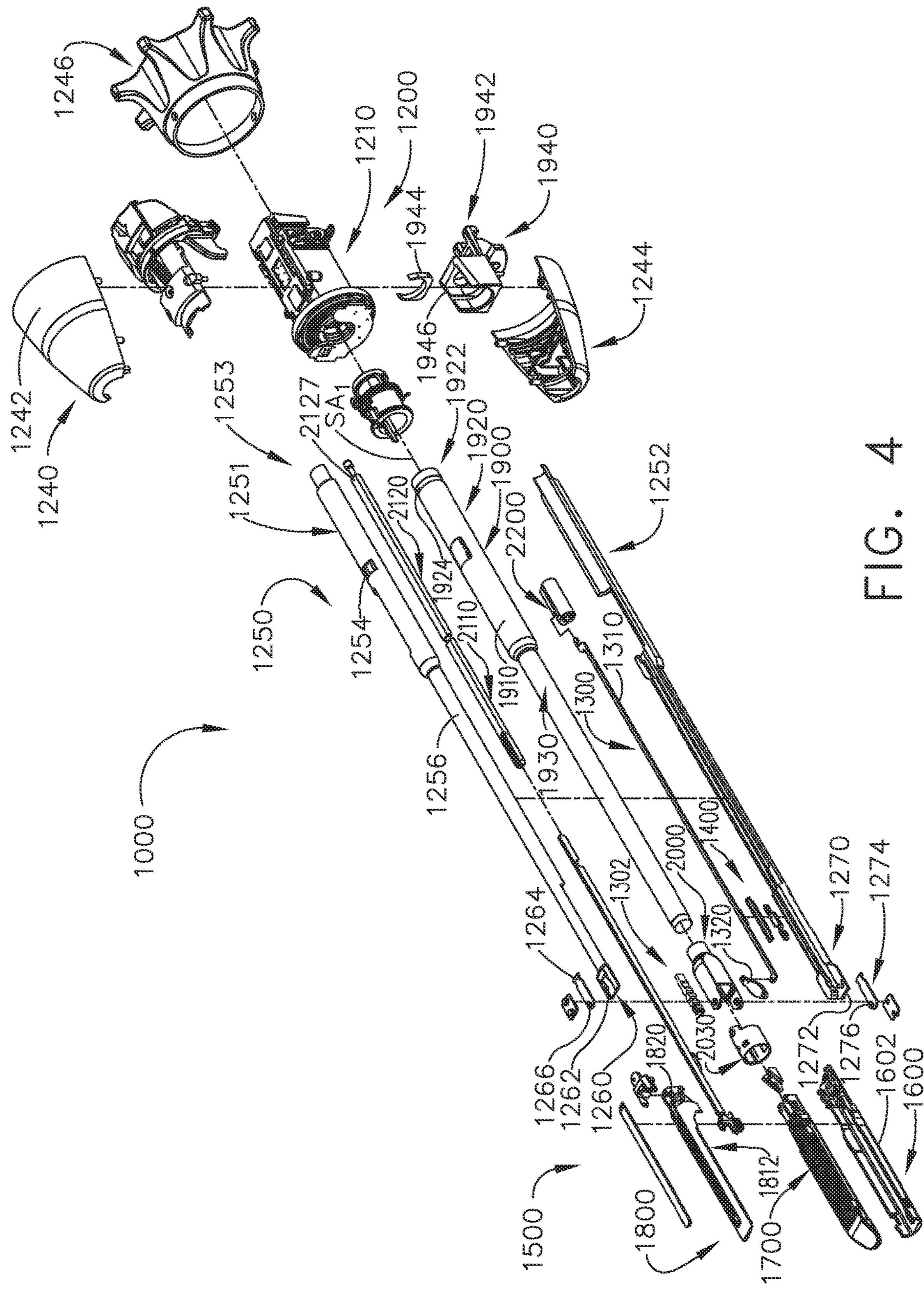
FIG. 4 is an exploded assembly view of the interchangeable surgical tool assembly of FIG. 3.

Turning now to FIGS. 3 and 4, the interchangeable surgical tool assembly 1000 includes a surgical end effector 1500 that comprises a first jaw 1600 and a second jaw 1800. In one arrangement, the first jaw 1600 comprises an elongate channel 1602 that is configured to operably support a surgical staple/fastener cartridge 1700 therein. The second jaw 1800 comprises an anvil 1810 that is pivotally supported relative to the elongate channel 1602. The interchangeable surgical tool assembly 1000 includes an articulation system 1300 that comprises an articulation joint 1302 and an articulation lock 1400 (FIGS. 4-6) which can be configured to releasably hold the surgical end effector 1500 in a desired articulated position relative to a shaft axis $SA_1$.

As can be further seen in FIGS. 4 and 7-9, the interchangeable surgical tool assembly 1000 includes a tool frame assembly 1200 that comprises a tool chassis 1210 that operably supports a nozzle assembly 1240 thereon. In one form, the nozzle assembly 1240 is comprised of nozzle portions 1242, 1244 as well as an actuator wheel portion 1246 that is configured to be coupled to the assembled nozzle portions 1242, 1244 by snaps, lugs, and/or screws, for example. The interchangeable surgical tool assembly 1000 includes a proximal closure assembly 1900 which is operably coupled to a distal closure assembly 2000 that is utilized to close and/or open the anvil 1810 of the surgical end effector 1500 as will be discussed in further detail below. In addition, the interchangeable surgical tool assembly 1000 includes a spine assembly 1250 that operably supports the proximal closure assembly 1900 and is coupled to the surgical end effector 1500. In various circumstances, for ease of assembly, the spine assembly 1250 may be fabricated from an upper spine segment 1251 and a lower spine segment 1252 that are interconnected together by snap features, adhesives, and/or welds, for example. In assembled form, the spine assembly 1250 includes a proximal end 1253 that is rotatably supported in the tool chassis 1210. In one arrangement, for example, the proximal end 1253 of the spine assembly 1250 is attached to a spine bearing that is configured to be supported within the tool chassis 1210. Such an arrangement facilitates the rotatable attachment of the spine assembly 1250 to the tool chassis 1210 such that the spine assembly 1250 may be selectively rotated about the shaft axis $SA_1$ relative to the tool chassis 1210. In particular, in at least one arrangement, the proximal end 1253 of the spine assembly 1250 includes an upper lug seat 1254 (FIGS. 4, 5, 7, 8, and 10) and a lower lug seat that are each configured to receive a corresponding nozzle lug 1245 extending inwardly from each of the nozzle portions 1242, 1244, for example. Such an arrangement facilitates the rotation of the spine assembly 1250 about the shaft axis $SA_1$ by rotating the actuator wheel portion 1246 of the nozzle assembly 1240.

Figure 5:
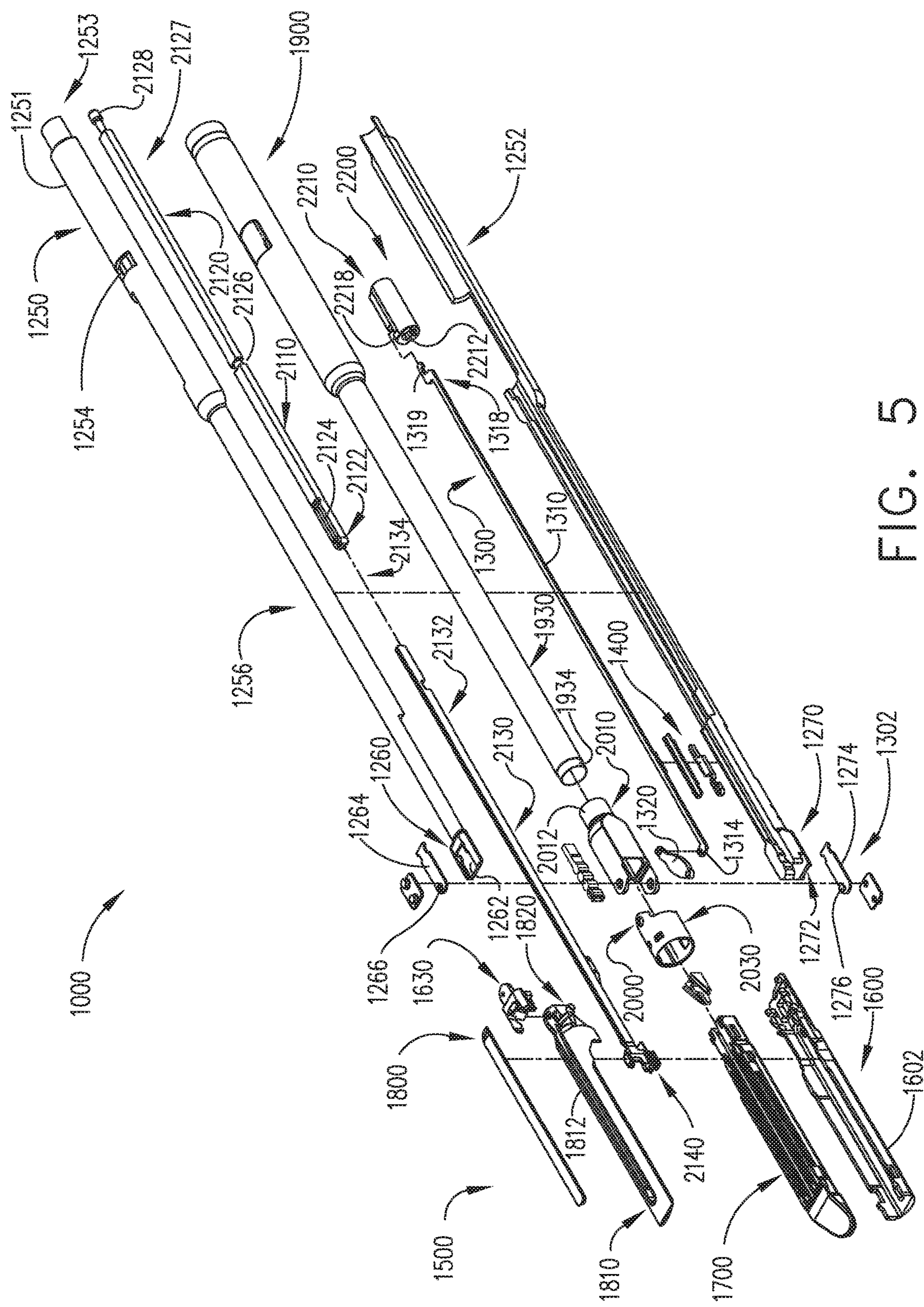
FIG. 5 is another exploded assembly view of a distal portion of the interchangeable surgical tool assembly of FIGS. 3 and 4.
Figure 6:
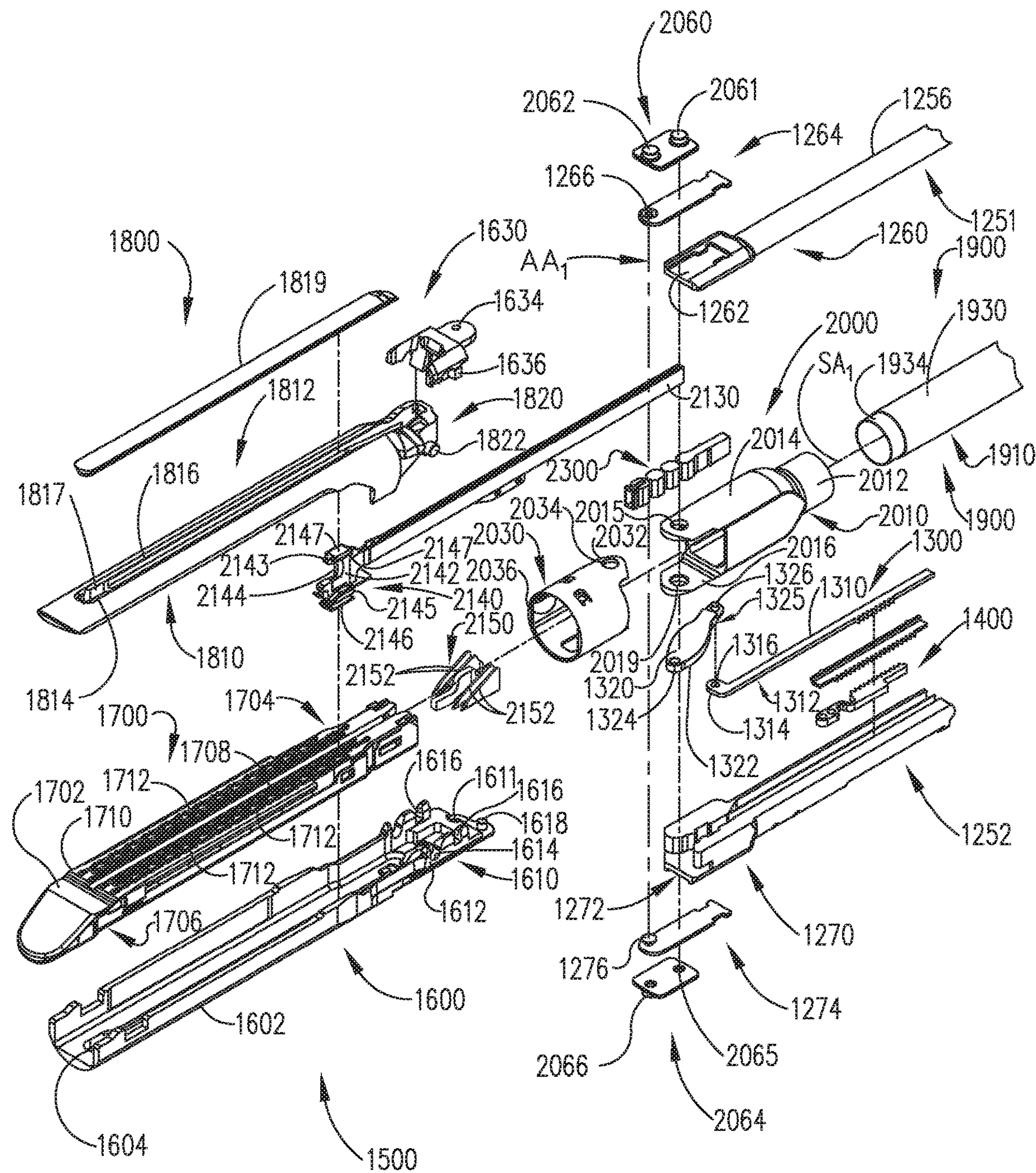
FIG. 6 is another exploded assembly view of a distal portion of the interchangeable surgical tool assembly of FIGS. 3-5.

As can be seen in FIGS. 4 and 5, the spine assembly 1250 further includes an intermediate spine shaft segment 1256 that has a diameter that is less than the diameter of the proximal end 1253 of the spine assembly 1250. The intermediate spine shaft segment 1256 of the upper spine segment 1251 terminates in an upper lug mount feature 1260 and the intermediate spine shaft segment of the lower spine segment 1252 terminates in a lower lug mount feature 1270. As can be seen in FIG. 6, the upper lug mount feature 1260 is formed with a lug slot 1262 therein that is adapted to mountingly support an upper mounting link 1264 therein. Similarly, the lower lug mount feature 1270 is formed with a lug slot 1272 therein that is adapted to mountingly support a lower mounting link 1274 therein. The upper mounting link 1264 includes a pivot socket 1266 therein that is offset from the shaft axis $SA_1$. The pivot socket 1266 is adapted to rotatably receive therein a pivot pin 1634 that is formed on a channel cap or anvil retainer 1630 that is attached to a proximal end portion 1610 of the elongate channel 1602. The lower mounting link 1274 includes a lower pivot pin 1276 that is adapted to be received within a pivot hole 1611 formed in the proximal end portion 1610 of the elongate channel 1602. See FIG. 6. The lower pivot pin 1276 as well as the pivot hole 1611 is offset from the shaft axis $SA_1$. The lower pivot pin 1276 is vertically aligned with the pivot socket 1266 to define an articulation axis $AA_1$ about which the surgical end effector 1500 may articulate relative to the shaft axis $SA_1$. Although the articulation axis $AA_1$ is transverse to the shaft axis $SA_1$, the articulation axis $AA_1$ is laterally offset therefrom and does not intersect the shaft axis $SA_1$.

Figure 15:
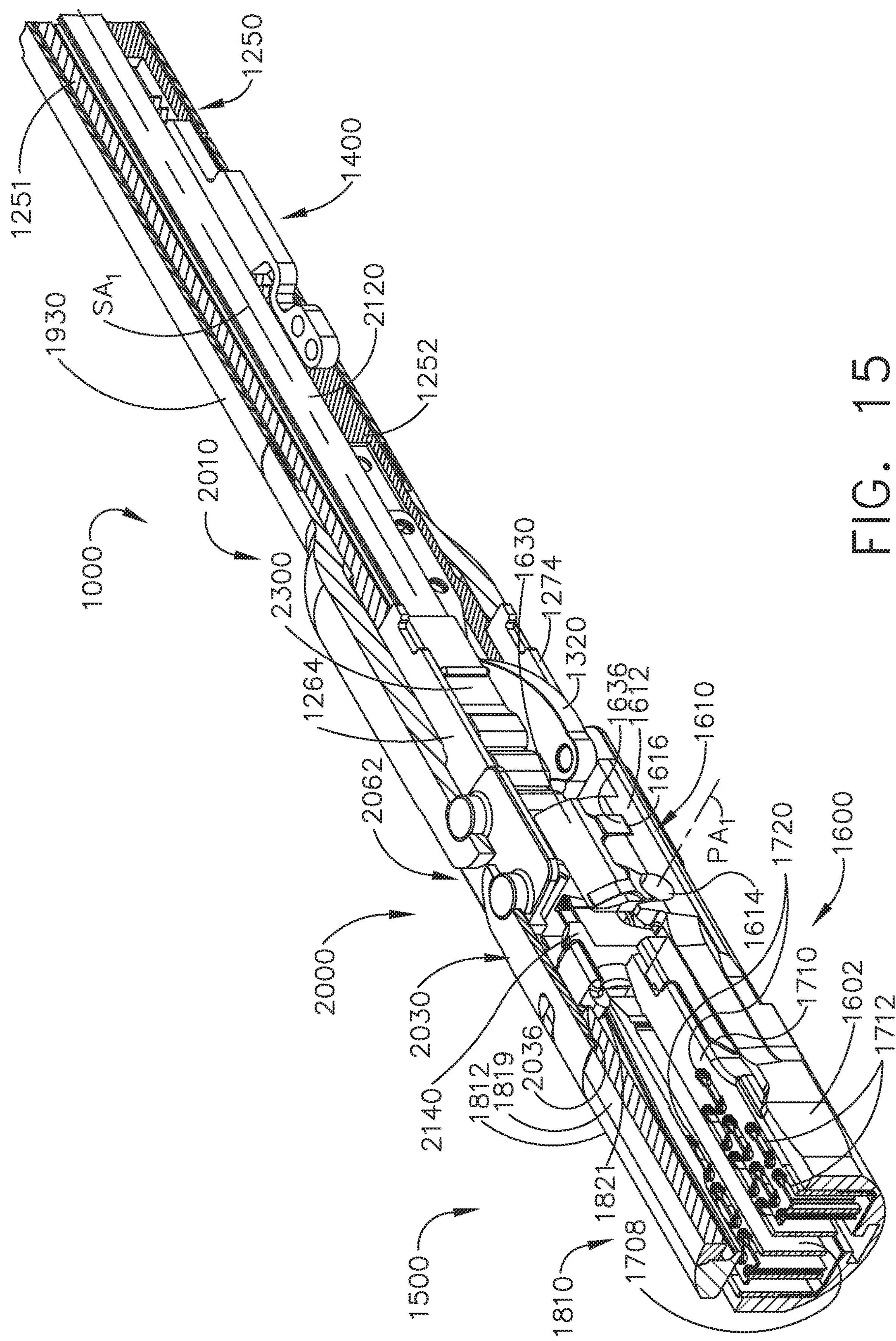
FIG. 15 is a cross-sectional perspective view of a distal portion of the interchangeable surgical tool assembly of FIGS. 3-14.

Referring now to FIGS. 6 and 15, the anvil 1810 includes an anvil body 1812 that terminates in anvil mounting portion 1820. The anvil mounting portion 1820 is movably or pivotably supported on the elongate channel 1602 for selective pivotal travel relative thereto about a fixed anvil pivot axis $PA_1$ (FIG. 15) that is transverse to the shaft axis $SA_1$. A pivot member or anvil trunnion 1822 extends laterally out of each lateral side of the anvil mounting portion 1820 to be received in a corresponding trunnion cradle 1614 formed in the upstanding walls 1612 of the proximal end portion 1610 of the elongate channel 1602. The anvil trunnions 1822 are pivotally retained in their corresponding trunnion cradle 1614 by the channel cap or anvil retainer 1630. The channel cap or anvil retainer 1630 includes a pair of attachment lugs 1636 that are configured to be retainingly received within corresponding lug grooves or notches 1616 formed in the upstanding walls 1612 of the proximal end portion 1610 of the elongate channel 1602.

The surgical end effector 1500 is selectively articulatable about the articulation axis $AA_1$ by the articulation system 1300. In one form, the articulation system 1300 includes a proximal articulation driver 1310 that is pivotally coupled to an articulation link 1320. As can be seen in FIG. 6, an offset attachment lug 1314 is formed on a distal end 1312 of the proximal articulation driver 1310. A pivot hole 1316 is formed in the offset attachment lug 1314 and is configured to pivotally receive therein a proximal link pin 1326 formed on the proximal end 1325 of the articulation link 1320. A distal end 1322 of the articulation link 1320 includes a pivot hole 1324 that is configured to pivotally receive therein a channel pin 1618 formed on the proximal end portion 1610 of the elongate channel 1602. Thus, axial movement of the proximal articulation driver 1310 will apply articulation motions to the elongate channel 1602 to articulate the surgical end effector 1500 about the articulation axis $AA_1$ relative to the spine assembly 1250.

Figure 7:
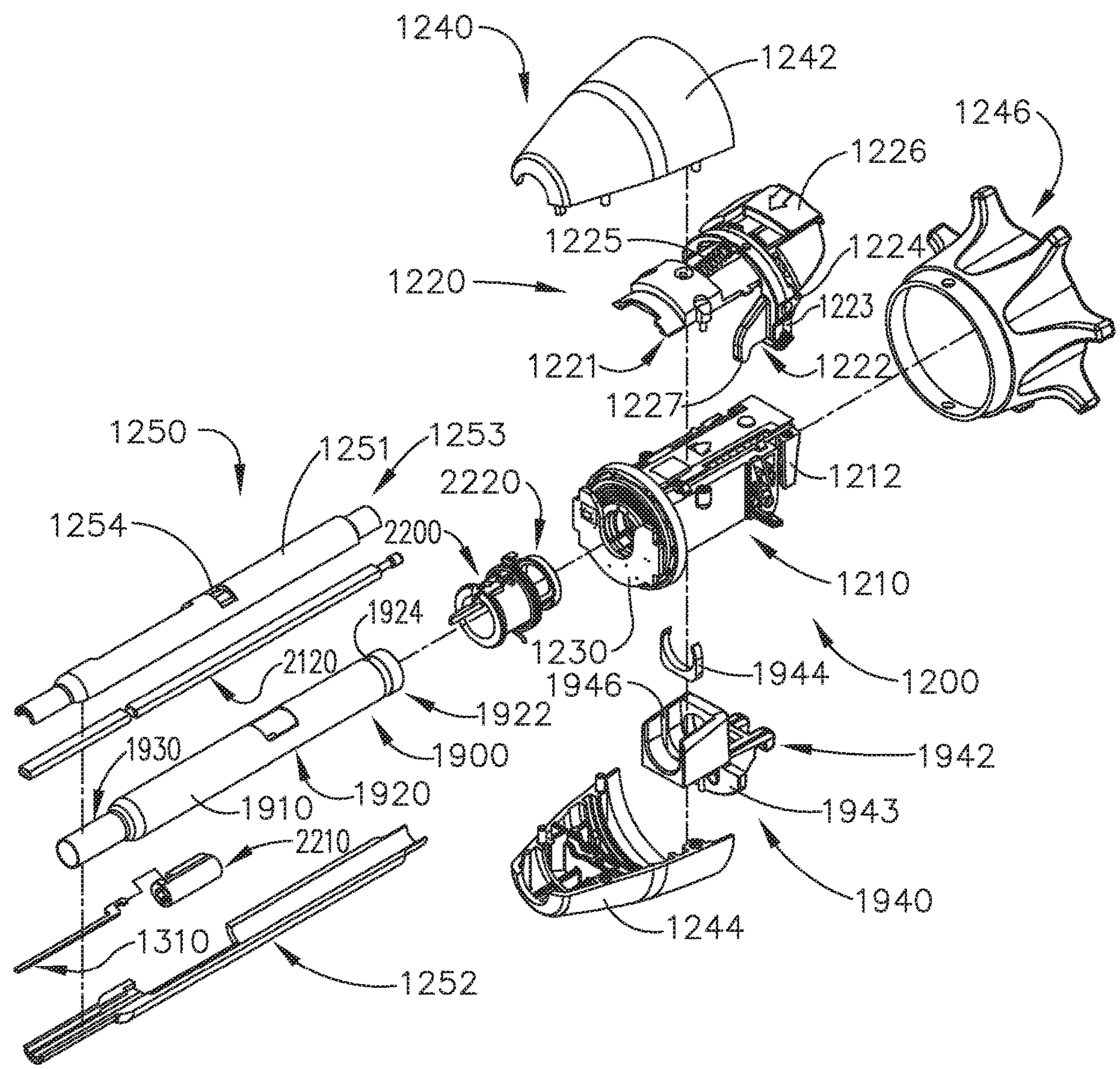
FIG. 7 is an exploded assembly view of a proximal portion of the interchangeable surgical tool assembly of FIGS. 3-6.
Figure 8:
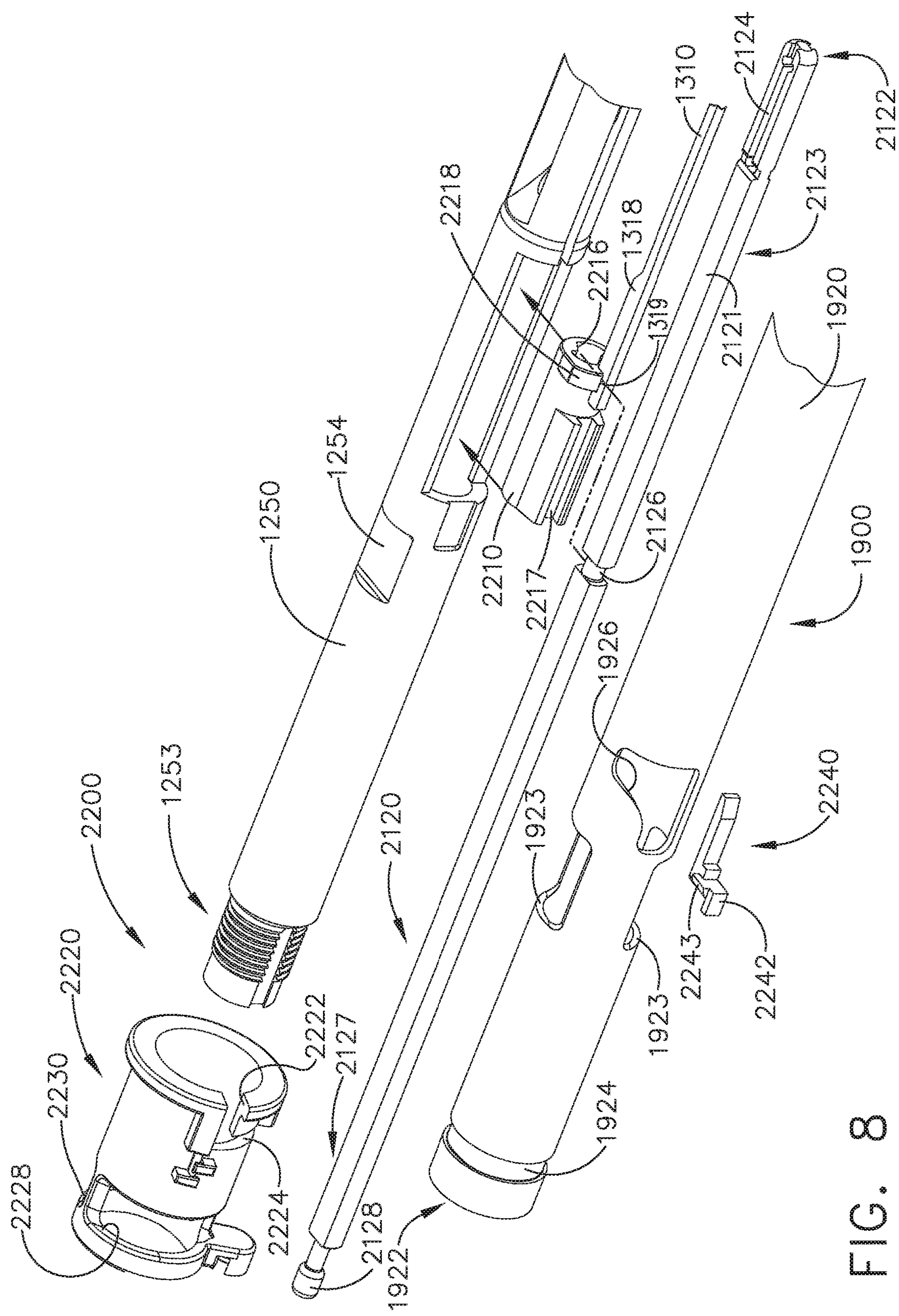
FIG. 8 is another exploded assembly view of a portion of the interchangeable surgical tool assembly of FIGS. 3-7.
Figure 9:
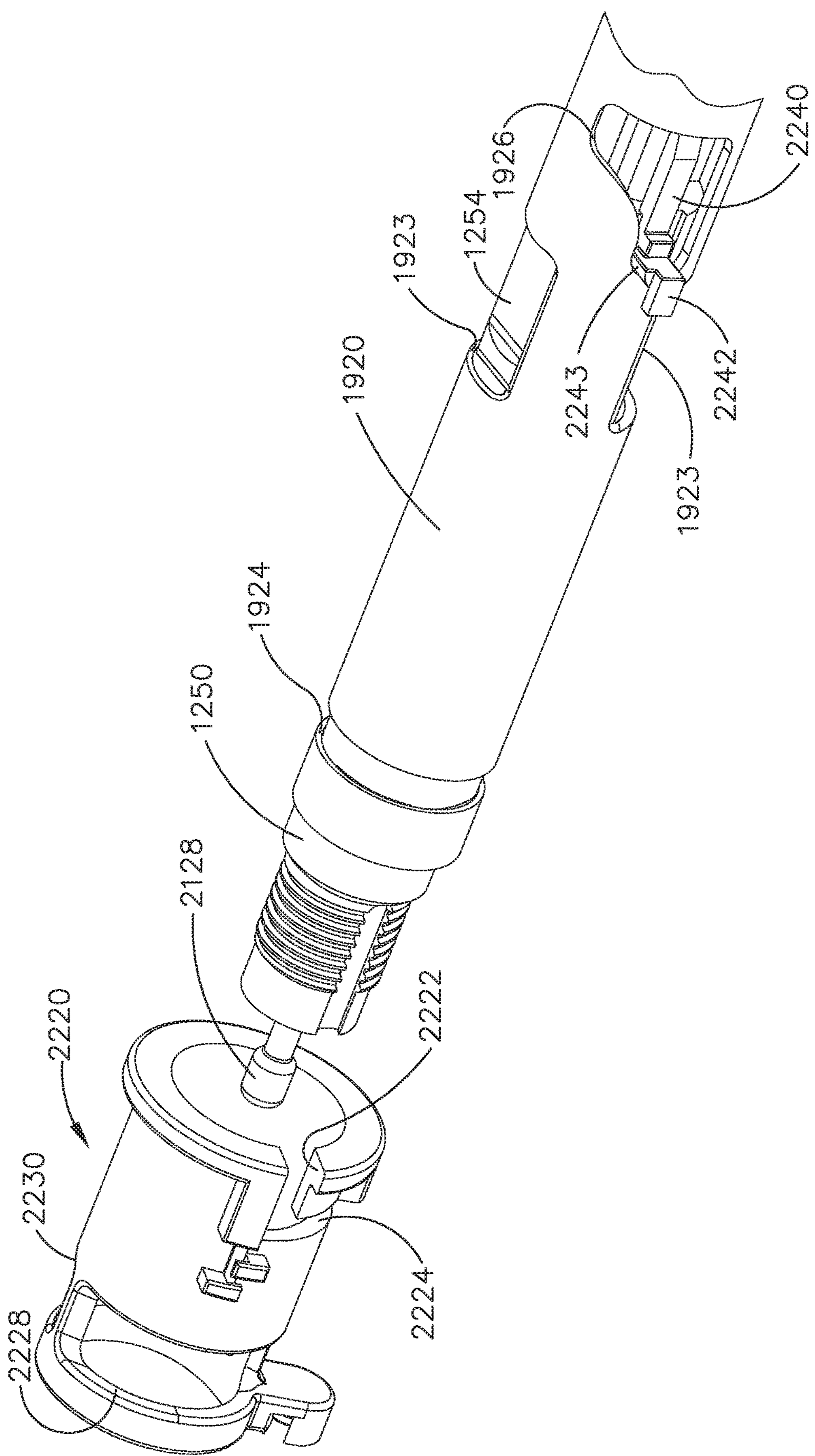
FIG. 9 is another exploded assembly view of a portion of the interchangeable surgical tool assembly of FIGS. 3-8.
Figure 10:
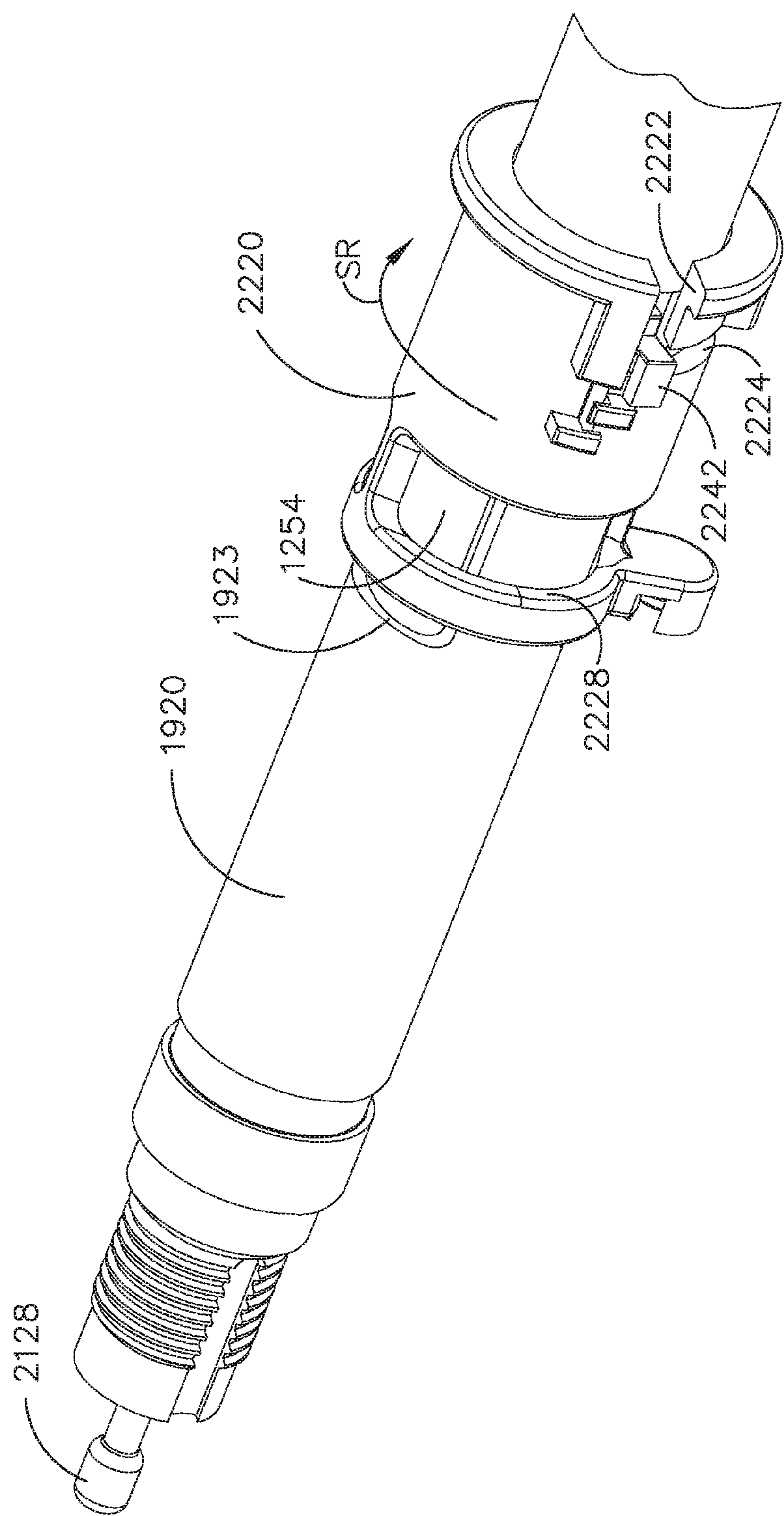
FIG. 10 is a perspective view of a proximal portion of the interchangeable surgical tool assembly of FIGS. 3-9.
Figure 11:
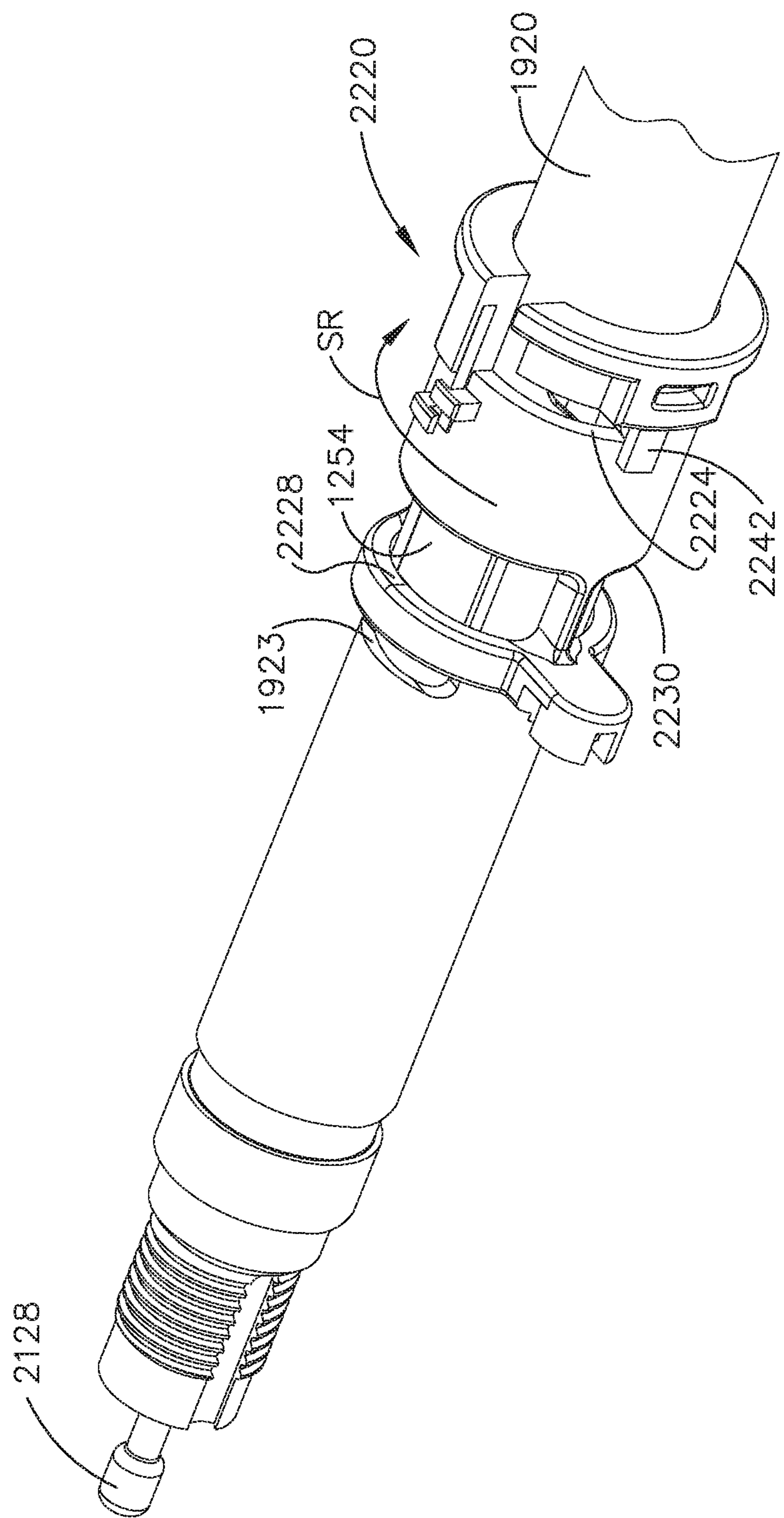
FIG. 11 is another perspective view of the proximal portion of the interchangeable surgical tool assembly of FIGS. 3-10.
Figure 12:
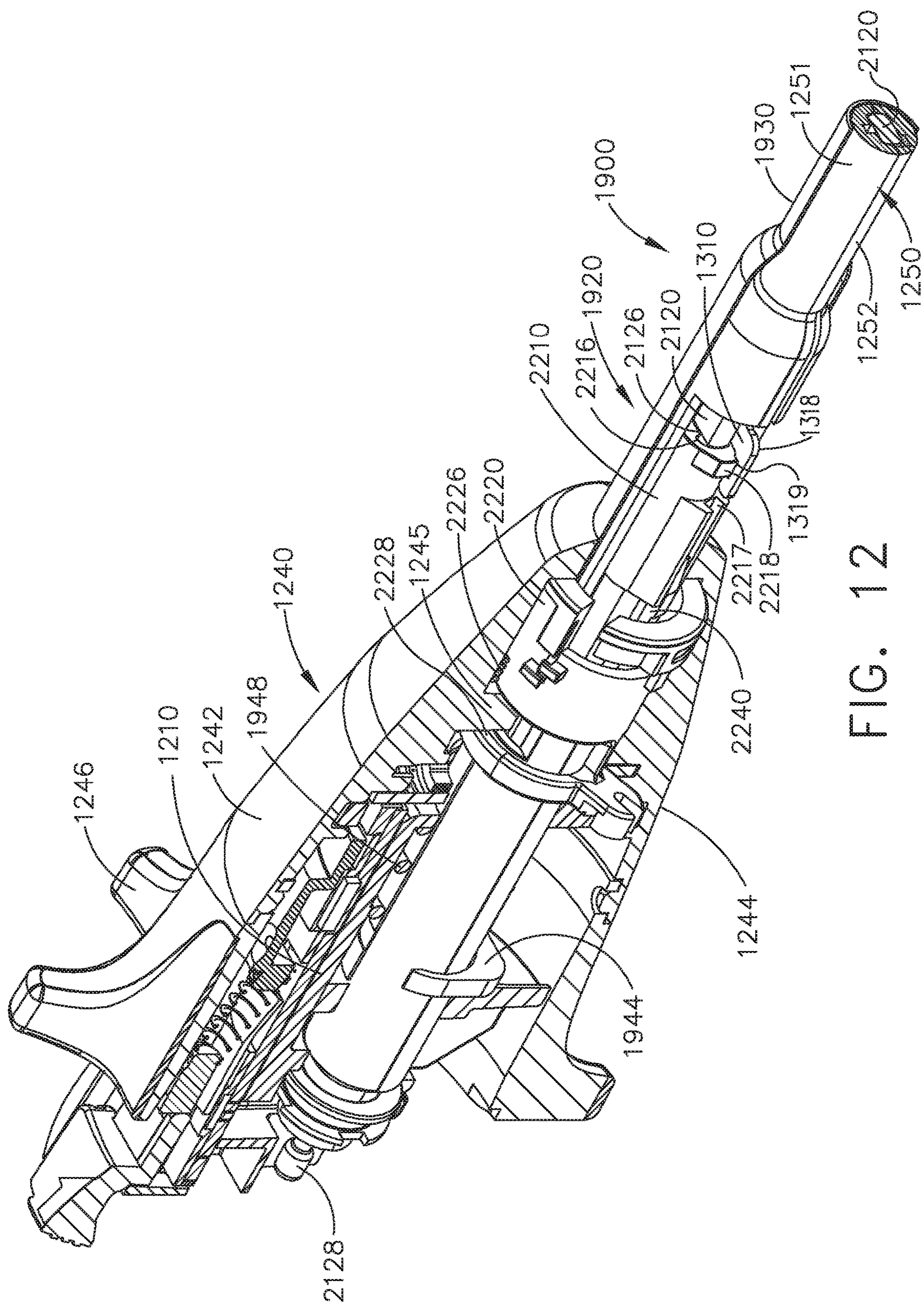
FIG. 12 is a cross-sectional perspective view of the proximal portion of the interchangeable surgical tool assembly of FIGS. 3-11.
Figure 13:
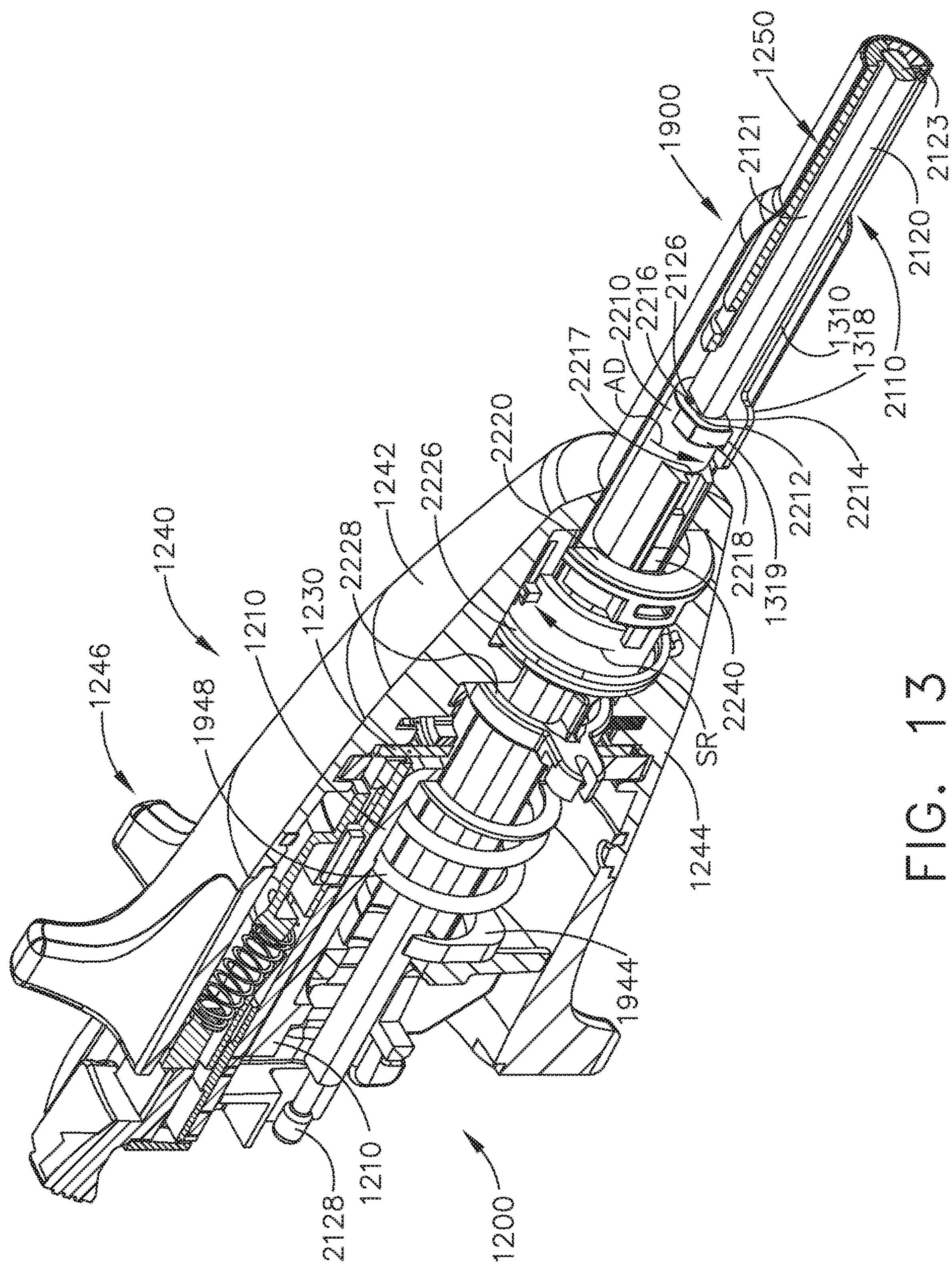
FIG. 13 is another cross-sectional perspective view of the proximal portion of the interchangeable surgical tool assembly of FIGS. 3-12.
Figure 14:
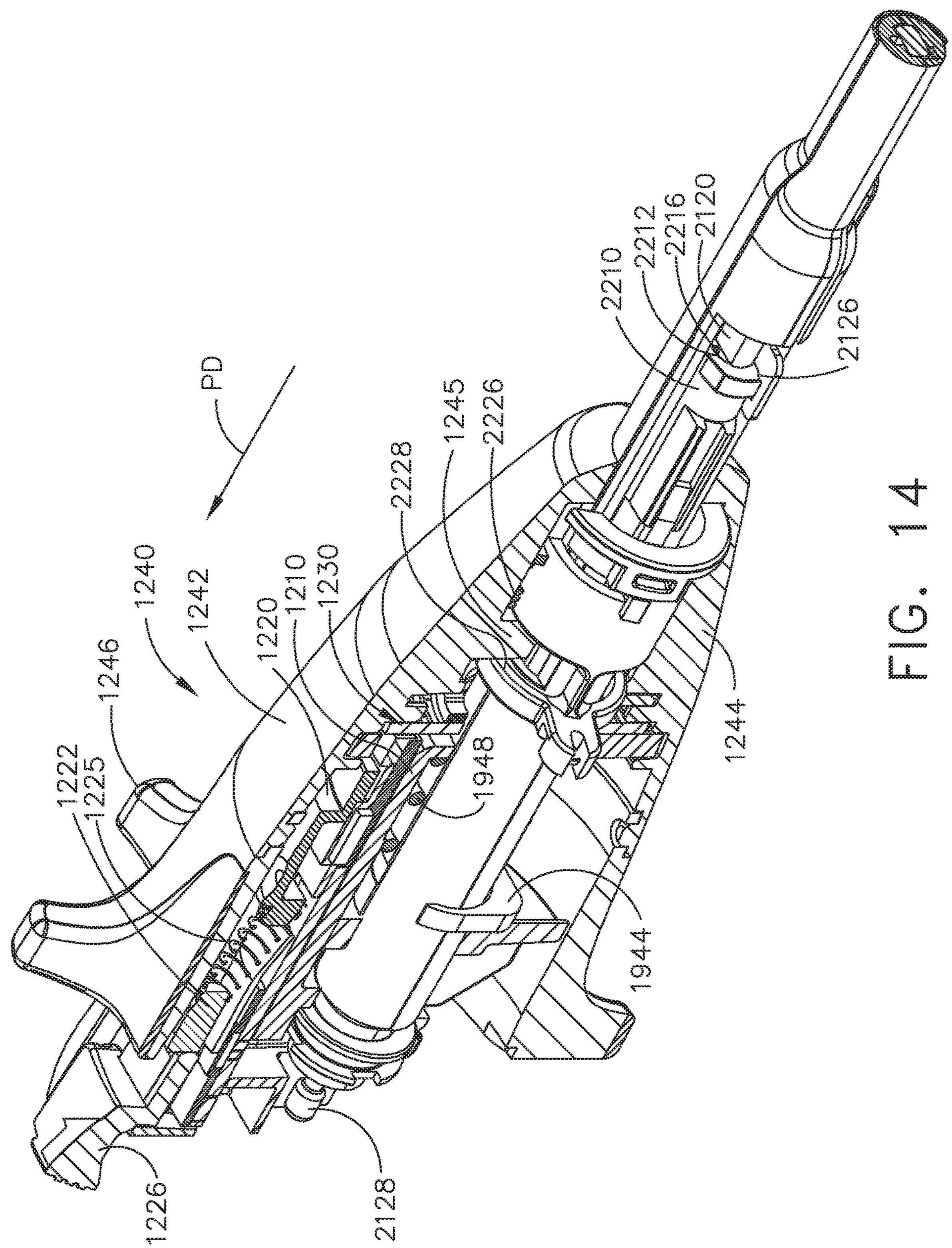
FIG. 14 is another cross-sectional perspective view of the proximal portion of the interchangeable surgical tool assembly of FIGS. 3-13.

Movement of the anvil 1810 relative to the elongate channel 1602 is effectuated by axial movement of the proximal closure assembly 1900 and the distal closure assembly 2000. Referring now to FIGS. 4 and 7, the proximal closure assembly 1900 comprises a proximal closure tube 1910 that has a proximal closure tube portion 1920 and a distal portion 1930. The distal portion 1930 has a diameter that is less than the diameter of the proximal closure tube portion 1920. The proximal end 1922 of the proximal closure tube portion 1920 is rotatably supported in a closure shuttle 1940 which is slidably supported within the tool chassis 1210 such that the closure shuttle 1940 may be axially moved relative to the tool chassis 1210. In one form, the closure shuttle 1940 includes a pair of proximally-protruding hooks 1942 that are configured to be attached to the attachment pin 516 that is attached to the closure linkage assembly 514 of the handle assembly 500. The proximal end 1922 of the proximal closure tube portion 1920 is rotatably coupled to the closure shuttle 1940. For example, a U-shaped connector 1944 is inserted into an annular slot 1924 in the proximal closure tube portion 1920 and is retained within vertical slots 1946 in the closure shuttle 1940. Such an arrangement serves to attach the proximal closure assembly 1900 to the closure shuttle 1940 for axial travel therewith while enabling the proximal closure assembly 1900 to rotate relative to the closure shuttle 1940 about the shaft axis $SA_1$. A closure spring 1948 (FIGS. 12-14) extends over the proximal closure tube portion 1920 to bias the closure shuttle 1940 in the proximal direction PD which can serve to pivot the closure trigger 512 on the handle assembly 500 (FIG. 2) into the unactuated position when the interchangeable surgical tool assembly 1000 is operably coupled to the handle assembly 500.

Referring now to FIGS. 5 and 6, a distal portion 1930 of the proximal closure tube 1910 is attached to the distal closure assembly 2000. The distal closure assembly 2000 includes an articulation connector 2010 that is coupled to a distal closure tube segment 2030. The distal closure tube segment 2030 has a diameter that is larger than the diameter of the distal portion 1930 of the proximal closure tube 1910. The articulation connector 2010 has a proximally extending end portion 2012 that is adapted to be received on a connection flange 1934 formed on the distal end of the distal portion 1930. The articulation connector 2010 may be retained on the connection flange 1934 by an appropriate fastener arrangement, adhesive, and/or welds, for example. The articulation connector 2010 includes upper and lower tangs 2014, 2016 that protrude distally from a distal end of the articulation connector 2010 that are movably coupled to an end effector closure sleeve, or distal closure tube segment, 2030. The distal closure tube segment 2030 includes an upper tang 2032 and a lower tang that protrude proximally from a proximal end thereof. An upper double pivot link 2060 includes proximal and distal pins 2061, 2062 that engage corresponding holes 2015, 2034 in the upper tangs 2014, 2032 of the articulation connector 2010 and distal closure tube segment 2030, respectively. Similarly, a lower double pivot link 2064 includes proximal and distal pins 2065, 2066 that engage corresponding holes 2019 in the lower tangs 2016 of the articulation connector 2010 and distal closure tube segment 2030, respectively. As will be discussed in further detail below, distal and proximal axial translation of the proximal closure assembly 1900 and distal closure assembly 2000 will result in the closing and opening of the anvil 1810 relative to the elongate channel 1602.

The interchangeable surgical tool assembly 1000 further includes a firing system generally designated as 2100. The firing system 2100 includes a firing member assembly 2110 that is supported for axial travel within the spine assembly 1250. The firing member assembly 2110 includes an intermediate firing shaft portion 2120 that is configured to be attached to a distal cutting portion, or knife bar, 2130. The firing member assembly 2110 may also be referred to herein as a "second shaft" and/or a "second shaft assembly". As can be seen in FIG. 5, the intermediate firing shaft portion 2120 may include a longitudinal slot 2124 in a distal end 2122 thereof which can be configured to receive a proximal end 2132 of the knife bar 2130. The longitudinal slot 2124 and the proximal end 2132 of the knife bar 2130 are sized and configured to permit relative movement therebetween and can comprise a slip joint 2134. The slip joint 2134 can permit the intermediate firing shaft portion 2120 of the firing member assembly 2110 to be moved to articulate the end effector 1500 without moving, or at least substantially moving, the knife bar 2130. Once the end effector 1500 has been suitably oriented, the intermediate firing shaft portion 2120 can be advanced distally until a proximal sidewall of the longitudinal slot 2124 comes into contact with a portion of the knife bar 2130 to advance the knife bar 2130 and fire the surgical staple/fastener cartridge 1700 positioned within the elongate channel 1602. A proximal end 2127 of the intermediate firing shaft portion 2120 has a firing shaft attachment lug 2128 formed thereon (FIG. 8) that is configured to be seated into an attachment cradle that is on the distal end of the longitudinally movable drive member of the firing drive system 530 within the handle assembly 500. Such an arrangement facilitates the axial movement of the intermediate firing shaft portion 2120 upon actuation of the firing drive system 530.

Further to the above, the interchangeable tool assembly 1000 can include a shifter assembly 2200 which can be configured to selectively and releasably couple the proximal articulation driver 1310 to the firing system 2100. In one form, the shifter assembly 2200 includes a lock collar, or lock sleeve 2210, positioned around the intermediate firing shaft portion 2120 of the firing system 2100 wherein the lock sleeve 2210 can be rotated between an engaged position in which the lock sleeve 2210 couples the proximal articulation driver 1310 to the firing member assembly 2110 and a disengaged position in which the proximal articulation driver 1310 is not operably coupled to the firing member assembly 2110. When the lock sleeve 2210 is in its engaged position, distal movement of the firing member assembly 2110 can move the proximal articulation driver 1310 distally and, correspondingly, proximal movement of the firing member assembly 2110 can move the proximal articulation driver 1310 proximally. When the lock sleeve 2210 is in its disengaged position, movement of the firing member assembly 2110 is not transmitted to the proximal articulation driver 1310 and, as a result, the firing member assembly 2110 can move independently of the proximal articulation driver 1310. In various circumstances, the proximal articulation driver 1310 can be held in position by the articulation lock 1400 when the proximal articulation driver 1310 is not being moved in the proximal or distal directions by the firing member assembly 2110.

The intermediate firing shaft portion 2120 of the firing member assembly 2110 is formed with two opposed flat sides 2121, 2123 with a drive notch 2126 formed therein. See FIG. 8. As can also be seen in FIG. 13, the lock sleeve 2210 comprises a cylindrical, or an at least substantially cylindrical, body that includes a longitudinal aperture 2212 that is configured to receive the intermediate firing shaft portion 2120 there through. The lock sleeve 2210 comprises diametrically-opposed, inwardly-facing lock protrusions 2214, 2216 that, when the lock sleeve 2210 is in one position, are engagingly received within corresponding portions of the drive notch 2126 in the intermediate firing shaft portion 2120 and, when in another position, are not received within the drive notch 2126 to thereby permit relative axial motion between the lock sleeve 2210 and the intermediate firing shaft portion 2120.

Referring now to FIGS. 8 and 12-14, the lock sleeve 2210 further includes a lock member 2218 that is sized to be movably received within a notch 1319 in a proximal end 1318 of the proximal articulation driver 1310. Such an arrangement permits the lock sleeve 2210 to slightly rotate into and out of engagement with the intermediate firing shaft portion 2120 while remaining in engagement with the notch 1319 in the proximal articulation driver 1310. For example, when the lock sleeve 2210 is in its engaged position, the lock protrusions 2214, 2216 are positioned within the drive notch 2126 in the intermediate firing shaft portion 2120 such that a distal pushing force and/or a proximal pulling force can be transmitted from the firing member assembly 2110 to the lock sleeve 2210. Such axial pushing or pulling motion is then transmitted from the lock sleeve 2210 to the proximal articulation driver 1310 to thereby articulate the surgical end effector 1500. In effect, the firing member assembly 2110, the lock sleeve 2210, and the proximal articulation driver 1310 will move together when the lock sleeve 2210 is in its engaged (articulation) position. On the other hand, when the lock sleeve 2210 is in its disengaged position, the lock protrusions 2214, 2216 are not received within the drive notch 2126 in the intermediate firing shaft portion 2120 and, as a result, a distal pushing force and/or a proximal pulling force may not be transmitted from the firing member assembly 2110 to the lock sleeve 2210 (and the proximal articulation driver 1310).

Relative movement of the lock sleeve 2210 between its engaged and disengaged positions may be controlled by a shifter assembly 2200 that interfaces with the proximal closure tube 1910 of the proximal closure assembly 1900. More specifically and with reference to FIGS. 8 and 9, the shifter assembly 2200 further includes a shifter key 2240 that is configured to be slidably received within a key groove 2217 formed in the outer perimeter of the lock sleeve 2210. Such an arrangement enables the shifter key 2240 to move axially with respect to the lock sleeve 2210. Referring to FIGS. 8-11, the shifter key 2240 includes an actuator lug 2242 that extends through a cam slot or cam opening 1926 in the proximal closure tube portion 1920. See FIG. 9. A cam surface 2243 is also provided adjacent the actuator lug 2242 which is configured to cammingly interact with the cam opening 1926 so as to cause the shifter key 2240 to rotate in response to axial motion of the proximal closure tube portion 1920.

The shifter assembly 2200 further includes a switch drum 2220 that is rotatably received on a proximal end portion of the proximal closure tube portion 1920. As can be seen in FIGS. 10-14, the actuator lug 2242 extends through an axial slot segment 2222 in the switch drum 2220 and is movably received within an arcuate slot segment 2224 in the switch drum 2220. A switch drum torsion spring 2226 (FIGS. 12-14) is mounted on the switch drum 2220 and engages nozzle portion 1244 to apply a torsional bias or rotation (arrow SR in FIGS. 10 and 11) which serves to rotate the switch drum 2220 until the actuator lug 2242 reaches the end of the arcuate slot segment 2224. See FIGS. 11 and 12. When in this position, the switch drum 2220 may provide a torsional bias to the shifter key 2240 which thereby causes the lock sleeve 2210 to rotate into its engaged position with the intermediate firing shaft portion 2120. This position also corresponds to the unactuated configuration of the proximal closure assembly 1900. In one arrangement, for example, the actuator lug 2242 is located in the upper portion of the cam opening 1926 in the proximal closure tube portion 1920 when the proximal closure assembly 1900 is in an unactuated configuration (anvil 1810 is in an open position spaced away from the surgical staple/fastener cartridge 1700). When in that position, the actuation of the intermediate firing shaft portion 2120 will result in the axial movement of the proximal articulation driver 1310. Once the user has articulated the surgical end effector 1500 to a desired orientation, the user may then actuate the proximal closure assembly 1900. The actuation of the proximal closure assembly 1900 will result in the distal travel of the proximal closure tube portion 1920 to ultimately apply a closing motion to the anvil 1810. This distal travel of the proximal closure tube portion 1920 will result in the cam opening 1926 cammingly interacting with the cam surface 2243 on the actuator lug 2242 to thereby cause the shifter key 2240 to rotate the lock sleeve 2210 in an actuation direction AD. Such rotation of the lock sleeve 2210 will result in the disengagement of the lock protrusions 2214, 2216 from the drive notch 2126 in the intermediate firing shaft portion 2120. When in such a configuration, the firing drive system 530 may be actuated to actuate the intermediate firing shaft portion 2120 without actuating the proximal articulation driver 1310. Further details concerning the operation of the switch drum 2220 and lock sleeve 2210, as well as alternative articulation and firing drive arrangements that may be employed with the various interchangeable surgical tool assemblies described herein, may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. patent application Ser. No. 15/019,196, filed Feb. 9, 2016, entitled SURGICAL INSTRUMENT ARTICULATION MECHANISM WITH SLOTTED SECONDARY CONSTRAINT, the entire disclosures of which are hereby incorporated by reference herein.

Referring again to FIGS. 8-13, the switch drum 2220 can further comprise at least partially circumferential openings 2228, 2230 defined therein which can receive circumferential lugs/mounts 1245 that extend from the nozzle portions 1242, 1244 and permit relative rotation, but not translation, between the switch drum 2220 and the nozzle assembly 1240. The nozzle lugs 1245 extend through corresponding openings 1923 in the proximal closure tube portion 1920 to be seated in lug seats 1254 in the spine assembly 1250. See FIGS. 8 and 9. Such an arrangement enables the user to rotate the spine assembly 1250 about the shaft axis by rotating the nozzle assembly 1240.

As also illustrated in FIGS. 7 and 12-14, the interchangeable tool assembly 1000 can comprise a slip ring assembly 1230 which can be configured to conduct electrical power to and/or from the surgical end effector 1500 and/or communicate signals to and/or from the surgical end effector 1500, back to a microprocessor 560 (FIG. 2) in the handle assembly 500 or a robotic system controller, for example. Further details concerning the slip ring assembly 1230 and associated connectors may be found in U.S. patent application Ser. No. 13/803,086, entitled ARTICULATABLE SURGICAL INSTRUMENT COMPRISING AN ARTICULATION LOCK, now U.S. Patent Application Publication No. 2014/0263541, and U.S. patent application Ser. No. 15/019,196, filed Feb. 9, 2016, entitled SURGICAL INSTRUMENT ARTICULATION MECHANISM WITH SLOTTED SECONDARY CONSTRAINT, which have each been herein incorporated by reference in their respective entirety as well as in U.S. patent application Ser. No. 13/800,067, entitled STAPLE CARTRIDGE TISSUE THICKNESS SENSOR SYSTEM, now U.S. Patent Application Publication No. 2014/0263552, which is hereby incorporated by reference herein in its entirety. As also described in further detail in the aforementioned patent applications that have been incorporated by reference herein, the interchangeable surgical tool assembly 1000 can also comprise at least one sensor that is configured to detect the position of the switch drum 2220.

Referring again to FIG. 2, the tool chassis 1210 includes at least one tapered attachment portion 1212 formed thereon that is adapted to be received within a corresponding dovetail slot 507 formed within the distal end portion of the handle frame 506 of the handle assembly 500. Various interchangeable surgical tool assemblies employ a latch system 1220 for removably coupling the interchangeable surgical tool assembly 1000 to the handle frame 506 of the handle assembly 500. In at least one form, as can be seen in FIG. 7, the latch system 1220 includes a lock member or lock yoke 1222 that is movably coupled to the tool chassis 1210, for example. The lock yoke 1222 has a U-shape with two spaced downwardly extending legs 1223. The legs 1223 each have a pivot lug formed thereon that are adapted to be received in corresponding holes formed in the tool chassis 1210. Such an arrangement facilitates the pivotal attachment of the lock yoke 1222 to the tool chassis 1210. The lock yoke 1222 may include two proximally protruding lock lugs 1224 that are configured for releasable engagement with corresponding lock detents or grooves 509 in the distal end of the handle frame 506 of the handle assembly 500. See FIG. 2. In various forms, the lock yoke 1222 is biased in the proximal direction by a spring or biasing member 1225. Actuation of the lock yoke 1222 may be accomplished by a latch button 1226 that is slidably mounted on a latch actuator assembly 1221 that is mounted to the tool chassis 1210. The latch button 1226 may be biased in a proximal direction relative to the lock yoke 1222. The lock yoke 1222 may be moved to an unlocked position by biasing the latch button 1226 in the distal direction which also causes the lock yoke 1222 to pivot out of retaining engagement with the distal end of the handle frame 506. When the lock yoke 1222 is in "retaining engagement" with the distal end of the handle frame 506, the lock lugs 1224 are retainingly seated within the corresponding lock detents or grooves 509 in the distal end of the handle frame 506.

The lock yoke 1222 includes at least one lock hook 1227 that is adapted to contact corresponding a lock lug portion 1943 that is formed on the closure shuttle 1940. When the closure shuttle 1940 is in an unactuated position, the lock yoke 1222 may be pivoted in a distal direction to unlock the interchangeable surgical tool assembly 1000 from the handle assembly 500. When in that position, the lock hooks 1227 do not contact the lock lug portions 1943 on the closure shuttle 1940. However, when the closure shuttle 1940 is moved to an actuated position, the lock yoke 1222 is prevented from being pivoted to an unlocked position. Stated another way, if the clinician were to attempt to pivot the lock yoke 1222 to an unlocked position or, for example, the lock yoke 1222 was inadvertently bumped or contacted in a manner that might otherwise cause it to pivot distally, the lock hooks 1227 on the lock yoke 1222 will contact the lock lug portions 1943 on the closure shuttle 1940 and prevent movement of the lock yoke 1222 to an unlocked position.

Referring again to FIG. 6, the knife bar 2130 may comprise a laminated beam structure that includes at least two beam layers. Such beam layers may comprise, for example, stainless steel bands that are interconnected by welds and/or pins, for example, at the proximal ends and/or at other locations along the length thereof. In alternative embodiments, the distal ends of the bands are not connected together to allow the laminates or bands to splay relative to each other when the end effector is articulated. Such an arrangement permits the knife bar 2130 to be sufficiently flexible to accommodate articulation of the end effector. Various laminated knife bar arrangements are disclosed in U.S. patent application Ser. No. 15/019,245, entitled SURGICAL INSTRUMENTS WITH CLOSURE STROKE REDUCTION ARRANGEMENTS which is hereby incorporated by reference in its entirety. As can also be seen in FIG. 6, a firing shaft support assembly 2300 is employed to provide lateral support to the knife bar 2130 as it flexes to accommodate articulation of the surgical end effector 1500. Further details concerning the operation of the firing shaft support assembly 2300 and alternative knife bar support arrangements may be found in U.S. patent application Ser. No. 15/019,245, entitled SURGICAL INSTRUMENTS WITH CLOSURE STROKE REDUCTION ARRANGEMENTS and U.S. patent application Ser. No. 15/019,220, entitled SURGICAL INSTRUMENT WITH ARTICULATING AND AXIALLY TRANSLATABLE END EFFECTOR, which are each hereby incorporated by reference herein in their respective entireties.

As can also be seen in FIG. 6, a firing member or knife member 2140 is attached to the distal end of the knife bar 2130. In one exemplary form, the firing member 2140 comprises a body portion 2142 that supports a knife or tissue cutting portion 2144. The body portion 2142 protrudes through an elongate slot 1604 in the elongate channel 1602 and terminates in a foot member 2146 that extends laterally on each side of the body portion 2142. As the firing member 2140 is driven distally through the surgical staple/fastener cartridge 1700, the foot member 2146 rides within a passage in the elongate channel 1602 that is located under the surgical staple/fastener cartridge 1700. In one arrangement, the body portion 2142 includes two laterally protruding central tabs 2145 that may ride above the central passage within the surgical staple/fastener cartridge 1700. See FIG. 6. The tissue cutting portion 2144 is disposed between a distally protruding top nose portion 2143 and the foot member 2146. As can be further seen in FIG. 6, the firing member 2140 may further include two laterally extending top tabs, pins or anvil engagement features 2147. As the firing member 2140 is driven distally, a top portion of the body portion 2142 extends through a centrally disposed anvil slot 1814 and the anvil engagement features 2147 ride on corresponding anvil ledges 1816 formed on each side of the anvil slot 1814. To facilitate assembly of the anvil 1810 and firing member 2140 arrangement, in one arrangement, the top of the anvil body 1812 has an opening 1817 therein. Once the anvil 1810 is assembled onto the elongate channel 1602 and the firing member 2140 is installed, the opening 1817 is covered by an anvil cap 1819 that is affixed to the anvil body 1812 by welds and/or other suitable fastening means.

Returning to FIG. 6, the firing member 2140 is configured to operably interface with a sled assembly 2150 that is operably supported within a body 1702 of the surgical staple/fastener cartridge 1700. The sled assembly 2150 is slidably displaceable within the surgical staple/fastener cartridge body 1702 from a proximal starting position adjacent the proximal end 1704 of the cartridge body 1702 to an ending position adjacent a distal end 1706 of the cartridge body 1702. The cartridge body 1702 operably supports therein a plurality of staple drivers that are aligned in rows on each side of a centrally disposed slot 1708. The centrally disposed slot 1708 enables the firing member 2140 to pass there through and cut the tissue that is clamped between the anvil 1810 and the surgical staple/fastener cartridge 1700. The drivers are associated with corresponding staple/fastener pockets 1712 that open through an upper deck surface 1710 of the cartridge body 1702. Each of the staple drivers supports one or more surgical staples or fasteners thereon. The sled assembly 2150 includes a plurality of sloped or wedge-shaped cams 2152 wherein each cam 2152 corresponds to a particular line of fasteners or drivers located on a side of the slot 1708.

To attach the interchangeable surgical tool assembly 1000 to the handle assembly 500, referring to FIG. 2, the clinician may position the tool chassis 1210 of the interchangeable surgical tool assembly 1000 above or adjacent to the distal end of the handle frame 506 such that the tapered attachment portions 1212 formed on the tool chassis 1210 are aligned with the dovetail slots 507 in the handle frame 506. The clinician may then move the surgical tool assembly 1000 along an installation axis IA that is perpendicular to the shaft axis $SA_1$ to seat the tapered attachment portions 1212 in “operable engagement” with the corresponding dovetail receiving slots 507 in the distal end of the handle frame 506. In doing so, the firing shaft attachment lug 2128 on the intermediate firing shaft portion 2120 will also be seated in the attachment cradle in the longitudinally movable drive member within the handle assembly 500 and the portions of attachment pin 516 on the closure link 514 will be seated in the corresponding hooks 1942 in the closure shuttle 1940. As used herein, the term “operable engagement” in the context of two components means that the two components are sufficiently engaged with each other so that, upon the application of an actuation motion thereto, the components carry out their intended action, function, and/or procedure.

During a typical surgical procedure, a clinician may introduce the surgical end effector 1500 into the surgical site through a trocar, or other opening in a patient, to access the target tissue. When doing so, the clinician axially aligns, or at least substantially aligns, the surgical end effector 1500 in an unarticulated state along the shaft axis and inserts the surgical end effector 1500 through the trocar. Once the surgical end effector 1500 has passed through the trocar, the clinician may need to articulate the end effector 1500 to advantageously position the end effector 1500 adjacent the target tissue. Further to the above, the firing drive system 530 is operated through a limited range of motion to move the articulation driver 1310 and articulate the end effector 1500. Such articulation occurs prior to closing the anvil onto the target tissue. Once the end effector has attained the desired articulated position, the clinician may then actuate the closure drive system 510 to close the anvil 1810 onto the target tissue. Such actuation of the closure drive system 510 actuates the shifter assembly 2200 and delinks the articulation driver 1310 from the intermediate firing shaft portion 2120. Thus, once the target tissue has been suitably captured in the surgical end effector 1500, the clinician may once again actuate the firing drive system 530 to axially advance the firing member 2140 through the surgical staple/fastener cartridge 1700 to fire the staples into and cut the target tissue. Other closure and firing drive arrangements, such as handheld, manual, automated, and/or robotic arrangements, for example, may be employed to control the axial movement of the closure system components, the articulation system components, and/or the firing system components of the surgical tool assembly 1000.

Figure 16A:
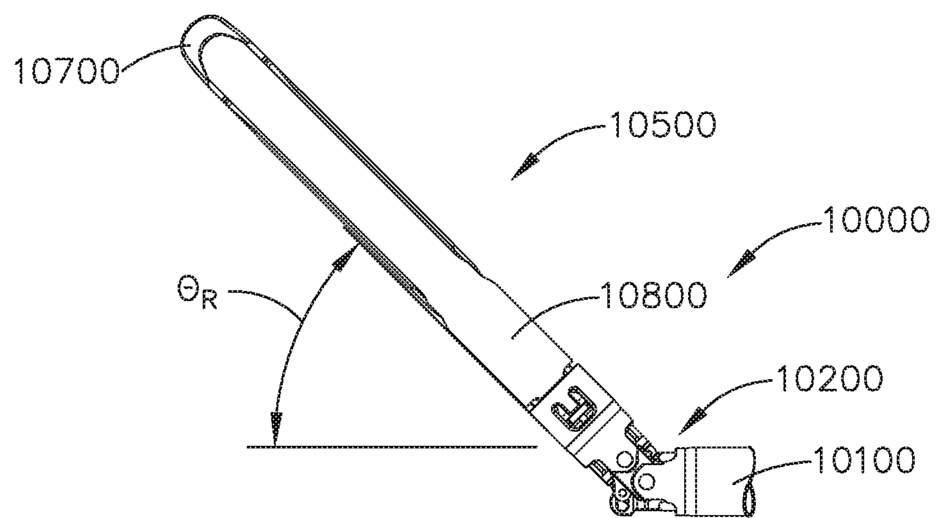
FIG. 16A is a partial plan view of the end effector of FIG. 16 illustrating the end effector articulated in a first direction.
Figure 16:
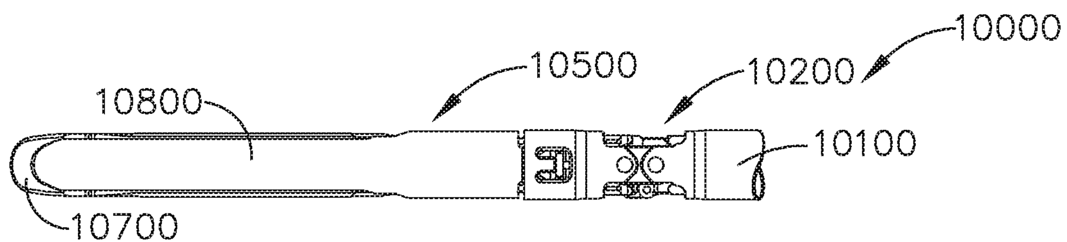
FIG. 16 is a partial plan view of an end effector of a surgical instrument in accordance with at least one embodiment.
Figure 16B:
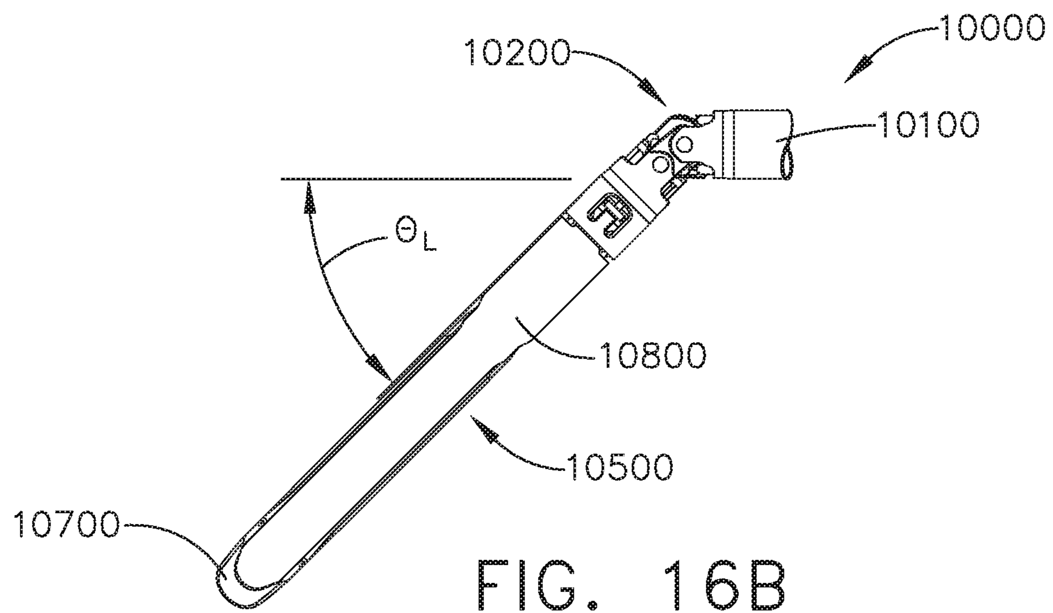
FIG. 16B is a partial plan view of the end effector of FIG. 16 illustrating the end effector articulated in a second direction.

An end effector 10500 of a surgical instrument 10000 is illustrated in FIGS. 16-16B. The end effector 10500 comprises a cartridge jaw 10600 (FIG. 18) including a staple cartridge 10700 and, in addition, an anvil 10800 configured to deform staples ejected from the staple cartridge 10700. In use, the anvil 10800 is rotatable between an open, unclamped position and a closed, clamped position; however, the cartridge jaw 10600 can be rotatable toward the anvil 10800 in other embodiments. The surgical instrument 10000 further comprises a shaft 10100 wherein the end effector 10500 is rotatably connected to the shaft 10100 about an articulation joint 10200. In use, the end effector 10500 is rotatable about the articulation joint 10200 between a fully-articulated right position (FIG. 16A), indicated by angle $\ominus_R$, and a fully-articulated left position (FIG. 16B), indicated by angle $\ominus_L$—and/or any suitable position there between. As discussed in greater detail below, the angles $\ominus_R$ and $\ominus_L$ are limited by the design of the articulation drive system of the surgical instrument 10000. In at least one instance the angles $\ominus_R$ and $\ominus_L$ are limited to approximately 45 degrees with respect to the unarticulated position of the end effector 10500 (FIG. 16).

Figure 18:
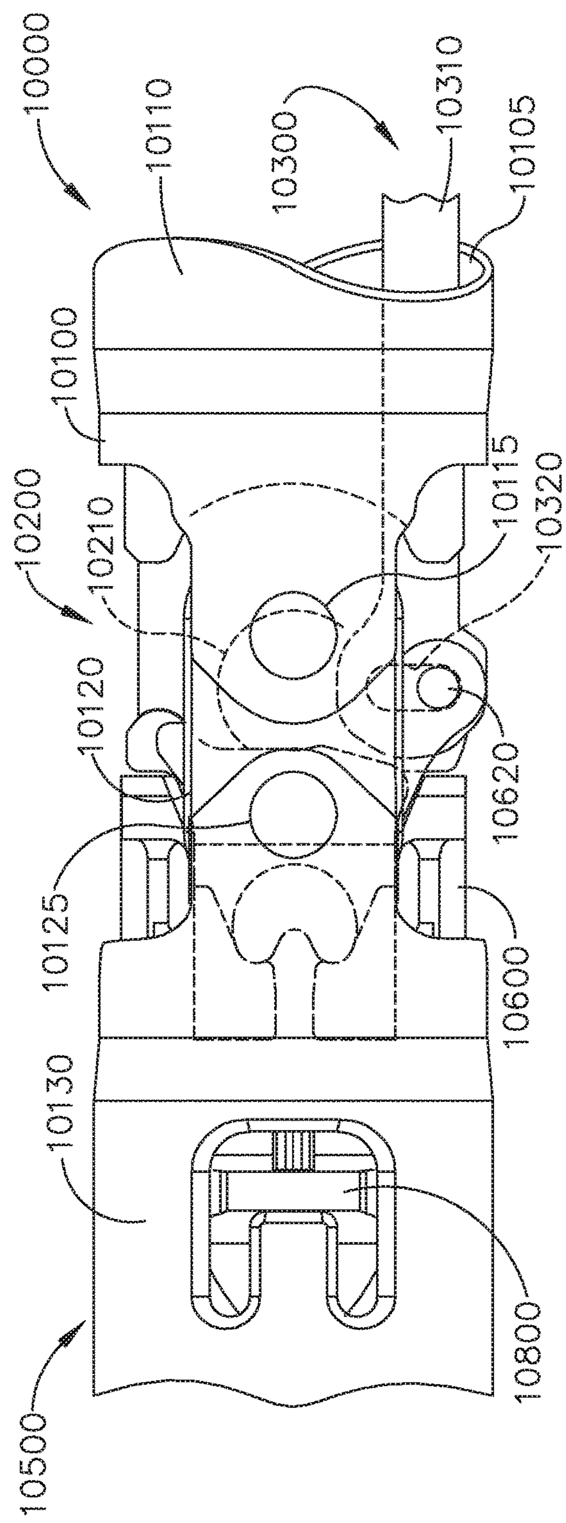
FIG. 18 is a partial plan view of the end effector of FIG. 16.

Referring to FIG. 18, the shaft 10100 of the surgical instrument 10000 comprises an outer closure tube including an outer housing 10110 which is movable distally to engage the anvil 10800 and move the anvil 10800 toward the staple cartridge 10700. The shaft 10100 further comprises a distal housing portion 10130 rotatably connected to the outer housing 10110 by two connector plates 10120 positioned on opposite sides of the articulation joint 10200. Each connector plate 10120 is connected to the outer housing 10110 at a pivot 10115 and, similarly, to the distal housing portion 10130 at a pivot 10125. The connector plates 10120 permit the closure tube to slide relative to the articulation joint 10200 when the end effector 10500 is in an articulated position and, as a result, the anvil 10800 can be opened and closed while the end effector 10500 is in an articulated position. Further to the above, the distal housing 10130 comprises an opening defined therein configured to receive a tab extending from the proximal end of the anvil 10800—a sidewall of which is configured to engage the tab and transfer a proximal, or opening motion, of the closure tube to the anvil 10800.

Figure 17A:
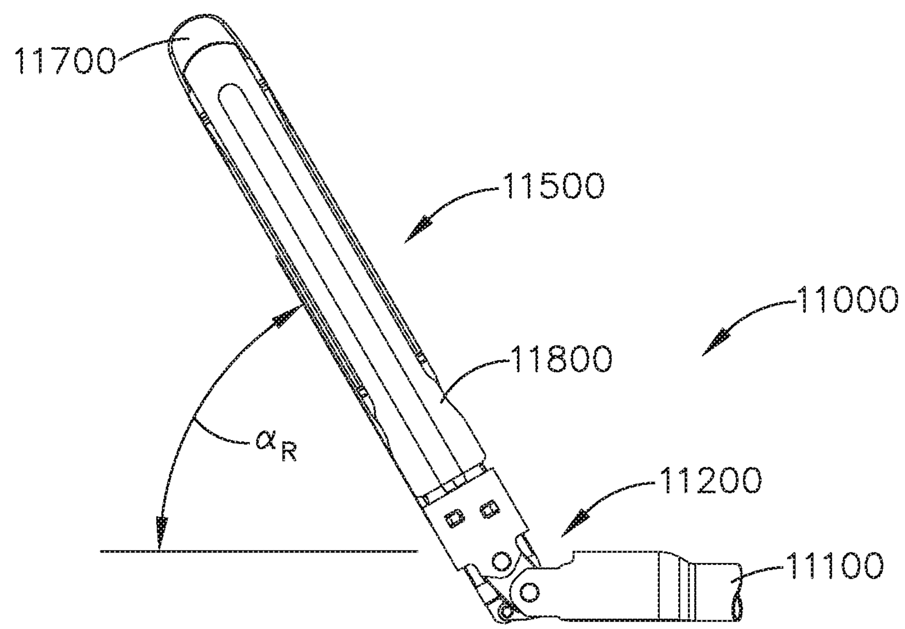
FIG. 17A is a partial plan view of the end effector of FIG. 17 illustrating the end effector articulated in a first direction.
Figure 17:
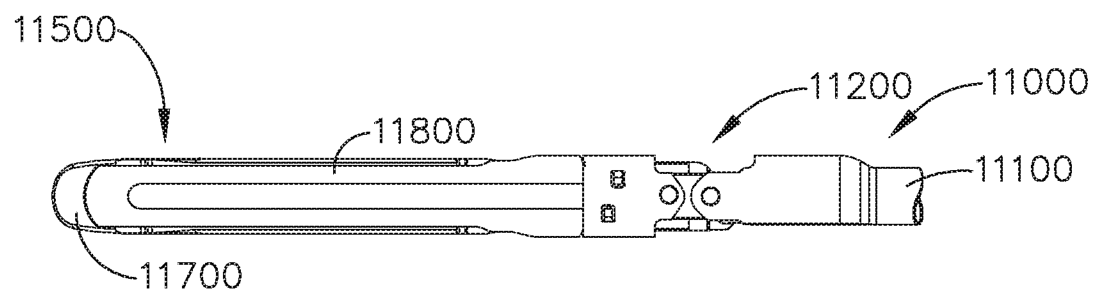
FIG. 17 is a partial plan view of an end effector of a surgical instrument in accordance with at least one embodiment.
Figure 17B:
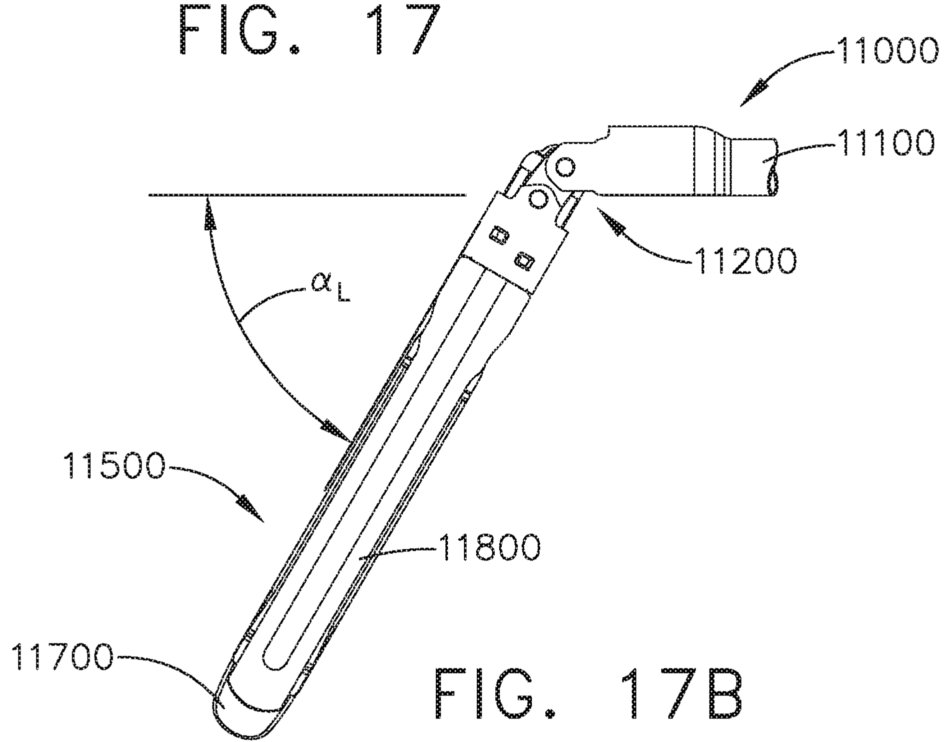
FIG. 17B is a partial plan view of the end effector of FIG. 17 illustrating the end effector articulated in a second direction.

An end effector 11500 of a surgical instrument 11000 is illustrated in FIGS. 17-17B. The end effector 11500 comprises a cartridge jaw 11600 (FIG. 19) including a staple cartridge 11700 and, in addition, an anvil 11800 configured to deform staples ejected from the staple cartridge 11700. In use, the anvil 11800 is rotatable between an open, unclamped position and a closed, clamped position; however, embodiments are envisioned in which the cartridge jaw 11600 is movable relative to the anvil 11800. The surgical instrument 11000 further comprises a shaft 11100 wherein the end effector 11500 is rotatably connected to the shaft 11100 about an articulation joint 11200. In use, the end effector 11500 is rotatable about the articulation joint 11200 between a fully-articulated right position (FIG. 17A), indicated by angle $\alpha_R$, and a fully-articulated left position (FIG. 17B), indicated by angle $\alpha_L$—and/or any suitable position there between. Although the angles $\alpha_R$ and $\alpha_L$ are ultimately limited by the design of the articulation drive system of the surgical instrument 11000, the angles $\alpha_R$ and $\alpha_L$ are larger. In at least one instance the angles $\alpha_R$ and $\alpha_L$ are approximately 60 degrees with respect to the unarticulated position of the end effector 11500 (FIG. 17), for example.

Figure 19:
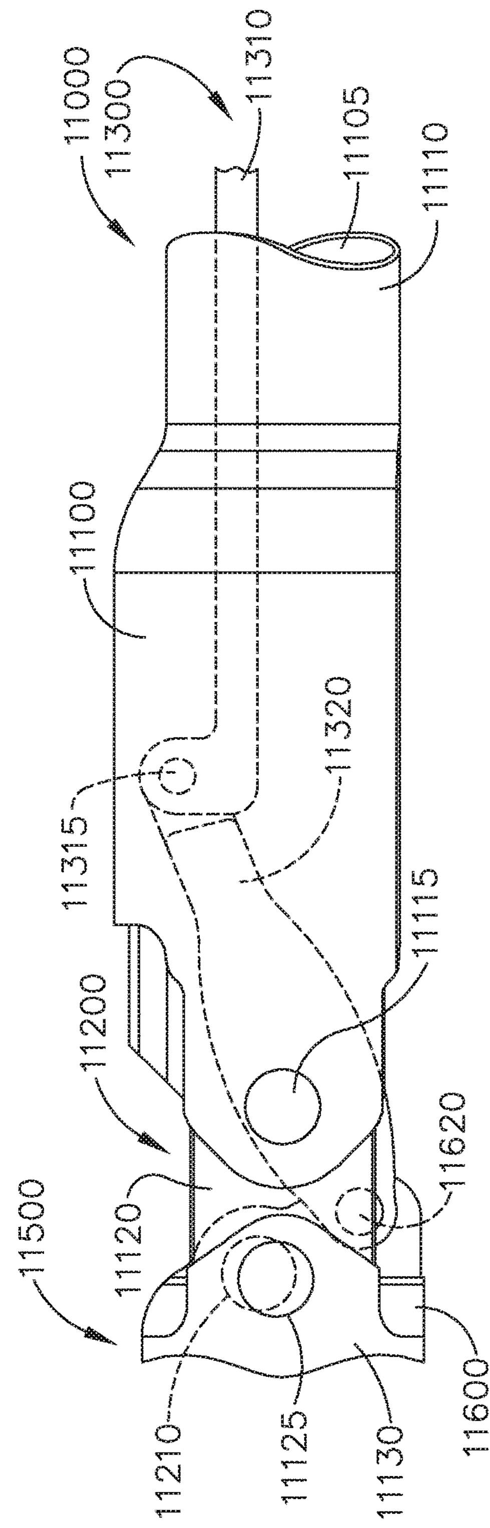
FIG. 19 is a partial plan view of the end effector of FIG. 17.

Referring to FIG. 19, the shaft 11100 of the surgical instrument 11000 comprises an outer closure tube including an outer housing 11110 which is movable distally to engage the anvil 11800 and move the anvil 11800 toward the staple cartridge 11700. The shaft 11100 further comprises a distal housing 11130 rotatably connected to the outer housing 11110 by two connector plates 11120 positioned on opposite sides of the articulation joint 11200. Each connector plate 11120 is connected to the outer housing 11110 at a pivot 11115 and, similarly, to the distal housing 11130 at a pivot 11125. Similar to the above, the connector plates 11120 permit the closure tube to slide relative to the articulation joint 11200 when the end effector 11500 is in an articulated position wherein, as a result, the anvil 11800 can be opened and closed while the end effector 11500 is in an articulated position. Further to the above, the distal housing 11130 comprises an opening defined therein configured to receive a tab extending from the proximal end of the anvil 11800—a sidewall of which is configured to engage the tab and transfer a proximal, or opening, motion of the closure tube to the anvil 11800.

Referring again to FIG. 18, the surgical instrument 10000 further comprises an articulation drive system 10300 including an articulation drive actuator 10310 extending through an interior aperture 10105 defined within the closure tube 10110 of the shaft 10100. The articulation drive actuator 10310 comprises a distal end operably engaged with the cartridge jaw 10600 of the end effector 10500. More specifically, the distal end of the articulation drive actuator 10310 comprises an opening, or slot, 10320 defined therein and the cartridge jaw 10600 comprises a pin 10620 extending into the slot 10320. When the articulation drive actuator 10310 is pushed distally, the end effector 10500 is driven to the right (FIG. 16A) about a fixed axis defined by a pivot 10210 which rotatably connects the cartridge jaw 10600 to a frame of the shaft 10100. Correspondingly, the end effector 10500 is rotated to the left (FIG. 16B) about the pivot 10210 when the articulation drive actuator 10310 is pulled proximally.

Referring again to FIG. 19, the surgical instrument 11000 further comprises an articulation drive system 11300 including an articulation drive actuator 11310 extending through an interior aperture 11105 defined within the closure tube 11110. The articulation drive system 11300 further comprises an articulation link 11320 rotatably coupled to a distal end of the articulation drive actuator 11310 about a pin 11315. Similarly, the articulation link 11320 is rotatably coupled to the cartridge jaw 11600 about a drive pin 11620 which extends through an aperture defined in the articulation link 11320. When the articulation drive actuator 11310 is pushed distally, the end effector 11500 is driven to the right (FIG. 17A) about a fixed axis defined by a pivot 11210 which rotatably connects the cartridge jaw 11600 to a frame of the shaft 11100. Correspondingly, the end effector 11500 is rotated to the left (FIG. 17B) about the pivot 11210 when the articulation drive actuator 11310 is pulled proximally.

Figure 21:
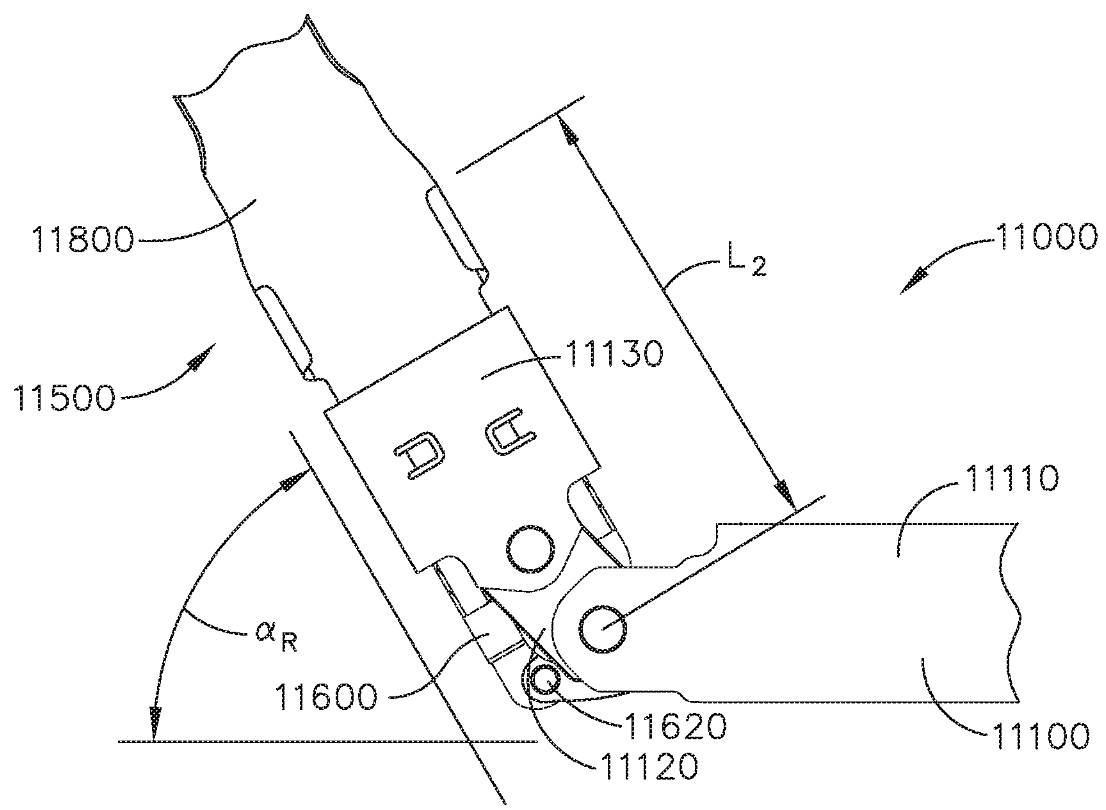
FIG. 21 is a partial plan view of the end effector of FIG. 17 in an articulated position.
Figure 20:
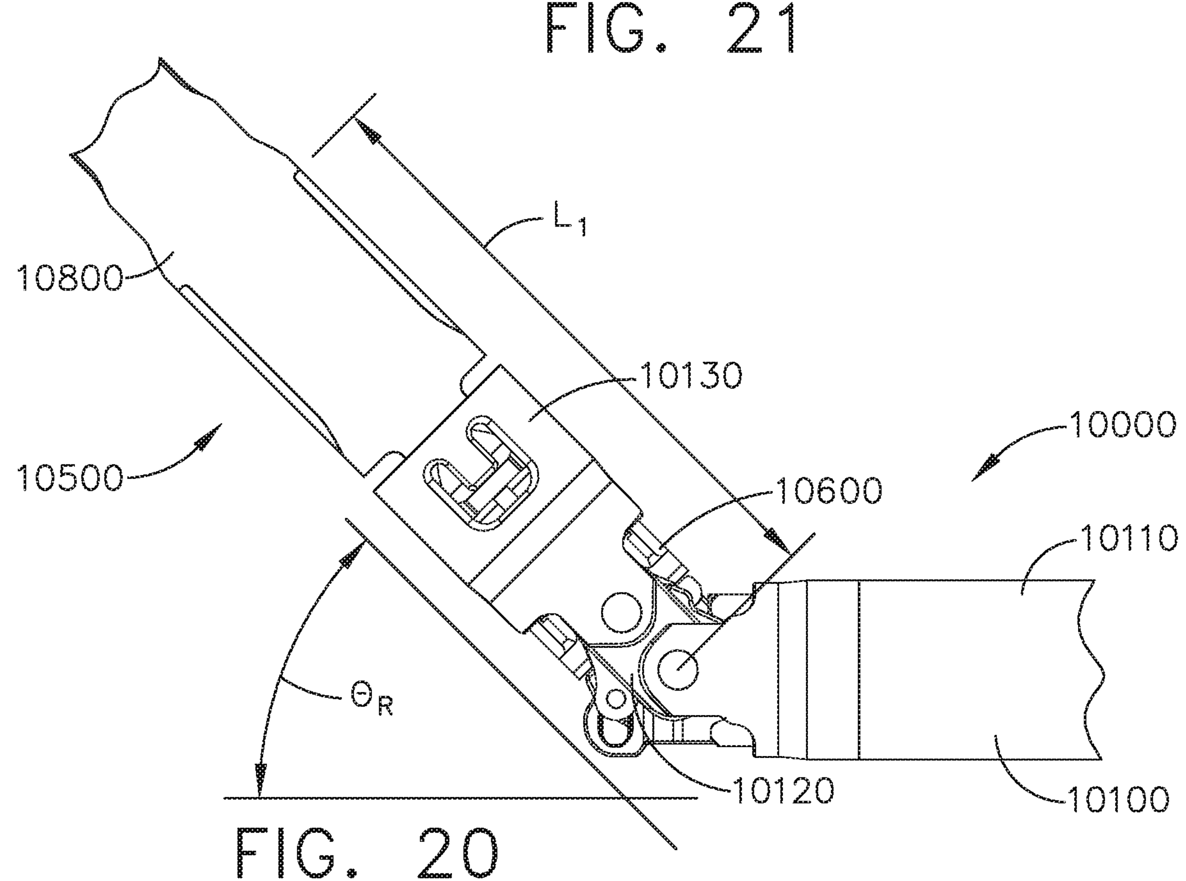
FIG. 20 is a partial plan view of the end effector of FIG. 16 in an articulated position.
Figure 22:
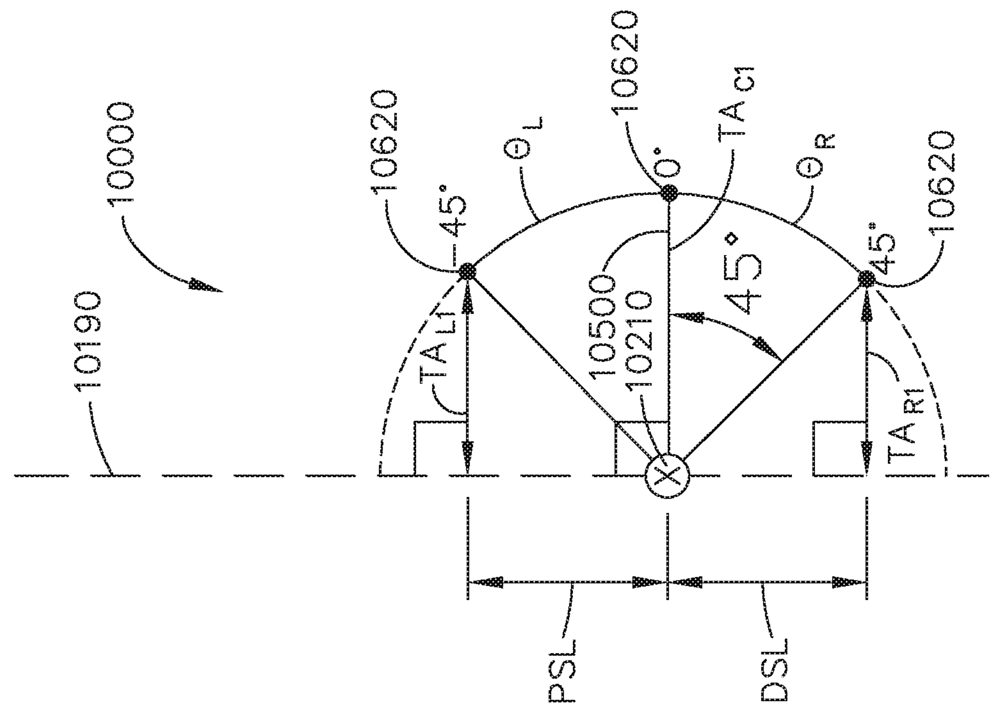
FIG. 22 is a schematic illustrating an articulation range of the end effector of FIG. 16.
Figure 23:
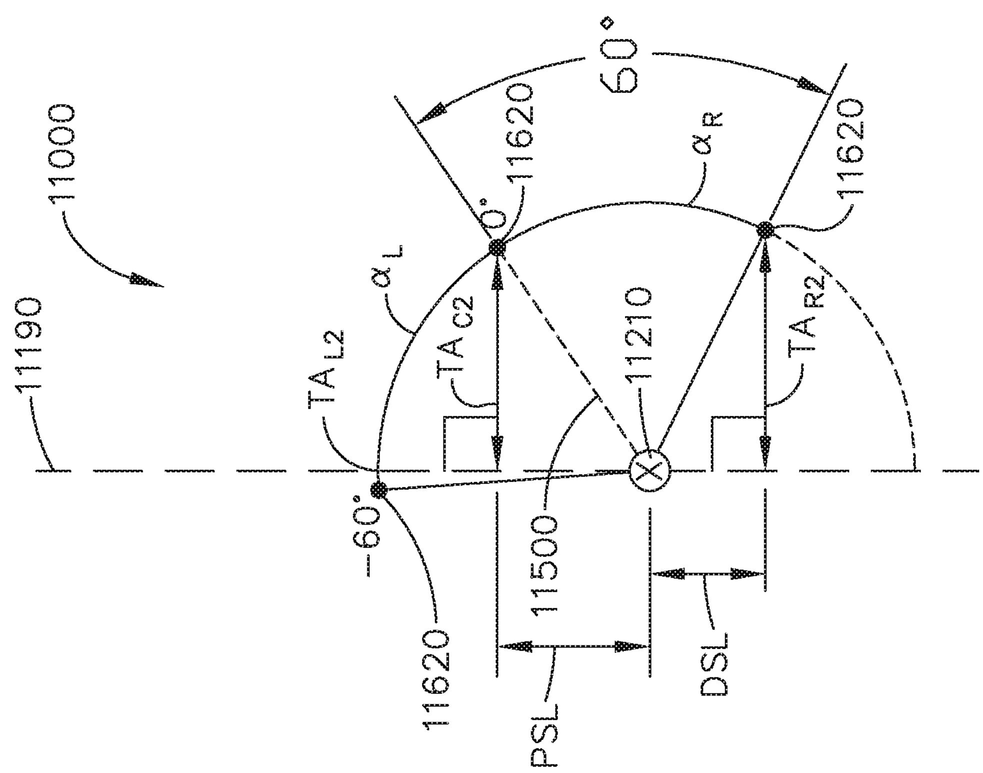
FIG. 23 is a schematic illustrating an articulation range of the end effector of FIG. 17.

Further to the above, the articulation link 11320 of the articulation system 11300 allows the end effector 11500 to be articulated through a larger range of articulation angles than the end effector 10500 for a given, or equal, stroke length of the articulation actuators 10310 and 11310. A side-by-side comparison of the end effectors 10500 and 11500 is provided in FIGS. 20 and 21 illustrating the end effectors 10500 and 11500 in their fully right-articulated configurations—and also illustrating that the end effector 11500 can be articulated further to the right than the end effector 10500. A similar comparison can be made showing the end effectors 10500 and 11500 in their fully left-articulated configurations. Moreover, FIG. 22 depicts the full articulation range of the end effector 10500 while FIG. 23 depicts the full articulation range of the end effector 11500.

Figure 31:
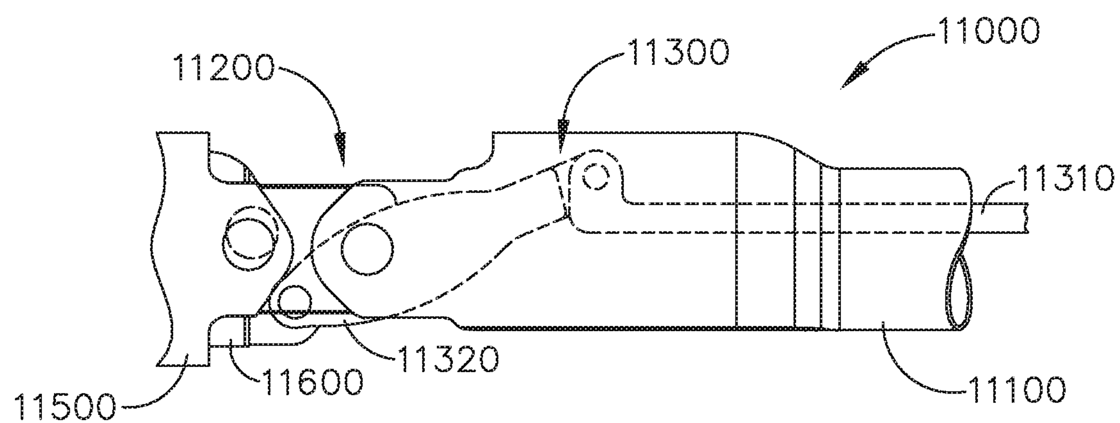
FIG. 31 is a partial plan view of the end effector of FIG. 17 illustrated in an unarticulated configuration.
Figure 31A:
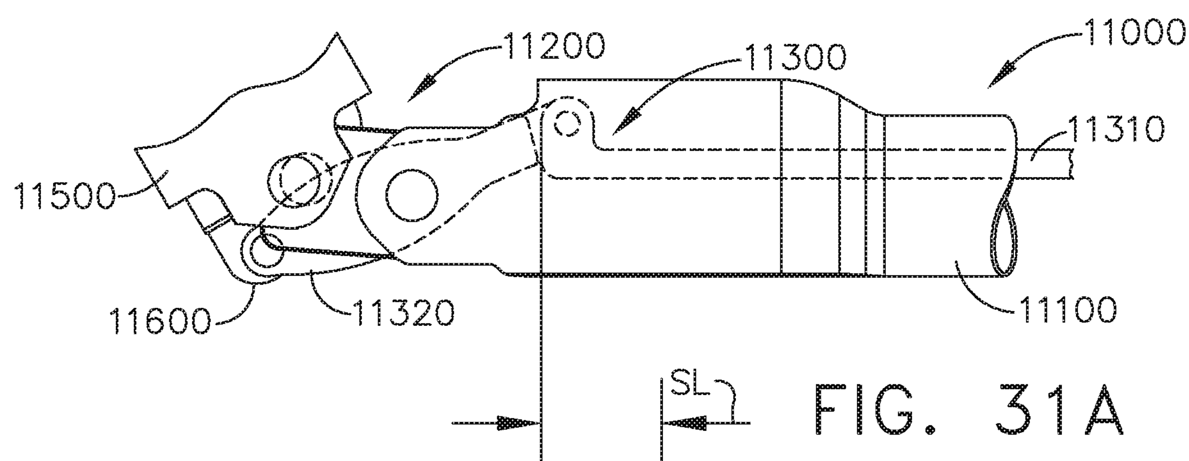
FIG. 31A is a partial plan view of the end effector of FIG. 17 illustrated in a fully-right articulated configuration.
Figure 31B:
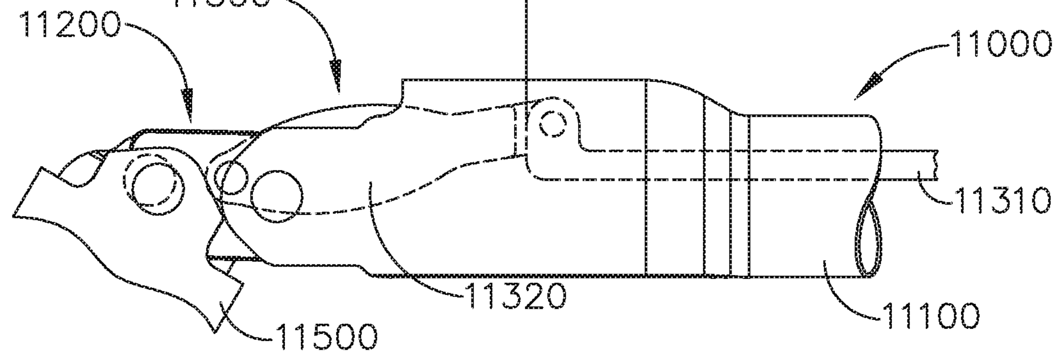
FIG. 31B is a partial plan view of the end effector of FIG. 17 illustrated in a fully-left articulated configuration.
Figure 32:
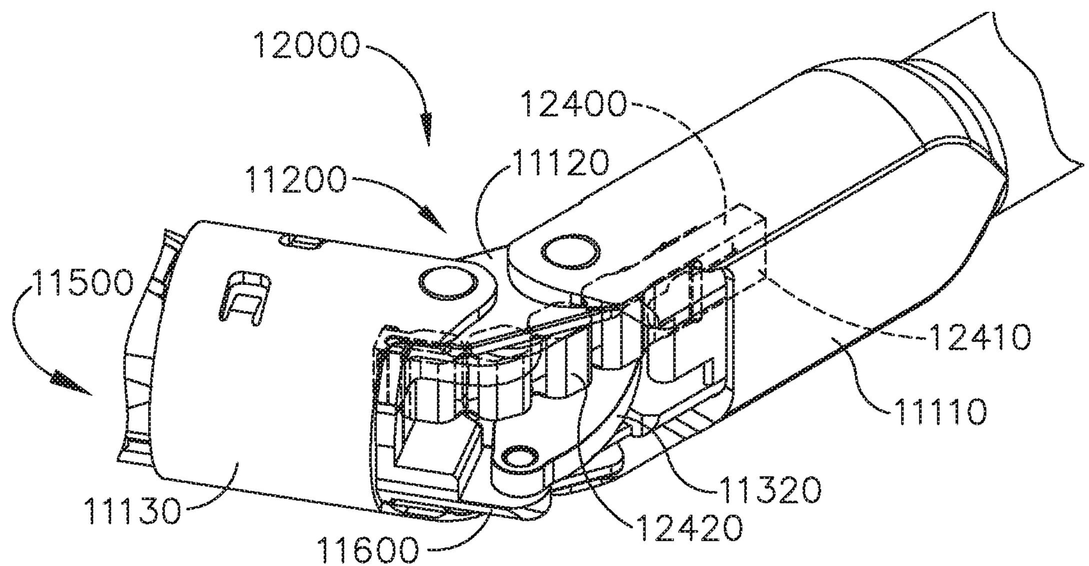
FIG. 32 is a partial perspective view of an end effector in accordance with at least one embodiment.
Figure 33:
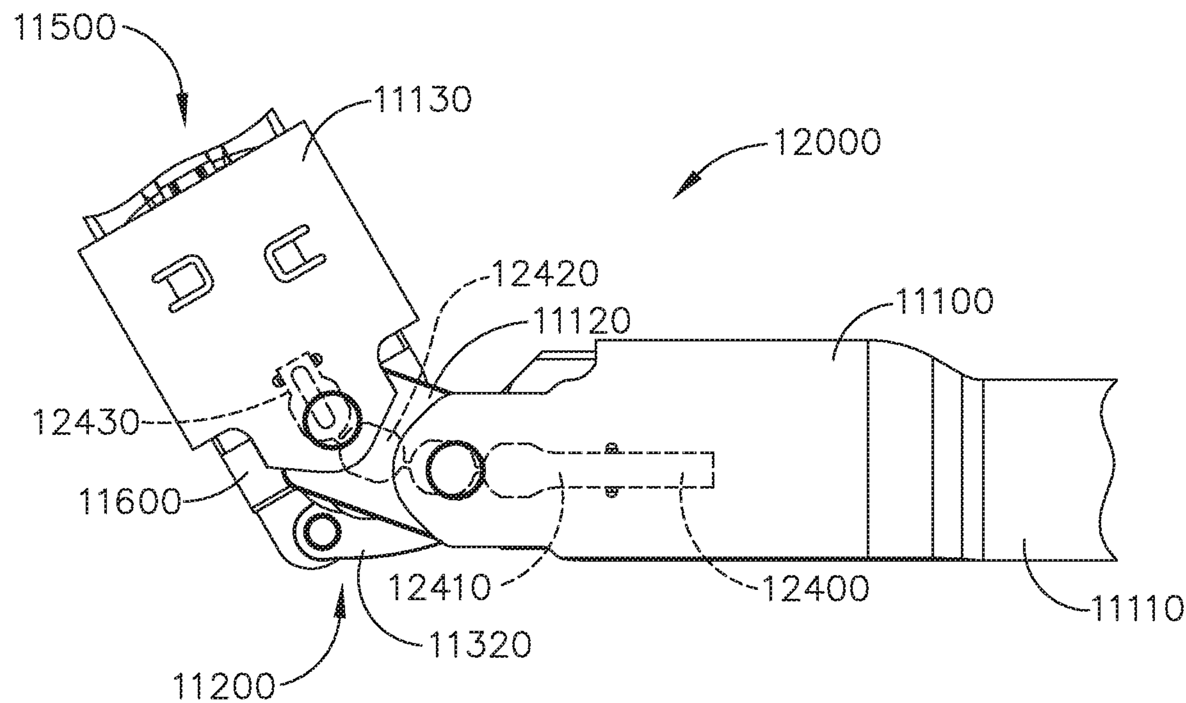
FIG. 33 is a partial plan view of the end effector of FIG. 32.

Referring again to FIG. 22, the articulation actuator 10310 of the surgical instrument 10000 is advanced a distal stroke length (DSL) with respect to its unarticulated position to fully articulate the end effector 10500 to the right. Correspondingly, the articulation actuator 10310 is retracted a proximal stroke length (PSL) with respect to its unarticulated position to fully articulate the end effector 10500 to the left. The distal stroke length (DSL) and the proximal stroke length (PSL) of the articulation actuator 10310 are equal, or at least substantially equal. Referring now to FIG. 23, the articulation actuator 11310 is advanced a distal stroke length (DSL) with respect to its unarticulated position to fully articulate the end effector 11500 to the right. Correspondingly, the articulation actuator 11310 is retracted a proximal stroke length (PSL) with respect to its unarticulated position to fully articulate the end effector 11500 to the left. The distal stroke length (DSL) and the proximal stroke length (PSL) of the articulation actuator 11310 are not equal—instead, the distal stroke length (DSL) is shorter than the proximal stroke length (PSL). In other embodiments, the proximal stroke length (DSL) is shorter than the distal stroke length (PSL). In any event, referring now to FIGS. 31-31B, the combination of the proximal stroke length (PSL) and the distal stroke length (DSL) equals the entire stroke length (SL).

Further to the above, the articulation actuator 10310 is configured to apply a torque to the first jaw 10600 of the end effector 10500 via the pin 10620 to rotate the end effector 10500 about the articulation joint 10200. Referring again to FIG. 22, a lateral torque arm defined between the pivot joint 10210 of the articulation joint 10200 and the pin 10620 has a length $TA_{C1}$ when the end effector 10500 is in its unarticulated position. The length $TA_{C1}$ is measured in an orthogonal direction with respect to a longitudinal axis 10190 extending through the articulation pivot joint 10210. Similarly, the lateral torque arm defined between the pivot joint 10210 and the pin 10620 has a length $TA_{R1}$ when the end effector 10500 is fully articulated to the right and, similarly, a length $TA_{L1}$ when the end effector 10500 is fully articulated to the left—both lengths of which are measured orthogonally with respect to the longitudinal axis 10190. Notably, the lengths $TA_{R1}$ and $TA_{L1}$, and the torque arms which they define, are equal, or at least substantially equal. Moreover, the lengths $TA_{R1}$ and $TA_{L1}$ are less than the unarticulated lateral torque arm length $TA_{C1}$. Thus, the largest torque arm, or mechanical advantage, of the articulation system 10300 exists when the end effector 10500 is in its unarticulated position.

In at least one instance, the arm length $TA_{C1}$ is approximately 0.180", the arm length $TA_{R1}$ is approximately 0.130", and the arm length $TA_{L1}$ is approximately 0.130", for example.

Figure 28:
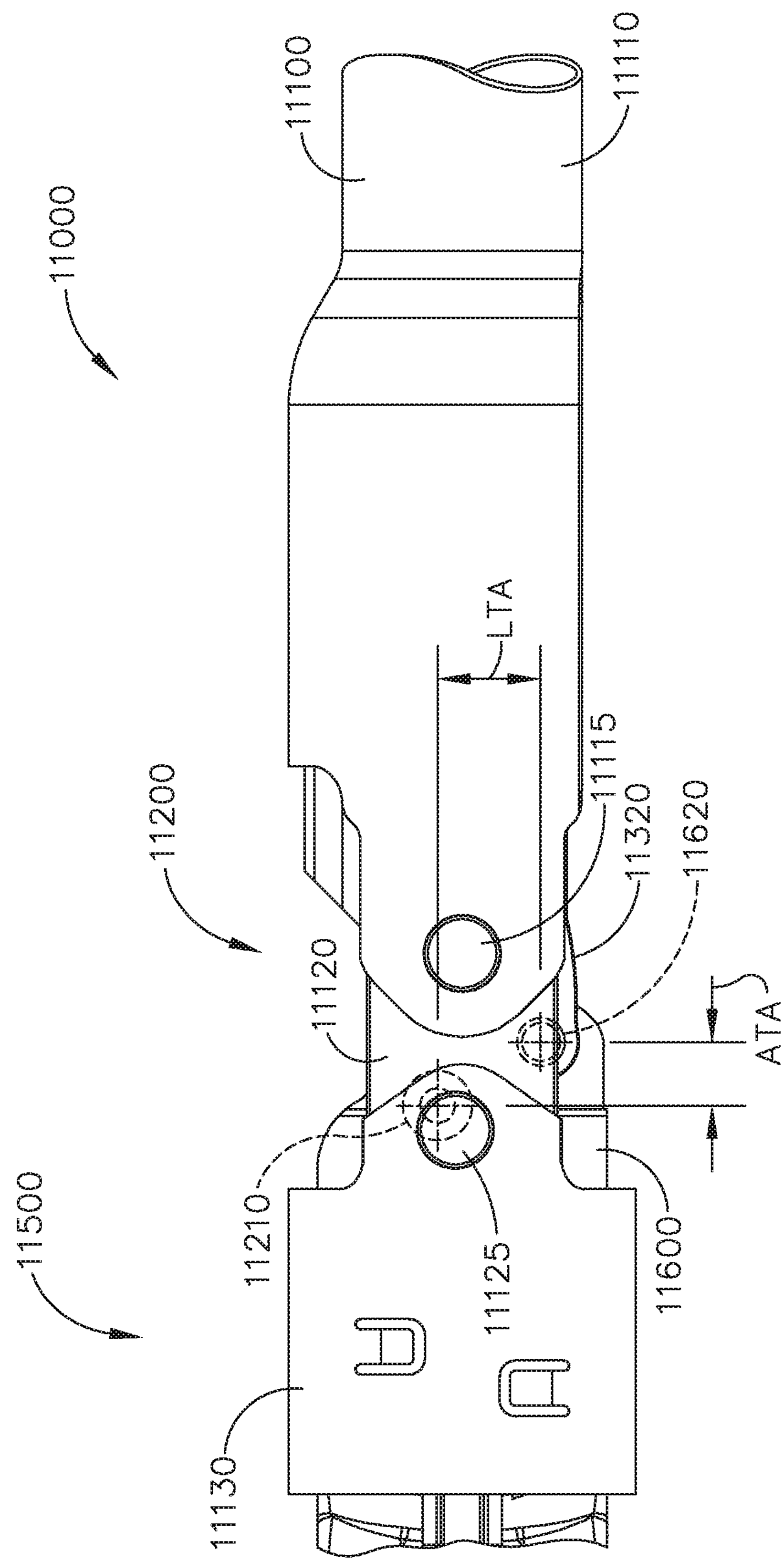
FIG. 28 is a partial plan view of the end effector of FIG. 17 illustrated in an unarticulated configuration.
Figure 29:
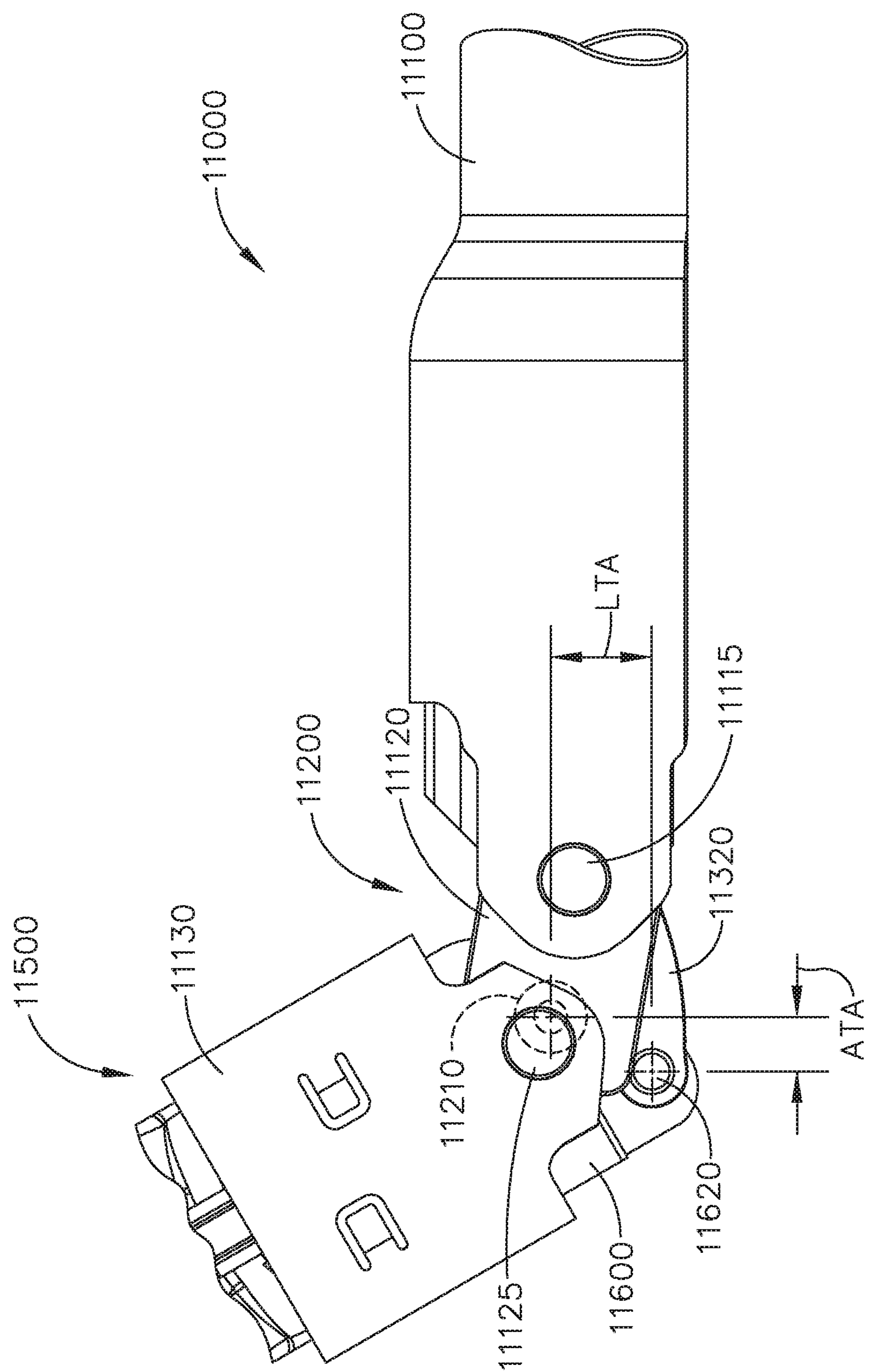
FIG. 29 is a partial plan view of the end effector of FIG. 17 illustrated in an articulated configuration.
Figure 30A:
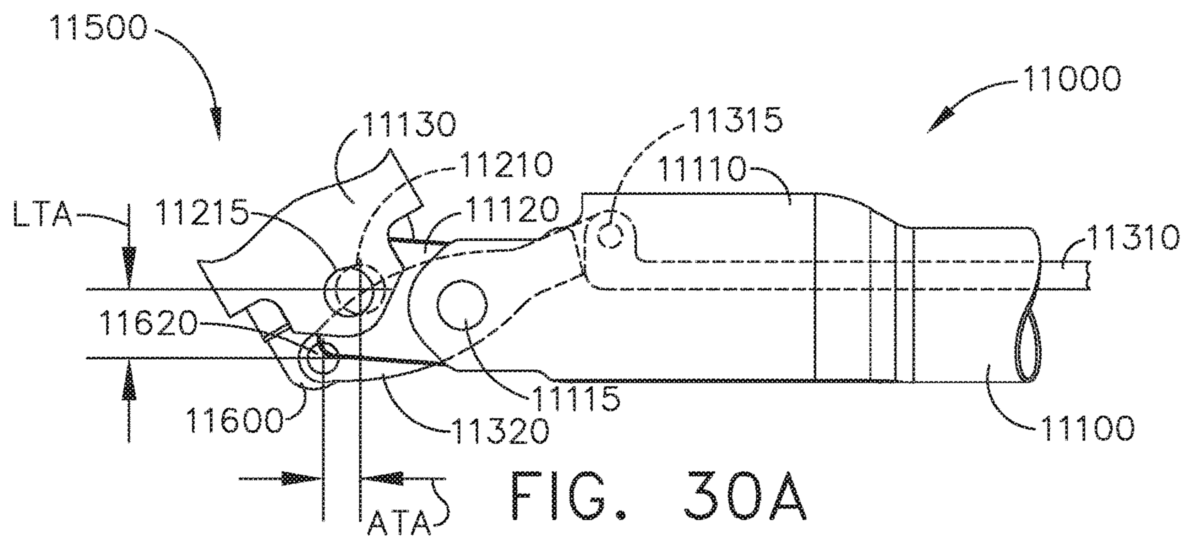
FIG. 30A is a partial plan view of the end effector of FIG. 17 illustrated in a fully-right articulated configuration.
Figure 30:
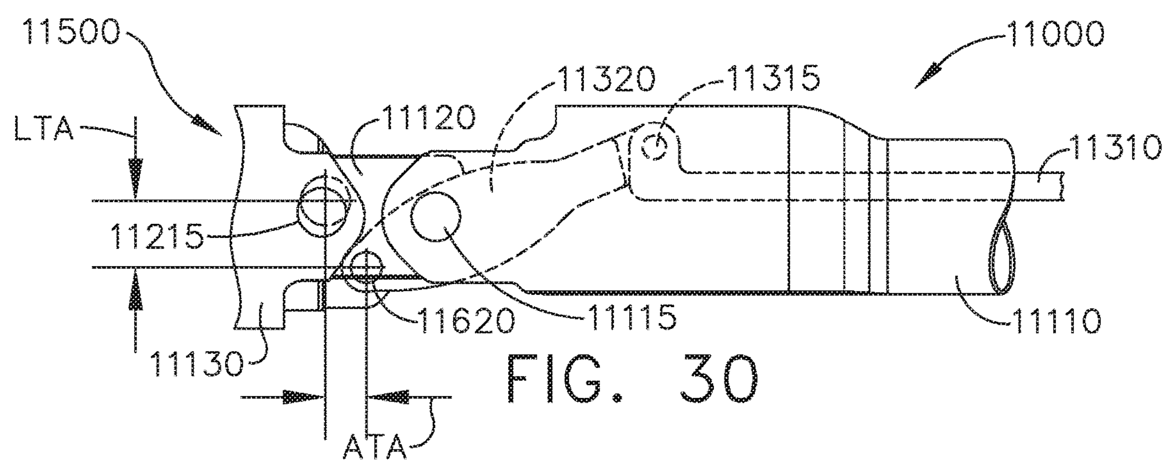
FIG. 30 is a partial plan view of the end effector of FIG. 17 illustrated in an unarticulated configuration.
Figure 30B:
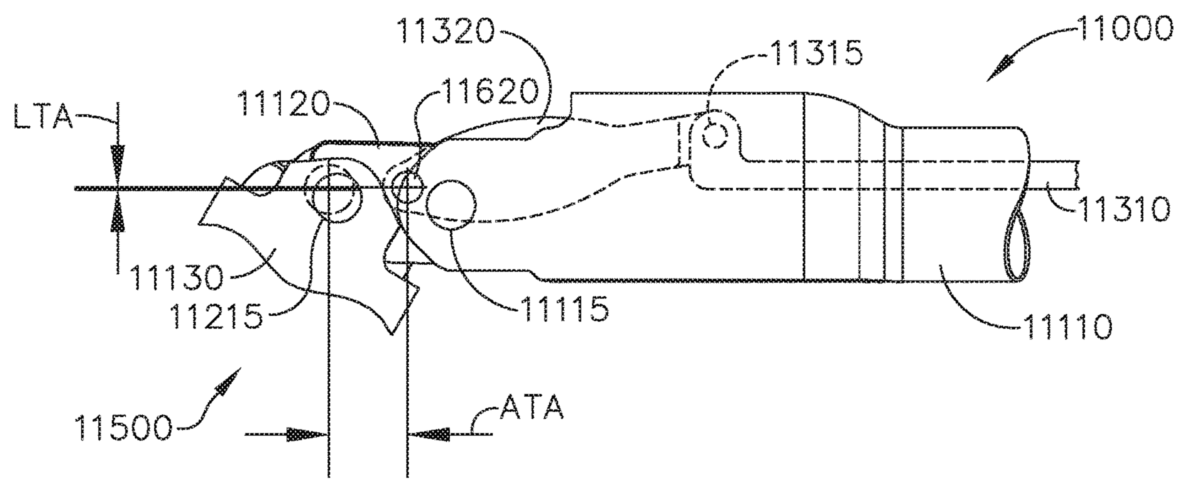
FIG. 30B is a partial plan view of the end effector of FIG. 17 illustrated in a fully-left articulated configuration.

Further to the above, the articulation actuator 11310 of the surgical instrument 11000 is configured to apply a torque to the first jaw 11600 of the end effector 11500 via the pin 11620 to rotate the end effector 11500 about the articulation joint 11200. Referring to FIGS. 23, 28, and 30, a lateral torque arm (LTA) defined between the pivot joint 11210 of the articulation joint 11200 and the pin 11620 is defined by a length $TA_{C2}$ when the end effector 11500 is in its unarticulated position. The length $TA_{C2}$ is measured in an orthogonal direction with respect to a longitudinal axis 11190 extending through the articulation pivot joint 11210. Notably, the longitudinal axis 11190 is offset and parallel with respect to the centerline of the shaft 11100, as discussed in greater detail below in connection with FIG. 25. Similar to the above, the lateral torque arm defined between the pivot joint 11210 and the pin 11620 is defined by a length $TA_{R2}$ when the end effector 11500 is fully articulated to the right (FIG. 30A) and, similarly, a length $TA_{L2}$ when the end effector 11500 is fully articulated to the left (FIG. 30B)—both lengths of which are measured orthogonally with respect to the longitudinal axis 11190. Notably, the length $TA_{R2}$ is larger than the unarticulated lateral torque arm length $TA_{C1}$ and the length $TA_{L2}$ is shorter than the unarticulated lateral torque arm length $TA_{C1}$. Moreover, the lengths $TA_{R2}$ and $TA_{L2}$, and the torque arms which they define, are not equal. Instead, the right-articulated torque arm length $TA_{R2}$ is considerably larger than the left-articulated torque arm length $TA_{L2}$. In fact, the right-articulated torque arm length $TA_{R2}$ and the left-articulated torque arm length $TA_{L2}$ extend in different directions. Such an arrangement provides for a larger pushing torque arm as compared to a smaller pulling torque arm. In various instances, as a result, the retraction pulling force applied by the articulation actuator 11310 to articulate the end effector 11500 to the left (FIG. 30B) may be, or may need to be, larger than the distal pushing force to articulate the end effector 11500 to the right (FIGS. 29 and 30A). Advantageously, the articulation actuator 11310 can accommodate such a larger pulling force as the articulation actuator 11310 is not subject to buckling failure when being pulled.

In at least one instance, the arm length $TA_{C2}$ is approximately 0.149", the arm length $TA_{R2}$ is approximately 0.154", and the arm length $TA_{L2}$ is approximately 0.015", for example.

Further to the above, the surgical instrument 11000 is configured and arranged to provide a large torque to the end effector 11500 while, at the same time, providing a large articulation range, or sweep, in response to a short articulation stroke. To wit, several design ratios for these relationships can be established and used to design the surgical instrument 11000. For instance, a first ratio comprises the fully-right articulated torque arm length (TA) divided by the full articulation stroke length (SL) of the articulation actuator 11310. The value of this first ratio is unitless. In at least one instance, the fully-right articulated torque arm length (TA) is 0.154" and the full articulation stroke length (SL) is 0.275", resulting in a ratio value of 0.56, for example. Larger ratio values for the first ratio indicate more efficient articulation systems. In various instances, the value for the first ratio is less than 1.0, but can be more than 1.0. In at least one instance, the fully-right articulated torque arm length (TA) is 2.79 mm and the full articulation stroke length (SL) is 11.43 mm, resulting in a ratio value of 0.24, for example.

The examples provided above for the first ratio were based on the torque arm length (TA) when the end effector 11500 is in its fully-right articulated position. This particular position of the end effector 11500 is notable because the articulation actuator 11310 is in compression and can undergo buckling when the load transmitted there through is excessive. That said, the first ratio could also be used to analyze any suitable position of the end effector 11500 such as its unarticulated position and its fully-left articulated position, for example. In at least one instance, the unarticulated torque arm length (TA) is 6.17 mm, resulting in a ratio value of 0.54 for a stroke length (SL) of 11.43 mm, for example. Also, in at least one instance, the fully-left articulated torque arm length (TA) is 1.41 mm, resulting in a ratio value of 0.12 for a stroke length (SL) of 11.43 mm, for example.

A second ratio includes the arc length in which the drive pin 11620 is swept through when the end effector 11500 is articulated between its fully-right articulated position and its fully-left articulated position, i.e., its arc length sweep (ALS). More specifically, the second ratio comprises the arc length sweep (ALS) of the drive pin 11620 divided by the full articulation stroke length (SL) of the articulation actuator 11310. The value of this second ratio is unitless. In at least one instance, the arc length sweep (ALS) of the drive pin 11620 is 0.387" and the full articulation stroke length (SL) is 0.275", resulting in a ratio value of 1.41, for example. In at least one instance, the arc length sweep (ALS) is 0.444" and the full articulation stroke length (SL) is 0.306", resulting in a ratio value of 1.45, for example. In at least one instance, the arc length sweep (ALS) is 12.94 mm and the full articulation stroke length (SL) is 11.43 mm, resulting in a ratio value of 1.13, for example. Larger ratio values for the second ratio indicate more efficient articulation systems. In various instances, the value for the second ratio is more than 1.0, such as between 1.0 and 3.0, for example. In at least one instance, the second ratio value is approximately 2.0, for example. In certain instances, the value for the second ratio is about 1.1, but between 0.9 and 1.3, for example.

A third ratio comprises the sum of the fully-right articulated torque arm length (TA) and the arc length sweep (ALS) of the drive pin 11620 divided by the full articulation stroke length (SL). The value of this third ratio is unitless. In at least one instance, the fully-right articulated torque arm length (TA) is 0.154", the arc length sweep (ALS) of the drive pin 11620 is 0.387", and the full articulation stroke length (SL) is 0.275", resulting in a ratio value of 1.97, for example. In at least one instance, the fully-right articulated torque arm length (TA) is 2.79 mm, the arc length sweep (ALS) of the drive pin 11620 is 12.94 mm, and the full articulation stroke length (SL) is 11.43 mm, resulting in a ratio value of 1.38, for example. Larger ratio values for the third ratio indicate more efficient articulation systems. In various instances, the value for the third ratio is more than 1.0, such as between 1.0 and 3.0, for example. In at least one instance, the third ratio value is approximately 2.0 or more than 2.0, for example.

Similar to the above, the third ratio could be used to evaluate the articulation system when the end effector 11500 is in any suitable position, such as its unarticulated and fully-left articulated positions, for example.

A fourth ratio comprises the product of the fully-right articulated torque arm length (TA) and the arc length sweep (ALS) of the drive pin 11620 divided by the full articulation stroke length (SL). The value of this fourth ratio is not unitless and is, instead, measured in distance. In at least one instance, the fully-right articulated torque arm length (TA) is 0.154", the arc length sweep (ALS) of the drive pin 11620 is 0.387", and the full articulation stroke length (SL) is 0.275", resulting in a ratio value of 0.217", for example. This value can be made unitless by dividing it by the stroke length (SL) once again resulting in a value of 0.79. In at least one instance, the fully-right articulated torque arm length (TA) is 2.79 mm, the arc length sweep (ALS) of the drive pin 11620 is 12.94 mm, and the full articulation stroke length (SL) is 11.43 mm, resulting in a ratio value of 3.15 mm, for example. In certain instances, the value for the fourth ratio is about 3.1 mm, but between 0.9 mm and 5.4 mm, for example. Similar to the above, this value can be made unitless by dividing it by the stroke length (SL) once again resulting in a value of 0.28. Larger ratio values for the fourth ratio indicate more efficient articulation systems.

Similar to the above, the fourth ratio could be used to evaluate the articulation system when the end effector 11500 is in any suitable position, such as its unarticulated and fully-left articulated positions, for example.

Figure 24:
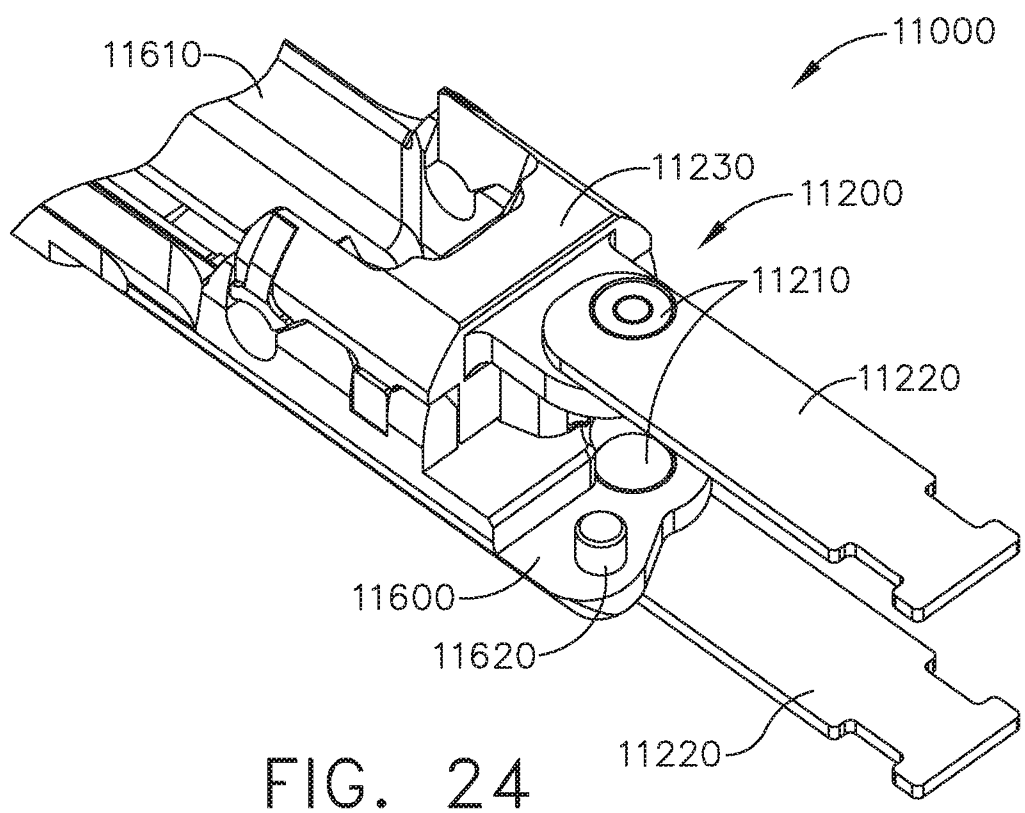
FIG. 24 is a partial perspective view of the end effector of FIG. 17 illustrated with some components removed.
Figure 25:
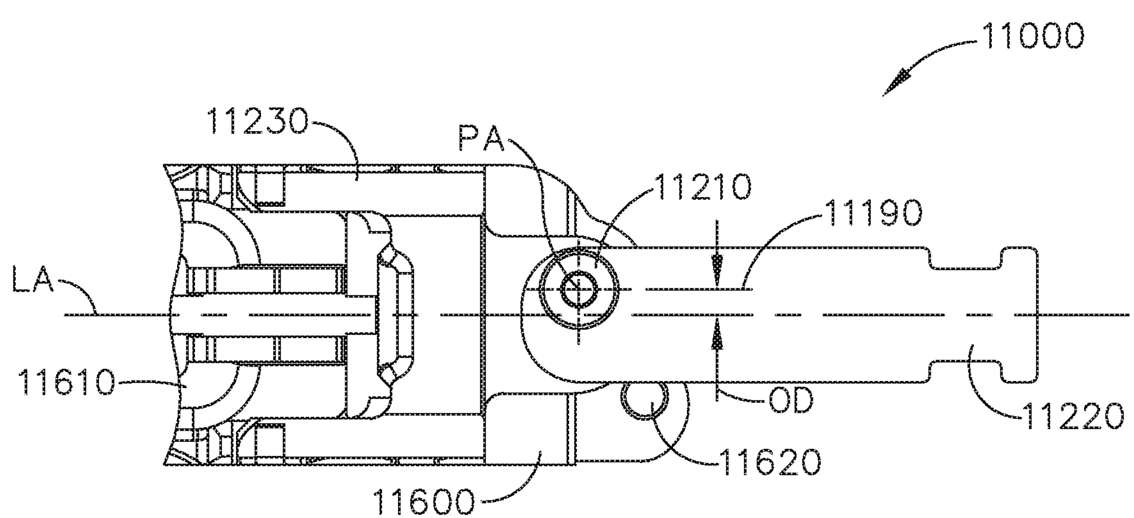
FIG. 25 is a partial plan view of the end effector of FIG. 17 illustrated with some components removed.

As discussed above, the end effector 11500 is rotatably mounted to the shaft 11100 about a fixed pivot 11210 of the articulation joint 11200. Referring now to FIGS. 24 and 25, the shaft 11100 comprises distal mounting tabs 11220 which extend from and are fixedly mounted to the frame, or spine, of the shaft 11100. A first distal mounting tab 11220 is mounted to the first jaw 11600, which comprises a lower frame portion, and a second distal mounting tab 11220 is mounted to an upper frame portion 11230. The interconnection between the mounting tabs 11220 and the first jaw 11600 and upper frame portion 11230 defines the fixed pivot 11210. As also discussed above, the fixed axis pivot 11210 is laterally offset with respect to a central longitudinal axis LA of the shaft 11100 by an offset distance OD. In at least one instance, the fixed axis pivot 11210 is laterally offset by approximately 0.036", for example. Moreover, referring to FIGS. 28-30B, the pin 11620 is longitudinally offset with respect to the fixed pivot 11210 which creates a longitudinal, or axial, torque arm (ATA).

Figure 26A:
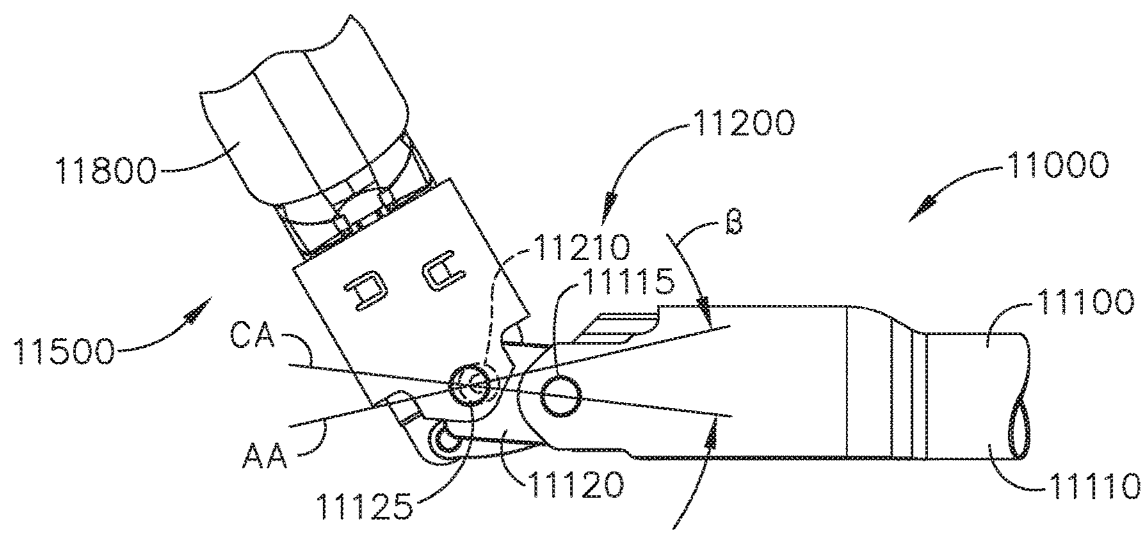
FIG. 26A is a partial plan view of the end effector of FIG. 17 illustrated in an open, fully-right articulated configuration.

As discussed above, the closure tube of the shaft 11100 is movable distally to engage the anvil jaw 11800 of the end effector 11500 and move the anvil jaw 11800 toward a staple cartridge 11700 positioned in the cartridge jaw 11600. Stated another way, the closure tube is configured to move the anvil 11800 from an open position (FIGS. 26-26B) to a closed position (FIGS. 27-27B) to clamp the tissue of a patient against the staple cartridge 11700. In such instances, the closure tube, comprising the housing 11110, the connector plates 11120, and the distal housing 11130, are slid distally with respect to the articulation joint 11200 during a closure stroke. When the end effector 11500 is in an open, unarticulated configuration, referring now to FIG. 26, the connector plates 11120 extend in a direction which is slightly transverse to the central longitudinal axis LA of the shaft 11100. More specifically, an axis CA extending between the joints 11115 and 11125 is slightly transverse with respect to the central longitudinal axis LA of the shaft 11100 when the end effector 11500 is in an open, unarticulated configuration. When the end effector 11500 is articulated relative to the right (FIG. 26A) or the right (FIG. 26B), the orientation of the axis CA relative to the central longitudinal axis LA can change.

In various instances, further to the above, the orientation of the axis CA will change relative to a longitudinal axis extending between the proximal end and the distal end of the end effector 11500. In at least one instance, the axis CA is transverse to such a longitudinal end effector axis except in one configuration in which the axis CA will be parallel to the longitudinal end effector axis.

Figure 26:
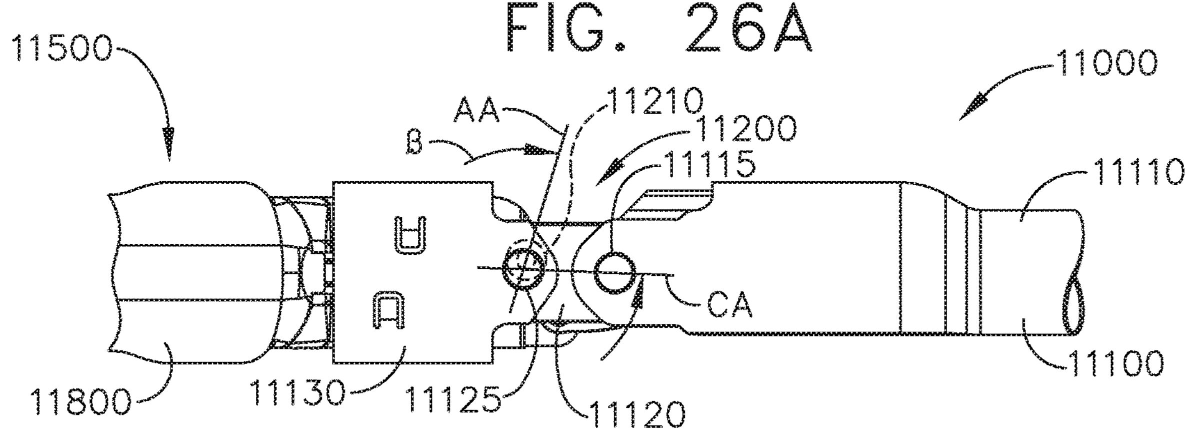
FIG. 26 is a partial plan view of the end effector of FIG. 17 illustrated in an open, unarticulated configuration.
Figure 26B:
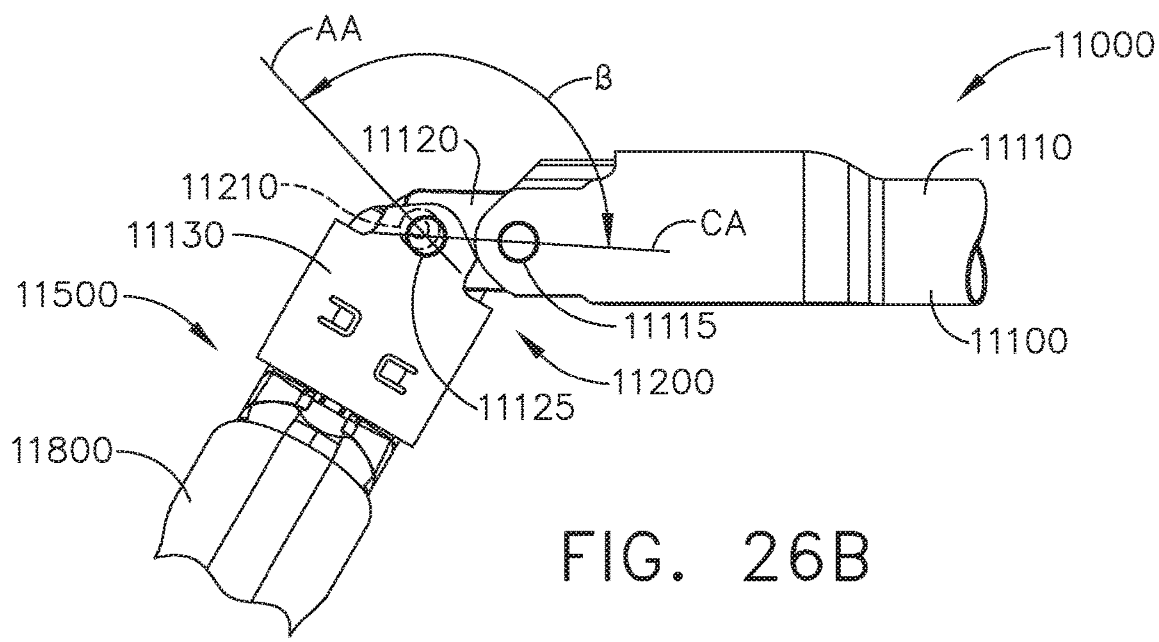
FIG. 26B is a partial plan view of the end effector of FIG. 17 illustrated in an open, fully-left articulated configuration.

Further to the above, the orientation of an axis AA defined between the articulation pivot 11210 and the distal pivot 11125 of the connector plates 11120 changes as the end effector 11500 is articulated. Referring to FIG. 26, the axis AA extends at an angle β with respect to the axis CA when the end effector 11500 is in an open, unarticulated configuration. When the end effector 11500 is articulated into an open, right configuration (FIG. 26A), the angle β decreases. When the end effector 11500 is articulated into an open, left configuration (FIG. 26B), the angle β increases. At no point, however, is the axis AA collinear with or parallel to the axis CA when the open end effector 11500 is articulated. Instead, the axis AA is transverse to the axis CA when the end effector 11500 is articulated in an open configuration.

Figure 27A:
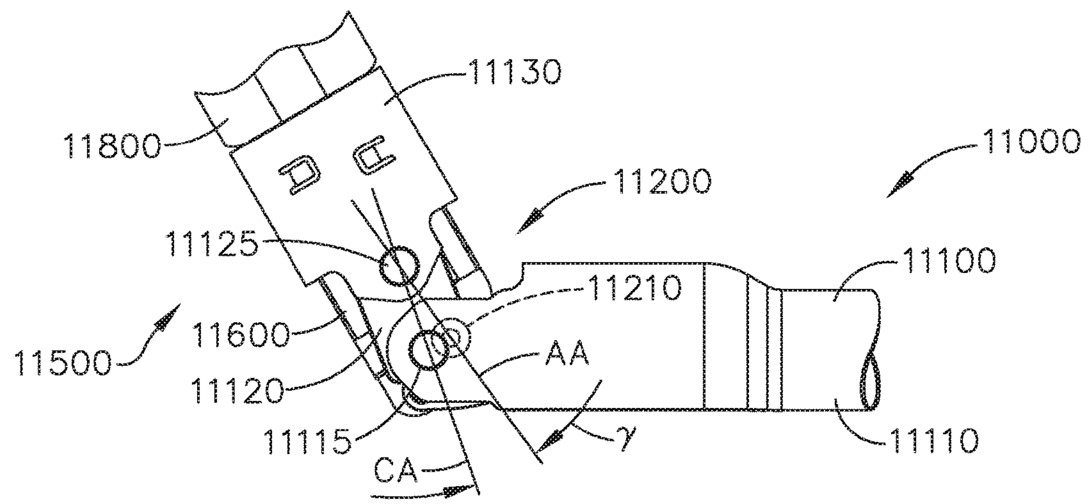
FIG. 27A is a partial plan view of the end effector of FIG. 17 illustrated in a closed, fully-right articulated configuration.
Figure 27:
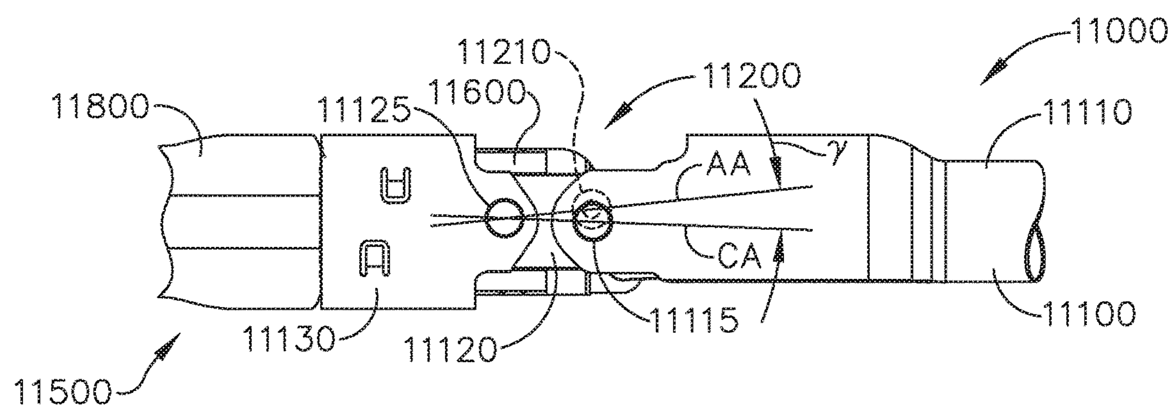
FIG. 27 is a partial plan view of the end effector of FIG. 17 illustrated in a closed, unarticulated configuration.
Figure 27B:
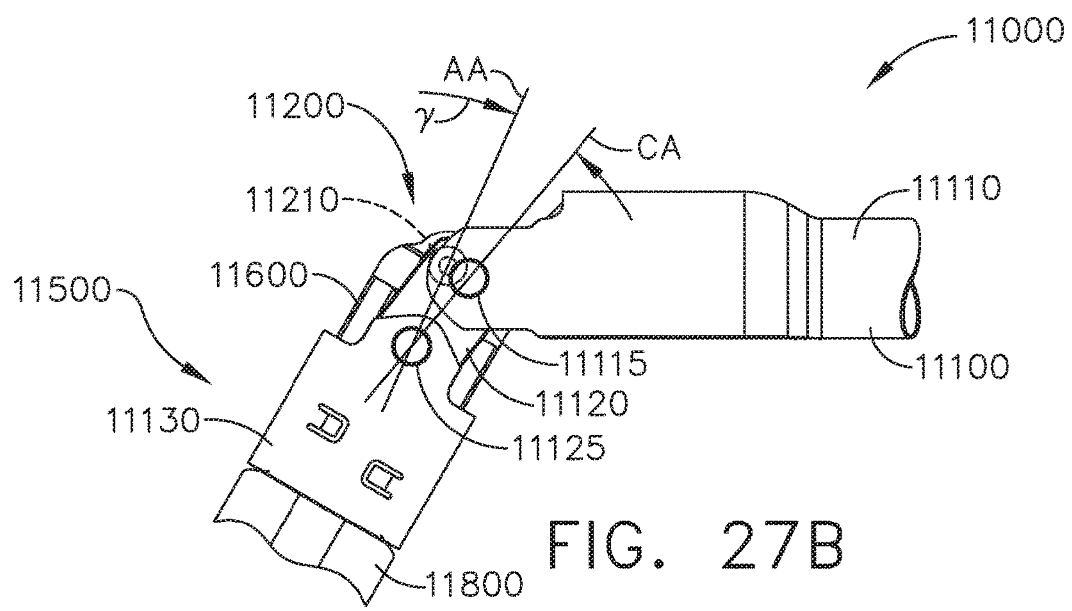
FIG. 27B is a partial plan view of the end effector of FIG. 17 illustrated in a closed, fully-left articulated configuration.

Referring to FIG. 27, the axis AA extends at an angle γ with respect to the axis CA when the end effector 11500 is in a closed, unarticulated configuration. When the end effector 11500 is articulated into a closed, right configuration (FIG. 27A), the angle γ increases. When the end effector 11500 is articulated into a closed, left configuration (FIG. 27B), the angle δ also increases. At no point, however, is the axis AA collinear with the axis CA when the end effector 11500 is articulated in a closed configuration, and/or any other configuration between an open configuration and a closed configuration. Instead, the axis AA is transverse to the axis CA when the end effector 11500 is articulated in a closed configuration and/or any other configuration between an open configuration and a closed configuration.

Referring again to FIGS. 20 and 21, the design of the surgical instrument 11000 can shorten the end effector 11500 as compared to the end effector 10500. Also, the distance between the articulation joint 10200 and the proximal end of the staple line that is applied to the tissue of a patient by the end effector 10500 is a distance L1—while the distance between the articulation joint 11200 and the proximal end of the staple line that is applied by the end effector 11500 is a distance L2, which is shorter than the distance L1.

Turning now to FIGS. 40-45, the surgical instrument 11000 further comprises an articulation lock 11400 configured to selectively lock the articulation drive system 11300 and the end effector 11500 in position. The articulation lock 11400 comprises a distal end 11402 mounted to a frame 11180 of the shaft 11100. More particularly, the shaft frame 11180 comprises pins, or projections, 11182 closely received and/or pressed within apertures defined in the distal end 11402. The articulation lock 11400 further comprises a proximal end 11404 configured to move relative to the distal end 11402. In at least one respect, the articulation lock 11400 comprises a cantilever beam where the distal end 11402 comprises a fixed end and the proximal end 11404 comprises a free end. The proximal end 11404 is positioned in a cavity 11184 defined in the shaft frame 11180 and is configured to move laterally toward and away from the articulation drive actuator 11310, as described in greater detail below.

Figure 40:
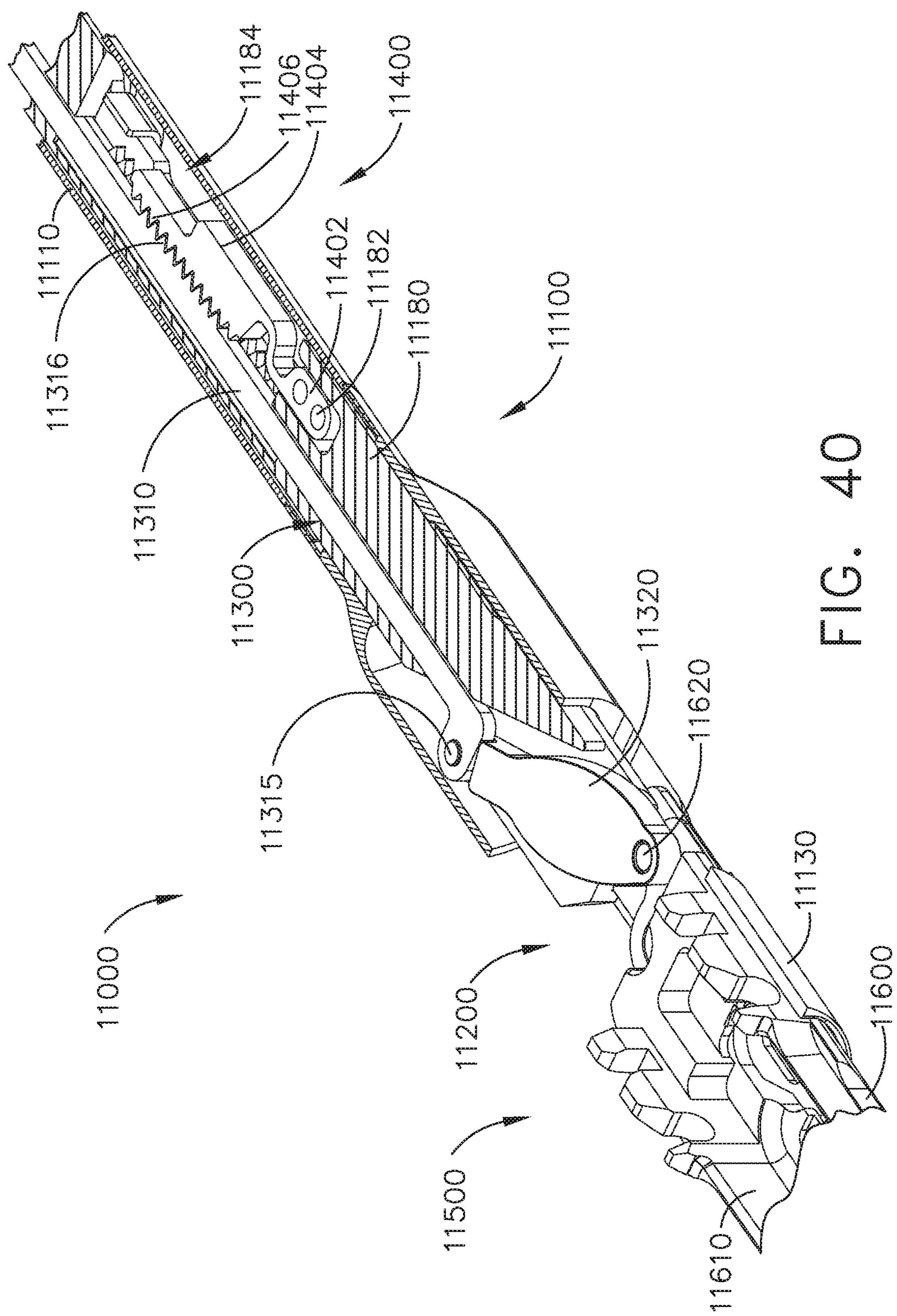
FIG. 40 is a partial cross-sectional view of an end effector comprising an articulation system including an articulation lock in accordance with at least one embodiment.
Figure 41:
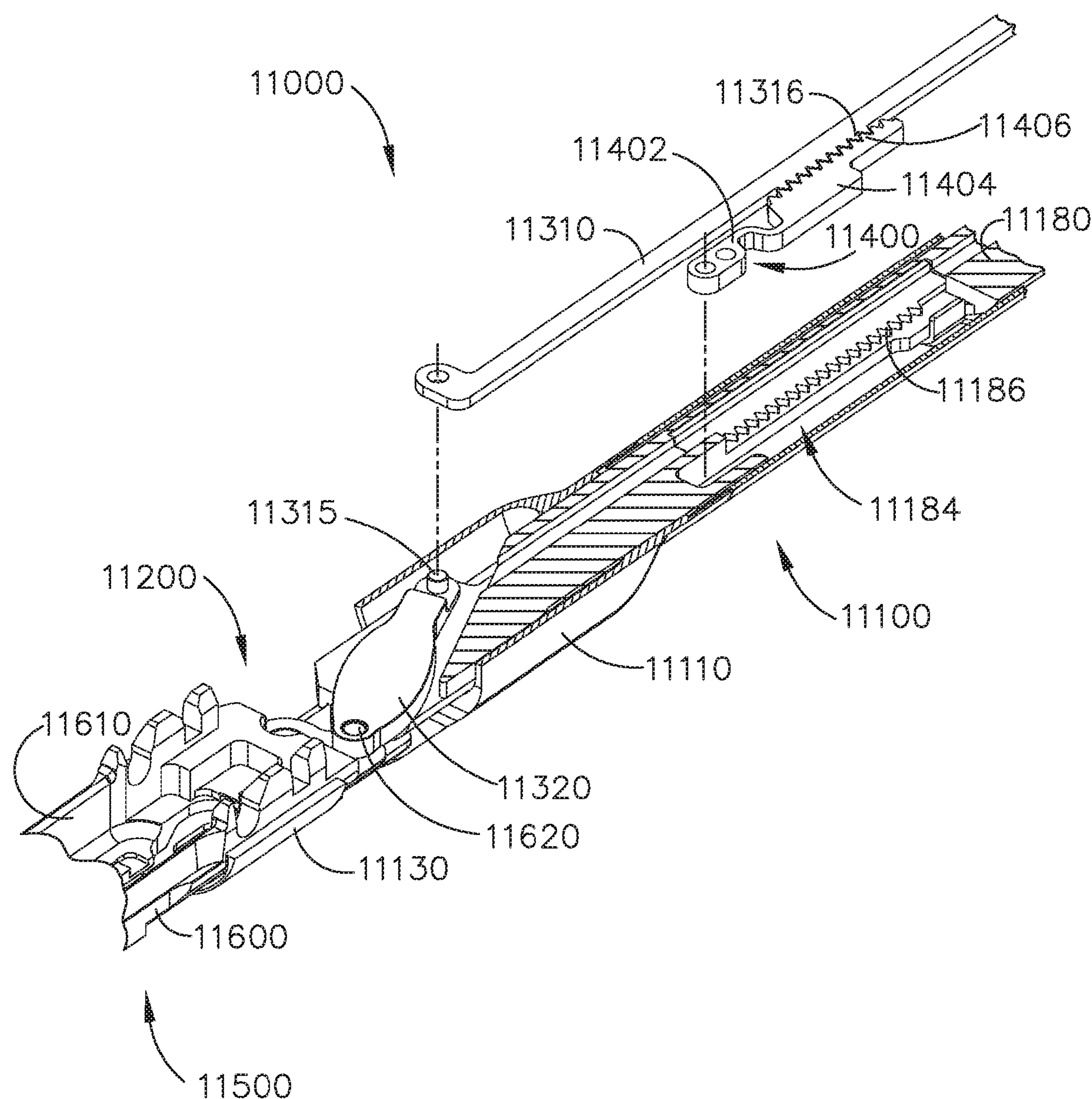
FIG. 41 is a partial exploded view of the end effector of FIG. 40.

Further to the above, the proximal end 11404 of the articulation lock 11400 comprises one or more teeth 11406 defined thereon which are configured to engage the articulation drive actuator 11310. As illustrated in FIG. 40, the teeth 11406 are arranged in a longitudinal array; however, any suitable arrangement may be used. The articulation drive actuator 11310 comprises a longitudinal array of teeth 11316 defined thereon which are configured to be engaged by the articulation lock teeth 11406. Referring to FIG. 41, the shaft frame 11180 further comprises a longitudinal array of teeth 11186 defined therein which are also configured to be engaged by the articulation lock teeth 11406. When the articulation lock 11400 is in a fully-locked state, as described in greater detail below, the articulation lock teeth 11406 are engaged with the drive actuator teeth 11316 and the shaft frame teeth 11186 such that the articulation lock 11400 locks the articulation drive actuator 11310 to the shaft frame 11180 and prevents, or at least inhibits, relative movement between the articulation drive actuator 11310 and the shaft frame 11180.

Figure 42:
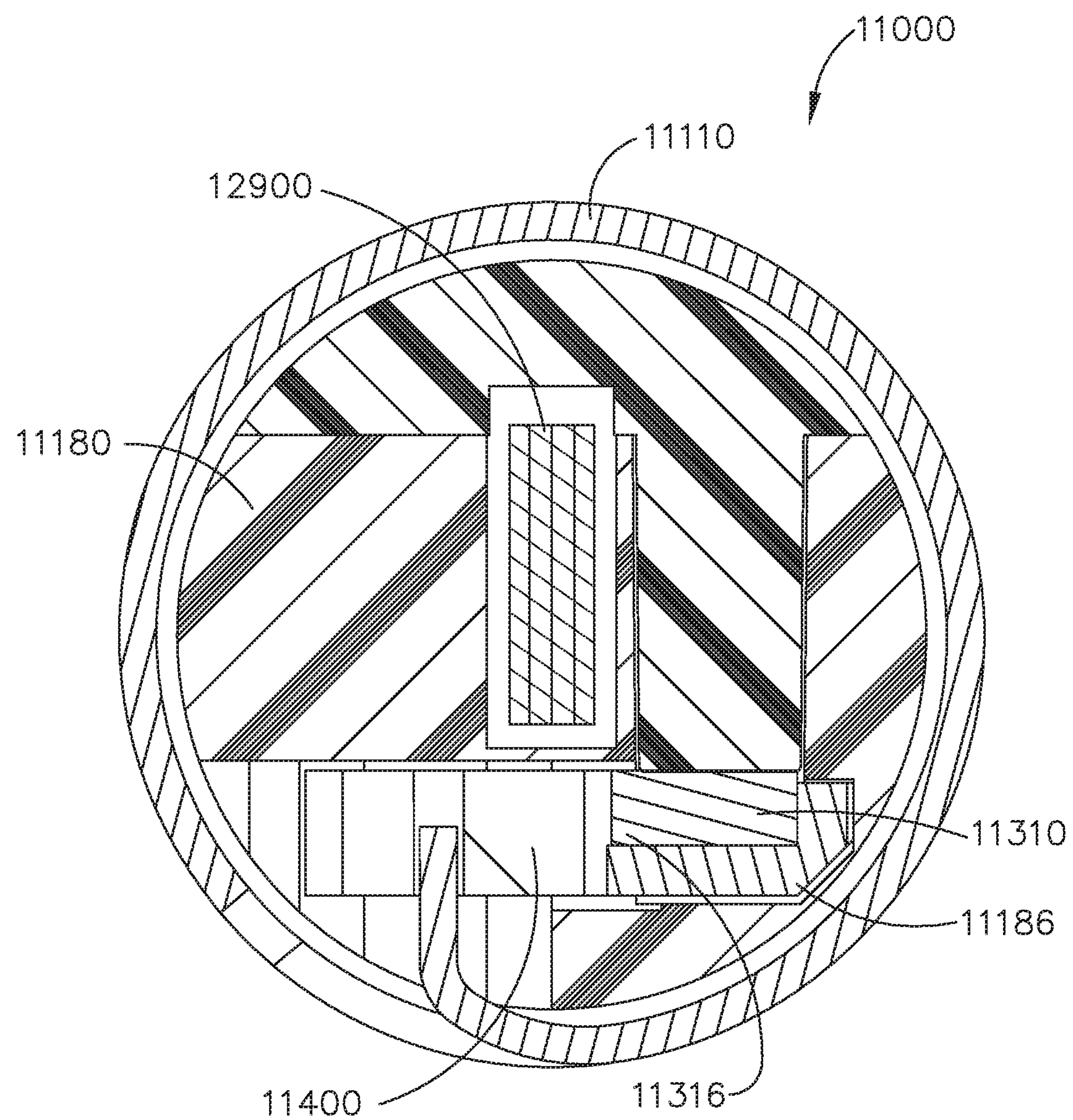
FIG. 42 is a cross-sectional end view of the end effector of FIG. 40.
Figure 43:
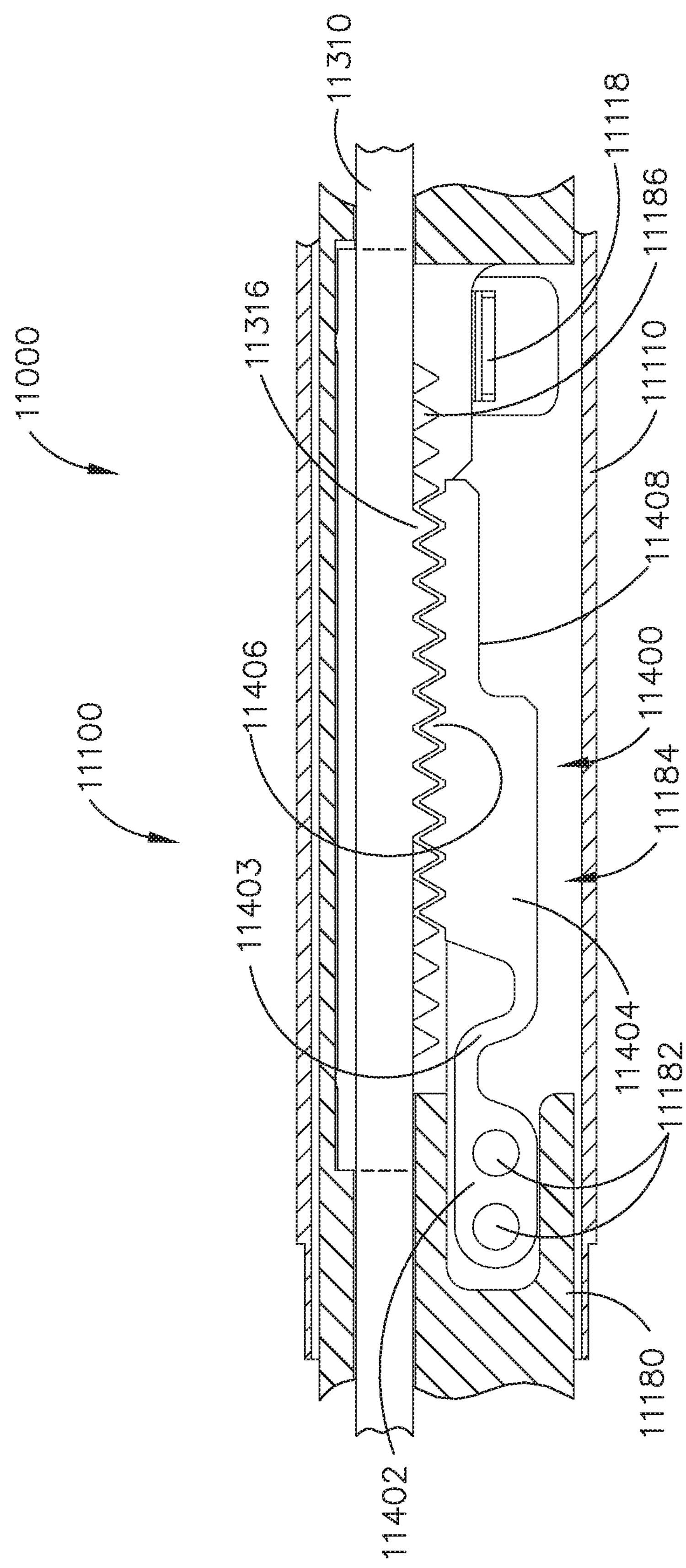
FIG. 43 is a partial cross-sectional view of the end effector of FIG. 40 illustrating the articulation lock in an engaged condition.
Figure 44:
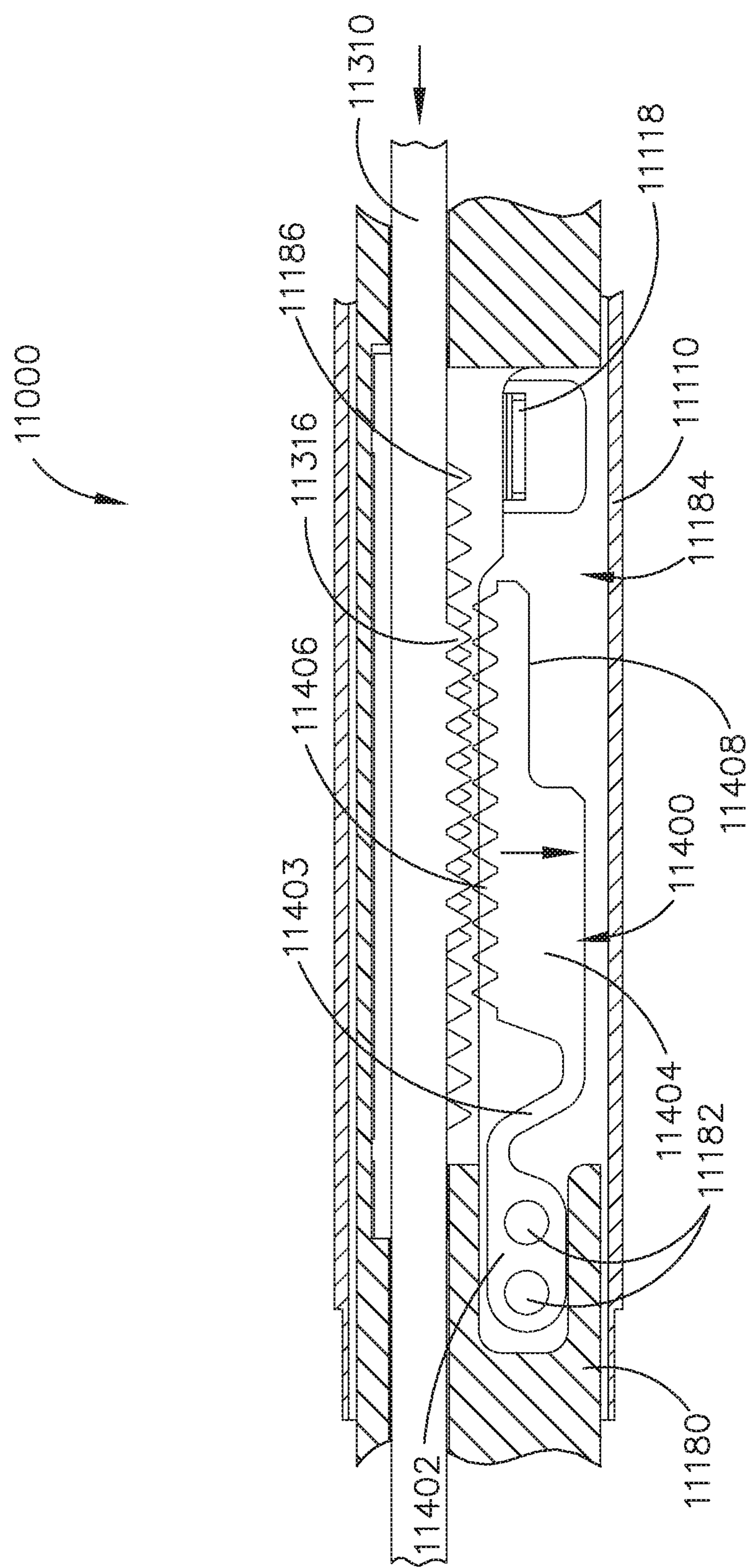
FIG. 44 is a partial cross-sectional view of the end effector of FIG. 40 illustrating the articulation lock in an unlocked condition.
Figure 45:
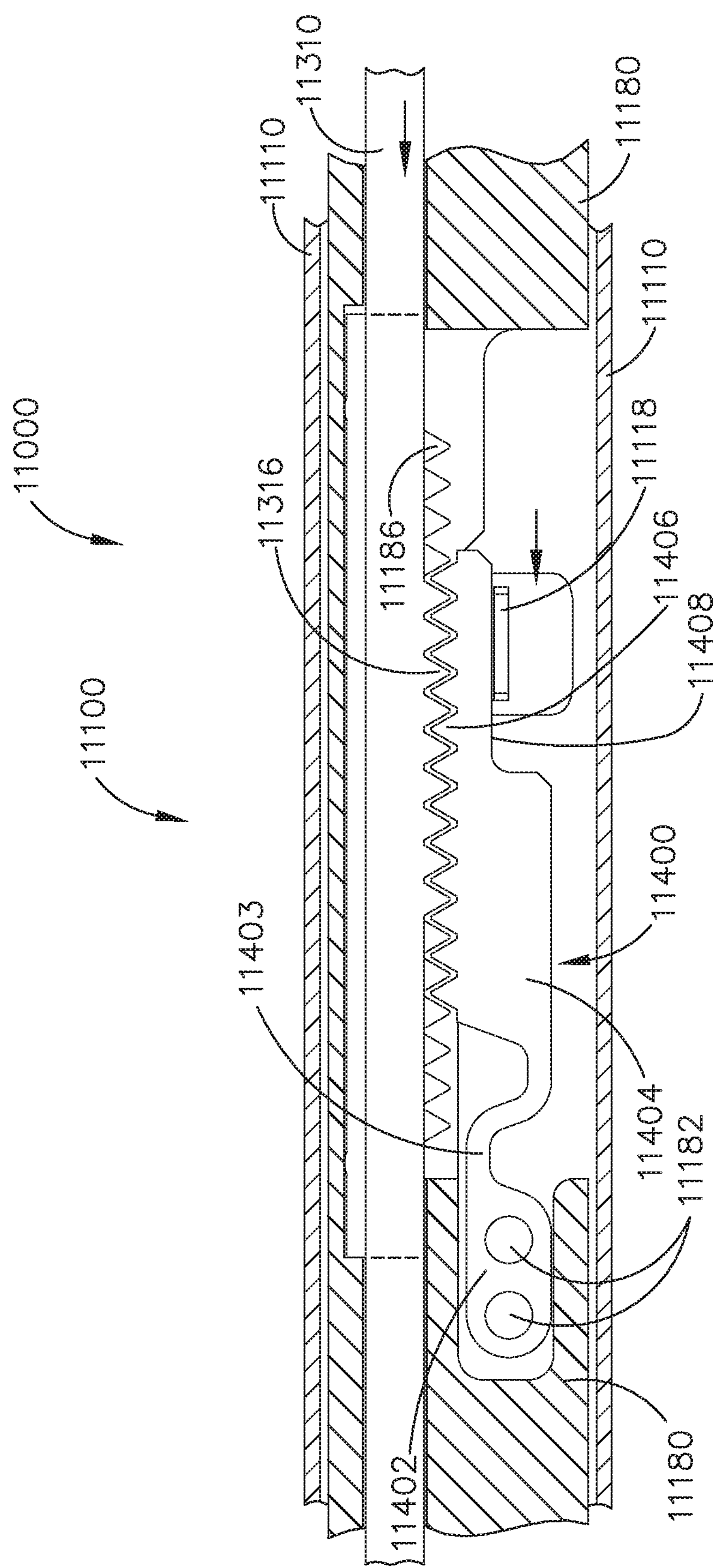
FIG. 45 is a partial cross-sectional view of the end effector of FIG. 40 illustrating the articulation lock in a locked condition.

Further to the above, the articulation lock 11400 is configurable in three states—a self-locked state, an unlocked state, and a fully-locked state. When the articulation lock 11400 is in a self-locked stated, referring to FIG. 43, the teeth 11406 of the articulation lock 11400 are engaged with the drive actuator teeth 11316 and the shaft frame teeth 11186. In such instances, the articulation lock 11400 can resist some force transmitted through the articulation drive actuator 11310; however, proximal and/or distal movement of the articulation drive actuator 11310 can overcome the holding force of the articulation lock 11400 and displace the articulation lock 11400 into its unlocked configuration, as illustrated in FIG. 44. In such instances, the articulation lock 11400 can flex or deflect laterally away from the drive actuator 11310. The articulation lock 11400 comprises a spring member 11403 extending between the distal portion 11402 and the proximal portion 11404 which is configured to resiliently return, or at least bias, the articulation lock toward its self-locked configuration (FIG. 42). As a result, the articulation drive system 11300 can lock and unlock itself as a result of its own motion and articulate the end effector 11500 unless the articulation lock 11400 is placed in its fully-locked position, as discussed below.

As discussed further above, the shaft 11100 of the surgical instrument 11000 comprises a closure tube 11110 that is advanced distally during a closure stroke to close the end effector 11500. Prior to the closure stroke, the articulation lock 11400 is movable between its self-locked and unlocked configurations to permit the end effector 11500 to be articulated by the articulation drive system 11300. During the closure stroke, however, the closure tube 11110 is configured to engage the articulation lock 11400 and place or hold the articulation lock 11400 in its fully-locked configuration. More specifically, the closure tube 11110 comprises a projection, or tab, 11118 configured to engage a cam surface 11408 defined on the back side of the articulation lock 11400 and prevent the articulation lock teeth 11406 from becoming demeshed from the drive actuator teeth 11316 and the shaft frame teeth 11186. When the closure tube 11110 is retracted proximally to open the end effector 11500, the tab 11118 disengages from the articulation lock 11400 and the articulation lock 11400 is free to move between its self-locked and unlocked positions, as discussed above, so that the end effector 11500 can be articulated once again.

The surgical instrument 11000 described above is further illustrated in FIGS. 80-82. The surgical instrument 11000 comprises a shaft 11100 which is configured for use with a trocar having a passageway defined therein. The surgical instrument shaft 11100 comprises different diameters at different points along the length of the surgical instrument shaft 11100. Among other things, the surgical instrument shaft 11100 comprises a central region 11160 comprising a smaller diameter than any other region of the surgical instrument shaft 11000. This geometry of the surgical instrument shaft 11100 provides significant advantages over previous designs and solves a long felt problem associated with the use of a trocar. Typically, when a surgical instrument is used in combination with a trocar during a surgical procedure, the surgical procedure is limited by the range of angles the instrument can take as a result of constrictions created by the trocar passageway. The configuration of the surgical instrument shaft 11100 is an improvement over existing shaft configurations because it increases the range of angles that a surgical instrument can take relative to the longitudinal axis of a trocar. As a result, the user of the surgical instrument 11000 can manipulate the surgical instrument 11000 in a variety of angles relative to the longitudinal axis of the trocar due to the smaller diameter of the central region 11160 of the surgical instrument shaft 11100.

Figure 80:
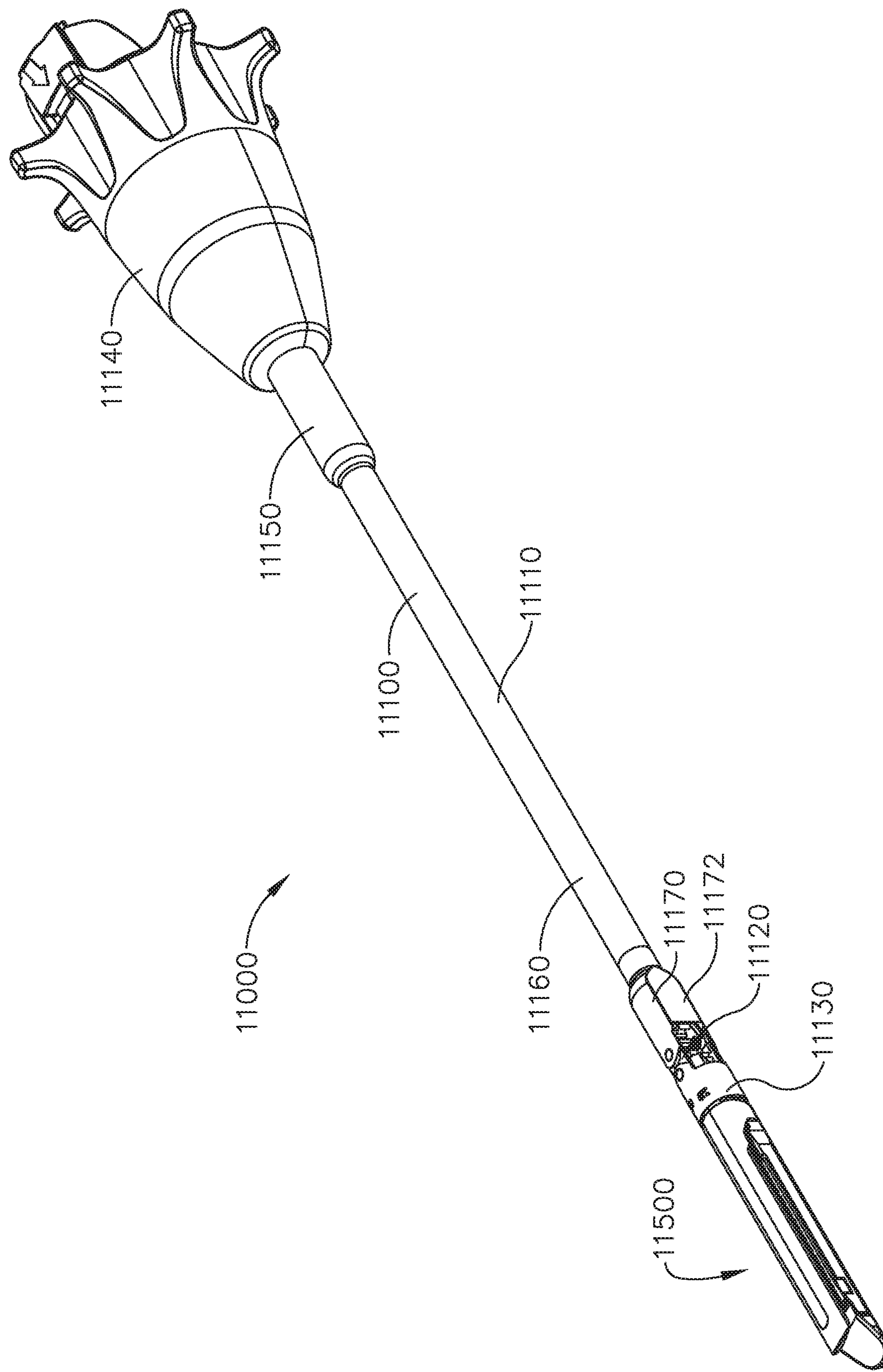
FIG. 80 is a perspective view of a surgical instrument in accordance with at least one embodiment comprising a shaft and an end effector.
Figure 81:
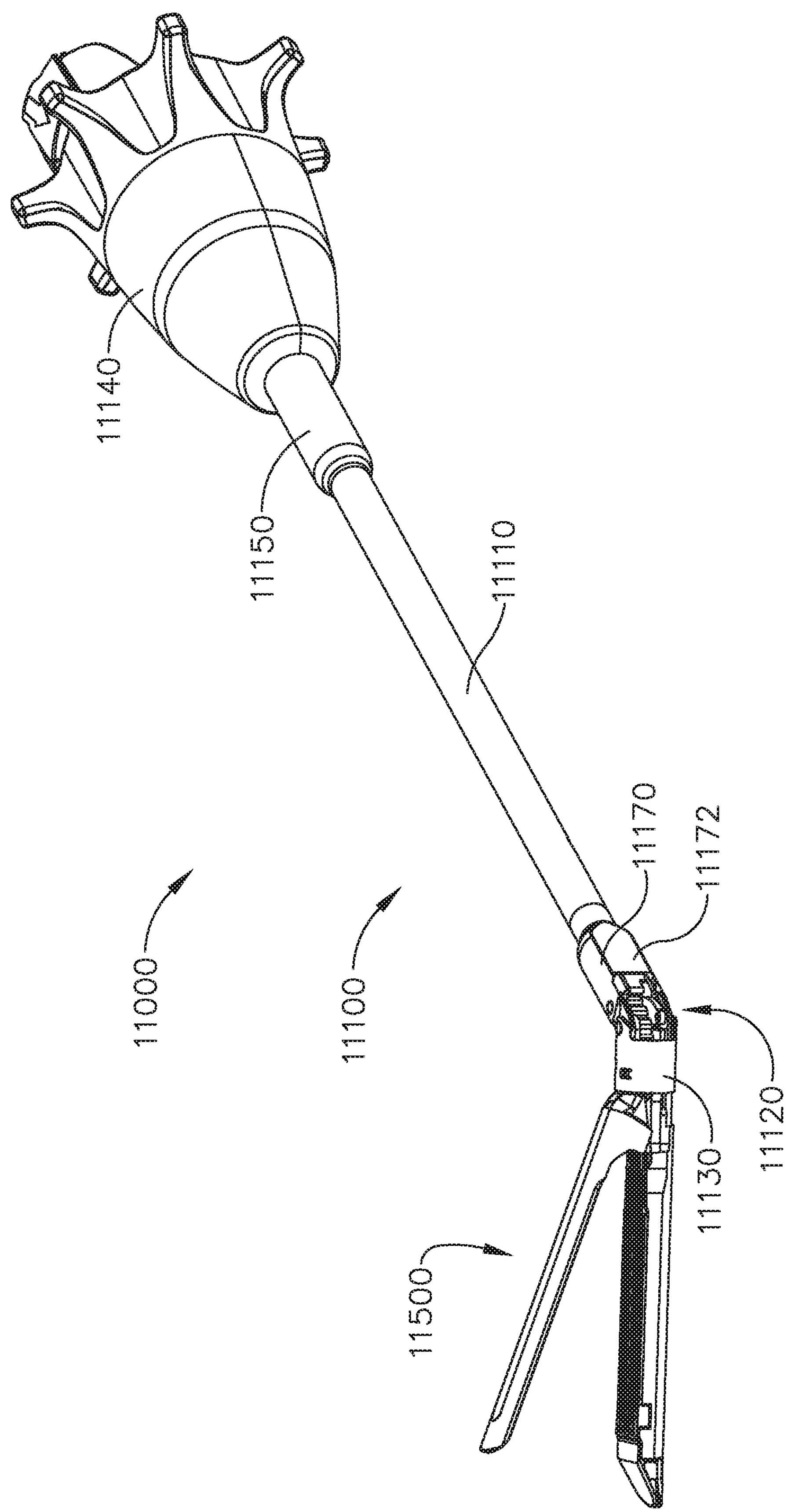
FIG. 81 is a perspective view of the surgical instrument in FIG. 80 illustrating the end effector articulated relative to the shaft.

Referring to FIGS. 80 and 81, the surgical instrument shaft further 11100 comprises a proximal region 11150 and a distal region 11170. The proximal region 11150 of the surgical instrument shaft 11000 is located adjacent to a nozzle assembly 11140 of the shaft 11100. The distal region 11170 is located closest to the end effector 11500. The proximal region 11150 of the surgical instrument shaft comprises a first diameter, and the central region 11160 comprises a second diameter. The distal region 11170 further comprises a third diameter. The first diameter of the proximal region 11150 is different than the second diameter of the central region 11160. Similarly, the second diameter of the central region 11160 is different than the third diameter of the distal region 11170. The first diameter of the proximal region 11150 is different than the third diameter of the distal region 11170; however, embodiments are envisioned in which the first diameter and the third diameter are the same.

Further to the above, the proximal region 11150 defines a central longitudinal axis. The central region 11160 extends along the central longitudinal axis and is centered with respect to the central longitudinal axis. The proximal region 11150 and the central region 11160 each define a circular profile, although they can comprise any suitable configuration. The distal region 11170 is not centered with respect to the central longitudinal axis. Instead, the distal region 11170 is offset laterally with respect to the central longitudinal axis. Moreover, more of the cross-section and/or perimeter of the distal region 11170 is positioned on a first side of the central longitudinal axis than a second side. In at least one instance, the distal region 11170 comprises an enlargement extending to one side of the central longitudinal axis. Additionally, the distal region 11170 does not define a circular profile.

Still referring to FIGS. 80 and 81, the central region 11160 comprises a second width that is smaller than the first width of the proximal region 11150. The central region further comprises a second width which is smaller than the third width of the distal region 11170. The proximal region 11150 further comprises a different width than the width of the distal region 11170. For example, the width of the proximal region 11150 is smaller than the width of the distal region 11170, but is still larger than the width of the central region 11160. Similarly, the width of the proximal region 11150 is larger than the width of the distal region 11170 and the width of the central region 11160. In other instances, the proximal region 11150 and the distal region 11170 comprise approximately the same width.

Figure 82:
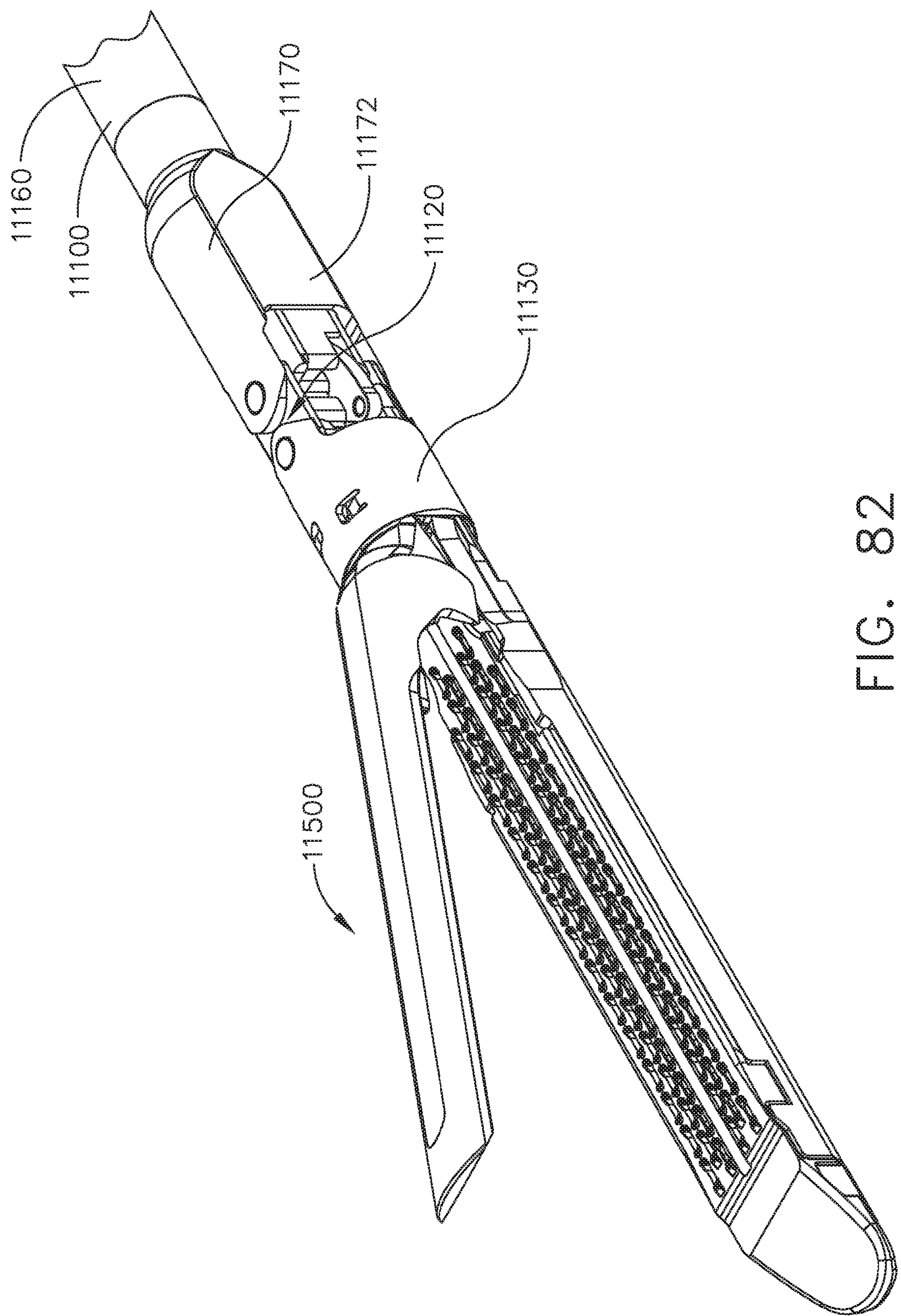
FIG. 82 is a perspective view of the end effector of FIG. 80 in an open configuration.

Referring to FIGS. 80-82, the surgical instrument shaft 11100 of the surgical instrument 11000 is configured to fit through a 12 mm trocar, for example. In at least one such instance, the central region 11160 of the surgical instrument shaft 11100 comprises a maximum diameter of approximately 9 mm. Such a diameter of the central region 11160 provides for a wider range of angles that the shaft 11100 can take relative to the centerline of the trocar. Also, such an arrangement can reduce the possibility of causing intercostal nerve damage associated with placing the surgical instrument shaft 11100 between the ribs of a patient during certain surgical procedures. The distal region 11170 of the surgical instrument shaft 11100 is configured to fit through a 12 mm trocar, and comprises one or more flat sides 11172 in order to provide for an increased level of access during procedures which require a high level of articulation. Other embodiments are envisioned in which the shaft 11100 is inserted through a 8 mm trocar and/or a 5 mm trocar, for example.

The proximal region 11150 comprises a stepped down, or tapered, region near the proximal end of the surgical instrument shaft 11100, where the surgical instrument shaft 11100 transitions from the proximal region 11150 to the central region 11160. The central region 11160 further comprises a stepped up, or tapered, region near the distal end of the surgical instrument shaft 11100, where the surgical instrument shaft 11100 transitions from the central region 11160 to the distal region 11170.

Still referring to FIGS. 80 and 81, the proximal region 11150 comprises a first circumference, the central region 11160 comprises a second circumference, and the distal region 11170 comprises a third circumference. The circumference of the proximal region 11150 is different than the circumference of the central region 11160, owing to the difference in diameters of such portions of the surgical instrument shaft 11100. Similarly, the circumference of the central region 11160 and the circumference of the distal region 11170 are different. The circumference of the proximal region 11150 and the circumference of the distal region 11170 are the same, but can be different in other embodiments.

Referring again to FIGS. 80 and 81, the surgical instrument shaft 11100 comprises a single, formed piece of material, although the surgical instrument shaft 11100 can comprise multiple pieces of material that are combined to form a single, cohesive surgical instrument shaft in other instances. The pieces of material can be assembled using any appropriate process. The surgical instrument shaft 11100 is configured to operate with a variety of surgical arrangements not limited to the surgical stapling instruments described above. The surgical instrument shaft 11100 can be used with other surgical instruments having articulatable end effectors. The other surgical instruments can include, for example, ultrasonic surgical devices, clip appliers, and fastener appliers. In addition, the surgical instrument shaft 11100 is configured for use with any surgical instrument wherein use of a trocar passageway is appropriate.

Further to the above, the outer tube 11110 of the shaft 11100 comprises a proximal end 11150 and a longitudinal portion 11160 comprising a diameter, or width, which is narrower than the diameter, or width, of the proximal end 11150. That said, the surgical instrument 11000 is configured and arranged to provide a large torque to the end effector 11500 while, at the same time, the longitudinal portion 11160 comprises a narrow diameter. To wit, at least one design ratio for this relationship can be established and used to design the surgical instrument 11000. For instance, one ratio comprises the diameter of the longitudinal portion 11160 (D) divided by the fully-right articulated torque arm length (TA). The value of this ratio is unitless. In at least one instance, the diameter of the longitudinal portion 11160 (D) is 0.316" and the torque arm length (TA) is 0.154", resulting in a ratio value of 2.06, for example. Smaller values for this ratio indicate more efficient articulation systems. In various instances, the value for this ratio is less than 2.0, such as between 1.0 and 2.0, for example. In at least one instance, the ratio value is between 2.0 and 3.0, for example. In certain instances, the ratio value is smaller than 3.38, for example.

Further to the above, the outer tube 11110 of the shaft 11100 comprises a longitudinal portion 11160 and an enlarged distal end 11170 (FIG. 80). Referring again to FIG. 40, the entirety of the articulation lock 11400 is positioned in the longitudinal portion 11160 and not the enlarged distal end 11170. Embodiments are envisioned, however, in which at least a portion of the articulation lock 11400 is positioned in the enlarged distal end 11170. In at least one such instance, the articulation lock 11400 is mounted to the shaft frame such that the distal end 11402 of the articulation lock 11400 is in the enlarged distal end 11170 of the outer tube 11110. In certain instances, the articulation lock 11400 is re-arranged such that the movable end of the articulation lock 11400 is positioned in the enlarged distal end 11170 of the outer tube 11110. In various instances, the entirety of the articulation lock 11400 is positioned in the enlarged distal end 11170.

Figure 46:
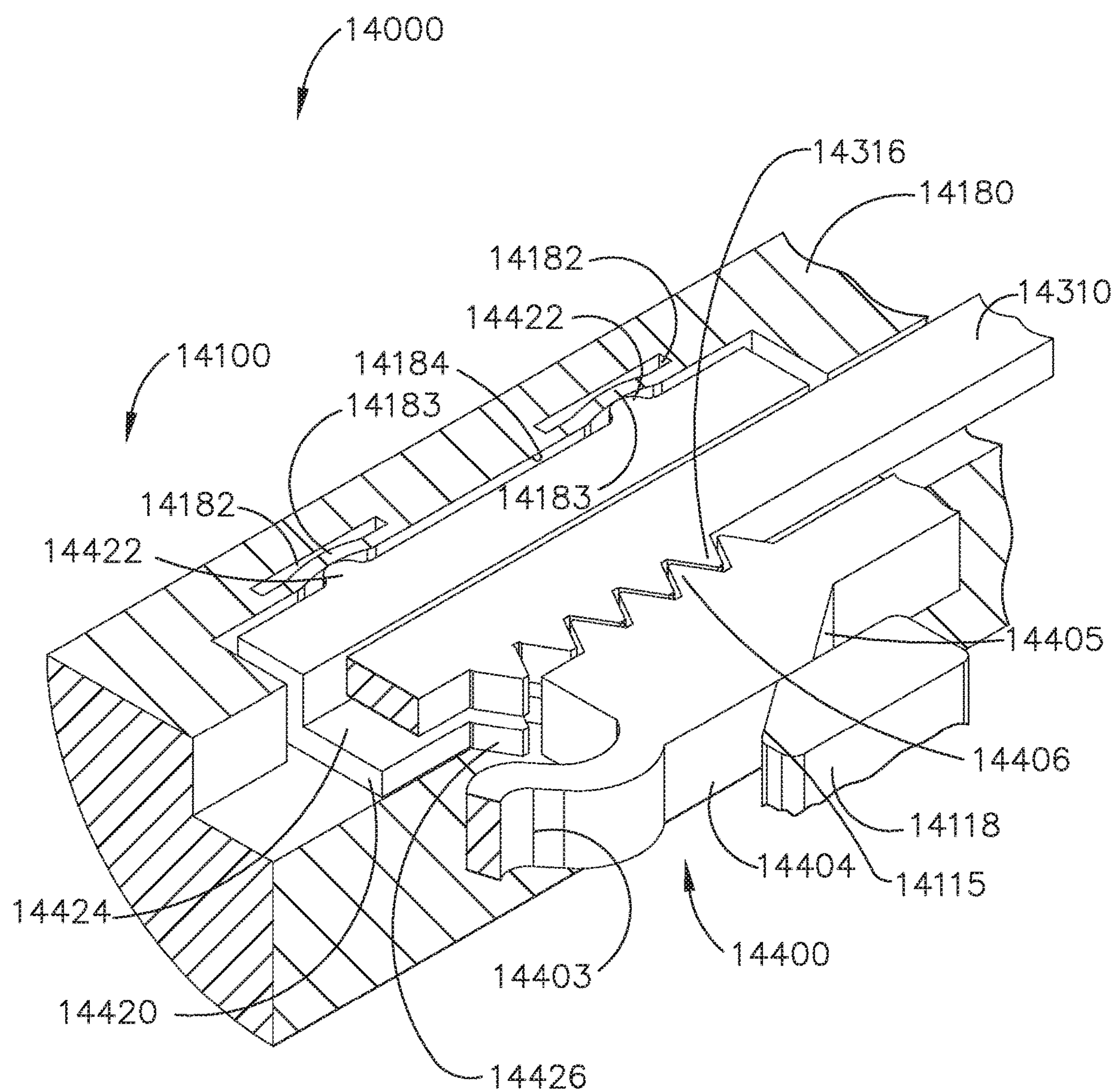
FIG. 46 is a partial cross-sectional view of an end effector including a slidable lock plate in accordance with at least one embodiment.

Turning now to FIG. 46, a surgical instrument 14000 comprises a shaft 14100, an end effector 11500, and, in addition, an articulation drive system including an articulation drive actuator 14310 configured to articulate the end effector 11500. The shaft 14100 comprises an articulation lock system configured to selectively lock the articulation drive actuator 14310 and the end effector 14500 in position. The articulation lock system comprises an articulation lock 14400 including proximal end and distal ends mounted to a frame 14180 of the shaft 14100. In at least one respect, the articulation lock 14400 comprises a beam fixedly and/or simply-supported at both ends. The articulation lock 14400 further comprises an intermediate portion 14404 positioned in a cavity 14184 defined in the shaft frame 14180 which is configured to move laterally toward and away from an articulation drive actuator 14310 of the articulation drive system 14300. Similar to the above, the articulation lock 14400 comprises one or more spring portions 14403 configured to permit the articulation lock 14400 to flex toward and away from the articulation drive actuator 14310.

Further to the above, the intermediate portion 14404 of the articulation lock 14400 comprises one or more teeth 14406 defined thereon which are configured to engage the articulation drive actuator 14310. The teeth 14406 are arranged in a longitudinal array; however, any suitable arrangement may be used. The articulation drive actuator 14310 comprises a longitudinal array of teeth 14316 defined thereon which are configured to be engaged by the articulation lock teeth 14406. The articulation lock system further comprises a lock plate 14420 slidably positioned in the shaft cavity 14184 which includes a longitudinal array of teeth 14226 defined therein which are also configured to be engaged by the articulation lock teeth 14406. When the articulation lock 14400 is in a fully-locked state, as described in greater detail below, the articulation lock teeth 14406 are engaged with the drive actuator teeth 14316 and the lock plate teeth 14226 such that the articulation lock 14400 locks the articulation drive actuator 14310 in position and prevents, or at least inhibits, relative movement between the articulation drive actuator 14310 and the shaft frame 14180.

The lock plate 14420 comprises a shoulder 14424 which is positioned under the articulation drive actuator 14310. The lock plate teeth 14426 are defined on a lateral edge of the shoulder 14424 and are substantially aligned with the teeth 14316 defined in the articulation drive actuator 14310. In at least one instance, the articulation drive actuator teeth 14316 are aligned along a first teeth axis and the lock plate teeth 14406 are defined along a second teeth axis which is parallel, or at least substantially parallel, to the first teeth axis. In various instances, the drive actuator teeth 14316 are defined in a plane which is parallel to a plane including the lock plate teeth 14406. Such arrangements permit the articulation lock 14400 to simultaneously engage the lock plate 14420 and the articulation drive actuator 14310. Although the first teeth axis and the second teeth axis are parallel to a longitudinal axis of the shaft 14100, embodiments are envisioned in which the first teeth axis and the second teeth axis are skew or transverse with respect to the longitudinal axis of the shaft 14100.

Referring again to FIG. 46, the lock plate 14420 is slidable longitudinally within the cavity 14184; however, the longitudinal movement of the lock plate 14420 is limited by proximal and distal end walls 14427. As a result, the lock plate 14420 can float within the shaft cavity 14184 between the end walls 14427. In various instances, the lock plate teeth 14426 may not be completely aligned with the drive actuator teeth 14316 when the articulation lock 14400 engages the teeth 14426 and 14316. In such instances, the lock plate 14420 can move longitudinally, to a certain degree, such that the lock plate teeth 14426 are aligned with the drive actuator teeth 14316. In various instances, the lock plate 14420 can move in response to a locking force applied thereto by the articulation lock 14400. In at least one instance, the lock plate 14420 can be permitted to move distally one tooth pitch distance and proximally one tooth pitch distance with respect to its centered position, for example, wherein a tooth pitch distance is the distance between the peaks of adjacent lock teeth 14426 of the lock plate 14420. In other instances, the lock plate 14420 can be permitted to move distally ¼ of a tooth pitch distance and proximally ¼ of a tooth pitch distance with respect to its centered position, for example. In various instances, the lock plate 14420 can be permitted to move proximally and distally more than one toot pitch distance.

Further to the above, the articulation lock 14400 is configurable in three states—a self-locked state, an unlocked state, and a fully-locked state. When the articulation lock 14400 is in a self-locked stated, the teeth 14406 of the articulation lock 14400 are engaged with the drive actuator teeth 14316 and the shaft frame teeth 14186. In such instances, the articulation lock 14400 can resist some force transmitted through the articulation drive actuator 14310; however, proximal and/or distal movement of the articulation drive actuator 14310 can overcome the holding force of the articulation lock 14400 and displace the articulation lock 14400 into its unlocked configuration. In such instances, the articulation lock 14400 can flex or deflect laterally away from the drive actuator 14310 so that the end effector 11500 can be articulated. Similar to the above, the spring members 14403 of the articulation lock 14400 can resiliently return, or at least bias, the articulation lock 14400 toward its self-locked configuration. As a result, the articulation drive system can lock and unlock itself as a result of its own motion unless it is placed in its fully-locked position, as discussed below.

Similar to the above, the shaft 14100 of the surgical instrument 14000 comprises a closure tube that is advanced distally during a closure stroke to close the end effector 11500. Prior to the closure stroke, the articulation lock 14400 is movable between its self-locked and unlocked configurations to permit the end effector 11500 to be articulated by the articulation drive system. During the closure stroke, the closure tube is configured to engage the articulation lock 14400 and place, block, and/or hold the articulation lock 14400 in its fully-locked configuration. More specifically, the closure tube comprises a cam 14118 configured to engage a cam surface 14405 defined on the back side of the articulation lock 14400 and prevent the articulation lock teeth 14406 from becoming de-meshed from the drive actuator teeth 14316 and the shaft frame teeth 14186. The cam 14118 comprises an angled surface 14115 which engages a corresponding angled surface defined on the cam surface 14405, although any suitable arrangement could be used. When the closure tube is retracted proximally to permit the end effector 11500 to be opened, the tab 14118 disengages from the articulation lock 14400 and the articulation lock 14400 is free to move between its self-locked and unlocked positions, as discussed above, so that the end effector 11500 can be articulated once again.

When the articulation lock 14400 is moved into its fully-locked configuration by the closure tube, referring again to FIG. 46, the articulation lock 14400 pushes the lock plate 14420 against a lateral sidewall 14183 of the shaft cavity 14184. In fact, the articulation lock 14400 engages the lock plate 14420 with sufficient force to pin the lock plate 14420 against the sidewall 14183 such that the lock plate 14420 cannot move, or at least substantially move, longitudinally with respect to the shaft frame 14180. The lock plate 14420 comprises one or more projections 14422 extending therefrom which are configured to dig into, bite, and/or deflect the sidewall 14183 of the shaft cavity 14184 when the lock plate 14420 is pushed against the sidewall 14183 to prevent, or at least reduce the possibility of, the lock plate 14420 from moving longitudinally relative to the shaft frame 14180.

Further to the above, the shaft frame 14180 comprises one or more cavities, or openings, defined therein which are configured to permit and/or facilitate the deflection of the sidewall 14183. For example, as illustrated in FIG. 46, the shaft frame 14180 comprises cavities 14182 defined therein which are aligned, or at least substantially aligned, with the projections 14422. When the lock plate 14420 is displaced laterally by the closure tube, as discussed above, the sidewall 14183 elastically displaces into the cavities 14182 and the lock plate 14420 is locked in position. In such instances, the engagement between the shaft frame 14180 and the lock plate 14420 prevents the articulation drive actuator 14310 from being moved longitudinally and locks the end effector 11500 in position. When the closure tube is retracted and disengaged from the articulation lock 14400, the sidewall 14183 can return to its unflexed state and displace the lock plate 14420 laterally. At such point, the lock plate 14420 is unlocked and the end effector 11500 can be articulated, as outlined above.

Figure 47:
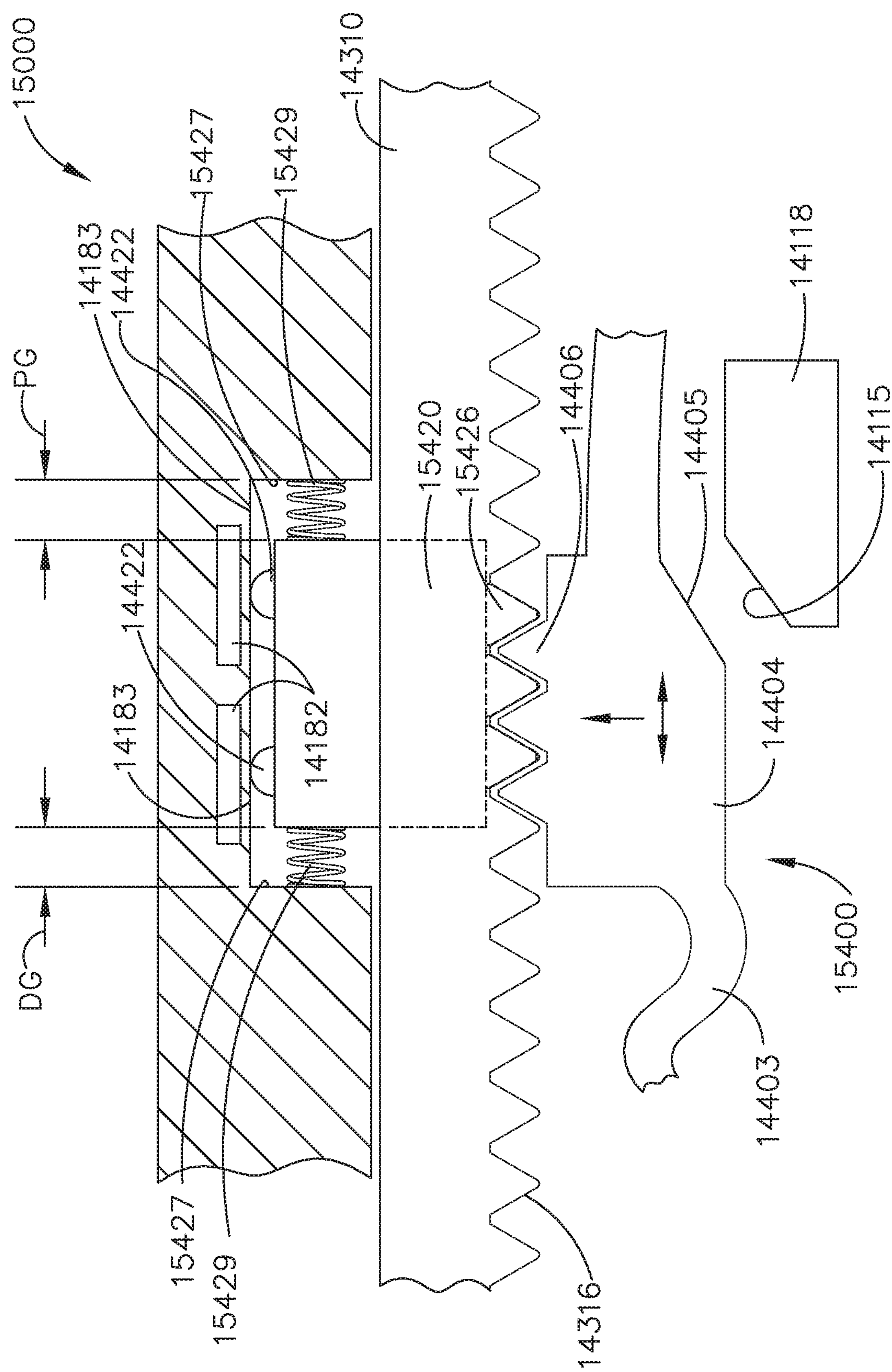
FIG. 47 is a partial cross-sectional view of another end effector including a slidable lock plate in accordance with at least one embodiment.
Figure 48:
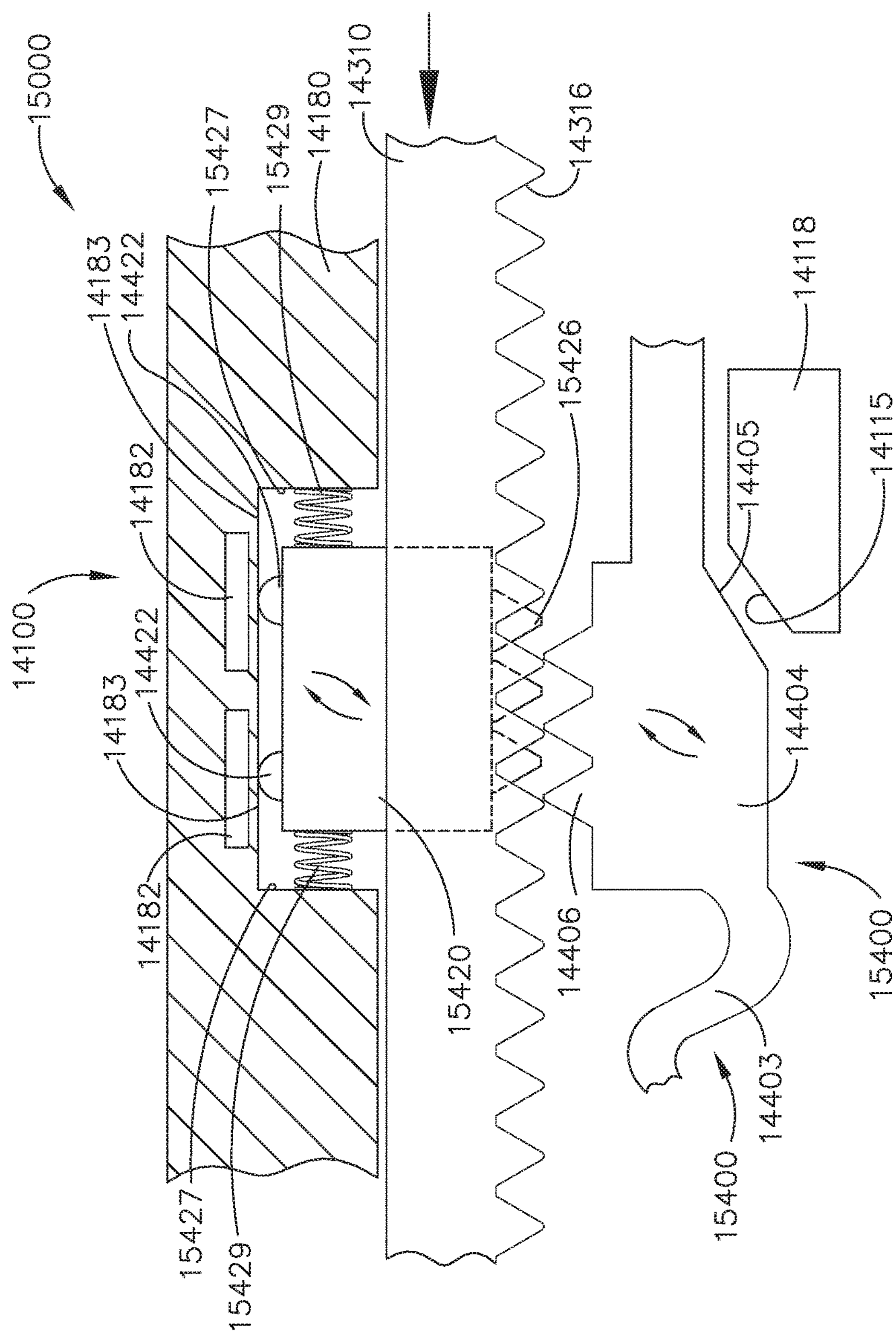
FIG. 48 is a partial cross-sectional view of the end effector of FIG. 47 illustrating self-adjustability of the lock plate.
Figure 49:
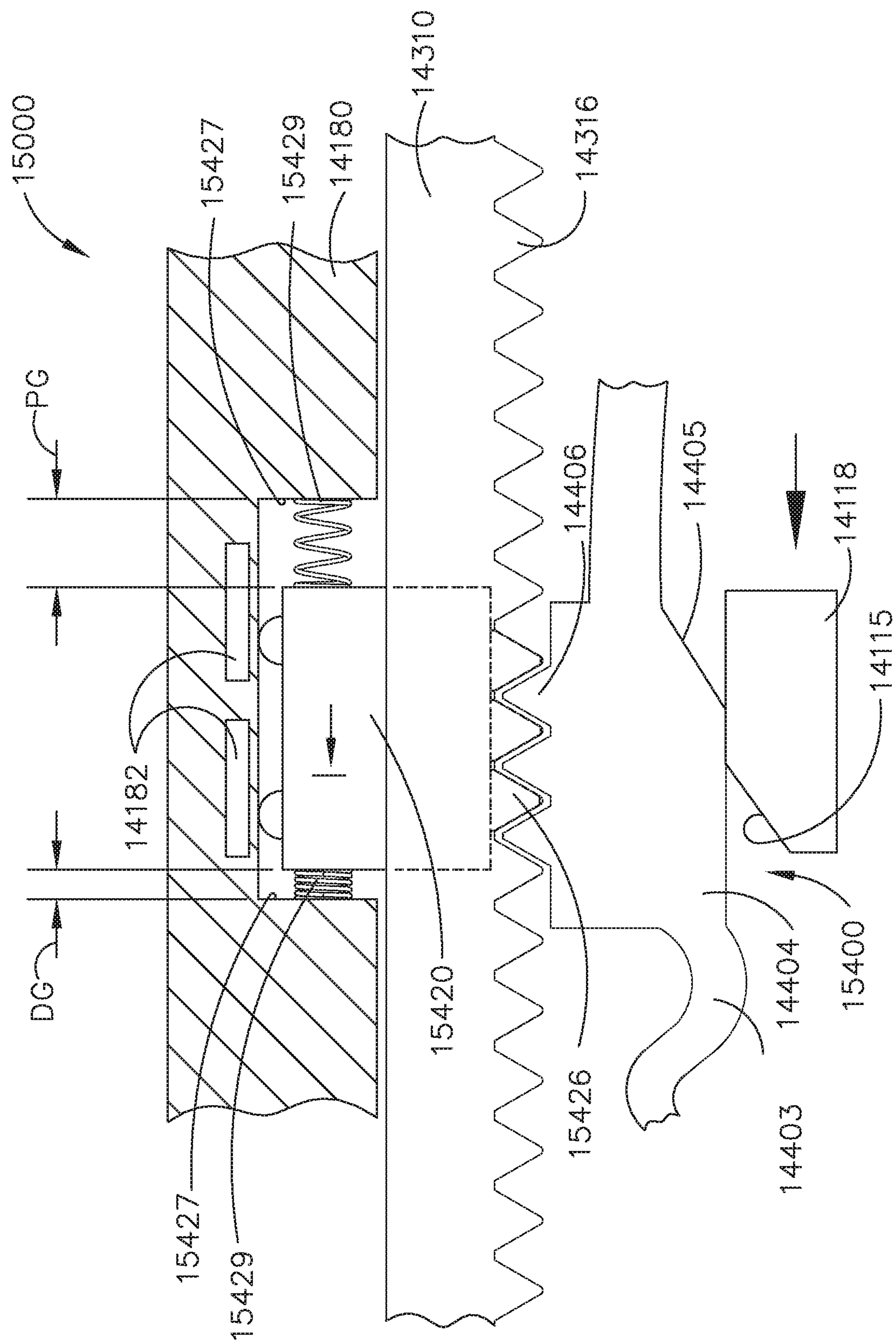
FIG. 49 is a partial cross-sectional view of the end effector of FIG. 47 in a locked condition.

A surgical instrument 15000 is illustrated in FIGS. 47-49 and is similar to the surgical instrument 14000 in many respects, most of which will not be repeated herein for the sake of brevity. Among other things, the surgical instrument 15000 comprises a shaft, an end effector 11500, and an articulation drive system including an articulation drive actuator 14310. The surgical instrument 15000 further comprises an articulation locking system including an articulation lock 15400 which is, similar to the above, movable between a self-locking position, an unlocked position, and a fully-locked position. The articulation locking system further comprises a lock plate 15420 which is similar to the lock plate 14420 in many respects. For instance, the lock plate 15420 is movable laterally into engagement with the wall 14183. Also, for instance, the lock plate 15420 is movable longitudinally to float into a suitable locked position in which an array of teeth 15426 defined on the lock plate 15420 are meshed with the teeth 14406 of the articulation lock 15400, as depicted in FIG. 48. That said, the shaft of the surgical instrument 15000 further comprises a distal spring 15429 positioned intermediate the lock plate 15420 and a distal end wall 15427 defined in the shaft frame and, in addition, a proximal spring 15429 positioned intermediate the lock plate 15420 and a proximal end wall 15427 defined in the shaft frame. The springs 15429 are configured to position the lock plate 15420 in a centered, or balanced, position between the end walls 15427, which is illustrated in FIG. 47. Such a centered position creates a proximal gap (PG) and a distal gap (DG) between the end walls 15427 and the lock plate 15420 which are equal, or at least substantially equal, to one another. That said, the springs 15429 may experience different deflections or loading when the lock plate 15420 seats itself into meshing engagement with the articulation lock 15400, as illustrated in FIG. 49, which may create unequal gaps PG and DG.

Figure 50:
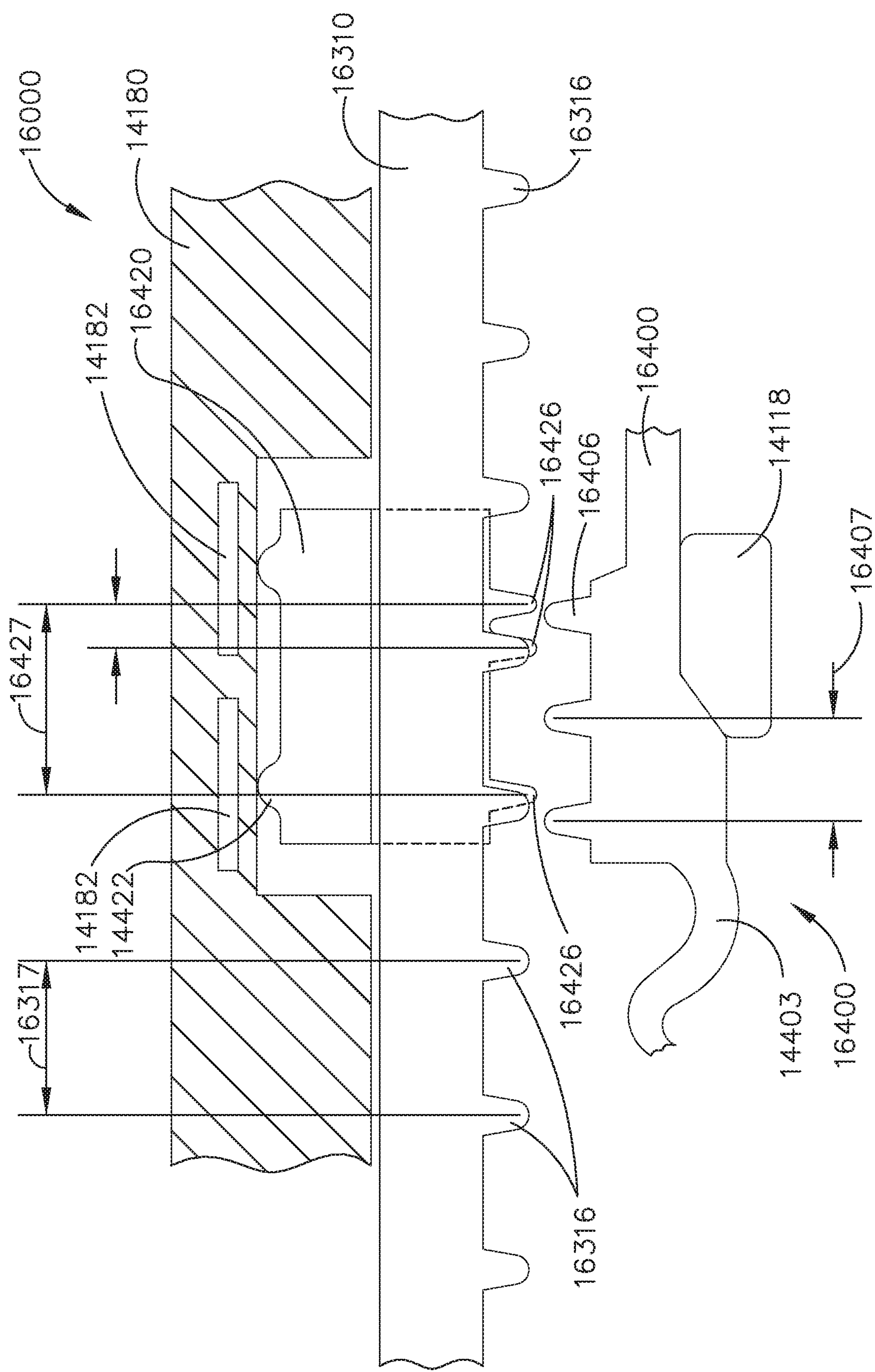
FIG. 50 is a partial cross-sectional view of an end effector including another slidable lock plate in accordance with at least one embodiment.
Figure 51:
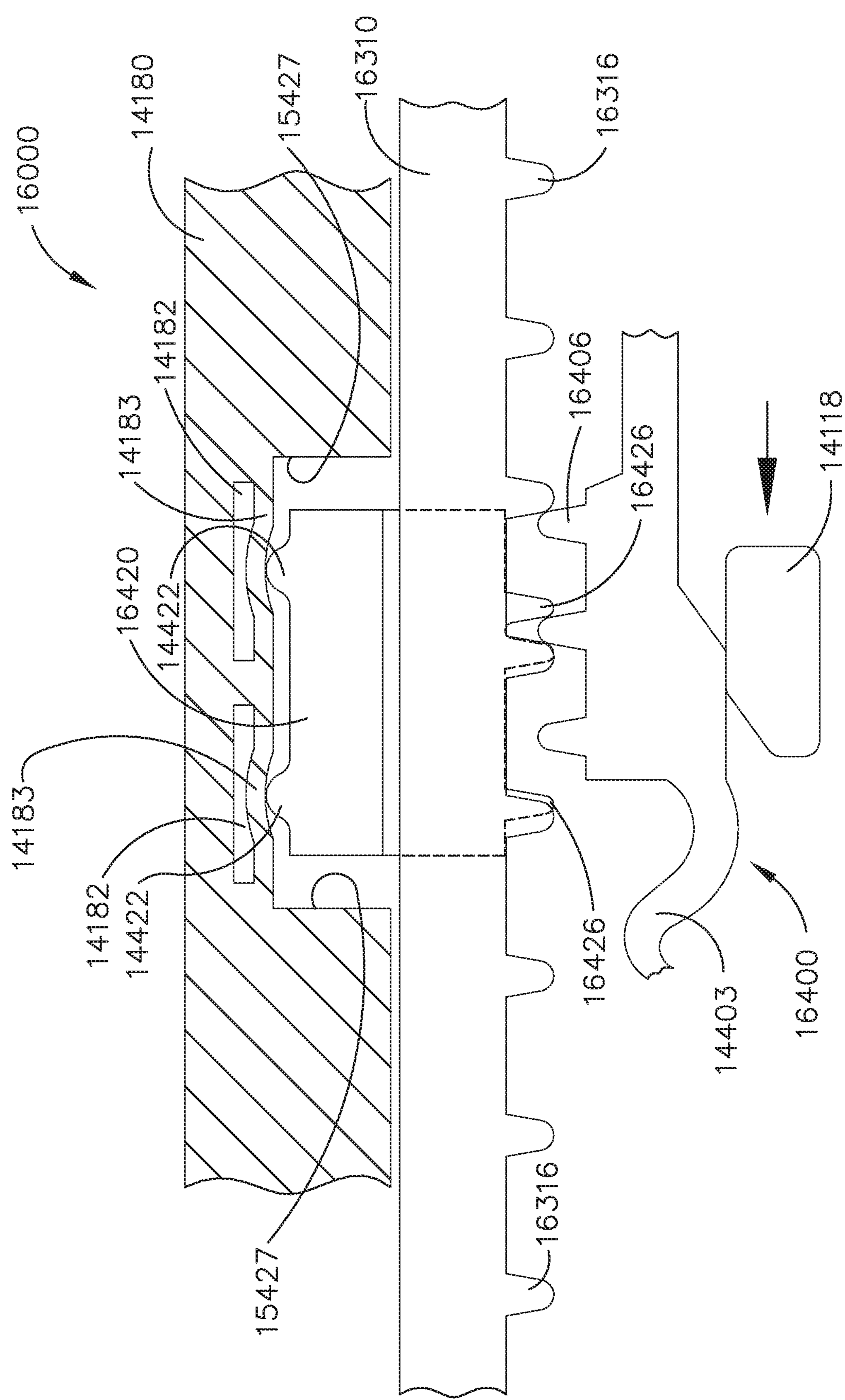
FIG. 51 is a partial cross-sectional view of the end effector of FIG. 50 illustrated in a locked condition.
Figure 52:
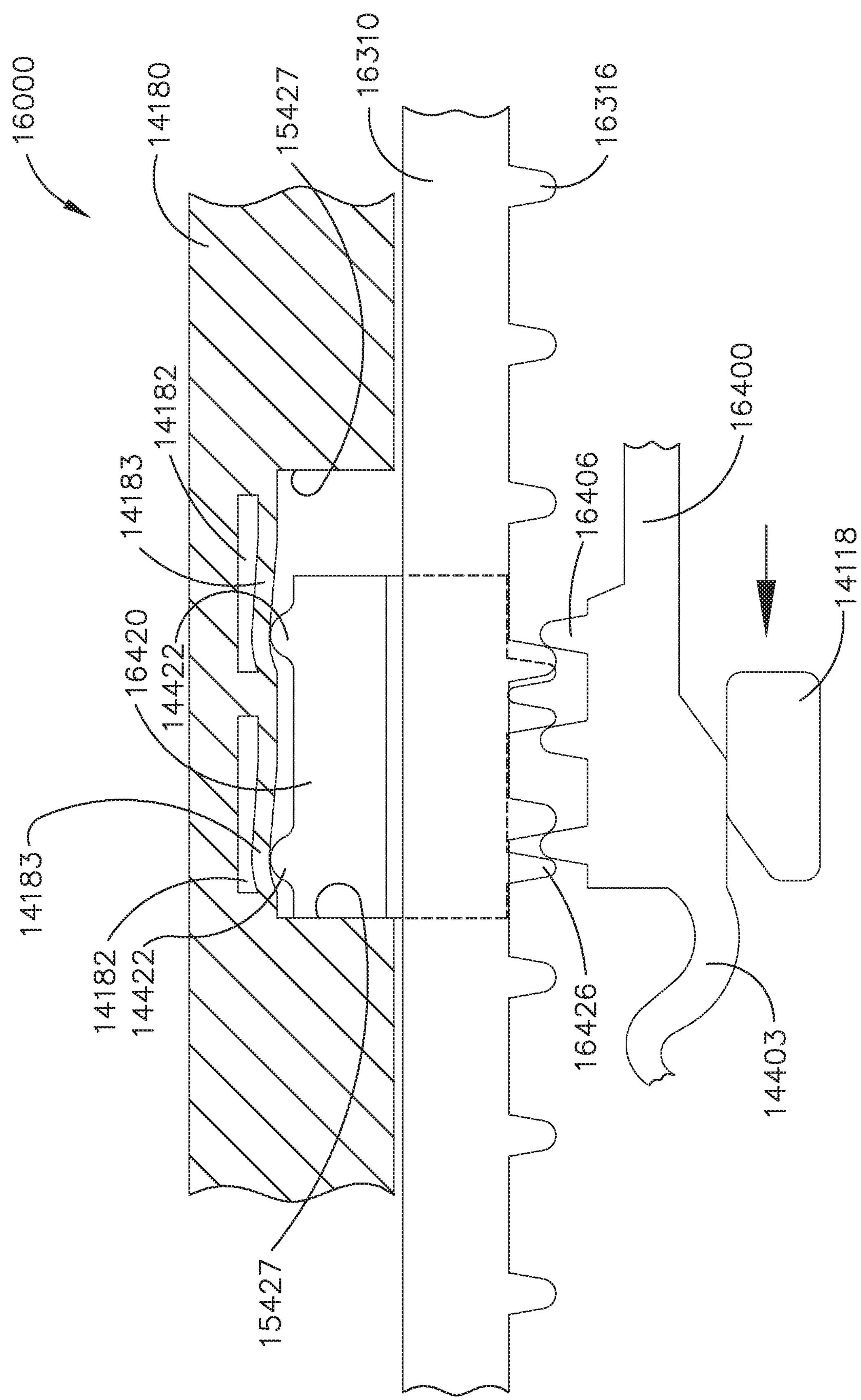
FIG. 52 is a partial cross-sectional view of the end effector of FIG. 50 illustrated in another locked condition.

A surgical instrument 16000 is illustrated in FIGS. 50-52 and is similar to the surgical instruments 14000 and 15000 in many respects, most of which will not be repeated herein for the sake of brevity. Among other things, the surgical instrument 16000 comprises a shaft, an end effector 11500, and an articulation drive system including an articulation driver 16310. Referring primarily to FIG. 50, the surgical instrument 16000 further comprises an articulation locking system including an articulation lock 16400 which is, similar to the above, configurable in a self-locking configuration, an unlocked configuration, and a fully-locked configuration. The articulation locking system further comprises a lock plate 16420 which is similar to the lock plate 14420 in many respects. For instance, the lock plate 16420 is movable laterally into engagement with the wall 14183, as illustrated in FIG. 51. Also, for instance, the lock plate 16420 is movable longitudinally to float into a suitable locked position in which teeth 16426 of the lock plate 16420 are meshed with the teeth 16406 of the articulation lock 16400, as depicted in FIG. 52. Moreover, the teeth 16406 of the articulation lock 16400, the teeth 16426 of the lock plate 16420, and the lock teeth 16316 of the articulation driver 16310 are configured and arranged to provide a plurality of positions, or permutations of positions, in which the articulation lock 16400 can lock the articulation driver 16310 to the lock plate 16420. For instance, the articulation lock system has reached a fully-locked configuration in a set of positions illustrated in FIG. 51 and a fully-locked configuration in a different set of positions illustrated in FIG. 52.

The above-discussed adaptability of the articulation locking system can be achieved via the tooth pitches of the articulation lock teeth 16406, the articulation driver teeth 16316, and the lock plate teeth 16426. For instance, referring primarily to FIG. 50, the articulation lock teeth 16406 are set at a first pitch 16407, the articulation driver teeth 16316 are set at a second pitch 16317, and the lock plate teeth 16426 are set at a third pitch 16427. The first pitch is different than the second pitch and the third pitch—the second pitch is different than the first pitch and the third pitch—and the third pitch is different than the first pitch and the second pitch, although embodiments are envisioned in which two of the first pitch, the second pitch, and the third pitch are the same. Referring again to FIG. 50, the third pitch 16427 of the lock plate teeth 16426 is larger than the second pitch 16317 of the articulation driver teeth 16316, and the second pitch 16317 is larger than the first pitch 16407 of the articulation lock teeth 16406, although any suitable arrangement can be used.

A surgical instrument 17000 is illustrated in FIGS. 53-56 and is similar to the surgical instrument 11000 in many respects, most of which will not be repeated herein for the sake of brevity. The surgical instrument 17000 comprises a shaft, an end effector 11500 rotatably connected to the shaft about an articulation joint 11200, and an articulation drive system configured to articulate the end effector 11500 about the articulation joint 11200. Similar to the above, the articulation drive system comprises an articulation link 17320 rotatably mounted to the jaw 11600 about a pin 11620 and an articulation driver 17310 rotatably mounted to the articulation link 17320 about a pin 17315. The surgical instrument 17000 further comprises an articulation lock 17400 movably mounted to a shaft frame of the surgical instrument 17000 which is movable between an unlocked position and a locked position. The articulation lock 17400 comprises a distal end 17402 fixedly mounted to the shaft frame and a proximal end 17404 slidably mounted to the shaft frame. More specifically, the shaft frame comprises a pin extending into an aperture defined in the distal end 17402 of the articulation lock 17400 and a guide projection 17114 extending into an elongate aperture defined in the proximal end 17404. In certain instances, the shaft frame can comprise two or more pins extending into apertures defined in the distal end 17402 of the articulation lock 17400 to fix the distal end 17402 to the shaft frame and prevent the distal end 17402 from rotating relative to the shaft frame. As a result of the above, at least the proximal end 17404 of the articulation lock 17400 is movable relative to the shaft frame to engage the articulation driver 17310 and lock the articulation system and end effector 11500 in position.

Figure 53A:
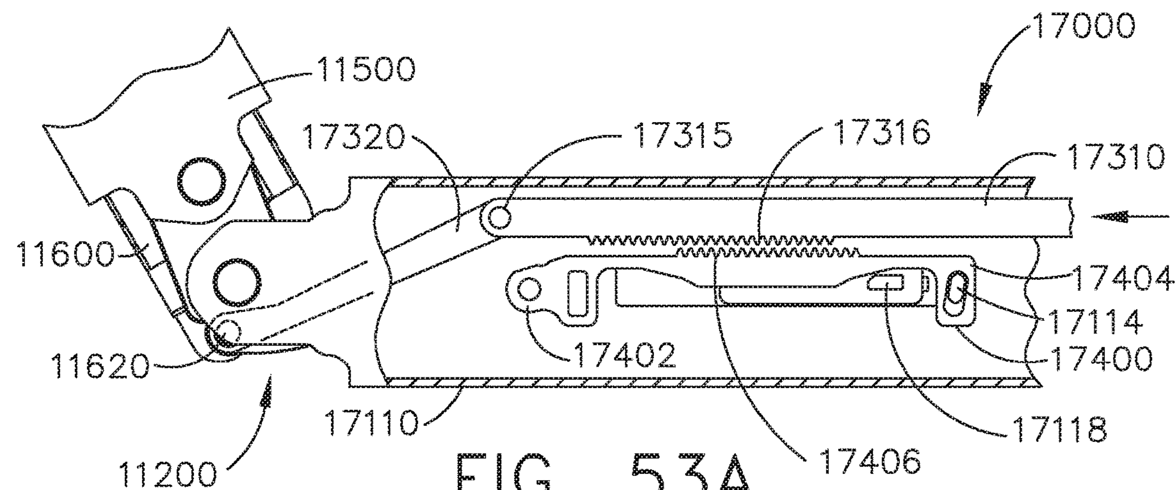
FIG. 53A is a partial cross-sectional view of the end effector of FIG. 53 articulated in a first direction.
Figure 53:
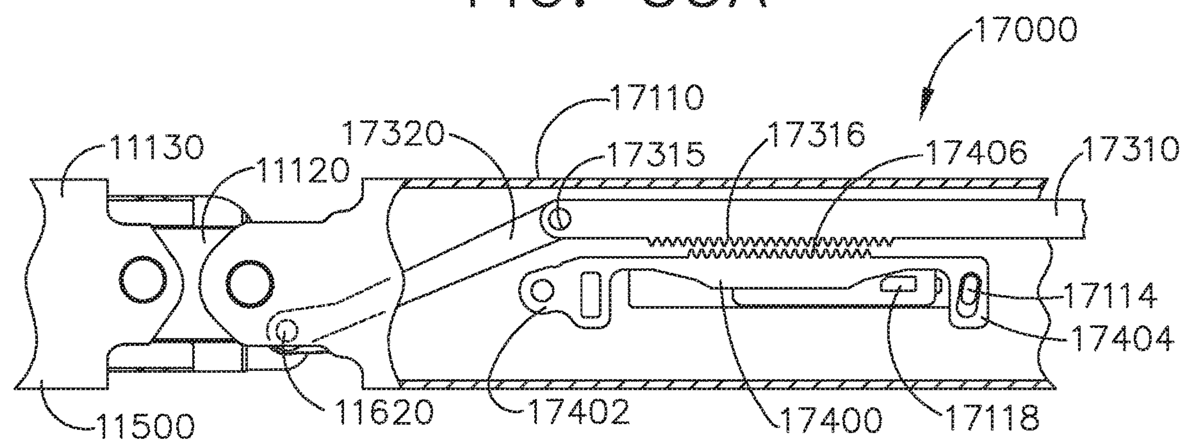
FIG. 53 is a partial cross-sectional view of an end effector comprising an articulation system and an articulation lock in accordance with at least one embodiment illustrated with some components removed.
Figure 53B:
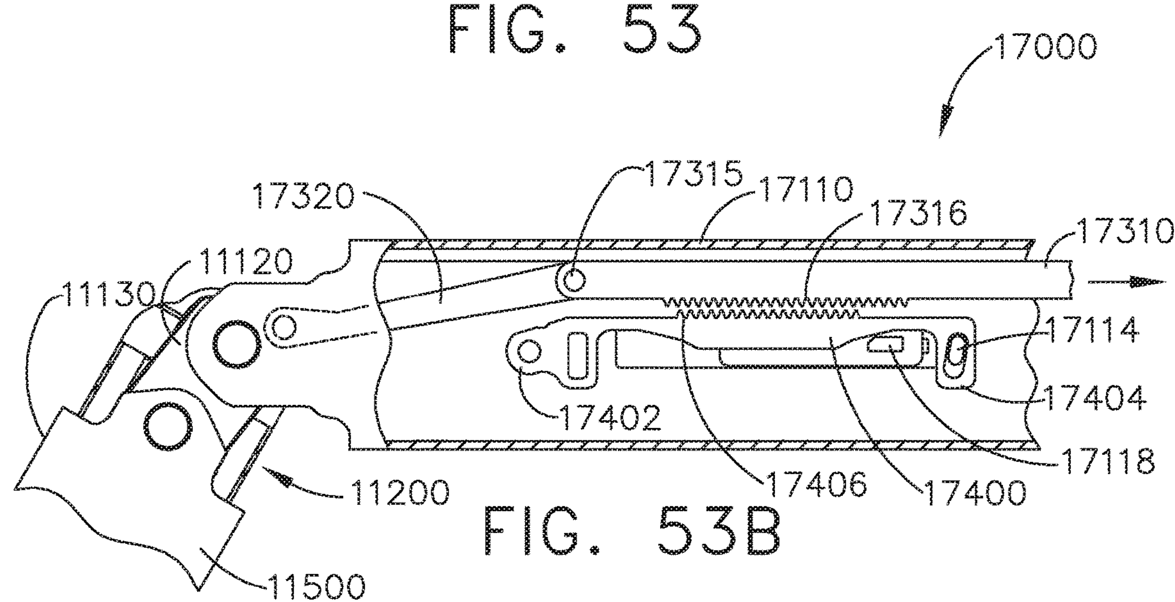
FIG. 53B is a partial cross-sectional view of the end effector of FIG. 53 articulated in a second direction.
Figure 54:
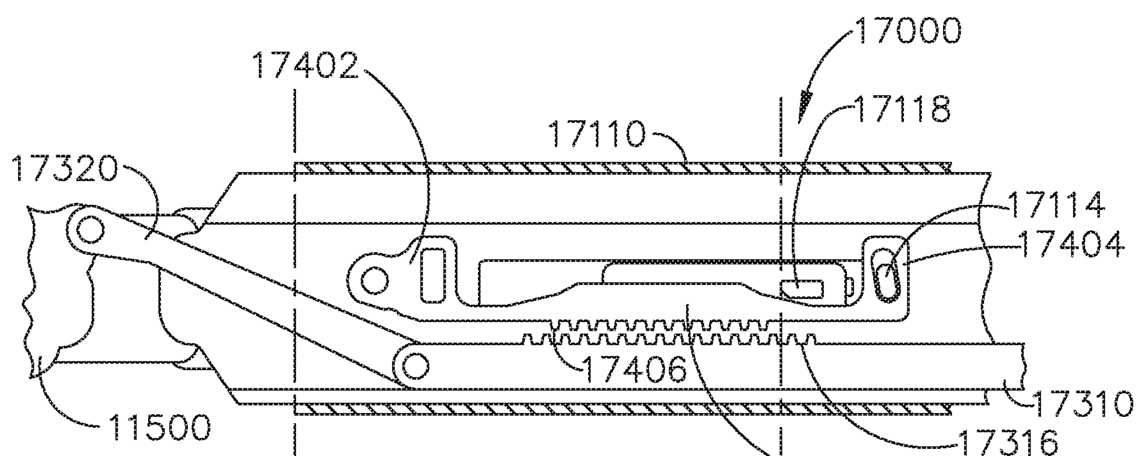
FIG. 54 is a partial cross-sectional view of the end effector of FIG. 53 in an unlocked condition.
Figure 55:
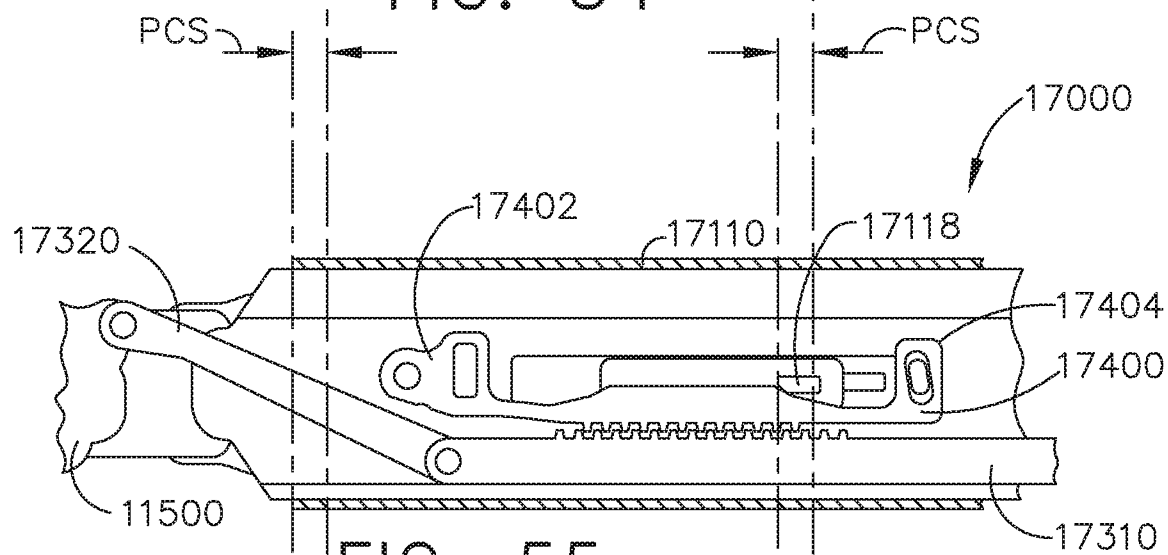
FIG. 55 is a partial cross-sectional view of the end effector of FIG. 53 in a partially-locked condition.
Figure 56:
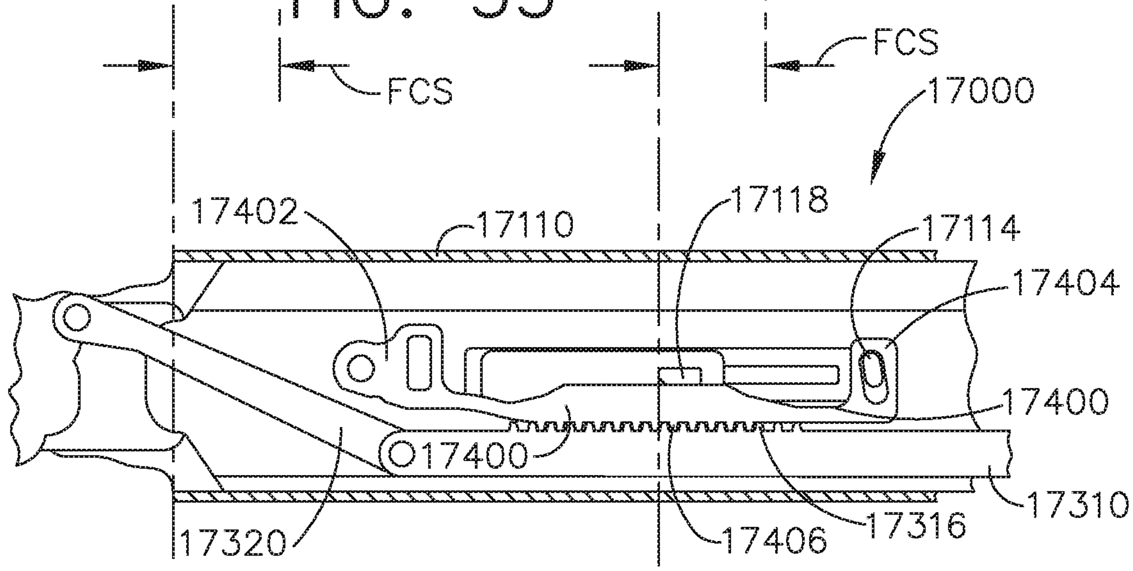
FIG. 56 is a partial cross-sectional view of the end effector of FIG. 53 in a locked condition.

Further to the above, the articulation driver 17310 comprises a longitudinal rack of teeth 17316 defined thereon and the articulation lock 17400 comprises a longitudinal rack of teeth 17406 defined thereon. When the articulation lock 17400 is in its unlocked position, as illustrated in FIGS. 53 and 54, the teeth 17406 of the articulation lock 17400 are not engaged with the teeth 17316 of the articulation driver 17310. In such instances, the articulation driver 17310 can move freely relative to the articulation lock 17400 to articulate the end effector 11500. When the articulation lock 17400 is in a partially-locked position, as illustrated in FIG. 55, the articulation lock teeth 17406 are partially engaged with the articulation driver teeth 17316. In such instances, the proximal and distal movement of the articulation driver 17310 is impeded by the articulation lock 17400; however, the articulation driver 17310 can still move relative to the articulation lock 17400 to articulate the end effector 11500. When the articulation lock 17400 is in a fully-locked position, as illustrated in FIG. 56, the articulation lock teeth 17406 are fully engaged with the articulation driver teeth 17316. In such instances, the proximal and distal movement of the articulation driver 17310, and the articulation of the end effector 11500, is prevented by the articulation lock 17400.

Further to the above, the surgical instrument 17000 does not include a biasing member configured to move the articulation lock 17400 toward the articulation driver 17310 other than a closure member, or tube, 17110. The closure tube 17110 is configured to engage the articulation lock 17400 and move the articulation lock 17400 from its unlocked position (FIG. 54) to its partially-locked (FIG. 55) and fully-locked positions (FIG. 56). Similar to the above, the closure tube 17110 comprises a cam 17118 configured to engage a cam surface defined on the articulation lock 17400, although other arrangements can be used. The closure tube 17110 is configured to move the articulation lock 17400 between its unlocked position and its partially-locked position when the closure tube 17110 is moved distally through a partial closing stroke (PCS) which at least partially closes the end effector 11500. In such instances, the end effector 11500 of the surgical instrument 17000 can be used to grasp the tissue of a patient, for example. The closure tube 17110 is configured to move the articulation lock 17400 into its fully-locked position when the closure tube 17110 is moved distally through a full closing stroke (FCS) which completely closes the end effector 11500. In such instances, the end effector 11500 of the surgical instrument 17000 can be used to fully clamp the tissue of a patient, for example.

Figure 57:
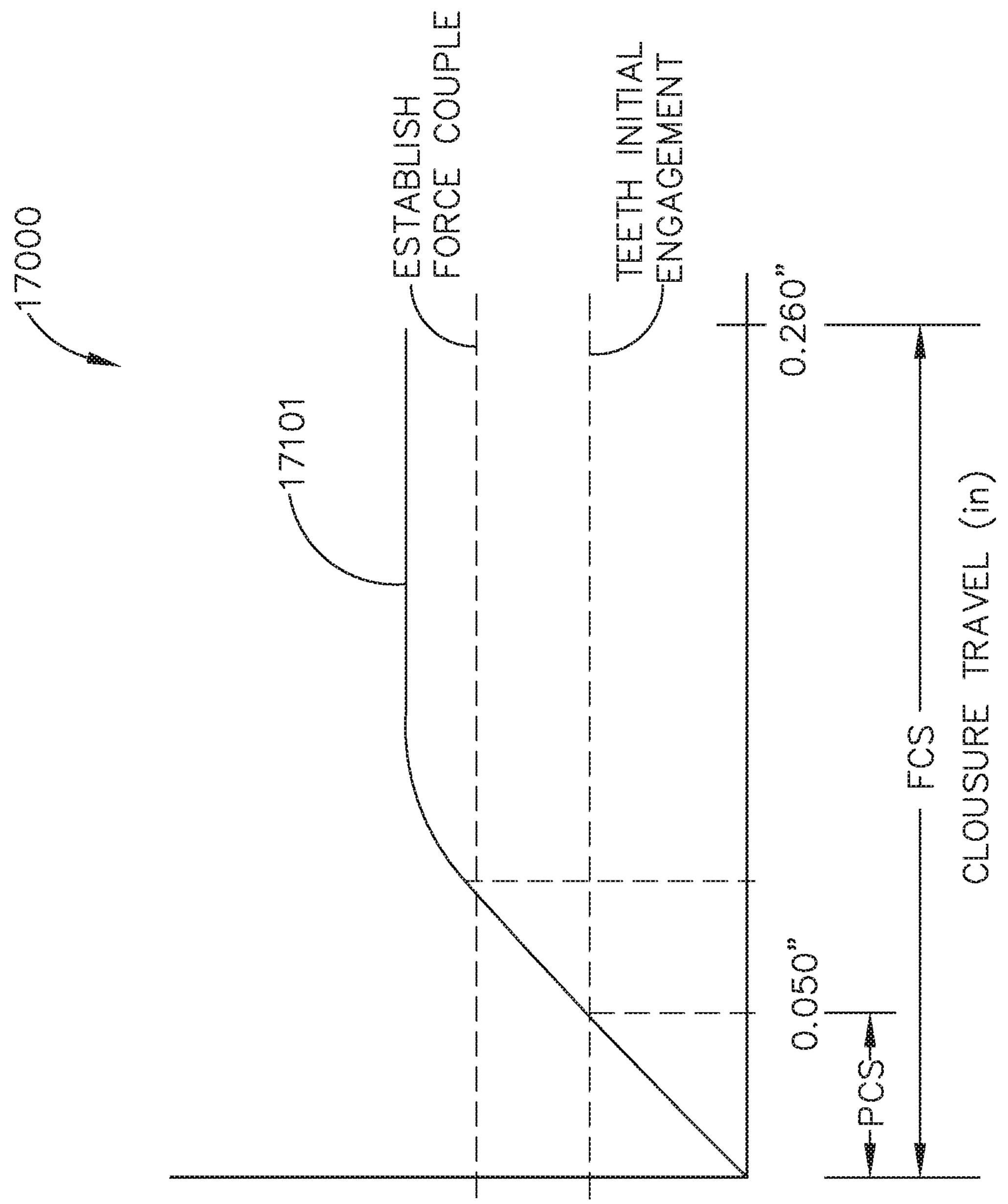
FIG. 57 is a chart illustrating the gradual locking of the end effector of FIG. 53.

As discussed above, the locking force applied to the articulation driver 17310 by the articulation lock 17400 increases as the closure tube 17110 is advanced distally. Stated another way, the articulation locking force is a function of the closure tube 17110 stroke. Further to the above, turning now to FIG. 57, the locking force between the articulation driver 17310 and the articulation lock 17400 is represented by line 17101. As illustrated in FIG. 57, the articulation lock teeth 17406 become initially engaged with the articulation driver teeth 17316 during the partial closure stroke. In at least one instance, such initial engagement of the teeth 17406 and 17316 occurs after approximately 0.050" of closure stroke of the closure tube 17110, although any suitable distance can be used. Notably, such initial engagement of the teeth 17406 and 17316 does not necessarily coincide with the end of the partial closing stroke; rather, it can occur at some point during the partial closure stroke (PCS). It also occurs at some point during the full closure stroke (FCS). Such an initial engagement, however, does not comprise a locking force couple. Instead, a locking force couple between the teeth 17406 and 17316 is only established at some during the full closing stroke (FCS). In at least one instance, the full closing stroke (FCS) has a length of approximately 0.260", for example.

Figure 58:
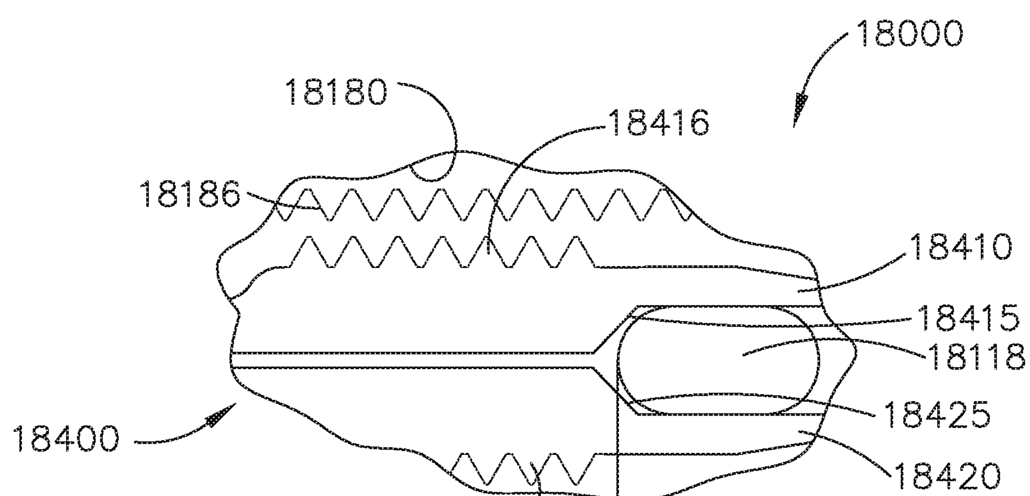
FIG. 58 is a partial cross-sectional view of an end effector comprising an articulation system and an articulation lock in accordance with at least one embodiment illustrated with some components removed.
Figure 59:
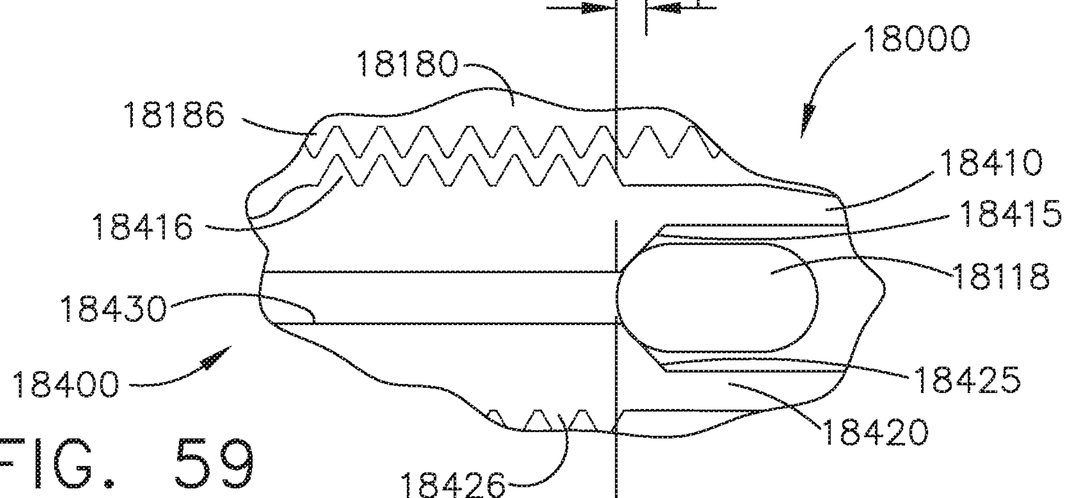
FIG. 59 is a partial cross-sectional view of the end effector of FIG. 58 illustrated in a partially-locked condition.
Figure 60:
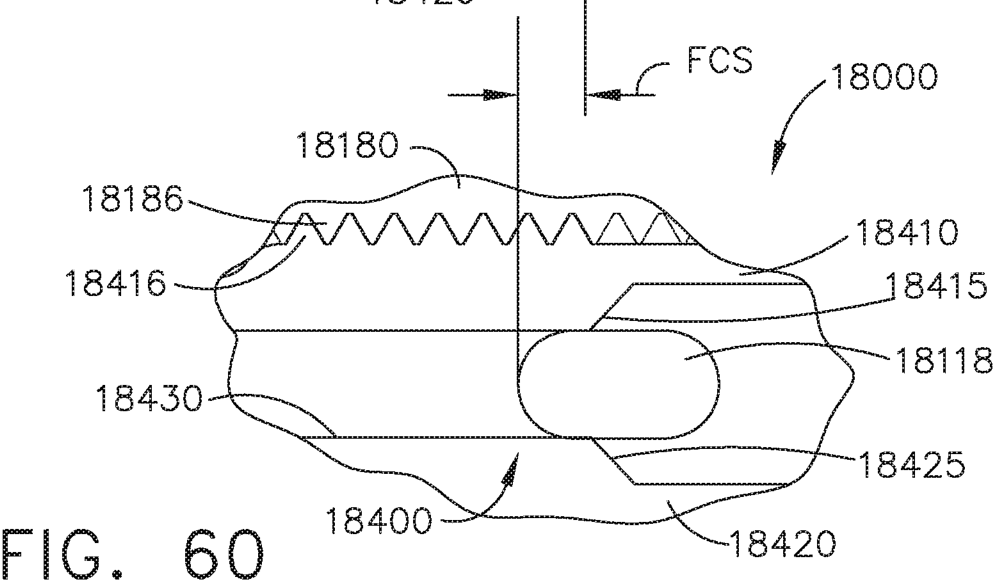
FIG. 60 is a partial cross-sectional view of the end effector of FIG. 58 in a locked condition.

A surgical instrument 18000 is illustrated in FIGS. 58-60 and is similar to the surgical instruments 11000 and 17000 in many respects, most of which will not be repeated herein for the sake of brevity. The surgical instrument 18000 comprises a shaft, an end effector 11500 rotatably connected to the shaft about an articulation joint, and an articulation system configured to articulate the end effector 11500. The shaft comprises a frame 18180 including first and second longitudinal racks of teeth 18186 which are parallel, or at least substantially parallel, to one another, although the racks of teeth 18186 can extend transversely to one another. The surgical instrument 18000 further comprises an articulation lock 18400 and a closure member including a cam 18118. The articulation lock 18400 includes a first lock arm 18410 configured to engage the first longitudinal rack of teeth 18186 and a second lock arm 18420 configured to engage the second longitudinal rack of teeth 18186. Referring primarily to FIGS. 59 and 60, the first lock arm 18410 comprises a first cam surface 18415 defined thereon and the second lock arm 18420 comprises a second cam surface 18425 defined thereon which are configured to be contacted by the cam 18118 during a closure stroke of the closure member and displaced or flexed outwardly into a fully-locked engagement with the longitudinal racks of teeth 18186. Moreover, one or both of the lock arms 18410 and 18420 also engage the articulation system to lock the end effector 11500 in place when the lock arms 18410 and 18420 are displaced outwardly into engagement with the shaft frame 18180.

Once displaced or flexed into their fully-locked states, the lock arms 18410 and 18420 define a longitudinal slot 18430 there between which is configured to permit the cam 18118 to pass thereby during the remainder of the closure stroke, for example. Moreover, in such instances, the cam 18118 wedges the articulation lock 18400 into engagement with the frame 18180 and securely holds the lock arms 18410 and 18420 in their fully-locked positions.

In at least one alternative embodiment, further to the above, the first lock arm 18410 of the articulation lock 18400 can be configured to engage the shaft frame 18180 of the surgical instrument 18000 while the second lock arm 18420 of the articulation lock 18400 can be configured to engage the articulation system of the surgical instrument 18000.

Figure 61:
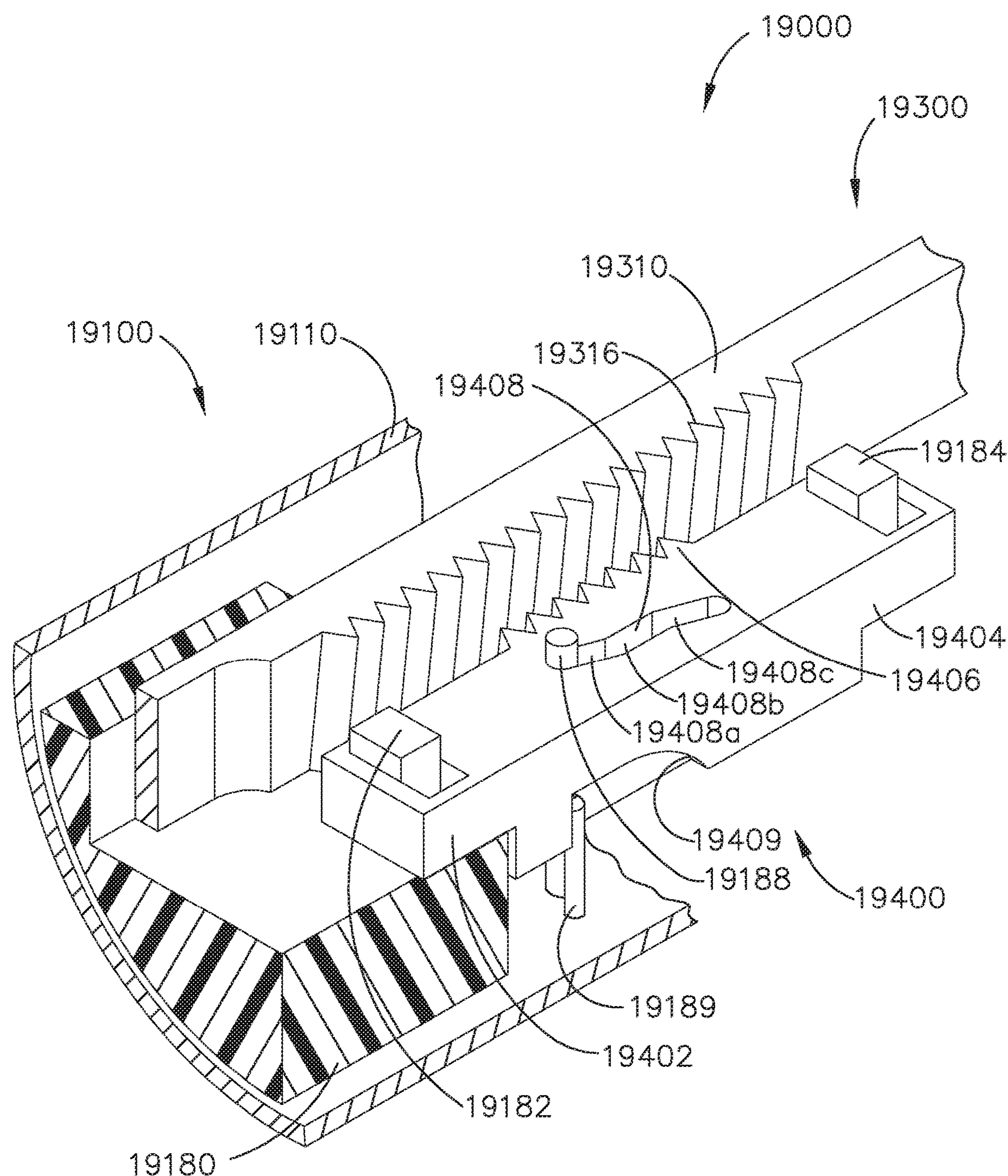
FIG. 61 is a partial cross-sectional view of an end effector comprising an articulation system and an articulation lock in accordance with at least one embodiment illustrated with some components removed.
Figure 62:
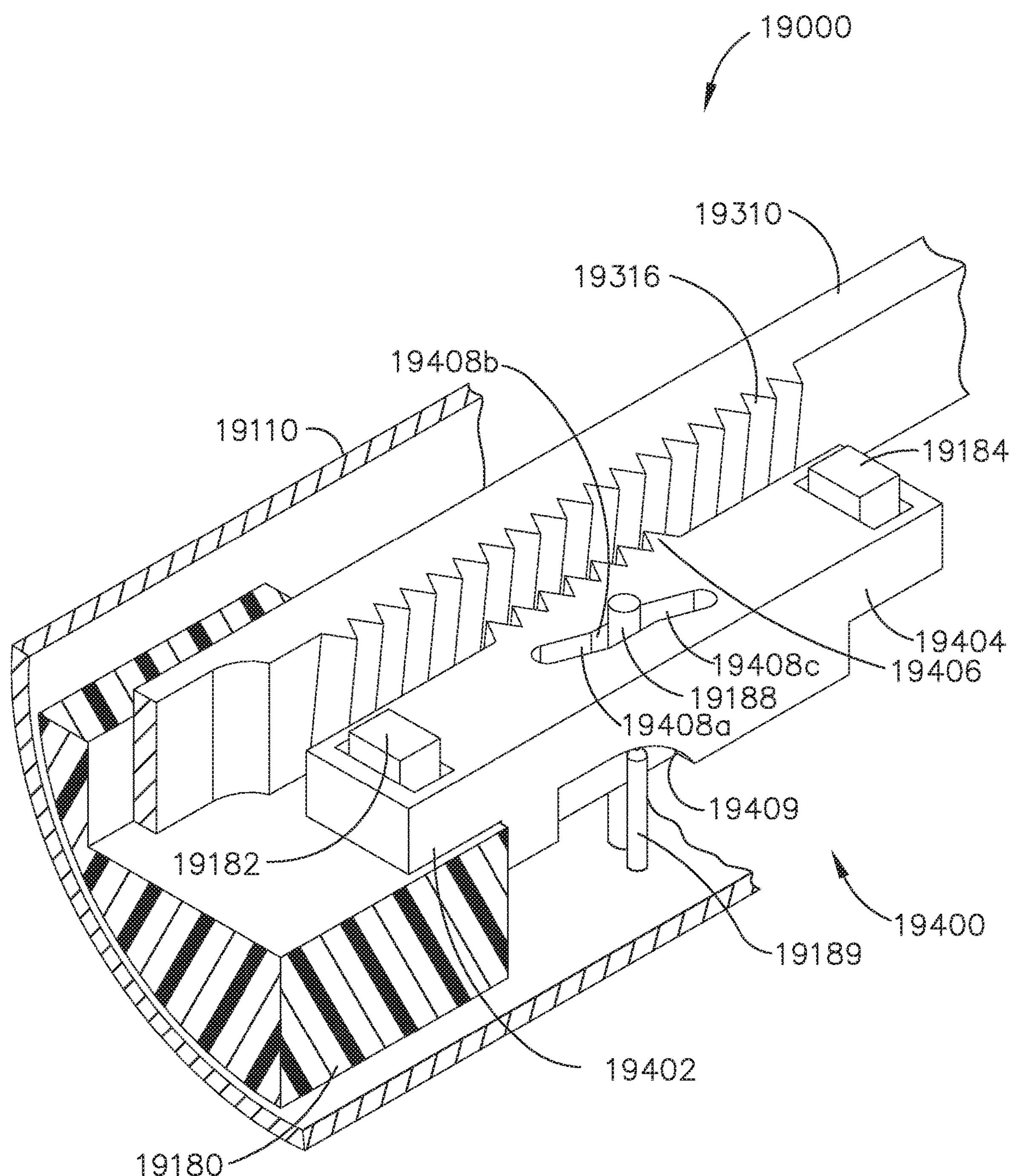
FIG. 62 is a partial cross-sectional view of the end effector of FIG. 61 illustrating the articulation lock being moved toward the articulation system.
Figure 63:
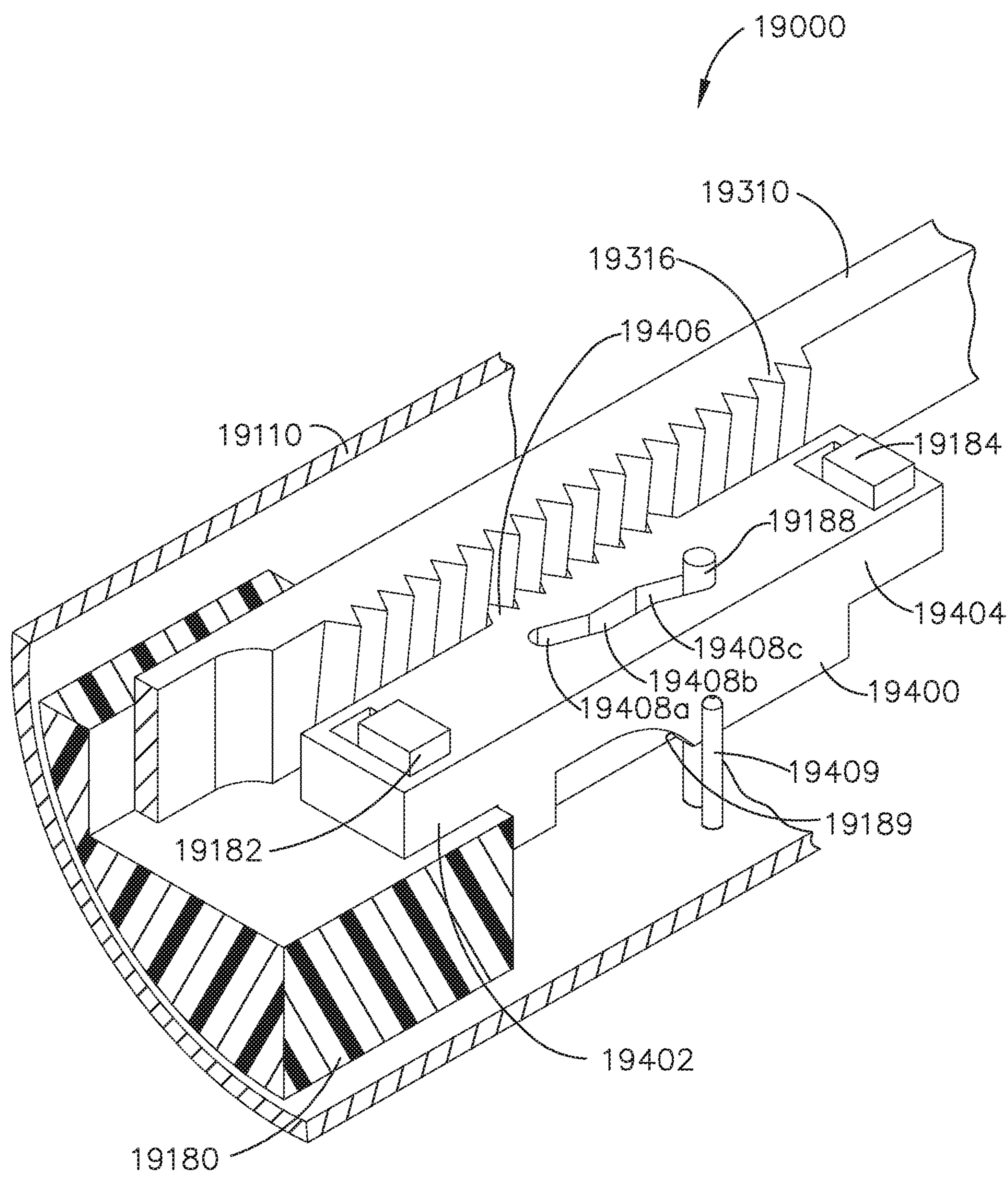
FIG. 63 is a partial cross-sectional view of the end effector of FIG. 61 illustrating the articulation lock engaged with the articulation system.
Figure 64:
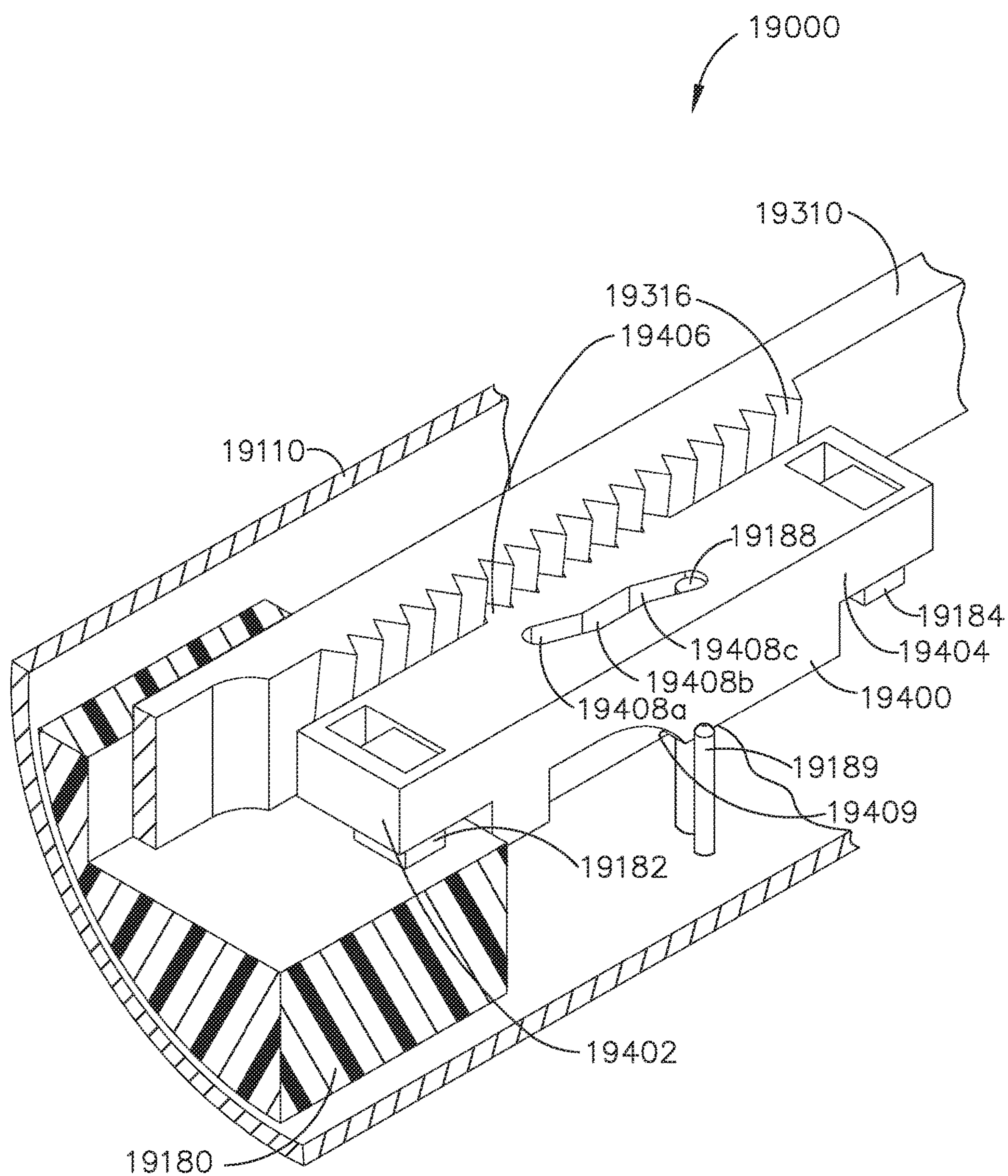
FIG. 64 is a partial cross-sectional view of the end effector of FIG. 61 illustrating the articulation lock in a locked condition.
Figure 65:
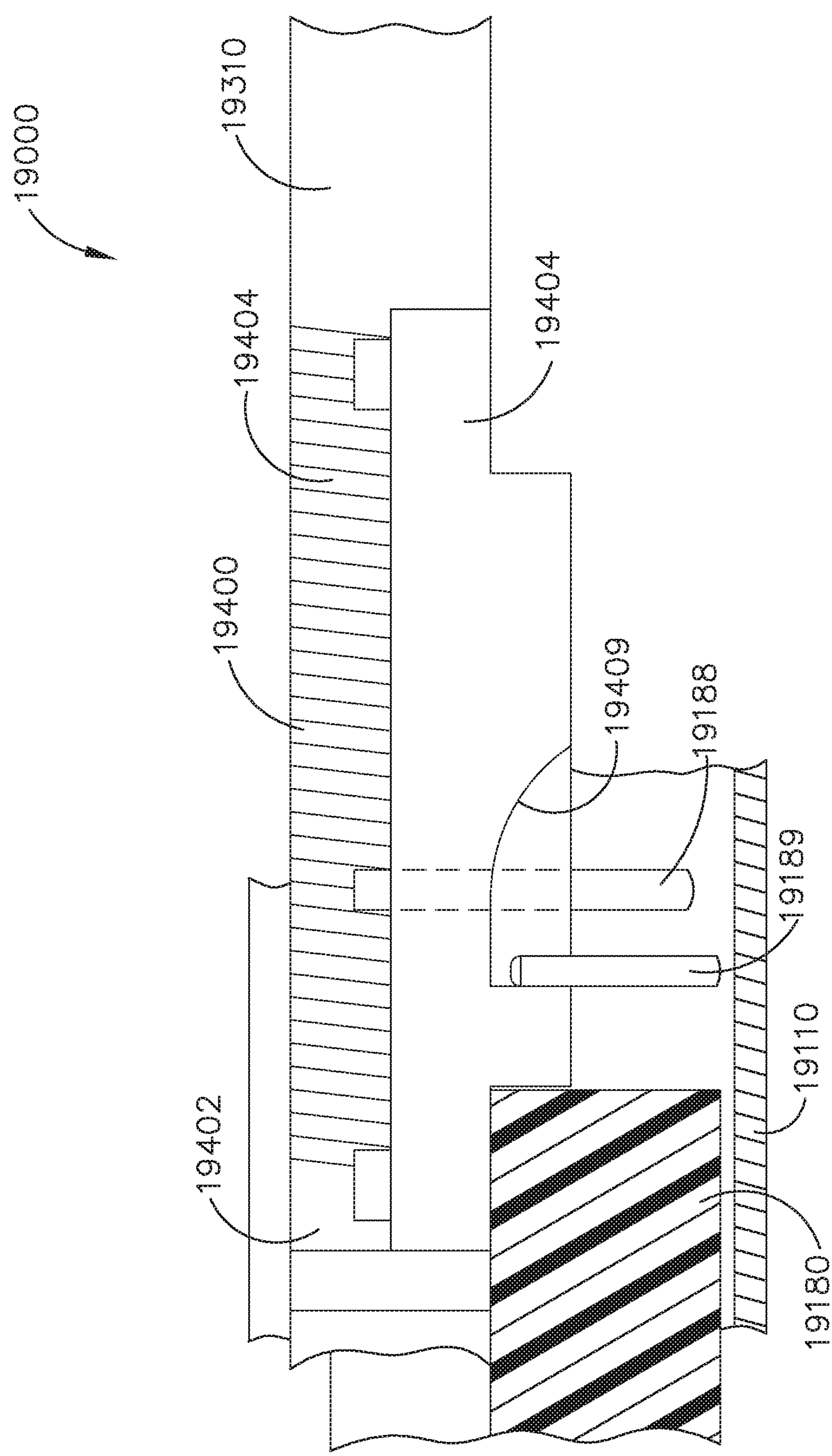
FIG. 65 is another partial cross-sectional view of the end effector of FIG. 61 illustrating the articulation lock in its locked condition.

A surgical instrument 19000 is illustrated in FIGS. 61-65 and is similar to the surgical instrument 11000 in many respects, most of which will not be repeated herein for the sake of brevity. The surgical instrument 19000 comprises a shaft 19100 including a closure member 19110, an end effector 11500 rotatably connected to the shaft 19100 about an articulation joint 11200, and an articulation drive system 19300 including an articulation driver 19310 configured to articulate the end effector 11500 about the articulation joint 11200. Referring primarily to FIG. 61, the surgical instrument 19000 further comprises an articulation lock 19400 configured to selectively engage the articulation drive system 19300 and lock the end effector 11500 in position. The shaft 19100 further comprises a frame 19180 and the articulation lock 19400 is movably mounted to the frame 19180 between an unlocked position (FIG. 61), a partially-locked position (FIG. 63), and a locked position (FIG. 64). As described in greater detail below, the articulation lock 19400 is movable laterally toward the articulation driver 19310 to bring the articulation lock 19400 into close approximation with the articulation driver 19310 (FIG. 63) and, also, transversely into interference with the articulation driver 19310 (FIG. 64).

Further to the above, the shaft frame 19180 comprises a proximal guide post 19182 and a distal guide post 19184. The proximal guide post 19182 extends into a lateral elongate slot defined in a proximal end 19402 of the articulation lock 19400 and, similarly, the distal guide post 19184 extends into a lateral elongate slot defined in a distal end 19404 of the articulation lock 19400. The lateral elongate slots permit the articulation lock 19400 to move laterally toward and away from the articulation driver 19310, as outlined above. The lateral elongate slots also define the lateral path of the articulation lock 19400 and prevent, or at least substantially prevent, longitudinal movement of the articulation lock 19400 relative to the shaft frame 19180. As a result, the elongate slots of the articulation lock 19400 can guide the articulation lock 19400 between an unlocked position (FIG. 61) in which the lock teeth 19406 of the articulation lock 19400 are not engaged with a longitudinal rack of teeth 19316 defined on the articulation driver 19310, a partially-locked position (FIG. 63) in which the lock teeth 19406 are partially engaged with the teeth 19316, and a fully-locked position (FIG. 64) in which the lock teeth 19406 are fully engaged with the teeth 19316.

Further to the above, the articulation lock 19400 further comprises a longitudinal cam slot 19408 defined therein and the closure member 19110 comprises a cam pin 19188 positioned in the cam slot 19408. When the closure member 19110 is in an unactuated, or open, position (FIG. 61), the cam pin 19188 is positioned in a proximal portion 19408*a* of the cam slot 19408. When the closure member 19110 is moved distally into a partially-actuated, or partially-closed, position, as illustrated in FIG. 62, the cam pin 19188 is moved into a central portion 19408*b* of the cam slot 19408. In such instances, the cam pin 19188 displaces the articulation lock 19400 toward the articulation driver 19310. In such instances, however, the teeth 19406 of the articulation lock 19400 may not be engaged with the teeth 19316 of the articulation driver 19310 and, as a result, the articulation driver 19310 can still be moved to articulate the end effector 11500 relative to the shaft 19100. As a result, the end effector 11500 can be articulated when the closure stroke of the closure member 19110 has only been partially completed.

When the closure member 19110 is moved further distally, as illustrated in FIG. 63, the cam pin 19188 is moved into a distal portion 19408*c* of the cam slot 19408. In such instances, the cam pin 19188 displaces the articulation lock 19400 into close approximation with the articulation driver 19310 and into partial intermeshment with the teeth 19316 of the articulation driver 19310. That said, such partial intermeshment between the teeth 19406 and 19316 can only resist a certain amount of force transmitted through the articulation driver 19310 and such resistance can be overcome to move the articulation driver 19310 relative to the articulation lock 19400 and articulate the end effector 11500.

Further to the above, the articulation lock 19400 is not transversely lifted or lowered relative to the shaft frame 19180 during the partial closure stroke of the closure member 19110 (FIGS. 61-63). Rather, the articulation lock 19400 is lifted upwardly such that teeth 19406 of the articulation lock 19400 fully engage the teeth 19316 of the articulation driver 19310 and lock the articulation driver 19310 in position during the final or last portion of the closure stroke of the closure member 19110, as illustrated in FIG. 64. The articulation lock 19400 is moved upwardly by a different cam pin extending from the closure member 19110, i.e., cam pin 19189 which engages the articulation lock 19400 at the end of the closure stroke of the closure member 19110. Notably, the cam pin 19189 is not engaged with the articulation lock 19400 at the beginning of the closure stroke or during the partial closure stroke of the closure member 19110. At most, the cam pin 19189 may slidingly touch the bottom of the articulation lock 19400 during the partial closure stroke. That said, referring primarily to FIG. 65, the articulation lock 19400 comprises a cut-out, or recess, 19409 defined therein which provides clearance between the cam pin 19189 and the articulation lock 19400 during the partial closure stroke. That said, the cam pin 19189 comes into contact with the articulation lock 19400 when the cam pin 19189 reaches the end of the recess 19409 and, in such instances, drives the articulation lock 19400 transversely upwardly such that the lock teeth 19406 interferingly engage with the teeth 19316 of the articulation driver 19310 and the articulation lock 19400 is placed in its fully-locked position, as illustrated in FIG. 64. At such point, the articulation driver 19310 is locked in position and cannot be moved longitudinally to articulate the end effector 11500.

Referring again to FIG. 65, the teeth 19316 of the articulation driver 19310 are angled, or tilted, relative to the longitudinal axis of the shaft 19100. The lock teeth 19406 of the articulation lock 19400 are not angled, or are angled at a different orientation than the teeth 19316. As a result, the lock teeth 19406 of the articulation lock 19400 can be partially engaged with the teeth 19316 of the articulation driver 19310 when the articulation lock 19400 is in its lowered position (FIG. 63) and fully engaged with the teeth 19316 when the articulation lock 19400 is in its raised position (FIG. 64).

In order to unlock the articulation system 19300 of the surgical instrument 19000, the closure member 19110 must be retracted to disengage the cam pin 19189 from the articulation lock 19400 so that the articulation lock 19400 can return to its lowered position. Once the cam pin 19189 has been disengaged from the articulation lock 19400, the proximal retraction of the cam pin 19188 can drive the articulation lock 19400 downwardly as the cam pin 19188 is pulled proximally through cam slot 19408. Moreover, the cam pin 19188 can displace the articulation lock 19400 away from the articulation driver 19310 when it is pulled proximally. In various embodiments, the shaft 19110 can comprise one or more biasing members, such as springs, for example, configured to bias or push the articulation lock 19400 downwardly to quickly reset the articulation lock to an unlocked position.

Figure 66:
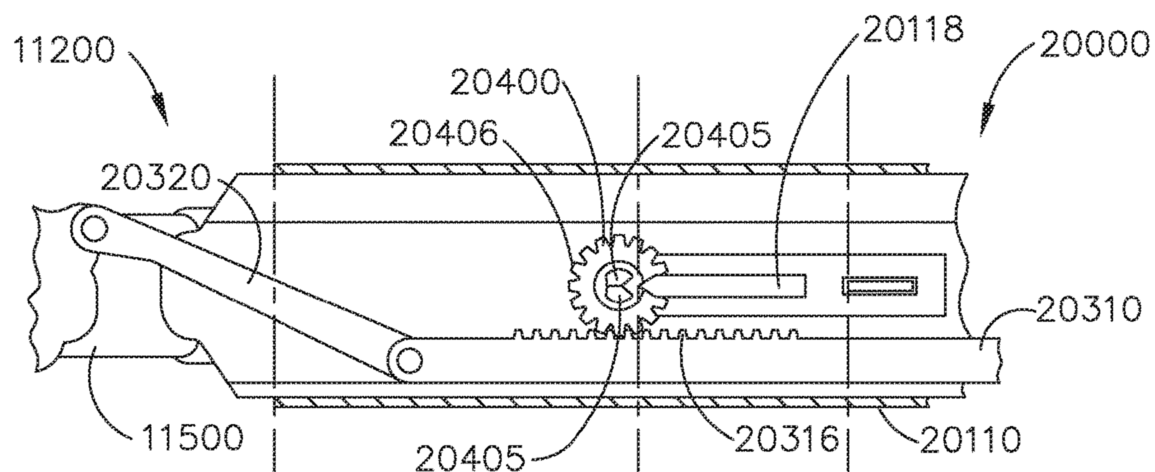
FIG. 66 is a partial cross-sectional view of an end effector comprising an articulation system and an articulation lock in accordance with at least one embodiment illustrated with some components removed.
Figure 67:
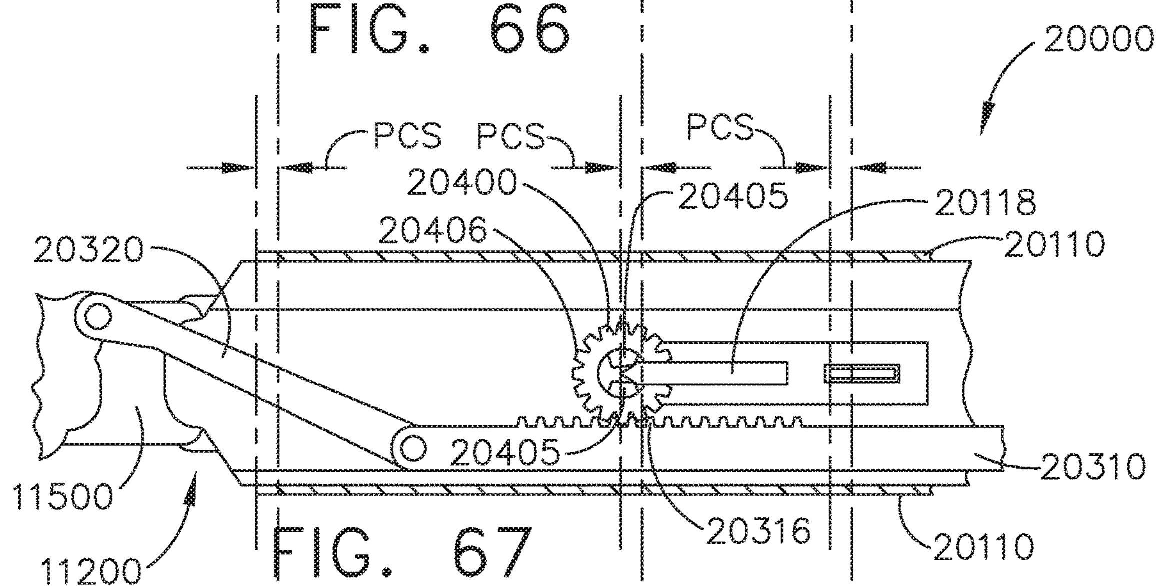
FIG. 67 is a partial cross-sectional view of the end effector of FIG. 66 illustrating the articulation lock engaged with the articulation system.
Figure 68:
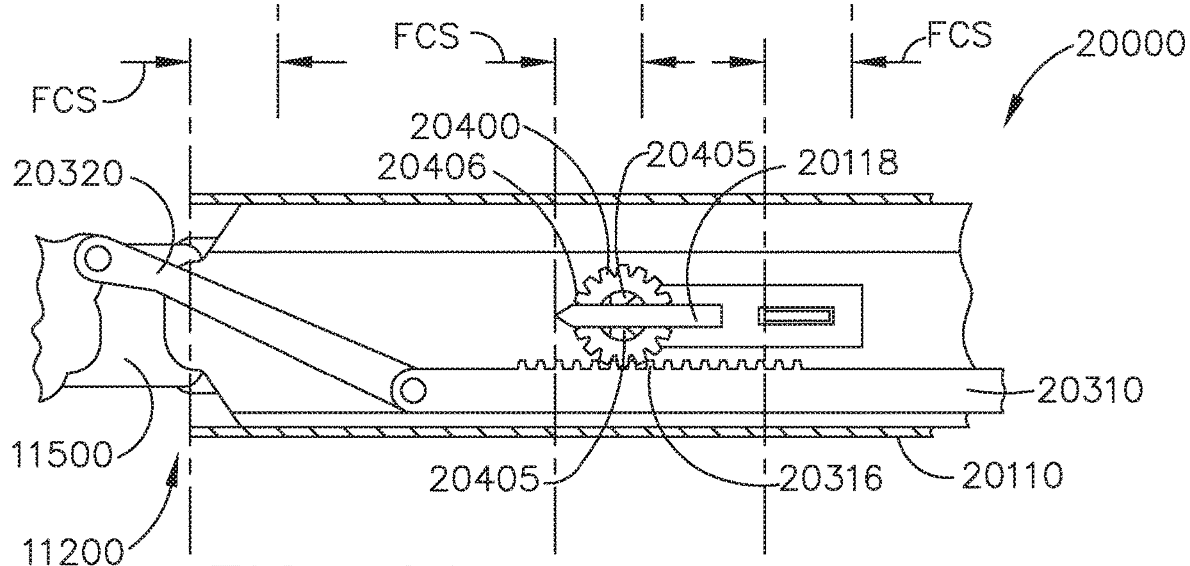
FIG. 68 is a partial cross-sectional view of the end effector of FIG. 66 illustrating the articulation lock in a locked condition.

A surgical instrument 20000 is illustrated in FIGS. 66-68 and is similar to the surgical instruments 11000, 17000, 18000, and 19000 in many respects, most of which will not be repeated herein for the sake of brevity. The surgical instrument 20000 comprises a shaft including a closure tube 20110, an end effector 11500 rotatably mounted to the shaft about an articulation joint 11200, and an articulation system configured to articulation the end effector 11500 relative to the shaft. Similar to the above, the articulation system comprises an articulation link 20320 rotatably pinned to the end effector 11500 and, in addition, an articulation actuator 20310 rotatably pinned to the articulation link 20320. In use, the articulation actuator 20310 is moved proximally and/or distally to drive the articulation link 20320 and articulate the end effector 11500. The surgical instrument 20000 further comprises an articulation lock system comprising an articulation lock gear 20400 rotatably mounted to a frame of the shaft about a fixed axis. The articulation lock gear 20400 comprises an annular array of teeth 20406 which is meshingly engaged with a longitudinal array of teeth 20316 defined on the articulation actuator 20310. As a result, referring generally to FIG. 66, the articulation lock gear 20400 will rotate in response to the proximal and/or distal movement of the articulation actuator 20310 until the articulation lock gear 20400 is locked in position by the closure tube 20110, as illustrated in FIG. 68.

Further to the above, the articulation lock system further comprises lock arms 20405 extending from the shaft frame into a central aperture defined in the articulation lock gear 20400 and, when the closure tube 20110 is moved distally during a closure stroke to close the end effector 11500, a cam, or wedge, 20118 of the closure tube 20110 is configured to engage the lock arms 20405 and splay the lock arms 20405 outwardly into engagement with the articulation lock gear 20400. Once the lock arms 20405 are engaged with the articulation lock gear 20400, the lock arms 20405 can prevent the rotation of the articulation lock gear 20400 and, also, the longitudinal movement of the articulation actuator 20310. In such instances, the lock arms 20405 can prevent, or at least substantially prevent, the articulation of the end effector 11500 until the wedge 20118 of the closure tube 20110 is retracted proximally during an opening stroke and the lock arms 20405 resiliently return to their unflexed, or unlocked, configurations.

Further to the above, the articulation system of the surgical instrument 20000 can be placed in an unlocked configuration (FIG. 66), a partially-locked configuration (FIG. 67), and a fully-locked configuration (FIG. 68). The articulation system can be placed in its partially-locked configuration (FIG. 67) when the closure tube 20110 is advanced distally through a partial closing stroke (PCS). In such instances, the end effector 11500 is at least partially closed but can still be articulated even though the lock arms 20405 may be partially engaged with the articulation lock gear 20400. More particularly, the articulation lock gear 20400 can still rotate despite drag created by the partial engagement of the lock arms 20405 against the articulation lock gear 20400. In at least one instance, the PCS is approximately 0.050", for example. The articulation system can be placed in its fully-locked configuration (FIG. 68) when the closure tube 20110 is advanced distally through a full closure stroke (FCS). In such instances, the end effector 11500 is completely closed and cannot be articulated until the articulation system is returned to its partially-locked and/or unlocked configurations.

Figure 69:
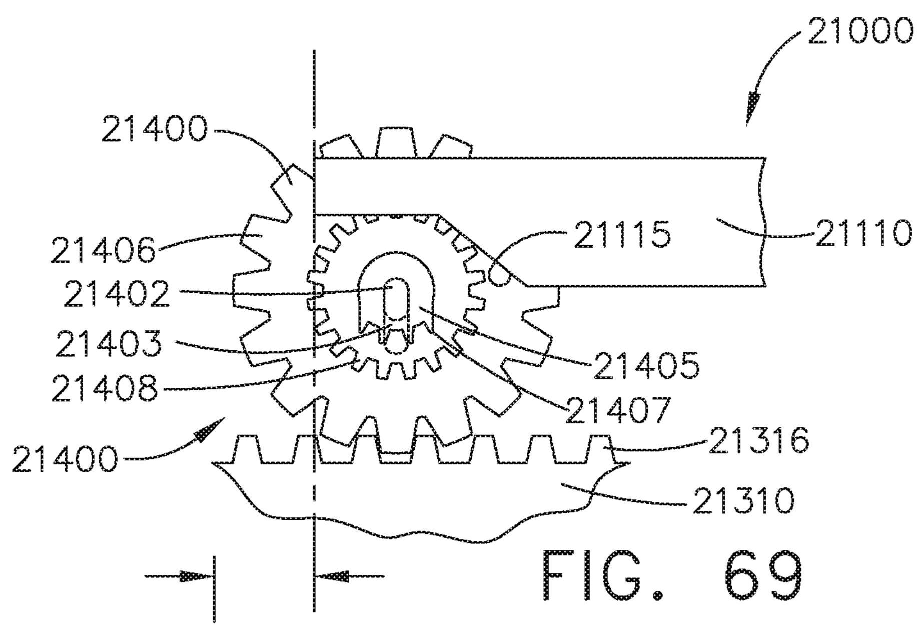
FIG. 69 is a partial cross-sectional view of an end effector comprising an articulation system and an articulation lock in accordance with at least one embodiment illustrated with some components removed.
Figure 70:
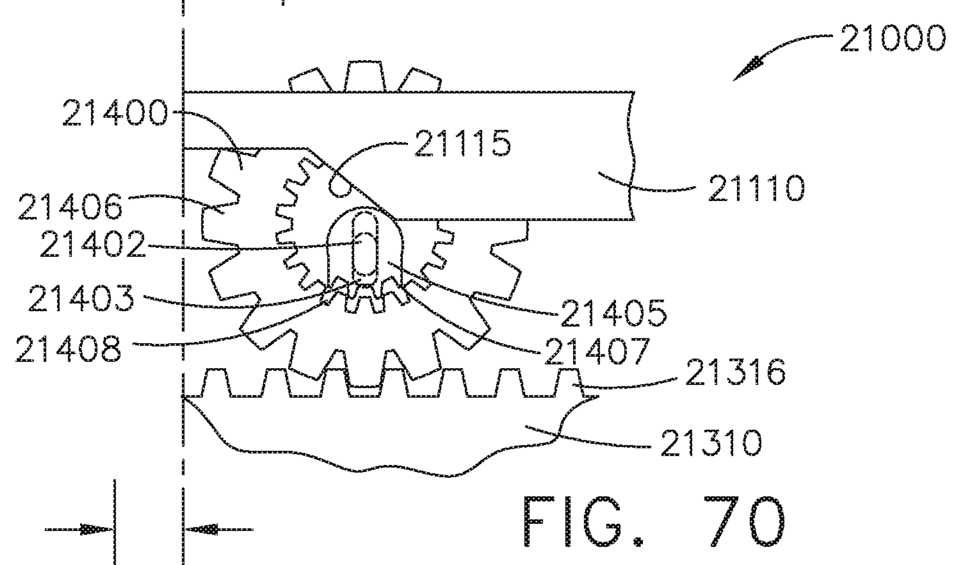
FIG. 70 is a partial cross-sectional view of the end effector of FIG. 69 illustrating the articulation lock being moved toward the articulation system.
Figure 71:
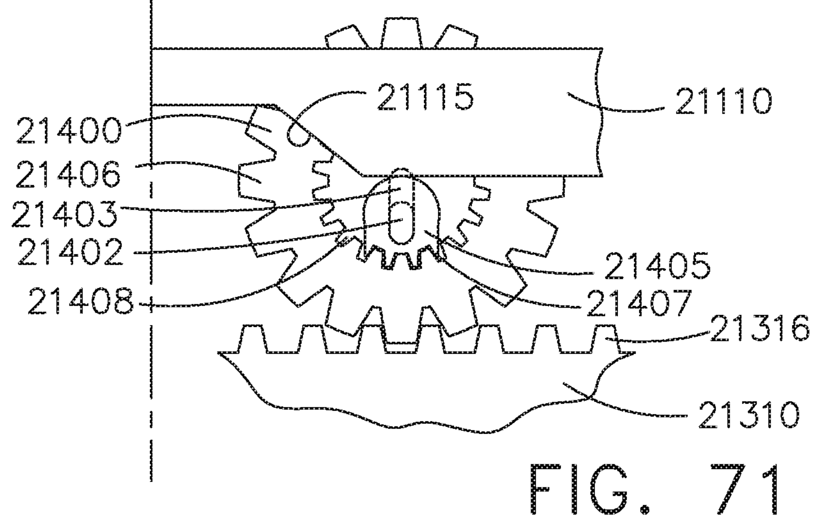
FIG. 71 is a partial cross-sectional view of the end effector of FIG. 69 illustrating the articulation lock in a locked condition.

A surgical instrument 21000 is illustrated in FIGS. 69-71 and is similar to the surgical instruments 11000, 17000, 18000, 19000, and 20000 in many respects, most of which will not be repeated herein for the sake of brevity. The surgical instrument 21000 comprises a shaft including a closure member 21110, an end effector 11500 rotatably mounted to the shaft about an articulation joint 11200, and an articulation system including an articulation actuator 21130 configured to articulate the end effector 11500 relative to the shaft. The surgical instrument 21000 further comprises an articulation lock system comprising an articulation lock gear 21400 rotatably mounted to a frame of the shaft about a fixed axis. The articulation lock gear 21400 comprises an annular array of teeth 21406 which is meshingly engaged with a longitudinal array of teeth 21316 defined on the articulation actuator 21310. As a result, referring generally to FIG. 69, the articulation lock gear 21400 rotates in response to the proximal and/or distal longitudinal movement of the articulation actuator 21310 until, as described in greater detail below, the articulation lock gear 21400 is locked in position by the closure member 21110 (FIG. 71).

Further to the above, the articulation lock system of the surgical instrument 21000 further comprises a movable lock element 21405 which is slidably mounted to the shaft frame. More specifically, referring primarily to FIG. 69, the lock element 21405 comprises a guide projection 21402 extending therefrom which extends into a lateral elongate slot 21403 defined in the shaft frame which is configured to permit the lock element 21405 to slide laterally toward and/or away from the articulation driver 21310. Moreover, referring primarily to FIG. 70, the lock element 21405 slides laterally within an aperture defined in the articulation lock gear 21400 between an unlocked position (FIG. 69) and a locked position (FIG. 71). The lock element 21405 comprises an annular array of lock teeth 21407 and the articulation lock gear 21400 comprises an annular array of lock teeth 21408 defined around the inner aperture thereof and, when the lock element 21405 is in its unlocked position (FIG. 69), the lock teeth 21407 of the lock element 21405 are not engaged with the lock teeth 21408 of the articulation lock gear 21400. When the lock element 21405 is in its locked position (FIG. 71), the lock teeth 21407 of the lock element 21405 are engaged with the lock teeth 21408 of the articulation lock gear 21400 such that the articulation lock gear 21400 cannot rotate and, as a result, the articulation actuator 21300 is prevented from being moved longitudinally to articulate the end effector 11500.

FIGS. 69-71 illustrate the distal progression of the closure member 21110 during a closure stroke. FIG. 69 illustrates the closure member 21110 in an unactuated, or open, position. In such a position, the closure member 21110 is not engaged with the lock element 21405. FIG. 70 illustrates the closure member 21110 in a partially closed position in which the closure member 21110 has at least partially closed the end effector 11500. In such a position, a cam surface 21115 of the closure member 21110 has engaged the lock element 21405. In at least one instance, the closure member 21110 moves distally approximately 0.050" from its open position (FIG. 69) to its partially closed position (FIG. 70). FIG. 71 illustrates the closure member 21110 in a fully closed position in which the closure member 21110 has completely closed the end effector 11500. In such a position, the cam surface 21115 has moved by the lock element 21405 and the lock element 21405 has been displaced by the full thickness of the closure member 21110.

In view of the above, a surgical instrument can include an articulation lock system configured to prevent the end effector of the surgical instrument from being articulated and/or unintentionally back-driven by a load, or torque, applied to the end effector. At least a portion of the articulation lock system can be moved into engagement with an articulation drive system of the surgical instrument to prevent the articulation of the end effector. In at least one instance, an articulation lock can be integral to the articulation drive system, as described in greater detail below.

Figure 72:
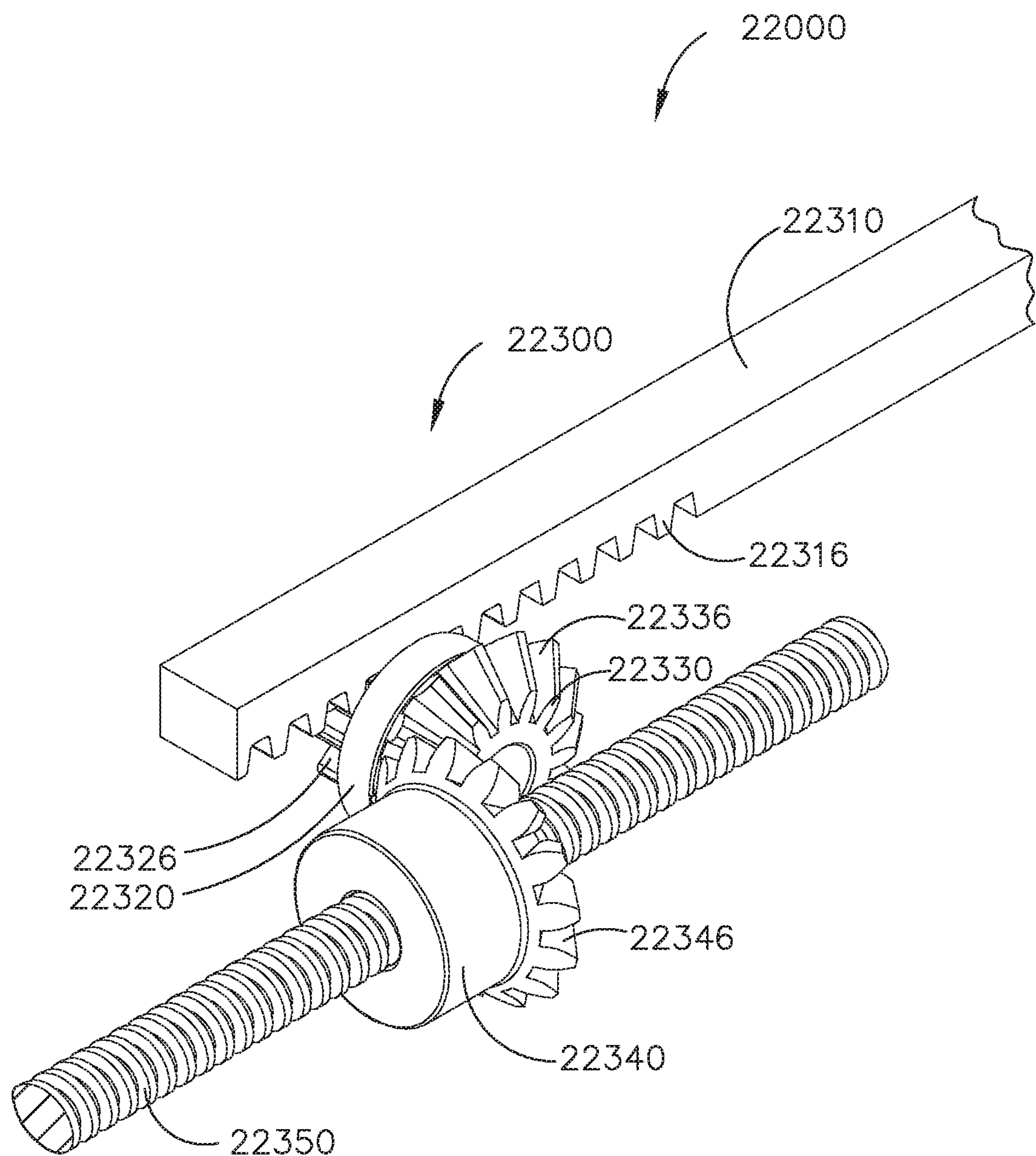
FIG. 72 is a partial perspective view of an end effector articulation drive system in accordance with at least one embodiment.
Figure 73:
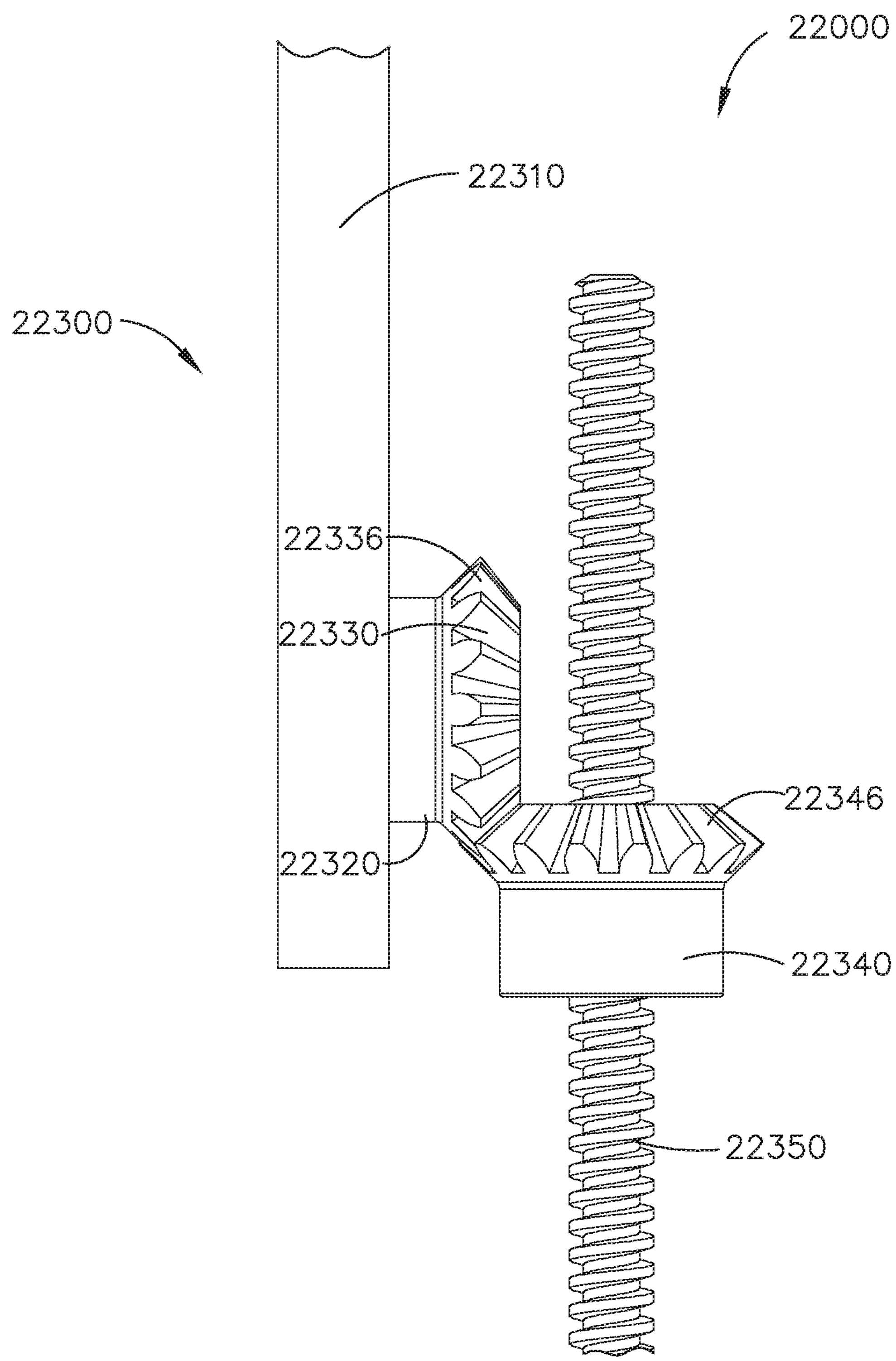
FIG. 73 is a plan view of the end effector articulation drive system of FIG. 72.
Figure 74:
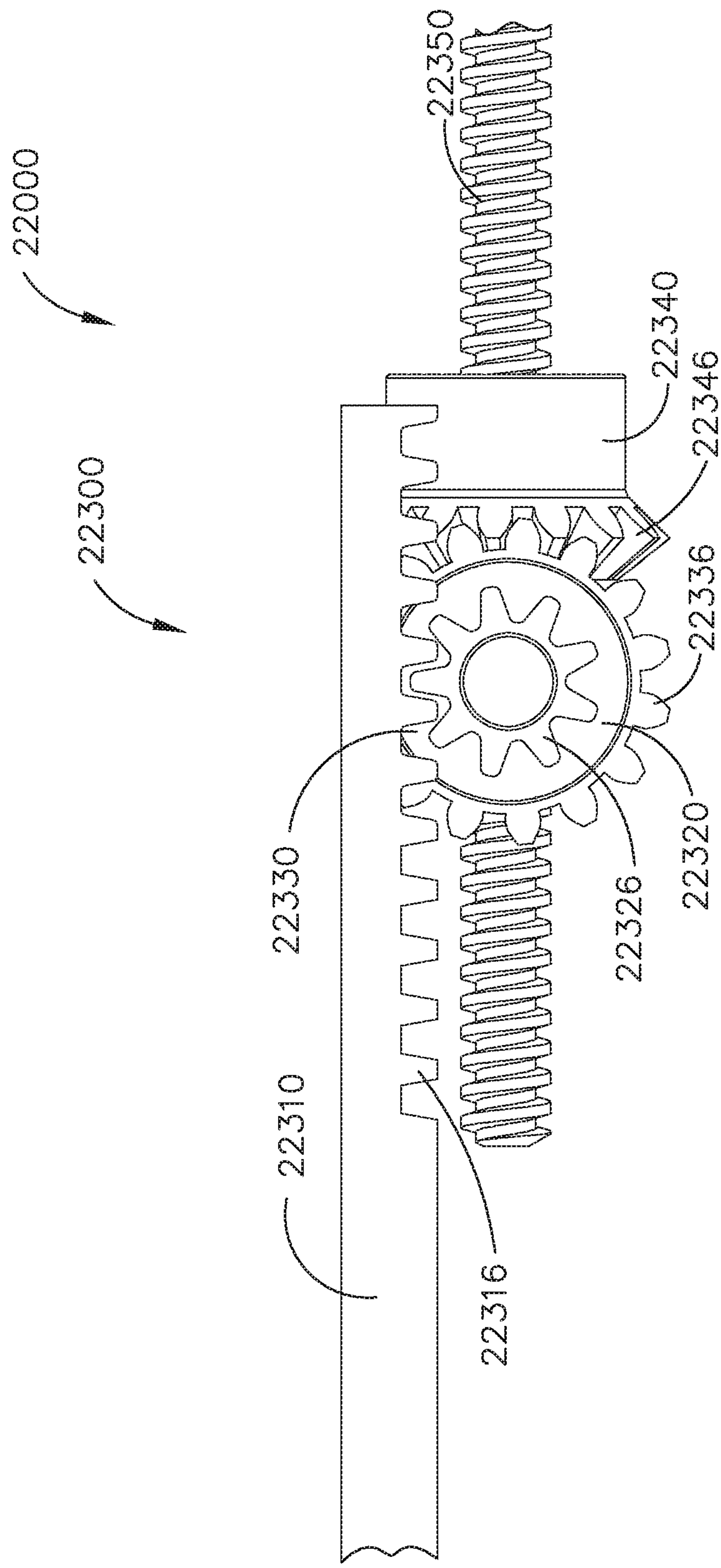
FIG. 74 is an elevational view of the end effector articulation drive system of FIG. 72.
Figure 75:
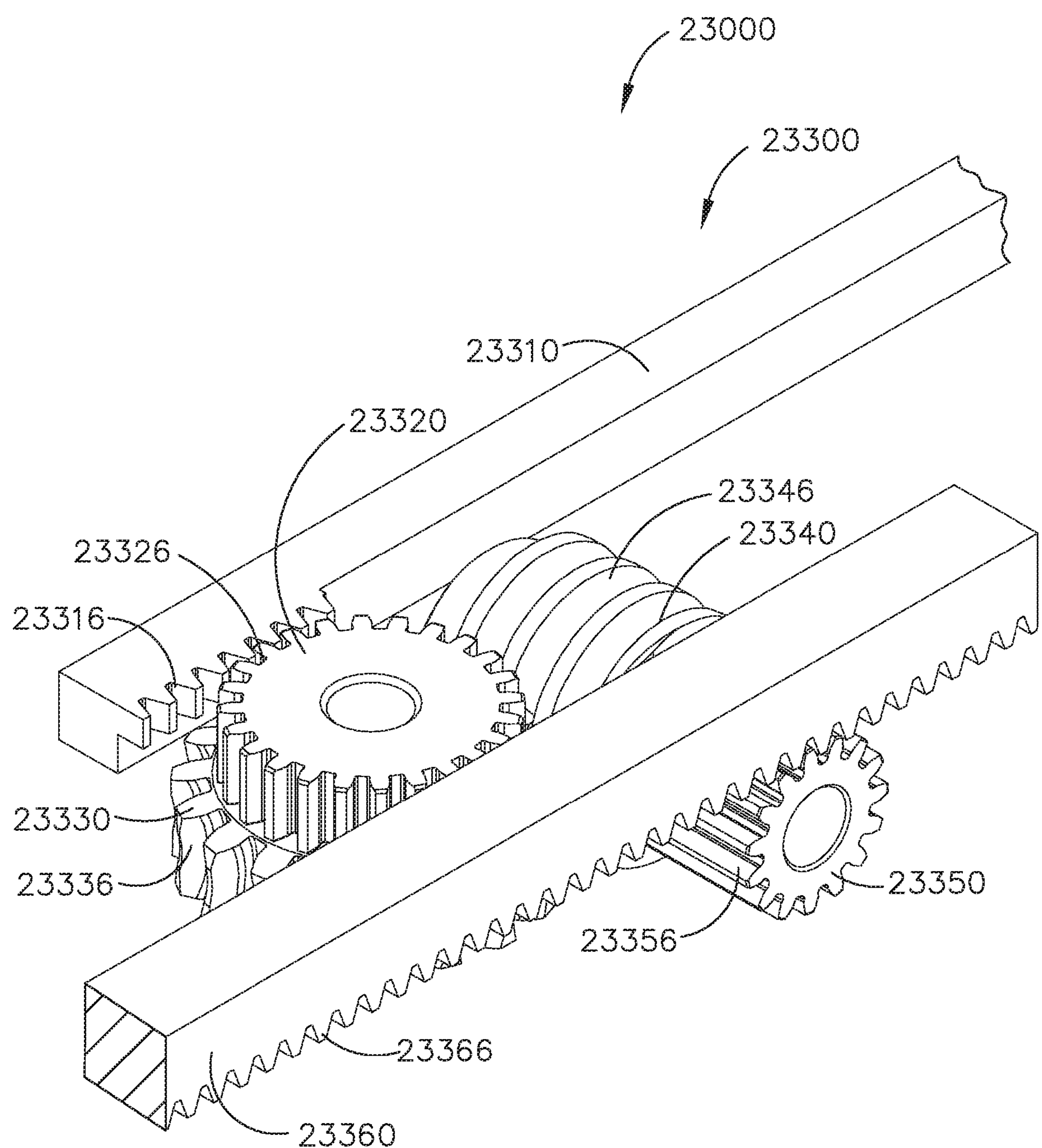
FIG. 75 is a partial perspective view of an end effector articulation drive system in accordance with at least one embodiment.
Figure 76:
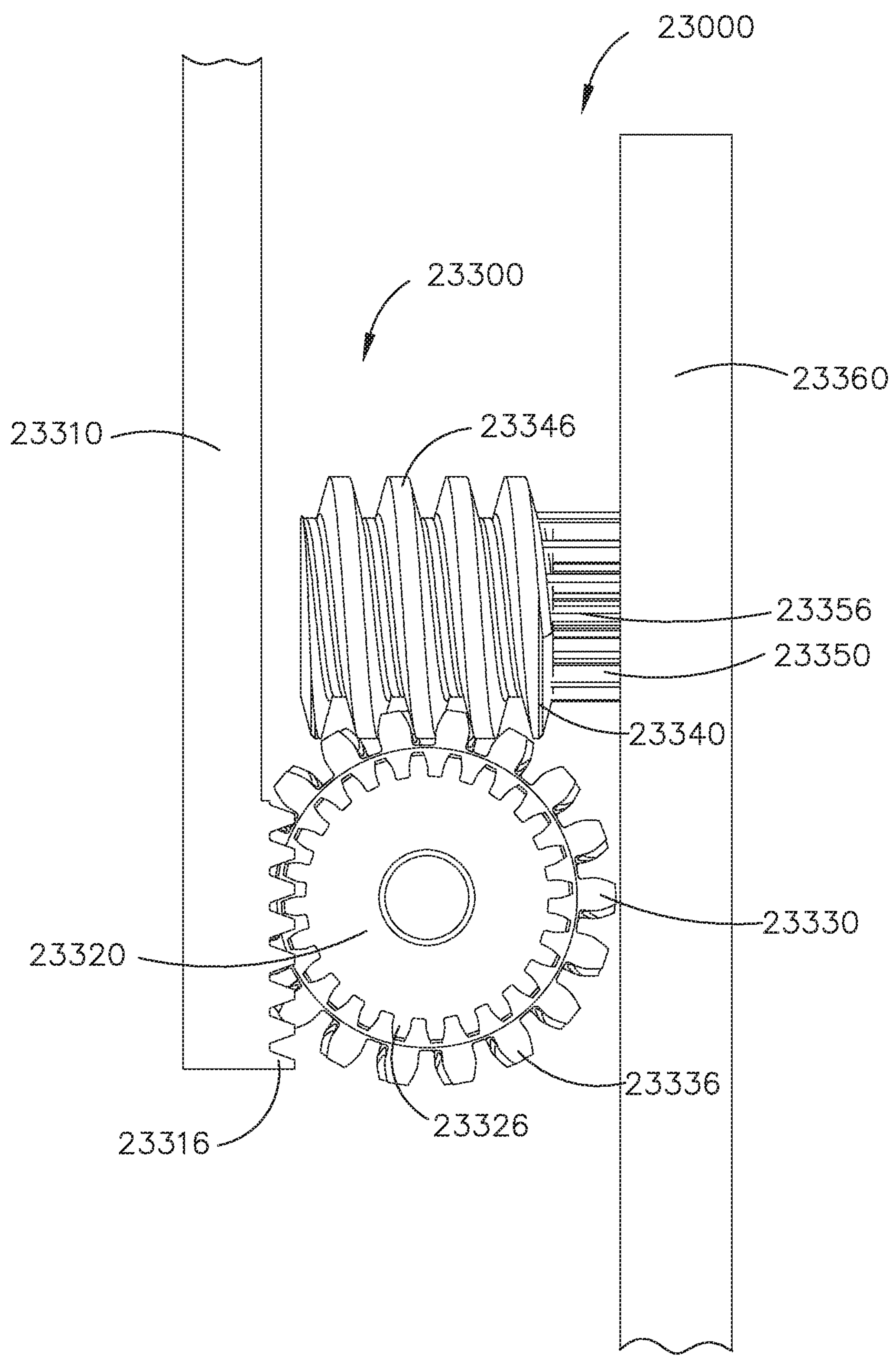
FIG. 76 is a plan view of the end effector articulation drive system of FIG. 75.
Figure 77:
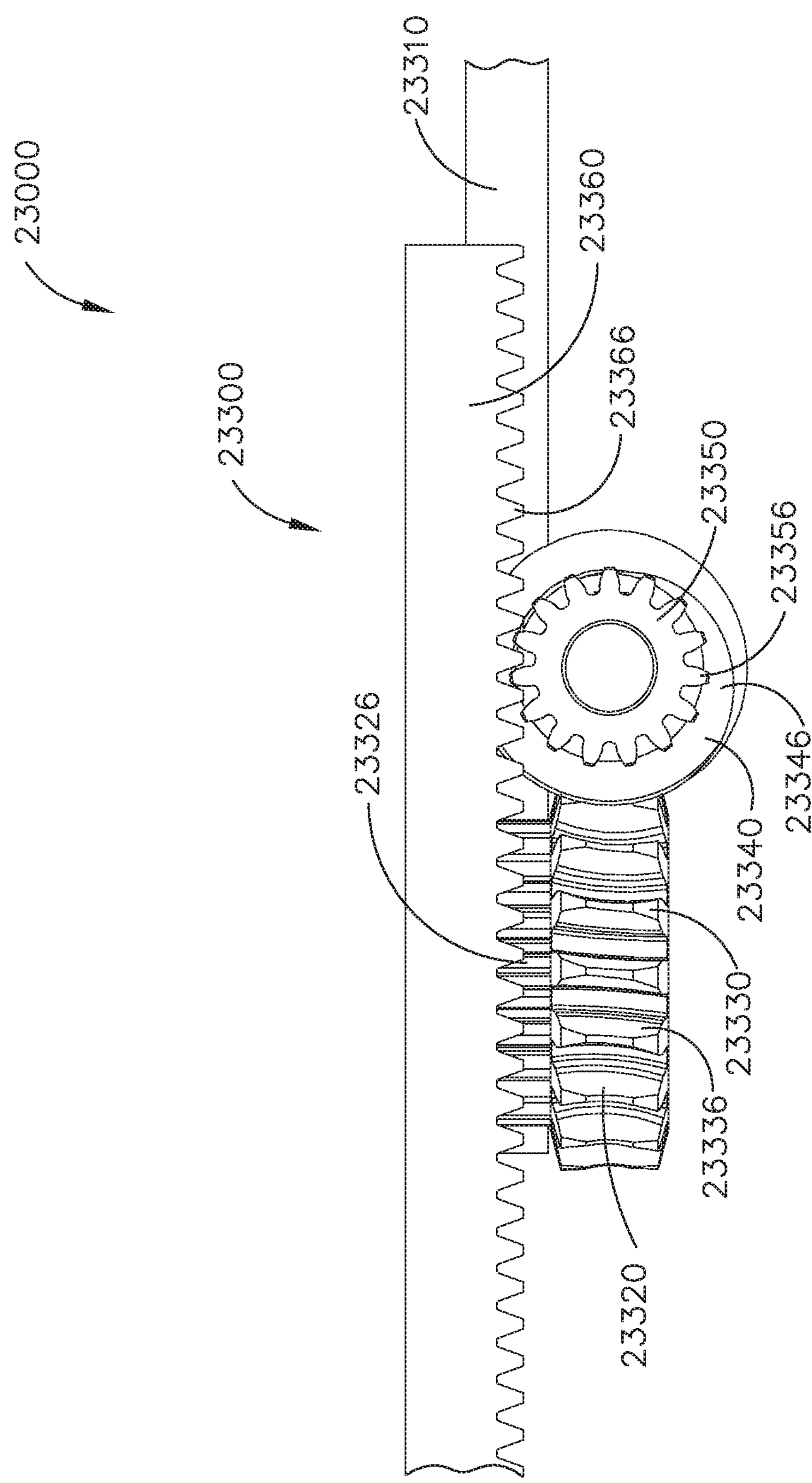
FIG. 77 is an elevational view of the end effector articulation drive system of FIG. 75.
Figure 78:
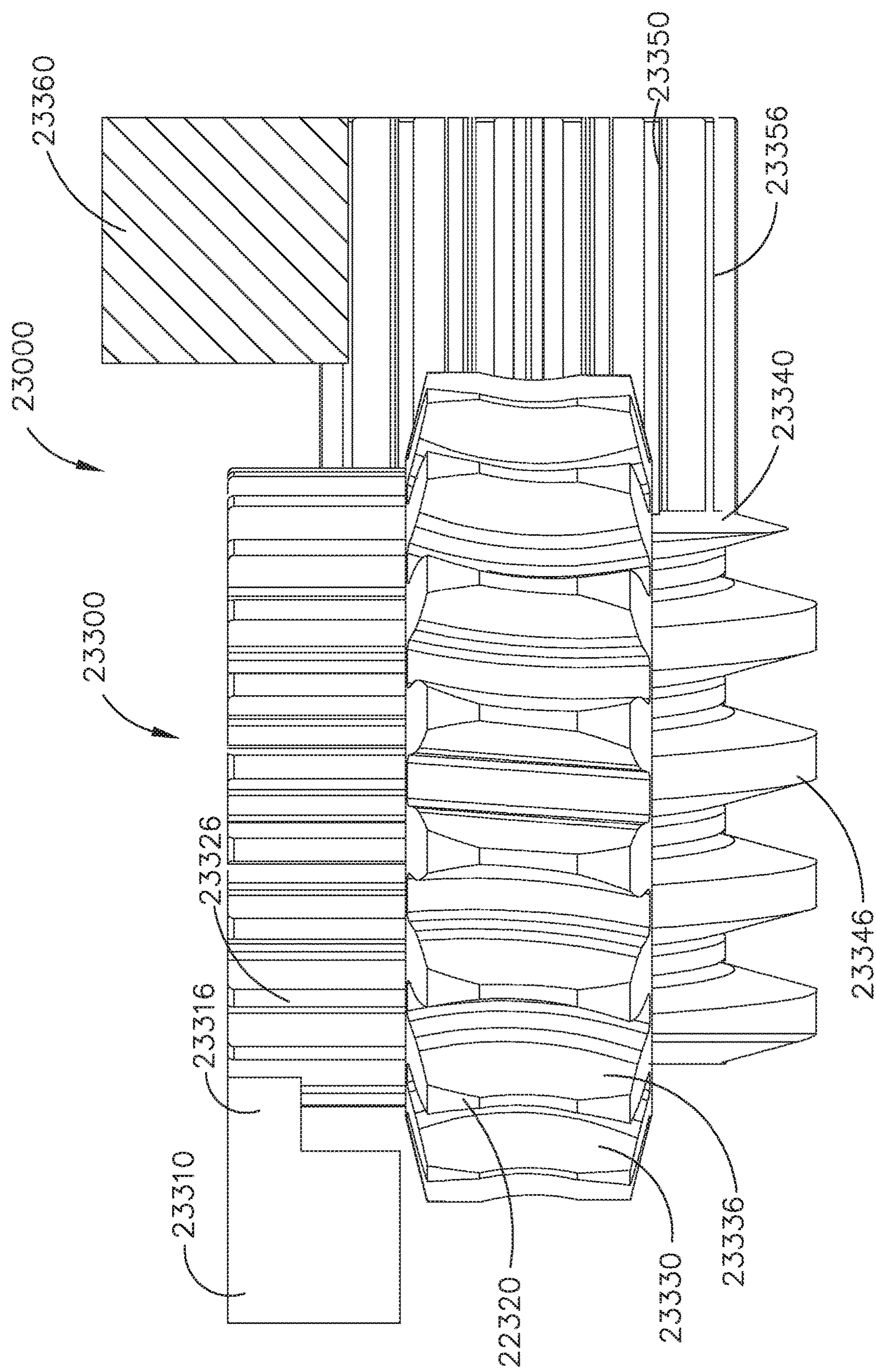
FIG. 78 is a detail view of the end effector articulation drive system of FIG. 75.
Figure 79:
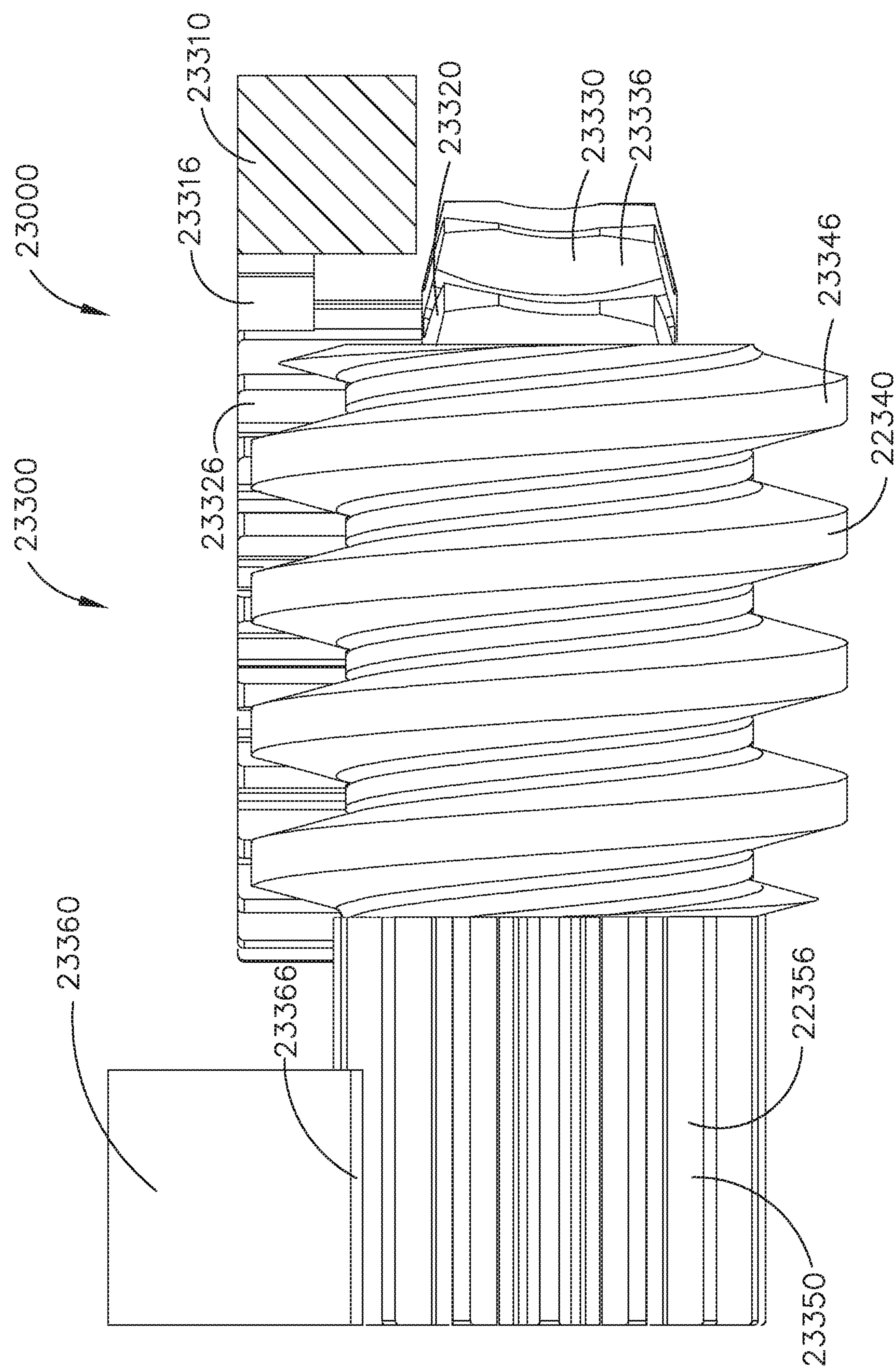
FIG. 79 is another detail view of the end effector articulation drive system of FIG. 75.

Referring to FIGS. 72-74, a surgical instrument 22000 comprises a shaft and an articulation drive system 22300 which is configured to articulate an end effector, such as an end effector 11500, for example, of the surgical instrument 22000 relative to the shaft. The articulation drive system 22300 comprises an articulation driver 22310 and a pinion gear 22320. The articulation driver 22310 comprises a longitudinal rack of teeth 22316 defined thereon which is operably meshed with teeth 22326 of the pinion gear 22320. When the articulation driver 22310 is translated distally, the pinion gear 22320 is rotated in a first direction. Correspondingly, the pinion gear 22320 is rotated in a second direction when the articulation driver 22310 is translated proximally. The pinion gear 22320 comprises a bevel gear 22330 fixedly mounted thereto such that the bevel gear 22330 rotates with the pinion gear 22320 about a common axis of rotation. The combined assembly of the pinion gear 22320 and the bevel gear 22330 is rotatably mounted in the shaft of the surgical instrument 22000.

Further to the above, teeth 22336 of the bevel gear 22330 are meshingly engaged with the teeth 22346 of a bevel gear 22340 which is rotatably mounted about a rotatable threaded articulation lead screw 22350. More specifically, the bevel gear 22340 comprises a nut portion which includes an at least partially threaded aperture which is threadably engaged with the articulation lead screw 22350. When the bevel gear 22340 is rotated in a first direction by the articulation driver 22310 via the bevel gear 22330, the bevel gear 22340 rotates the articulation lad screw 22350 in a first direction. Correspondingly, the bevel gear 22340 rotates the articulation lead screw 22350 in a second direction when the bevel gear 22340 is rotated in a second direction. Moreover, the end effector 11500 is rotated in a first direction when the articulation lead screw 22350 is rotated in its first direction and, correspondingly, in a second direction when the threaded articulation driver shaft 22350 is rotated in its second direction.

Further to the above, the pitch of the threads on the threaded articulation lead screw 22350 can be selected to prevent back-driving within the articulation drive system 22300. Stated another way, a steep pitch of the threads defined on the articulation lead screw 22350 would be able to resist a force and/or torque transmitted proximally from the end effector 11500 through the articulation drive system 22300 and, as a result, can prevent the end effector 11500 from being unintentionally articulated. As such, the thread pitch can serve as an articulation lock integral to the articulation drive system 22300. In at least one instance, the articulation lead screw comprises an ACME lead screw, for example.

Referring to FIGS. 75-79, a surgical instrument 23000 comprises a shaft and an articulation drive system 23300 which is configured to articulate an end effector, such as an end effector 11500, for example, of the surgical instrument 23000 relative to the shaft. The articulation drive system 23300 comprises an articulation driver 23310 and a pinion gear 23320. The articulation driver 23310 comprises a longitudinal rack of teeth 23316 defined thereon which is operably meshed with the teeth 23326 of the pinion gear 23320. When the articulation driver 23310 is translated distally, the pinion gear 23320 is rotated in a first direction. Correspondingly, the pinion gear 23320 is rotated in a second direction when the articulation driver 23310 is translated proximally. The pinion gear 23320 comprises a worm gear 23330 fixedly mounted thereto such that the worm gear 23330 rotates with the pinion gear 23320 about a common axis of rotation. The combined assembly of the pinion gear 23320 and the worm gear 23330 is rotatably mounted in the shaft of the surgical instrument 23000.

Further to the above, teeth 23336 of the worm gear 23330 are meshingly engaged with the teeth 23346 of a worm 23340 which is rotatably mounted to the shaft frame. The worm 23340 comprises a pinion gear 23350 fixedly mounted thereto such that the pinion gear 23350 rotates with the worm 23340 about a common axis of rotation. The pinion gear 23350 is operably engaged with a translatable articulation output driver 23360. More specifically, the pinion gear 23350 comprises teeth 23356 which are meshingly engaged with a rack of teeth 23366 defined on the output driver 23360. When the worm 23340 is rotated in a first direction by the articulation driver 23310 via the worm gear 23330, the pinion gear 23350 drives the output driver 23360 distally. Correspondingly, the worm 23340 and the pinion gear 23350 drive the output driver 23360 proximally when the worm 23340 is rotated in a second direction by the worm gear 23330. Moreover, the end effector 11500 is rotated in a first direction when the output driver 23350 is driven distally by the articulation drive system 23330 and in a second direction when the output driver 23350 is driven proximally by the articulation drive system 23330.

Further to the above, the pitch of the threads on the worm 23340 can be selected to prevent back-driving within the articulation drive system 23300. Stated another way, a steep pitch of the threads defined on the worm 23340, for instance, would be able to resist a force and/or torque transmitted proximally from the end effector 11500 through the articulation drive system 23300 and can prevent the end effector 11500 from being unintentionally articulated. As such, the thread pitch can serve as an articulation lock integral to the articulation drive system 23300.

A surgical instrument 12000, illustrated in FIGS. 32-34B, is similar to the surgical instrument 11000 in several respects, many of which will not be repeated herein in the interest of brevity. In addition to a shaft 11100, an end effector 11500, and an articulation joint 11200, the surgical instrument 12000 further comprises a staple firing system 12900, for example, including a firing bar 12910 extending through the articulation joint 11200. In use, the firing bar 12910 is translatable distally to perform a staple firing stroke and retractable proximally after at least a portion of the staple firing stroke has been completed. The firing bar 12910 extends through a channel, or slot, 11190 defined in the frame 11180 of the shaft 11100 which is configured to closely receive and/or guide the firing bar 12910 as the firing bar 12910 moves relative to the shaft 11100. Similarly, the end effector 11500 comprises a channel, or slot, 11590 defined in the frame 11580 of the end effector 11500 which is also configured to closely receive and/or guide the firing bar 12910 as the firing bar 12910 moves relative to the end effector 11500

Figure 34A:
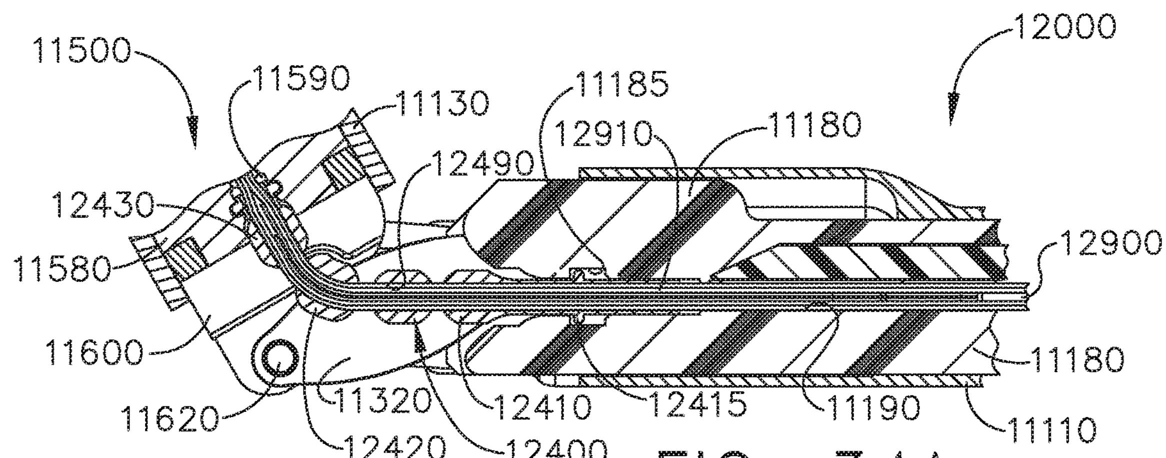
FIG. 34A is a cross-sectional view of the end effector of FIG. 32 illustrated in an articulated configuration.
Figure 34:
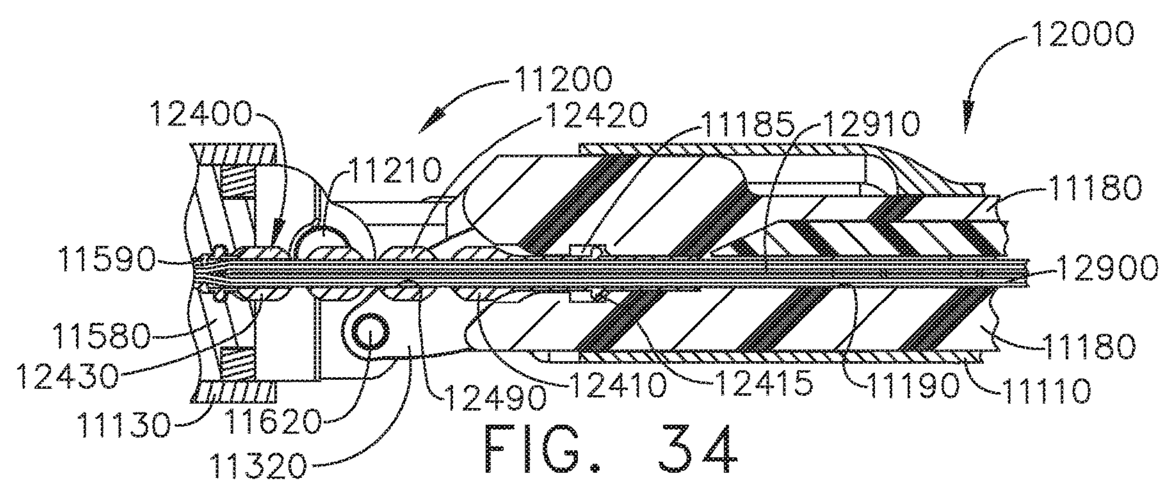
FIG. 34 is a cross-sectional view of the end effector of FIG. 32 illustrated in an unarticulated configuration.
Figure 34B:
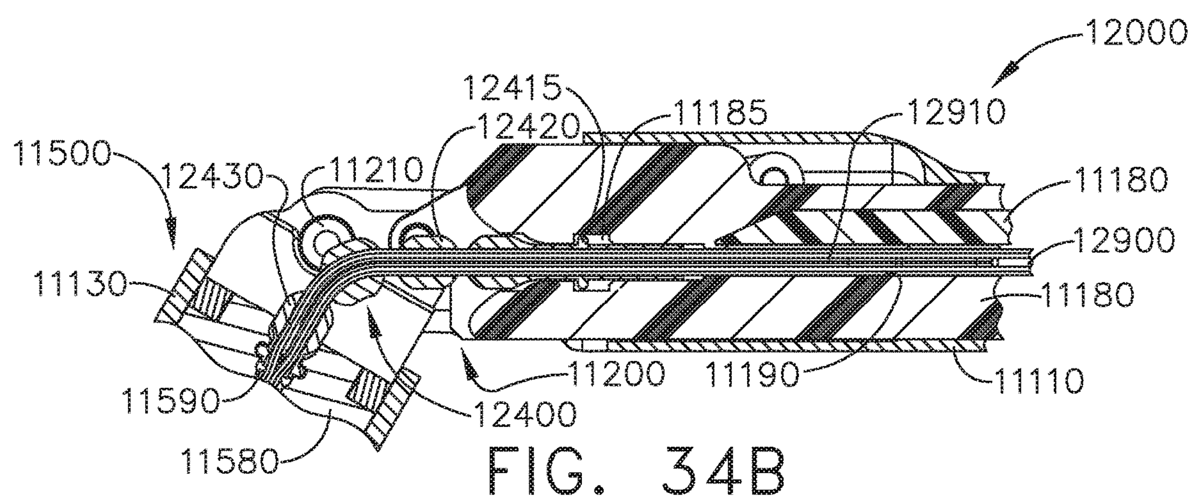
FIG. 34B is a cross-sectional view of the end effector of FIG. 32 illustrated in an articulated configuration.
Figure 35:
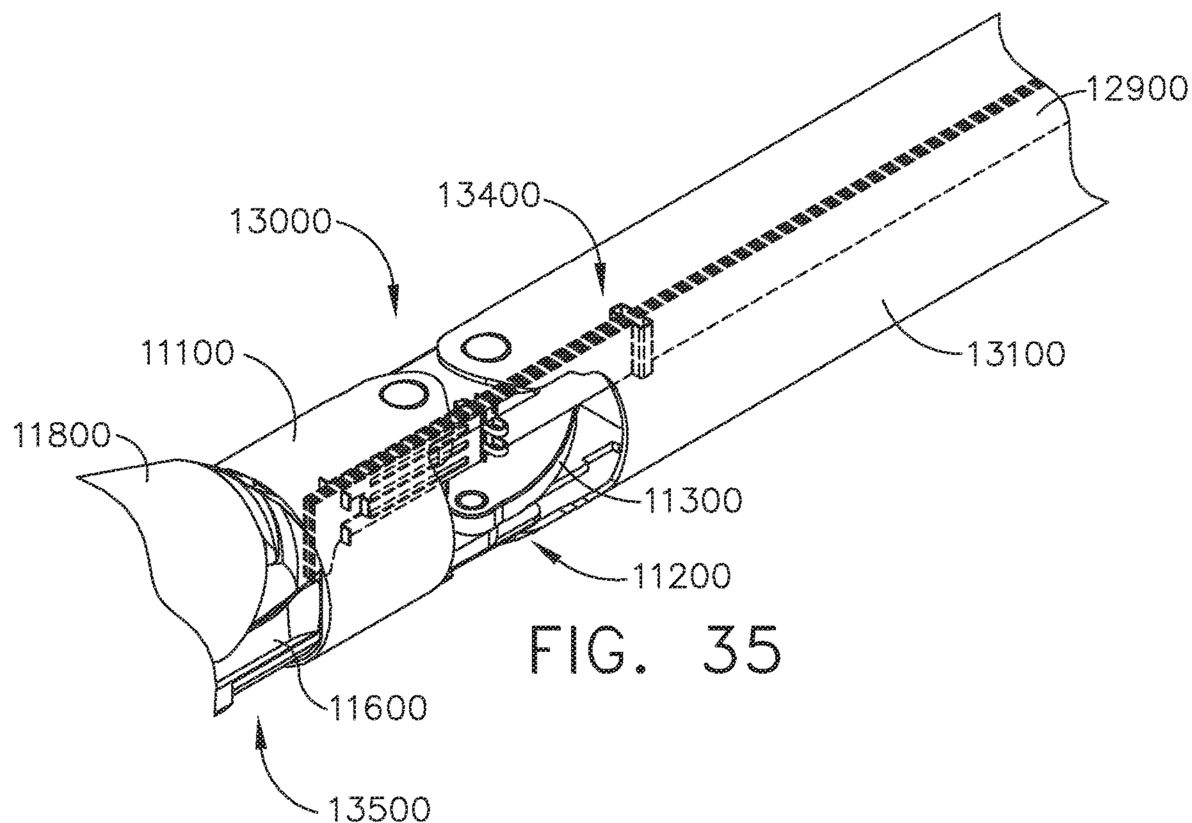
FIG. 35 is a partial perspective view of an end effector in accordance with at least one embodiment.
Figure 36:
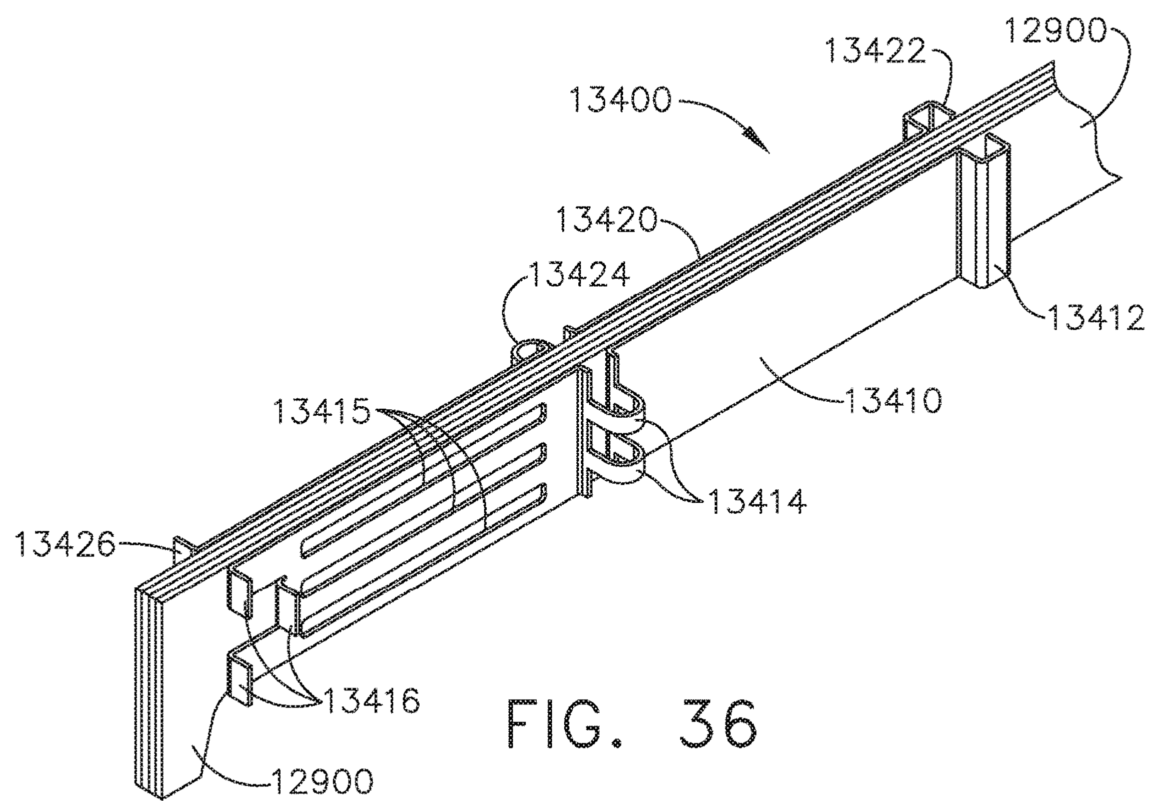
FIG. 36 is a partial perspective view of the end effector of FIG. 35 illustrated with some components removed.
Figure 37:
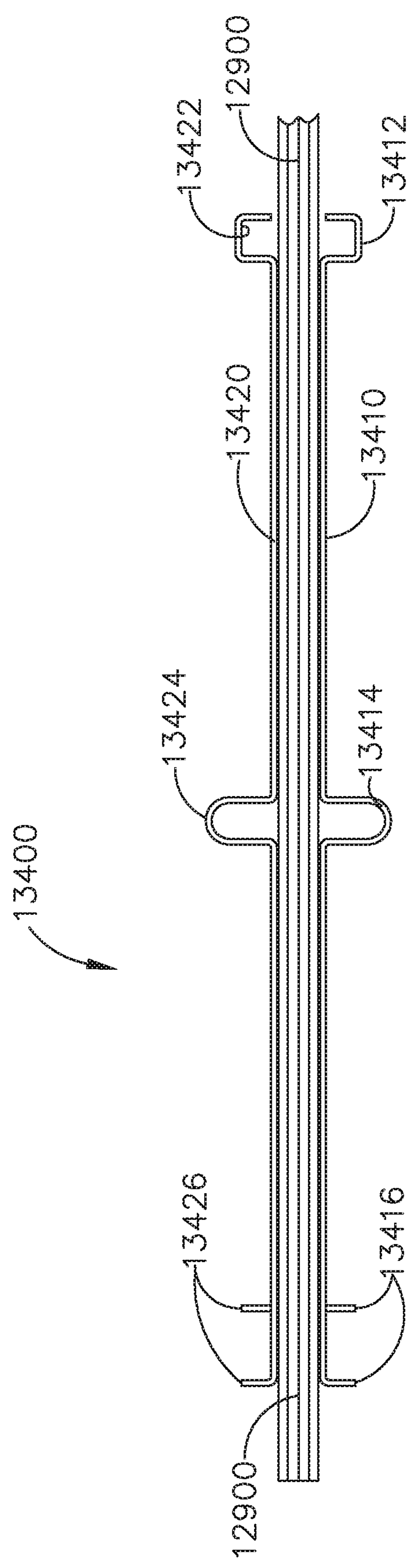
FIG. 37 is a partial plan view of the end effector of FIG. 35 illustrated with some components removed.
Figure 38:
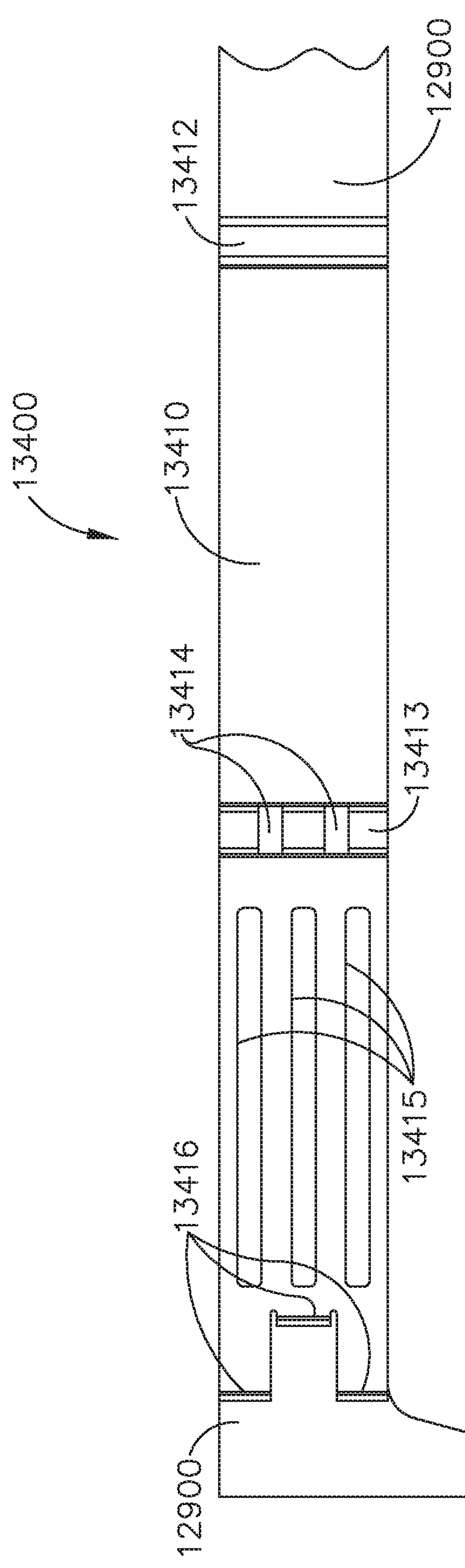
FIG. 38 is a partial elevational view of the end effector of FIG. 35 illustrated with some components removed.

Further to the above, the channels 11190 and 11590 do not extend into the articulation joint 11200 and, without more, the firing bar 12910 may be unsupported within the articulation joint 11200. When the end effector 11500 is in an unarticulated configuration (FIG. 34), the firing bar 12910 is unlikely to buckle within the articulation joint 11120 during the staple firing stroke—however, the likelihood of the firing bar 12910 buckling laterally during the staple firing stroke increases when the end effector 11500 is in an articulated configuration (FIGS. 34A and 34B). To reduce the possibility of such buckling, the surgical instrument 12000 further comprises a firing bar support 12400 configured to support the firing bar 12910. The firing bar support 12400 comprises a proximal portion 12410 connected to the shaft frame 11180, a distal portion 12430 connected to the end effector frame 11580, and an intermediate portion 12420 extending between the proximal portion 12410 and the distal portion 12430. The portions 12410, 12420, and 12430 of the firing bar support 12400 are integrally formed; however, other embodiments are envisioned in which the portions 12410, 12420, and 12430 are assembled to one another and/or comprise separate components.

Further to the above, the distal portion 12430 of the firing bar support 12400 is fixedly mounted to the end effector frame 11580 and does not move, or at least substantially move, relative to the end effector frame 11580. The intermediate portion 12420 of the firing bar support 12400 comprises one or more portions having a reduced cross-section which, among other things, allows the firing bar support 12400 to flex within the articulation joint 11200 when the end effector 11500 is articulated. The proximal portion 12410 of the firing bar support 12400 is slideably mounted to the shaft frame 11180 such that the firing bar support 12400 can translate relative to the shaft frame 11180 when the end effector 11500 is articulated. That said, the proximal portion 12410 of the firing bar support 12400 comprises a proximal head 12415 that is slideable within a chamber, or cavity, 11185 defined within the shaft frame 11180 which can limit the travel of the firing bar support 12400. Embodiments are envisioned, however, without such a travel constraint. In any event, the proximal portion 12410, intermediate portion 12420, and distal portion 12430 of the firing bar support 12400 co-operatively define a channel, or slot, 12490 which is configured to support the firing bar 12910—especially within the articulation joint 11200—and reduce the possibility of the firing bar 12910 buckling during the staple firing stroke, for instance.

In various instances, the firing bar 12910 is comprised of a plurality of parallel, or at least substantially parallel, layers. The layers are affixed to a distal cutting member and can partially translate or slide longitudinally relative to one another—especially within the articulation joint 11200. Each such layer is configured to transmit a load in the same direction, i.e., proximally or distally, even though such layers can move, or slide, relative to one another. Further to the above, such layers may splay laterally relative to one another—especially within the articulation joint 11200—when the end effector 11500 has been articulated. The intermediate portion 12420 of the firing bar support 12400 comprises a plurality of connected control elements which can at least reduce, if not prevent, the relative lateral splay of the firing bar layers. Alternatively, as mentioned above, one or more of the control elements can be unconnected to one another.

In addition to or in lieu of the firing bar support 12400, the surgical instrument 12000 comprises one or more dividers which separate and control the layers of the firing bar 12910. Referring to FIGS. 34-34B, the shaft 11110 comprises a divider 12920 positioned within the layers of the firing bar 12910. Two layers of the firing bar 12910 are positioned on one side of the divider 12920 while two layers are positioned on the other side of the divider 12920, although any suitable arrangement can be used. The divider 12920 prevents half of the layers of the firing bar 12910 from splaying outwardly when the end effector 11500 is articulated. Stated another way, the divider 12920 prevents the two right-most firing bar layers from splaying to the left when the end effector 11500 is articulated to the right (FIG. 34A) and, similarly, the divider 12920 prevents the two left-most firing bar layers from splaying to the right when the end effector 11500 is articulated to the left (FIG. 34B). The divider 12920 extends through the articulation joint 11200 and the firing bar support 12400 and into the end effector 11500 and can bend when the end effector 11500 is articulated. Accordingly, in such instances, the divider 12920 is flexible. The divider 12920 is mounted to the frame 11180 of the shaft 11110 and does not move relative to the frame 11180; however, embodiments are envisioned in which the divider 12920 is not mounted to the frame 11180 and can float within the firing bar layers.

Figure 39A:
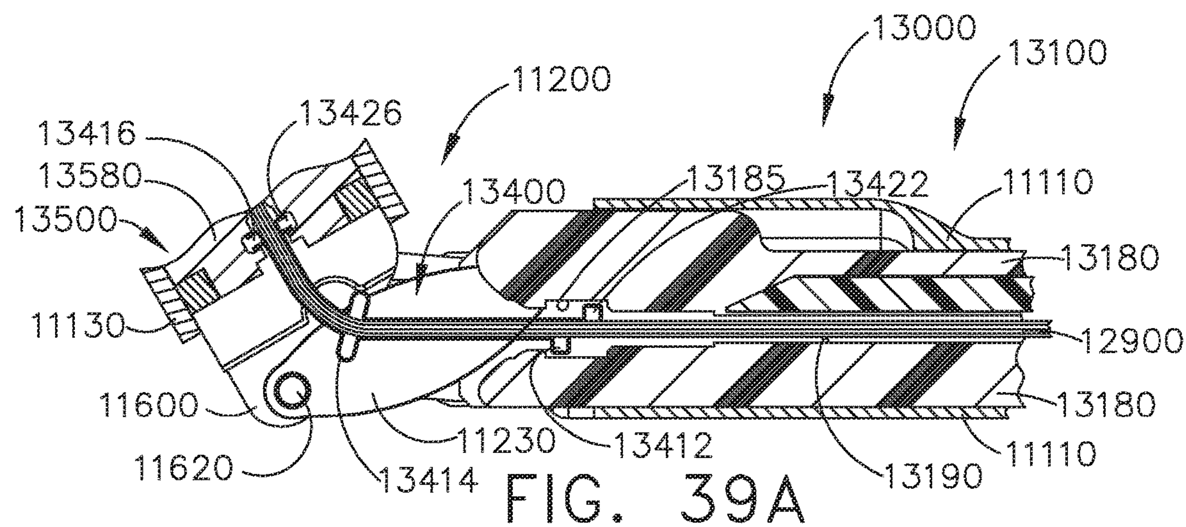
FIG. 39A is a cross-sectional view of the end effector of FIG. 35 illustrated in an articulated configuration.
Figure 39:
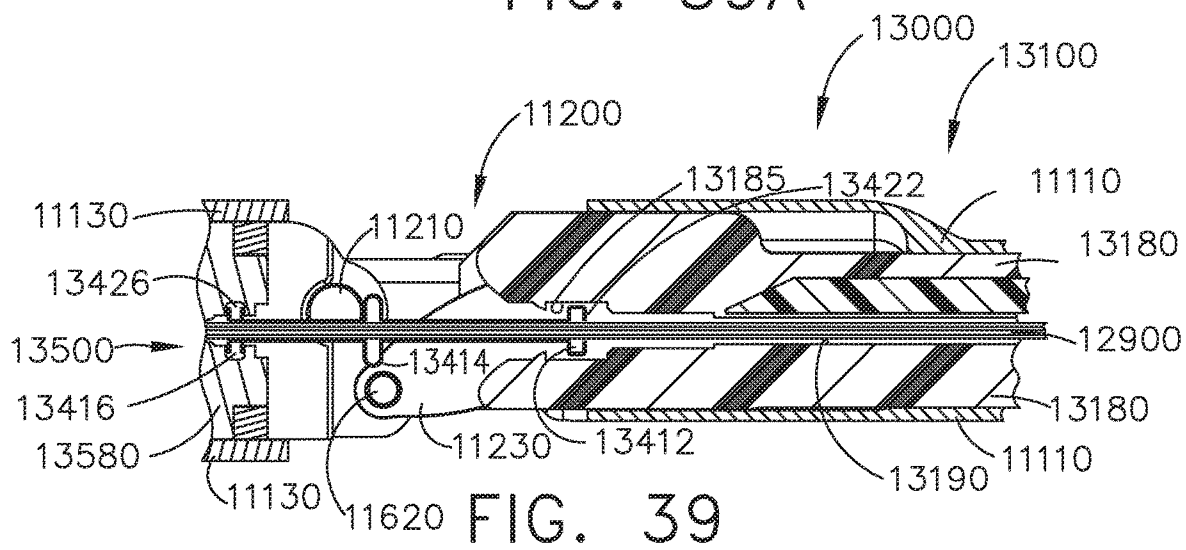
FIG. 39 is a cross-sectional view of the end effector of FIG. 35 illustrated in an unarticulated configuration.
Figure 39B:
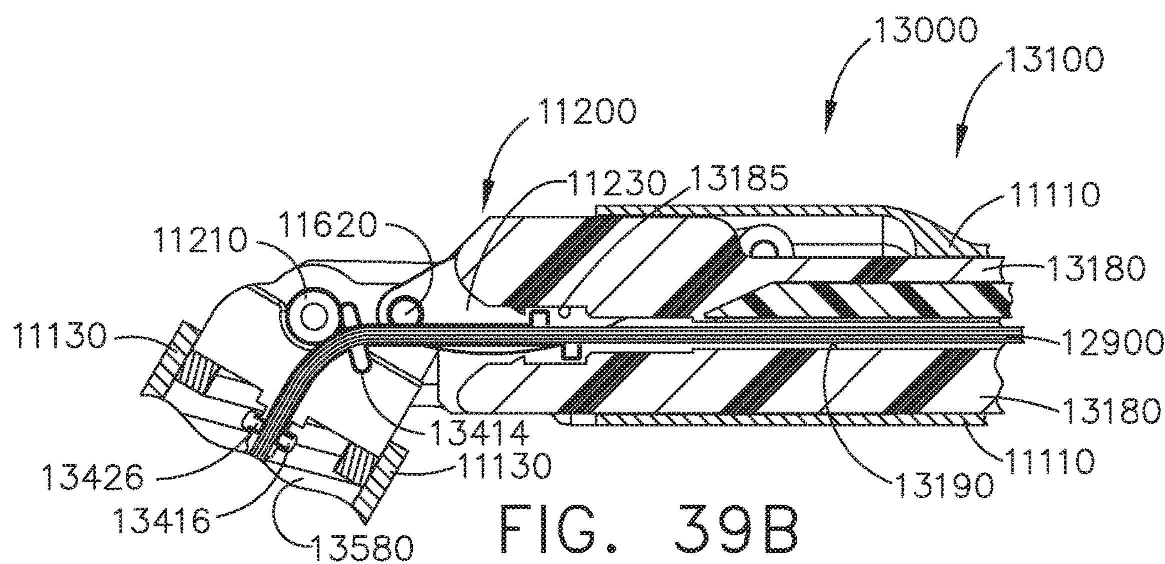
FIG. 39B is a cross-sectional view of the end effector of FIG. 35 illustrated in an articulated configuration.

A surgical instrument 13000, illustrated in FIGS. 35-39B, is similar to the surgical instruments 11000 and 12000 in several respects, many of which will not be repeated herein in the interest of brevity. In addition to a shaft 13100, an end effector 13500, and an articulation joint 11200, the surgical instrument 13000 further comprises a staple firing system 12900, for example, including a firing bar 12910 extending through the articulation joint 11200. In use, the firing bar 12910 is translatable distally to perform a staple firing stroke and retractable proximally after at least a portion of the staple firing stroke has been completed. Referring primarily to FIGS. 39-39B, the firing bar 12910 extends through a channel, or slot, 13190 defined in the frame 13180 of the shaft 13100 which is configured to closely receive and/or guide the firing bar 12190 as the firing bar 12910 moves relative to the shaft 11100. Similarly, the end effector 13500 comprises a channel, or slot, defined in the frame 13580 of the end effector 13500 which is also configured to closely receive and/or guide the firing bar 12190 as the firing bar 12910 moves relative to the end effector 13500

When the end effector 13500 is in an unarticulated configuration (FIG. 39), further to the above, the firing bar 12910 is unlikely to buckle within the articulation joint 11120 during the staple firing stroke—however, the likelihood of the firing bar 12910 buckling laterally during the staple firing stroke increases when the end effector 13500 is in an articulated configuration (FIGS. 39A and 39B). To reduce the possibility of such buckling, the surgical instrument 13000 further comprises a firing bar support 13400 configured to support the firing bar 12190. The firing bar support 13400 comprises a first lateral plate 13410 and a second lateral plate 13420. The lateral plates 13410 and 13420 are positioned on opposite sides of the firing bar 12910. Each lateral plate 13410, 13420 comprises a proximal portion connected to the shaft frame 13180, a distal portion connected to the end effector frame 13580, and an intermediate portion extending between the proximal portion and the distal portion. The portions of each plate 13410, 13420 are integrally formed; however, other embodiments are envisioned in which the portions are assembled to one another and/or comprise separate components.

Further to the above, the first lateral plate 13410 comprises a distal portion 13416 which is fixedly mounted to the end effector frame 13580 and does not move, or at least substantially move, relative to the end effector frame 13580. Similarly, the second lateral plate 13420 comprises a distal portion 13426 which is fixedly mounted to the end effector frame 13580 and does not move, or at least substantially move, relative to the end effector frame 13580. The first lateral plate 13410 comprises a proximal portion 13412 which is slideably mounted to the shaft frame 13180 such that the first lateral plate 13410 can translate relative to the shaft frame 13180 when the end effector 13500 is articulated. The proximal portion 13412 comprises a head that is slideable within a chamber, or cavity, 13185 defined within the shaft frame 13180 which can limit the travel of the firing bar support 13400. Similarly, the second lateral plate 13420 comprises a proximal portion 13422 which is slideably mounted to the shaft frame 13180 such that the firing bar support 13400 can translate relative to the shaft frame 13180 when the end effector 13500 is articulated. The proximal portion 13422 comprises a head that is slideable within the chamber 13185 defined within the shaft frame 13180 which can also limit the travel of the firing bar support 13400.

The first lateral plate 13410 comprises a flexible portion 13414 positioned in the articulation joint 11200 which permits the distal portion 13416 of the first lateral plate 13410 to flex relative to the proximal portion 13412 and accommodate the articulation of the end effector 13500. The flexible portion 13414 extends laterally from the first lateral plate 13410 and comprises a hinge including gaps 13413 defined therein which permit rotation within the first lateral plate 13410. In addition to or in lieu of the above, the first lateral plate 13410 comprises longitudinal openings 13415 defined therein which permit the first lateral plate 13410 to flex within the end effector 13500 and accommodate the articulation of the end effector 13500. The first lateral plate 13410 can comprise any suitable number and configuration of openings and/or recesses defined therein at any suitable location which are configured to permit the first lateral plate 13410 to flex during the articulation of the end effector 13500. Similarly, the second lateral plate 13412 comprises a flexible portion 13424 positioned in the articulation joint 11200 which permits the distal portion 13426 of the second lateral plate 13420 to flex relative to the proximal portion 13422 and accommodate the articulation of the end effector 13500. The flexible portion 13424 extends laterally from the first lateral plate 13420 and comprises a hinge including gaps defined therein which permit rotation within the second lateral plate 13420. In addition to or in lieu of the above, the second lateral plate 13420 comprises longitudinal openings defined therein which permit the second lateral plate 13420 to flex within the end effector 13500 and accommodate the articulation of the end effector 13500. The second lateral plate 13420 can comprise any suitable number and configuration of openings and/or recesses defined therein at any suitable location which are configured to permit the second lateral plate 13420 to flex during the articulation of the end effector 13500.

Further to the above, the lateral plates 13410 and 13420 are flexible and can resiliently return to their unflexed configurations when the end effector 13500 is returned to its unarticulated configuration. In various instances, the lateral plates 13410 and 13420 comprise springs which resiliently bias the end effector 13500 into its unarticulated configuration.

Figure 83:
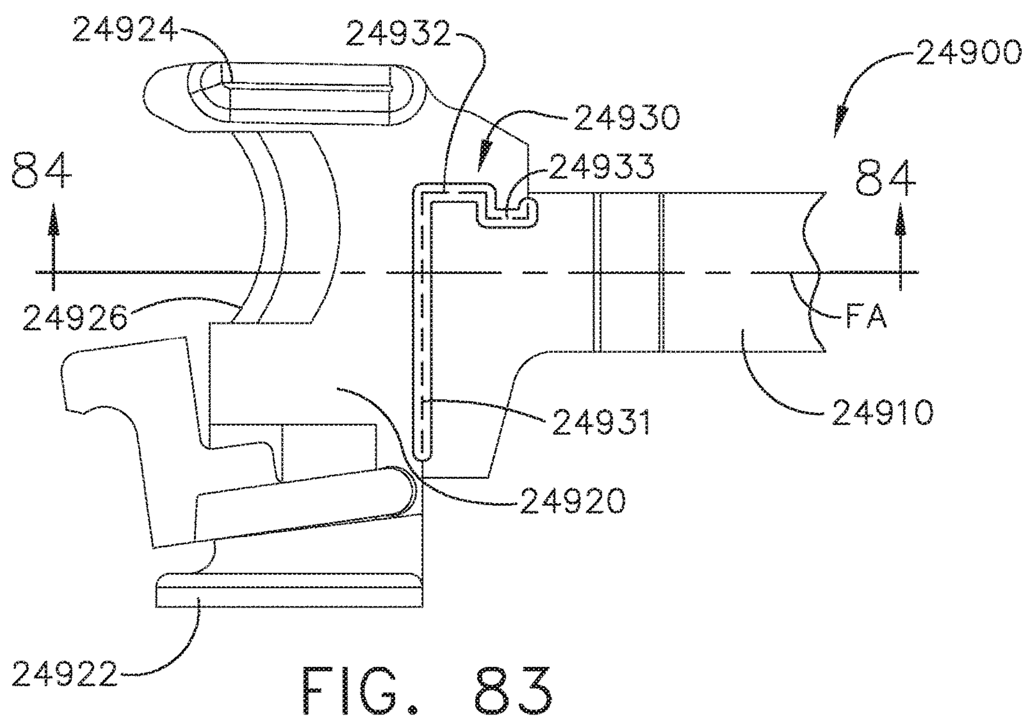
FIG. 83 is a partial elevational view of a firing member in accordance with at least one embodiment.
Figure 84:
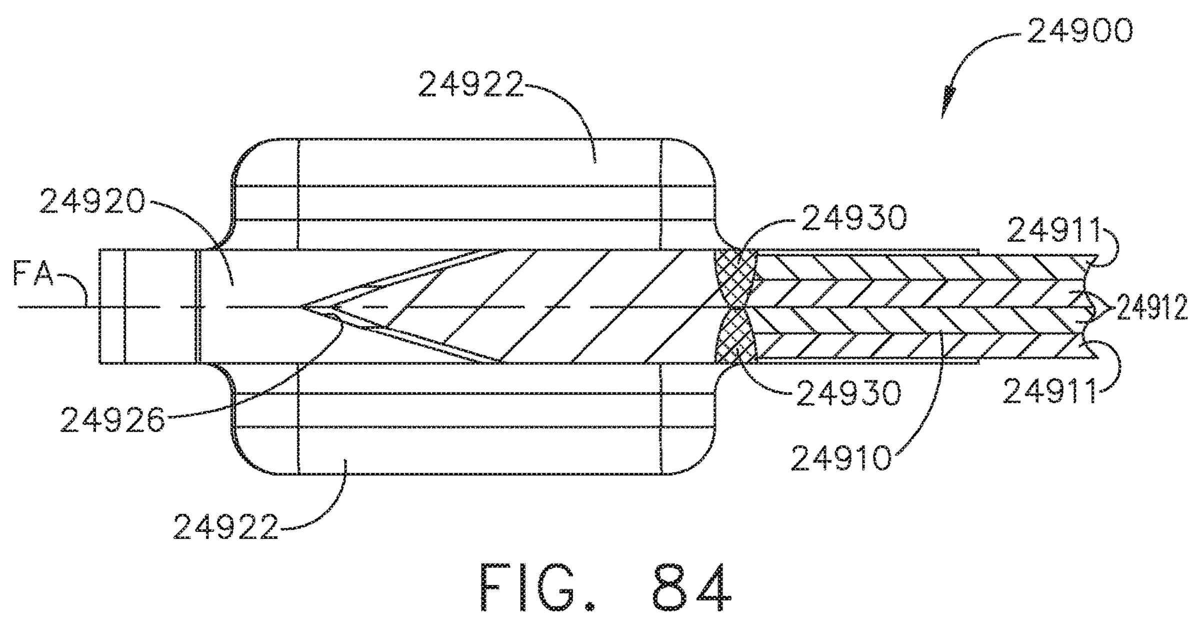
FIG. 84 is a partial cross-sectional plan view of the firing member of FIG. 83.

A firing member 24900 is illustrated in FIGS. 83 and 84 and can be used with any of the surgical stapling instruments disclosed herein. The firing member 24900 comprises a firing bar 24910 which, similar to the above, comprises a plurality of layers. More specifically, the firing bar 24910 comprises two exterior layers 24911 and two interior layers 24912. The firing member 24900 further comprises a distal cutting member 24920 which includes a tissue cutting edge 24926. The distal cutting member 24920 further comprises a first cam 24922 configured to engage a first jaw of an end effector and a second cam 24924 configured to engage a second jaw of the end effector. That said, embodiments are envisioned in which the distal cutting member 24920 is configured to only engage one jaw of an end effector or, alternatively, neither jaw of an end effector.

The layers 24911 and 24912 of the firing bar 24910 are welded to the distal cutting member 24920 at welds 24930. As illustrated in FIG. 84, a first weld 24930 is present on a first side of the firing member 24900 and a second weld 24930 is present on a second side of the firing member 24900. The first weld 24930 penetrates a first exterior layer 24911 and the adjacent interior layer 24912. In various instances, the first weld 24930 penetrates entirely through the adjacent interior layer 24912 and/or also penetrates into the other interior layer 24912. The second weld 24930 penetrates a second exterior layer 24911 and the adjacent interior layer 24912. In various instances, the second weld 24930 penetrates entirely through the adjacent interior layer 24912 and/or also penetrates into the other interior layer 24912.

Referring primarily to FIG. 83, each weld 24930 of the firing member 24900 comprises a weld line which is configured to securely hold the firing bar 24910 to the cutting member 24920 and, at the same time, provide a flexible connection there between. Each weld 24930 comprises a butt weld 24931 connecting the cutting member 24920 to the distal ends of the plates 24911 and 24912 and is placed in tension and/or compression when a longitudinal firing force is transmitted through the firing member 24900. The butt weld is orthogonal to, or at least substantially orthogonal to, a longitudinal firing axis (FA) of the firing member 24900. The butt weld 24931 can comprise any suitable configuration, such as a square, closed square, single-bevel, double-bevel, single-J, double-J, single-V, double-V, single-U, double-U, flange, flare, and/or tee configuration, for example.

Further to the above, each weld 24930 further comprises a distal hook weld portion 24932 and a proximal hook weld portion 24933. Each hook weld portion 24932 and 24933 comprises a longitudinal portion which is aligned with, or is parallel to, the longitudinal firing axis (FA) of the firing member 24900 and is placed in shear when a longitudinal firing force is transmitted through the firing member 24900. In addition, each hook weld portion 24932 and 24933 comprises a butt portion which is orthogonal, or at least substantially orthogonal, to the longitudinal firing axis (FA) and is placed in tension and/or compression when a longitudinal firing force is transmitted through the firing member 24900. Notably, each set of hook weld portions 24932 and 24933 comprises an interlocking connection between the firing bar 24910 and the cutting member 24920 which can transmit a flow of stress there between without failing and/or yielding unsuitably.

Each weld 24930 is generally L-shaped, for example; however, the welds 24930 can comprise any suitable configuration.

Although the surgical instruments 10000, 11000, 12000, 13000, 14000, 15000, 16000, 17000, 18000, 19000, 20000, 21000, 22000, and 23000 are surgical staplers, their designs can be readily adapted to other surgical instruments having articulatable end effectors, among others. Such other surgical instruments can include, for example, clip appliers, fastener appliers, and/or surgical instruments capable of delivering electrical and/or vibrational energy to tissue.

Figures 85, 86:
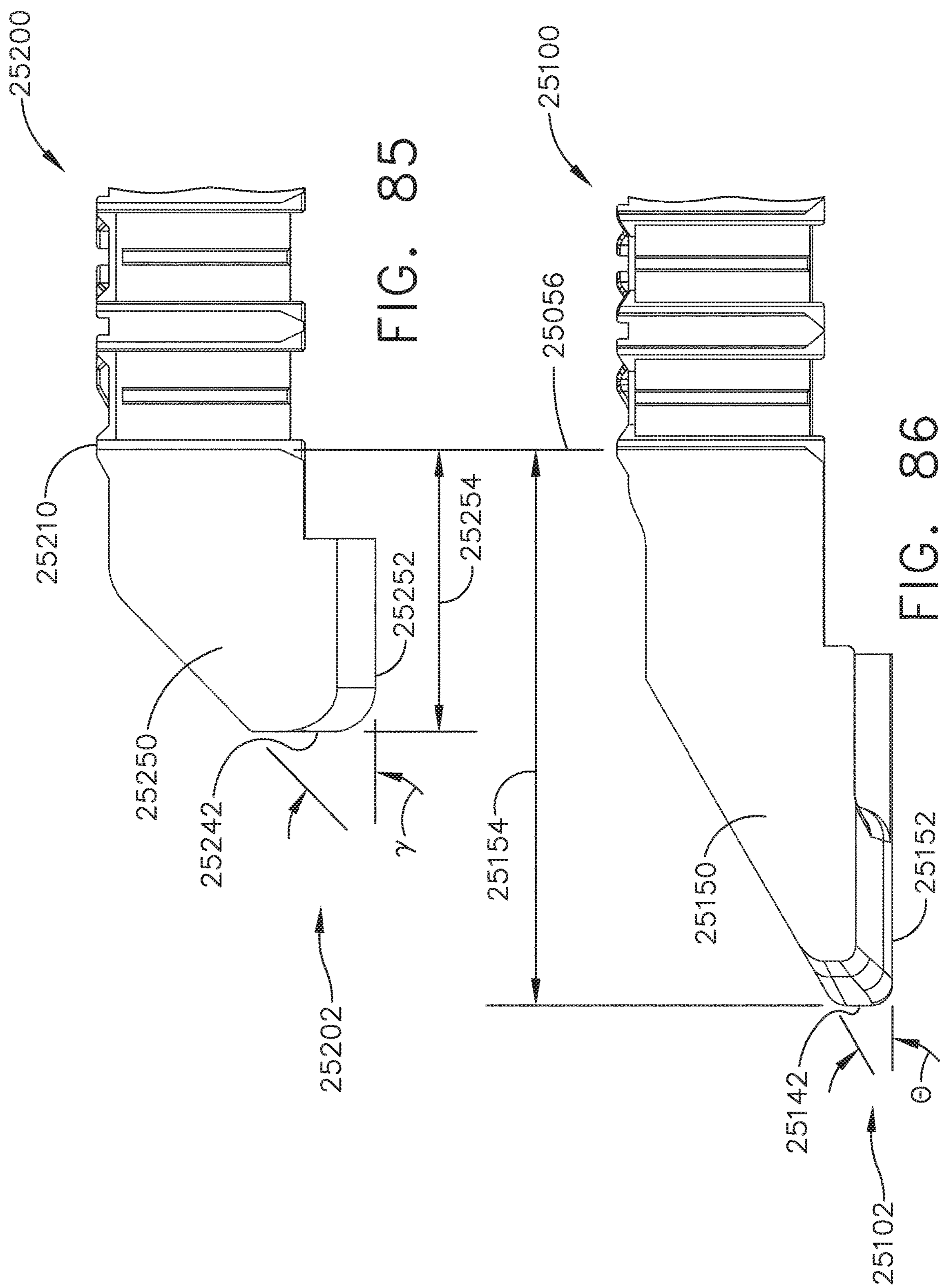
FIG. 85 is a partial cross-sectional view of a distal end of a staple cartridge with a shortened nose in accordance with at least one embodiment.
FIG. 86 is a partial cross-sectional view of a distal end of a staple cartridge with an elongate nose in accordance with at least one embodiment.

FIG. 86 depicts a surgical staple cartridge 25100 comprising an elongate nose 25150 located at a distal end thereof, generally denoted as 25102. The elongate nose 25150 has a base 25152 that is defined by a first length 25154 extending a distance between the end of the staple line 25056 and a distal tip 25142 of the staple cartridge 25100. The distal tip 25142 is formed at an angle σ from the base 25152 of the staple cartridge 25100. The distal tip 25142 on the staple cartridge 25100 is pointed and configured to serve as a parking area for a wedge sled, not shown, of the firing system upon the completion of a staple firing stroke.

In an effort to shorten the overall length of the staple cartridge without sacrificing length of stapled tissue, the surgical staple cartridge 25200 depicted in FIG. 85 comprises a cartridge body 25210 including a shortened nose 25250 located at a distal end thereof, generally denoted as 25202. The shortened nose 25250 has a base 25252 that is defined by a second length 25254 extending a distance between the end of the staple line 25056 and a blunted distal tip 25242 of the staple cartridge 25200. The second length 25254 of the shortened nose 25250 is minimized by blunting the parking area for the wedge sled 25270 (See FIG. 89). While the blunt, shortened nose 25250 of the staple cartridge 25200 in FIG. 85 still provides a parking area for the wedge sled, additional accommodations for storage may have to be made, as will be discussed below. The blunted distal tip 25242 is formed at an angle γ from the base 25252 of the staple cartridge 25200.

Upon comparing the staple cartridges 25200 and 25100 depicted in FIGS. 85 and 86, respectively, the reader should recognize that the second length 25254 is shorter than the first length 25154. As a result, the length of the staple cartridge 25200 beyond the end of the staple line 25056 is minimized to allow for improved spatial access within a surgical site, among other things. The shortened nose 25250 also prevents the blunted distal tip 25242 from puncturing a seal on a trocar system, as discussed further below. Furthermore, one will recognize the angle γ of the blunted distal tip 25242 of the staple cartridge 25200 with respect to the base 25252 is greater than the angle σ of the pointed distal tip 25142 of the staple cartridge 25100 with respect to the base 25152. For example, the blunted distal tip 25242 can extend at an angle of approximately 45-50 degrees with respect to the base 25252 of the staple cartridge 25200, while the pointed distal tip 25142 can extend at an angle of approximately 30 degrees with respect to the base 25152 of the staple cartridge 25100. The steeper angle of the blunted distal tip 25242 provides increased stability throughout distal regions of the structure of the staple cartridge 25200.

Figure 89:
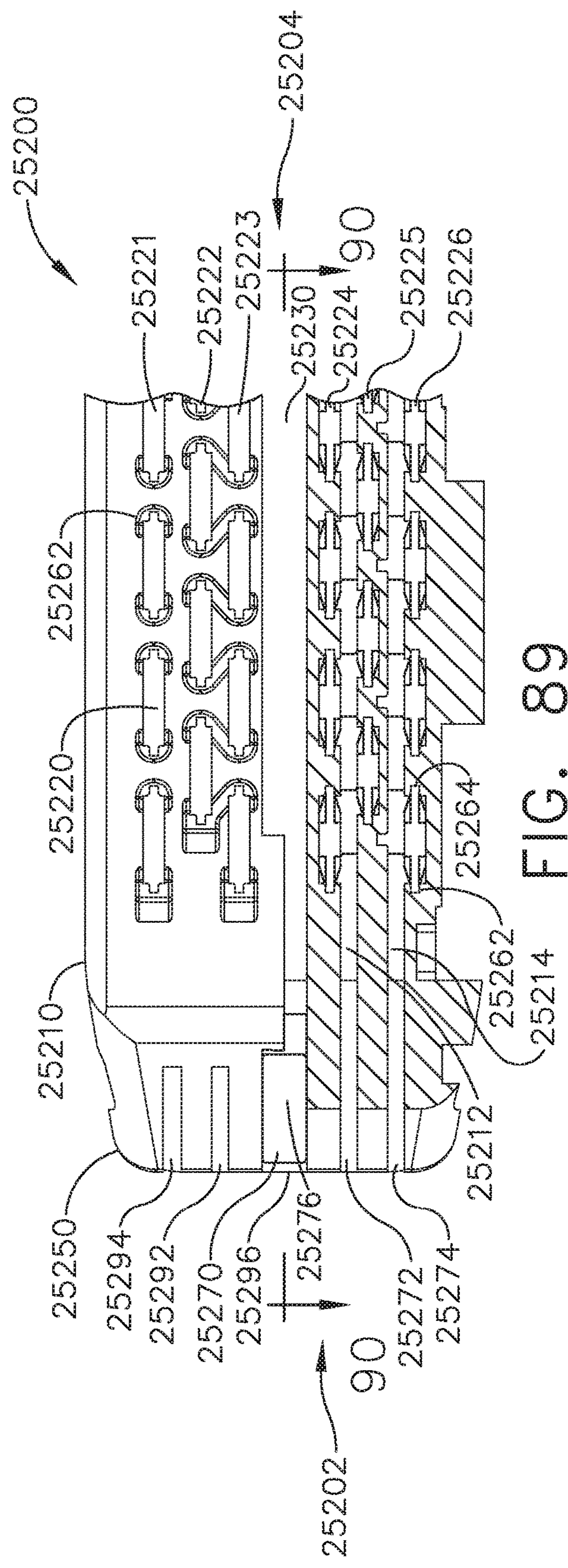
FIG. 89 is a partial plan view of the staple cartridge of FIG. 85 illustrating one side of the staple cartridge deck in cross-section and showing the position of the sled of FIG. 88 within recesses defined in the shortened nose of the cartridge after the completion of a firing stroke.

FIG. 89 is a plan view of the staple cartridge 25200. The cartridge body 25210 of the staple cartridge 25200 comprises an elongate slot 25230 that extends from a proximal end 25204 of the staple cartridge 25200 toward the distal, shortened nose 25250. A plurality of staple cavities 25220 are formed within the cartridge body 25210. Staple cavities 25220 extend between the proximal end 25204 and the distal end 25202 of the staple cartridge 25200. The staple cavities 25220 are arranged in six laterally-spaced longitudinal rows 25221, 25222, 25223, 25224, 25225, 25226, with three rows on each side of the elongate slot 25230. Removably positioned within the staple cavities 25220 are staples 25260.

Figure 87:
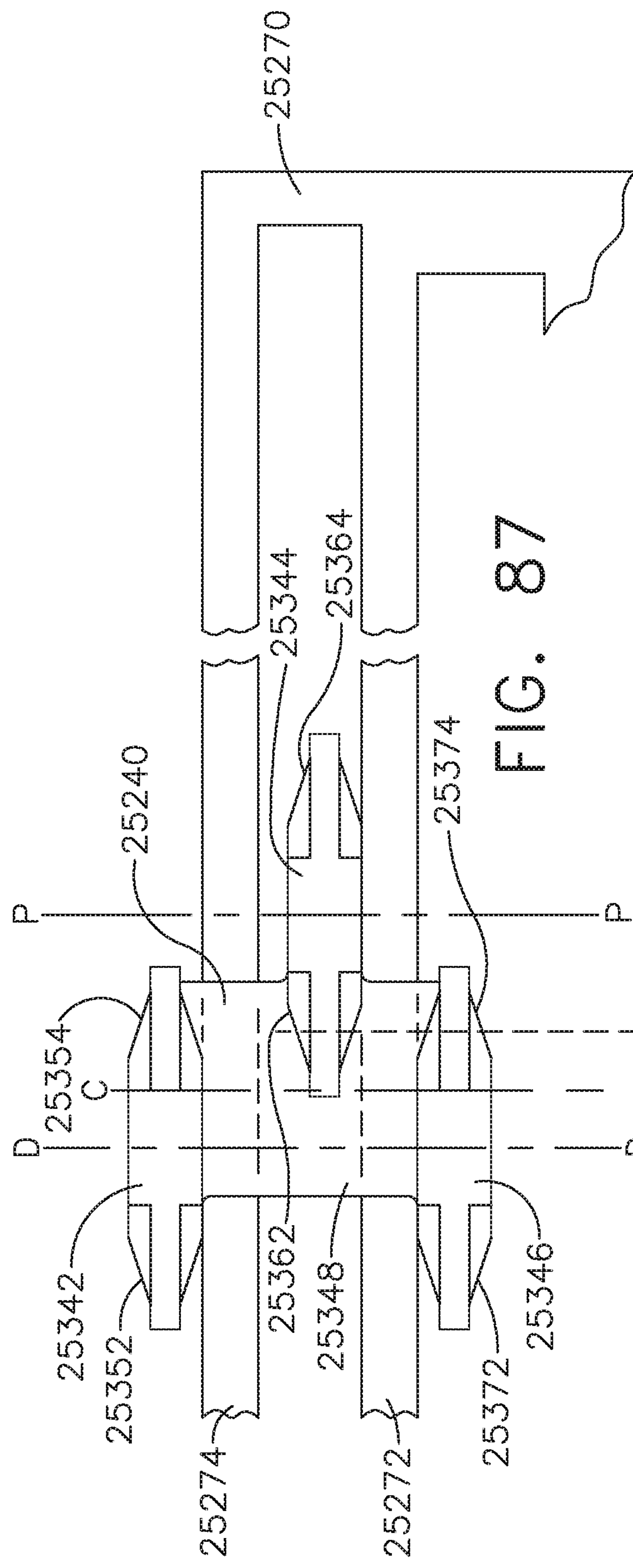
FIG. 87 is a top view of various internal components of the staple cartridge of FIG. 85 illustrating a triple staple driver spanning across three longitudinal rows of staple cavities positioned on top of a portion of a wedge sled.

FIG. 87 illustrates one embodiment of a triple staple driver 25240 within the staple cartridge 25200 for supporting and driving three staples 25260. The staple driver 25240 comprises a first driver portion 25342, a second driver portion 25344, and a third driver portion 25346. A central base member 25348 connects the first driver portion 25342 and the third driver portion 25346 to the second driver portion 25344. The first driver portion 25342 is positioned at least partially distal to the second driver portion 25344. Additionally, the third driver portion 25346 is positioned at least partially distal to the second driver portion 25344. A plurality of first staple drivers 25240 are slidably mounted within corresponding staple cavities 25220 from the three longitudinal rows 25221, 25222, 25223 on one side of the elongate slot 25230. In other words, each first staple driver 25240 is configured to support three staples 25260: a staple 25260 stored within a staple cavity 25220 in the first longitudinal row 25221; a staple 25260 stored within a staple cavity 25220 in the second longitudinal row 25222; and a staple 25260 stored within a staple cavity 25220 in the third longitudinal row 25223. Due to the distal position of the first driver portion 25342 and the third driver portion 25346 relative to the second driver portion 25344, the staples 25260 are fired in a reverse arrow configuration. As shown in FIG. 89, the last staples 25260 in the first longitudinal row 25221 and the third longitudinal row 25223 are closer to the shortened nose 25250 of the staple cartridge 25200 than the last staple 25260 in the second longitudinal row 25222.

On the other side of the elongate slot 25230, a plurality of second staple drivers are mounted within corresponding staple cavities 25220 in the three longitudinal rows 25224, 25225, 25226. Similar to the staple driver 25240, the second staple drivers each comprise a first driver portion 25342, a second driver portion 25344, and a third driver portion 25346. A central base member 25348 connects the first driver portion 25342 and the third driver portion 25346 to the second driver portion 25344. The first driver portion 25342 is positioned at least partially distal to the second driver portion 25344. Additionally, the third driver portion 25346 is positioned at least partially distal to the second driver portion 25344. As the staple driver 25240 above, each second staple driver is configured to support three staples 25260: a staple 25260 stored within a staple cavity 25220 in the fourth longitudinal row 25224, a staple 25260 stored within a staple cavity 25220 in the fifth longitudinal row 25225, and a staple 25260 stored within a staple cavity 25220 in the sixth longitudinal row 25226. Due to the distal position of the first driver portion 25342 and the third driver portion 25346 relative to the second driver portion 25344, the staples 25260 are fired in a reverse arrow configuration. As shown in FIG. 89, the last staples 25260 in the fourth longitudinal row 25224 and the sixth longitudinal row 25226 are closer to the shortened nose 25250 of the staple cartridge 25200 than the last staple 25260 in the fifth longitudinal row 25225.

The first driver portion 25342 of the staple driver 25240 has a first forward support column 25352 and a first rearward support column 25354 protruding upward from a first driver portion base. The first forward support column 25352 and the first rearward support column 25354 are spaced from each other and collectively form a first staple cradle for supporting a staple 25260 in an upright position (i.e., the prongs of the staple facing the anvil). Similarly, the second driver portion 25344 has a second forward support column 25362 and a second rearward support column 25364 protruding upward from a second driver portion base. The second forward support column 25362 and the second rearward support column 25364 are spaced from each other and collectively form a second staple cradle for supporting a staple 25260 in an upright position (i.e., the prongs of the staple facing the anvil). The third driver portion 25346 has a third forward support column 25372 and a third rearward support column 25374 protruding upward from a third driver portion base. The third forward support column 25372 and the third rearward support column 25374 are spaced from each other and collectively form a third staple cradle for supporting a staple 25260 in an upright position (i.e., the prongs of the staple facing the anvil).

Figure 88:
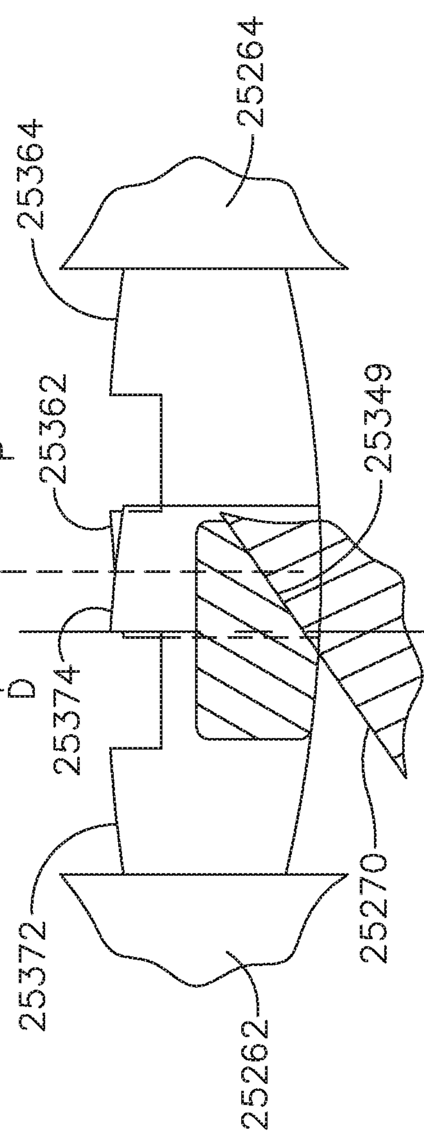
FIG. 88 is a cross-sectional view of the triple staple driver of FIG. 87 illustrating the centerline of the triple staple driver with respect to the sled.

The center of mass of the first and third driver portions 25342, 25346 is represented by the dashed line D-D. Similarly, the dashed line P-P represents the center of mass of the second driver portion 25344. The combined center of mass of the triple staple driver 25240 is represented in FIGS. 87 and 88 as dashed line C-C. As such, staple driver 25240 is less likely to roll forward. Notably, C-C is closer to D-D than P-P which makes the staple driver 25240 very stable.

Figure 90:
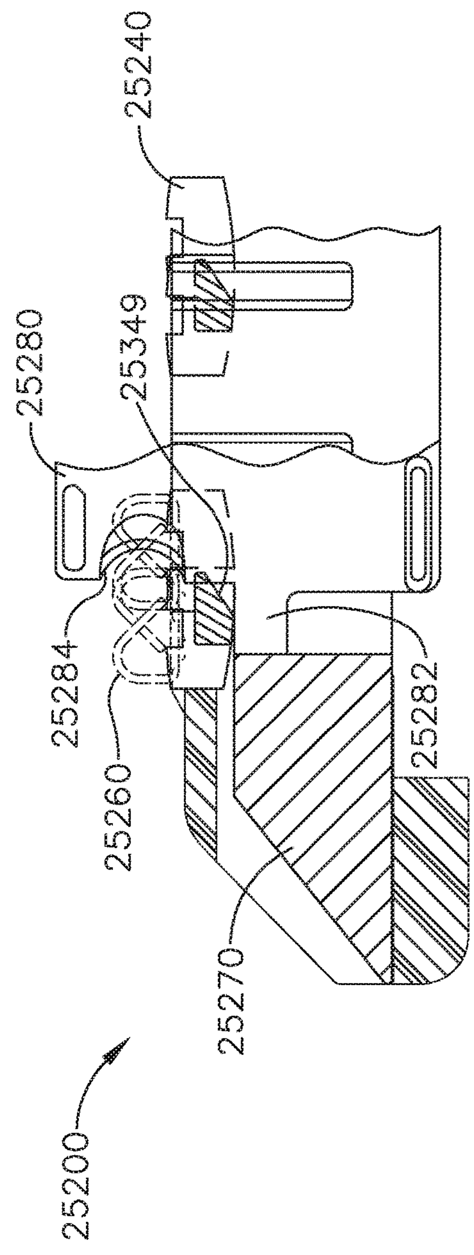
FIG. 90 is a partial cross-sectional view of the staple cartridge of FIG. 85 taken along line 90-90 in FIG. 89 illustrating the position of the sled after the completion of a firing stroke.

As discussed above, the central base member 25348 of the staple driver 25240, depicted in FIG. 88, attaches the first driver portion 25342 and the third driver portion 25346 to the second driver portion 25344. The central base member 25348 extends laterally between the proximal ends of the first and third rearward support columns 25354, 25374 on the first and third driver portions 25342, 25346, respectively, and the proximal end of the second forward support column 25362 on the second driver portion 25344. As can be seen in FIG. 90, the central base member 25348 has an angled rearwardly facing edge 25349 adapted to be engaged by a wedge sled 25270, as will be discussed in further detail below. Due to the extension of the central base member 25348 between all three driver portions 25342, 25344, 25346, the midpoint of the rearwardly facing edge 25349 may be bifurcated into a portion which is closer to the first portion 25342 and a portion which is closer to the third portion 25346. Such an arrangement can balance moments created during the firing and formation of the staples 25260 stored within the staple cavities 25220.

Referring primarily to FIG. 89, each staple cavity 25220 defined in the cartridge body 25210 of the staple cartridge 25200 comprises a proximal wall 25264 and a distal wall 25262. The reverse arrow orientation formed by the arrangement of the first, second, and third driver portions 25342, 25344, 25346 of the triple staple driver 25240 discussed above, reduces forward and/or lateral roll of the staple driver 25240 during a staple firing stroke. In various instances, the distal end of the first forward support column 25352 and the distal end of the third forward support column 25372 are pushed into the distal walls 25262 of their respective staple cavities 25220, which stabilize the driver 25240. Thus, when the sled 25270 (FIG. 89) lifts the staple driver 25240 upwardly during the staple firing stroke, two distal walls 25262 of the staple cavities 25220 provide an opposing force against the forward support columns 25352, 25372, preventing any unwanted movement or rolling of the staple driver 25240.

As illustrated in FIGS. 87-90, the elongate slot 25230 of the staple cartridge 25200 is configured to receive a portion of a firing assembly 25280. The firing assembly 25280 is configured to push the sled 25270 distally to eject the staples 25260 stored within the staple cavities 25220 and deform the staples 25260 against an anvil positioned opposite the staple cartridge 25200. More specifically, a coupling member 25282 pushes the wedge sled 25270 of the staple cartridge 25200 distally. The wedge sled 25270 has four rails, two inner rails 25272 and two outer rails 25274 which are connected to each other by a central member 25276. One inner rail 25272 and one outer rail 25274 are positioned on one side of the elongate slot 25230, while the other inner rail 25272 and the other outer rail 26274 are positioned on the opposite side of the elongate slot 25230. When driven distally, the inner rails 25272 pass through inner channels 25212 defined within the cartridge body 25210 and engage the rearwardly facing edge 25349 of the drivers 25240 supporting the staples 25260 to cause the firing of the staples toward the anvil. Likewise, the outer rails 25274 pass through outer channels 25214 defined within the cartridge body 25210 and engage portions of the drivers 25240 supporting the staples 25260 to push the staples toward the anvil. Distal movement of the wedge sled 25270 causes the rails 25272, 25274 to make contact with the rearwardly facing edges 25349 of the staple drivers 25240, pushing drivers 25240 upwards to eject the staples 25260 from the staple cartridge 25200 into tissue captured between the staple cartridge 25200 and an opposing anvil. The coupling member 25282 also comprises a cutting edge 25284 which incises the tissue as the coupling member 25282 is advanced distally to eject the staples 25260 from the cartridge body 25210.

Referring again to FIG. 87, the positioning of the first, second, and third driver portions 25342, 25344, 25346 of the staple driver 25240 between or adjacent an inner rail 25272 and an outer rail 25274 of the wedge sled 25270 provides increased lateral stability. Two rails, one inner rail 25272 and one outer rail 25274, straddle the staple driver 25240, providing increased support and stability of throughout a firing stroke. In addition to providing enhanced stability to the staple driver 25240, another benefit of having a staple driver 25240 spanning across two rails 25272, 25274 of a wedge sled 25270 is a reduced force required to perform a firing stroke. The required force is decreased as there is less deflection and loss within the system. Additionally, the additional drive surface provided by the rearwardly facing edge 25349 allows for the rails 25272, 25274 of the wedge sled 25270 to extend at a steeper angle from the base 25278 of the wedge sled 25270. The steeper angle of the wedge sled 25270 allows for an overall decrease in the length of the base 25278 of the wedge sled 25270, further contributing to the reduction in length of the shortened nose 25250 of the staple cartridge 25200. Upon the completion of the staple firing stroke, referring again to FIG. 89, the wedge sled 25270 of the firing assembly 25280 is parked within the shortened nose 25250 of the staple cartridge 25200.

FIG. 89 depicts the wedge sled 25270 of the firing assembly 25280 parked in the shortened nose 25250 upon the completion of the staple firing stroke. The shortened nose 25250 comprises a plurality of openings 25292, 25294 at the distal end of the shortened nose 25250 to receive the four rails 25272, 25274. The shortened nose 25250 further comprises an opening 25296 configured to receive the central sled member 25276 of the wedge sled 25270. Thus, portions of the rails 25272, 25274 and central sled member 25276 of the wedge sled 25270 are exposed at the distal end 25202 of the staple cartridge 25200. The openings 25292, 25294 are continuations of the channels 25212, 25214 within which the rails 25272, 25274 of the wedge sled 25270 slidably travel. Two inner openings 25292 are configured to receive the two inner rails 25272 of the wedge sled 25270, while two outer openings 25294 are configured to receive the two outer rails 25274 of the wedge sled 25270. A central opening 25296 in the center of the distal portion 25202 of the shortened nose 25250 is configured to receive the central member 25276 of the wedge sled 25270. The openings 25292, 25294, 25296 at the distal end 25202 of the shortened nose 25250 allow for the staple firing stroke to be completed and for the wedge sled 25270 to be parked in a shortened distal end.

Referring again to FIG. 89, the staple cartridge 25200 further includes projections 25262 extending around the proximal and distal ends of the staple cavities 25220. The projections 25262 in the first longitudinal row 25221 are shown to be singular, while the projections in the second and third longitudinal rows 25222, 25223 are shown to be connected. The projections 25262 are configured to provide additional support to the staples 25260 as they are fired upwardly out of their staple cavities 25220. Furthermore, the projections 25264 formed on the distalmost staple cavity 25220 are ramped to control the flow of tissue into the end effector. A more detailed discussion of the projections can be found in U.S. Patent Application Publication No. 2015/0297228, entitled FASTENER CARTRIDGES INCLUDING EXTENSIONS HAVING DIFFERENT CONFIGURATIONS, filed on Jun. 30, 2014, the entire disclosure of which is incorporated by reference.

Figure 91:
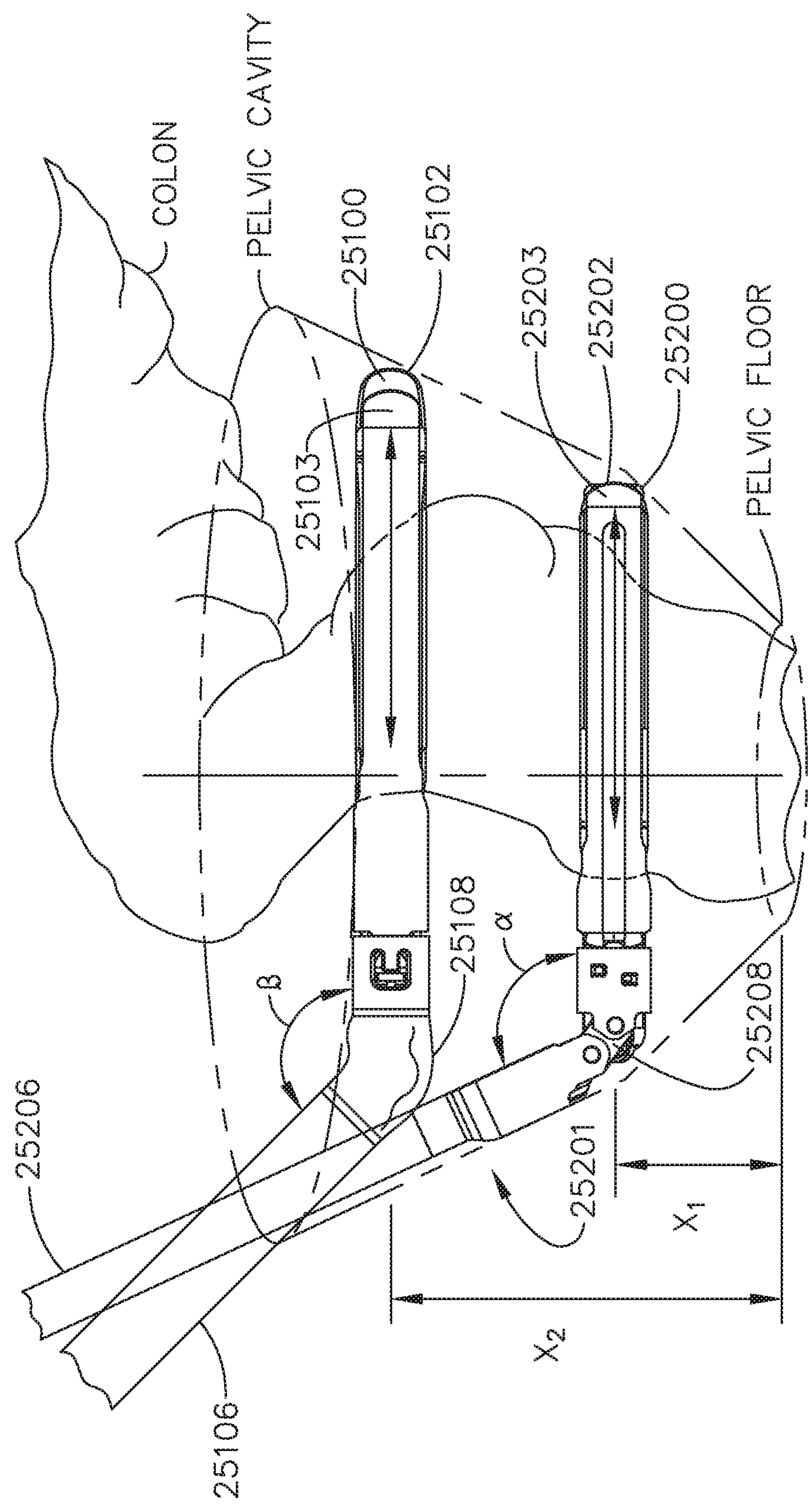
FIG. 91 is a diagram comparing the accessibility of end effectors comprising the staple cartridges in FIGS. 85 and 86 during a surgical procedure in a pelvic cavity.

FIG. 91 illustrates some of the advantages gained by using the shortened staple cartridge 25200 from FIG. 85 instead of the elongate staple cartridge 25100 from FIG. 86. Both staple cartridges are suitable for various surgical procedures, including, for example, Low Anterior Resection Surgery (LAR). LAR is a common treatment for colorectal cancer, for example. Such procedures require precise dissection and sealing of tissue deep within the pelvic cavity of a patient. As will be discussed in more detail below, the shortened length of the staple cartridge 25200, owing to the shortened nose 25250 in FIG. 85, among other things, allows the end effector of the surgical instrument to gain greater access to tissue within the pelvic cavity. The reader should understand that the staple cartridges described herein can be used in various surgical treatments and are not to be limited by the specific procedures discussed herein.

Further to the above, the short staple cartridge 25200 is part of a first end effector 25202 on a first surgical instrument 25201 which also includes an anvil 25203. The first surgical instrument 25201 further comprises a first shaft 25206 that is rotatably connected to the first end effector 25202. The first end effector 25202 is articulatable about an articulation joint 25208 positioned intermediate the first end effector 25202 and the first shaft 25206. The first end effector 25202 is capable of being articulated to an angle α with respect to the first shaft 25206. Similarly, the elongate staple cartridge 25100 is part of a second end effector 25102 on a second surgical instrument 25101 which also includes an anvil 25103. Also, the second surgical instrument 25101 further comprises a second shaft 25106 that is rotatably connected to the second end effector 25102. The second end effector 25102 is articulatable about an articulation joint 25108 positioned intermediate the second end effector 25102 and the second shaft 25106. The second end effector 25102 is capable of being articulated to an angle β with respect to the second shaft 25106.

Further to the above, in use, a clinician inserts the end effector 25202 through a cannula, or trocar, and into a patient when the end effector 25202 is in its unarticulated condition. Once through the trocar, the end effector 25202 can be articulated as illustrated in FIG. 91. At such point, the shaft 25206 can be moved to position the end effector 25202 in the pelvic cavity. Similar steps would be used to position the end effector 25102.

The first end effector 25202 is able to reach a distance $X_1$ from the pelvic floor within the pelvic cavity during a LAR procedure. The second end effector 25102 is able to reach a distance $X_2$ from the pelvic floor within the pelvic cavity during a LAR procedure. Distance $X_1$ is shorter than distance $X_2$, allowing the first surgical instrument 25201 to be placed deeper into the pelvic cavity than the second surgical instrument 25101, giving the surgeon the capability to, among other things, target, access, and remove a greater array of diseased tissue from the colon. Additionally, the articulation capabilities of the first surgical instrument 25201 allow deeper access to tissue within the surgical site while inflicting minimal trauma to surrounding tissue. The first end effector 25202 is able to be articulated to a greater degree than the second end effector 25102, as β is larger than α. For example, the first end effector 25202 may be articulated to an angle 115 degrees from the first shaft 25206, while the second end effector 25102 may only be articulated to an angle 135 degrees from the second shaft 25106.

As illustrated in FIG. 91, the staple cartridge 25100 and the anvil 25103 of the end effector 25102 have approximately the same length, but the staple cartridge 25100 is noticeably longer than the anvil 25103. Comparatively, the staple cartridge 25200 and the anvil 25203 of the end effector 25202 are substantially the same length, if not the same length. In any event, the difference in length between the staple cartridge 25200 and the anvil 25203 of the end effector 25202, if any, is much smaller than the end effector 25102.

Figure 93:
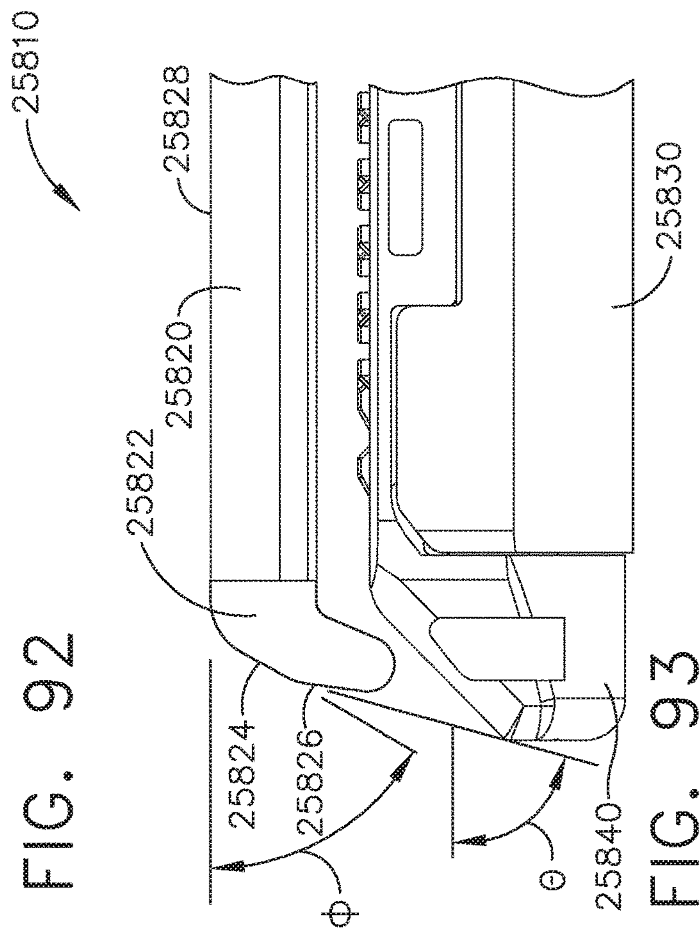
FIG. 93 is a partial elevational view of the end effector of FIG. 92.
Figure 92:
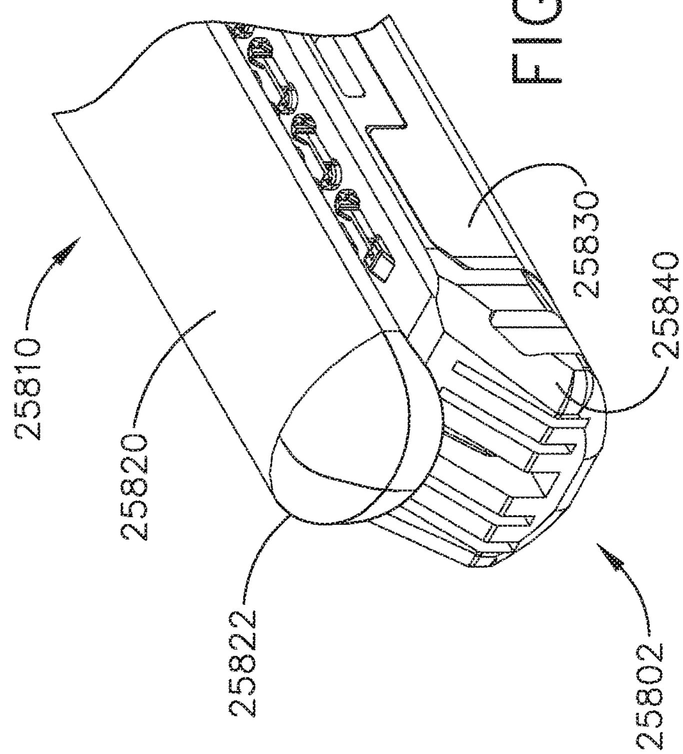
FIG. 92 is a partial perspective view of an end effector comprising the staple cartridge of FIG. 85 and a shortened opposing anvil with a protective tip in accordance with at least one embodiment.

An extreme difference between the distal end of a staple cartridge and a distal end of an anvil can cause damage to a trocar when the end effector is inserted there through. Referring to FIG. 92, an end effector 25810 comprises a distal end 25802, an anvil 25820, and a staple cartridge 25830. The staple cartridge 25830 has a blunt, shortened nose 25840 similar to the shortened nose 25250 on the staple cartridge 25200 in FIG. 85. As can be seen in FIGS. 92 and 93, the anvil 25820 has a protective tip 25822 thereon. The protective tip 25822 is sized and positioned on the anvil 25820 in a way that causes the anvil 25820 to be shorter in length than the staple cartridge 25830. Thus, the shortened nose 25840 of the staple cartridge 25830 extends distally relative to the anvil 25820. The protective tip 25822 may be integrally formed (molded, machined, etc.) on the distal end 25802 of the anvil 25820 or it may comprise a separate piece configured to receive a complementary portion of the anvil. A more extensive discussion of protective tips can be found U.S. Patent Application Publication No. 2008/0169328, entitled IMPROVED BUTTRESS MATERIAL FOR USE WITH A SURGICAL STAPLER, the entire disclosure of which is hereby incorporated by reference in its entirety.

As can be seen in FIGS. 92 and 93, the protective tip 25822 of the anvil 25820 has a first curved, or angled, outer surface 25824 and a second curved, or angled, outer surface 25826 configured to form a stubby distal end on the anvil 25820. The first angled outer surface 25824 extends downwardly from a top surface 25828 of the anvil 25820 at a first angle ϕ. The second angled outer surface 25826 extends downwardly from the first angled outer surface 25824 toward the staple cartridge 25830 at a second angle θ. The second angle θ is greater than the first angle ϕ. Various embodiments are envisions in which angle θ is approximately 90 degrees, for example. Other embodiments of the protective tip 25822 are envisioned having only one of either a first angled outer surface 25824 or a second angled outer surface 25826. The first angled outer surface 25824 serves to deflect a centering ring of a trocar seal assembly during the insertion of the end effector 25810 through the trocar. When the second angle θ gets farther from 90 degrees, and/or when the first and second curved outer surfaces 25824, 25826 are not continuous, the anvil 25820 might pierce through a trocar seal or can displace the centering ring of a trocar seal system, as will be discussed in greater detail below.

Figure 94:
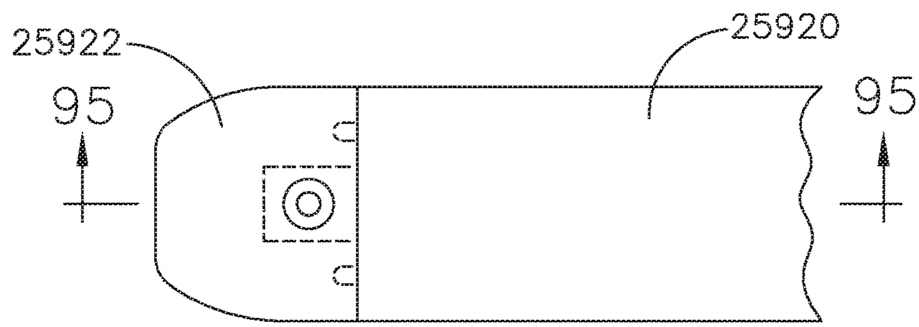
FIG. 94 is a partial plan view of one embodiment of the anvil depicted in FIG. 92 with a protective tip in an assembled configuration.
Figure 95:
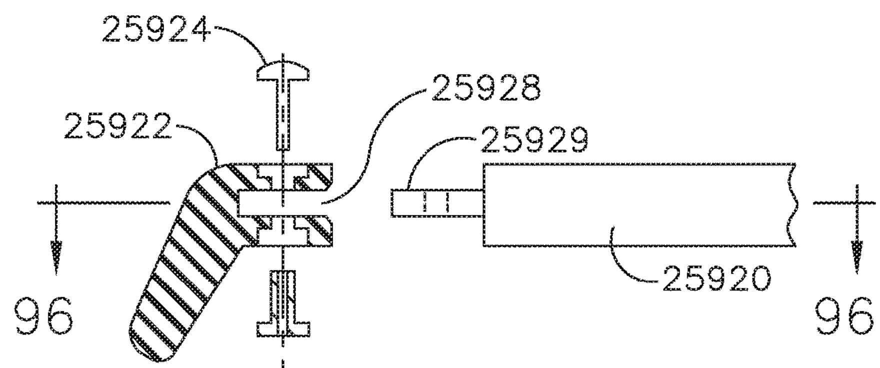
FIG. 95 is a partial cross-sectional view of the anvil depicted in FIG. 94 taken along line 95-95 in FIG. 94 and illustrated in a partially disassembled configuration showing exemplary attachment means for removably affixing the protective tip to the anvil.
Figure 96:
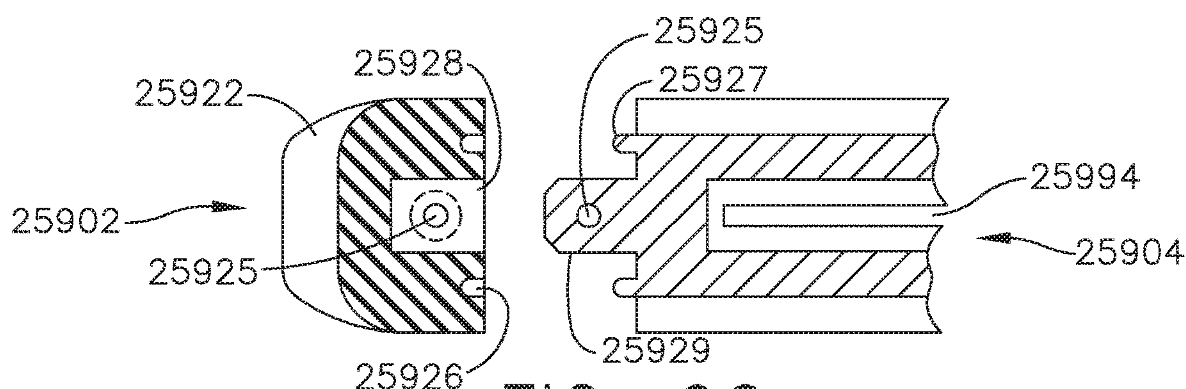
FIG. 96 is a partial cross-sectional view of the anvil depicted in FIG. 95 taken along line 96-96 in FIG. 95 and illustrated in a partially disassembled configuration showing the geometry of an attachment feature on the anvil for connection to corresponding geometry on the protective tip.

A protective tip can be attached to an anvil in any suitable manner. FIGS. 94-99 illustrate exemplary embodiments of separately formed protective tips 25922, 26022, and various methods for their attachment to an anvil. As depicted in FIGS. 94-96, a distal portion of an anvil 25920 comprises an attachment feature including attachment members 25927, 25929 which are configured to retainingly mate with complementary retention channels 25926, 25928 formed in the protective tip 25922. More specifically, a central retention channel 25928 is formed within the protective tip 25922 to receive a central attachment member 25929 of the anvil 25920. A pair of side retention channels 25296 is formed within the protective tip 25922 to receive a pair of corresponding side attachment members 25927 on the anvil 25920. FIG. 96 is a cross-sectional view of the anvil 25920 of FIG. 94 taken along the line 96-96 in FIG. 95 in a disassembled configuration showing the alignment of the retention channels 25926, 25928 with their respective attachment members 25927, 25929. An elongate slot 25994 extends longitudinally from the proximal end 25904 of the anvil 25920 toward the distal end 25902 of the anvil 25920. The elongate slot 25994 is configured to receive a portion of the firing assembly discussed herein.

In addition, or in the alternative, to the above, the protective tip 25922 may be secured to the anvil 25920 using rivets 25924. As shown in FIG. 96, a through-hole 25925 extends through the central retention channel 25928 of the protective tip 25922. A through-hole 25925 also extends through the central attachment member 25929 of the anvil 25920 so that when the protective tip 25922 is attached to the anvil 25920, the through-holes 25925 line up to facilitate the insertion of a rivet 25924 therein. FIG. 95 is a cross-sectional view of the anvil 25920 of FIG. 94 taken along line 95-95 in FIG. 94 in a disassembled configuration illustrating a rivet assembly for removably affixing the protective tip 25922 to the anvil 25920. In addition, or in the alternative, to the above, the protective tip 25922 may be affixed to the anvil 25920 by adhesives such as, for example, cyanoacrylates, light-curable acrylics, polyurethanes, silicones, epoxies, and/or ultra-violet curable adhesives such as HENKEL LOCTITE®. In any event, a combination of attachment members and retention channels may be provided on the anvil 25920 and the protective tip 25922. Still other forms of attachments and attachment arrangements may be used to affix the protective tip 25922 to the anvil 25920.

Figure 97:
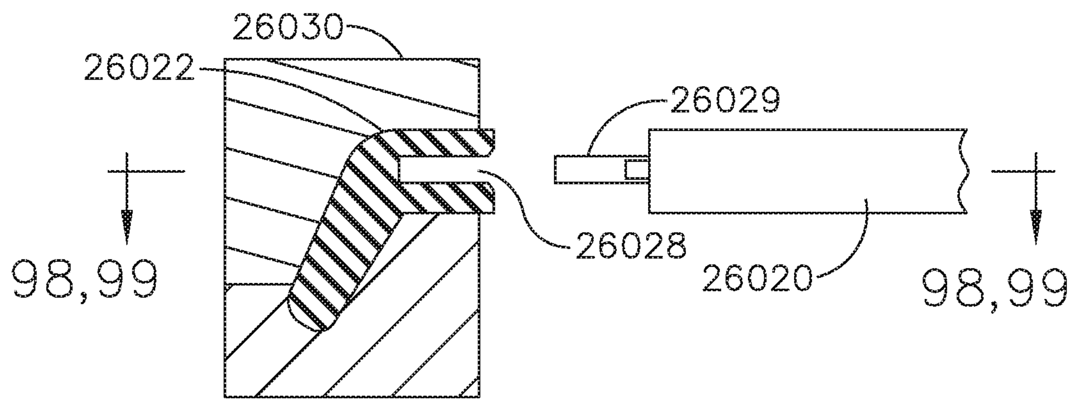
FIG. 97 is a partial cross-sectional view of an additional embodiment of the anvil depicted in FIG. 92 in a partially disassembled configuration, illustrating a protective tip positioned within a temporary holder.
Figure 98:
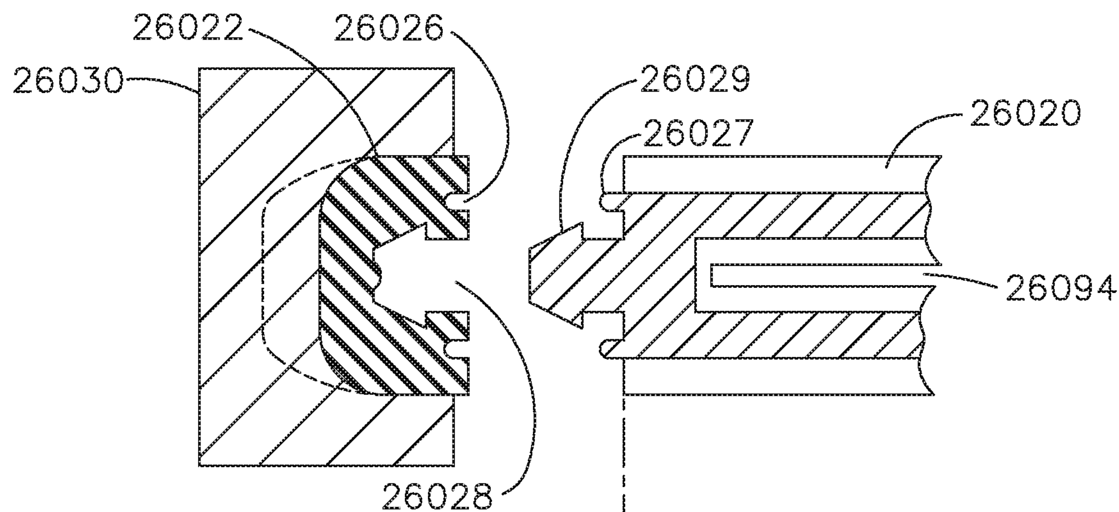
FIG. 98 is a cross-sectional view of the anvil depicted in FIG. 97 taken along line 98-98 in FIG. 97 in a partially disassembled configuration, showing the geometry of a tip attachment feature on the anvil.
Figure 99:
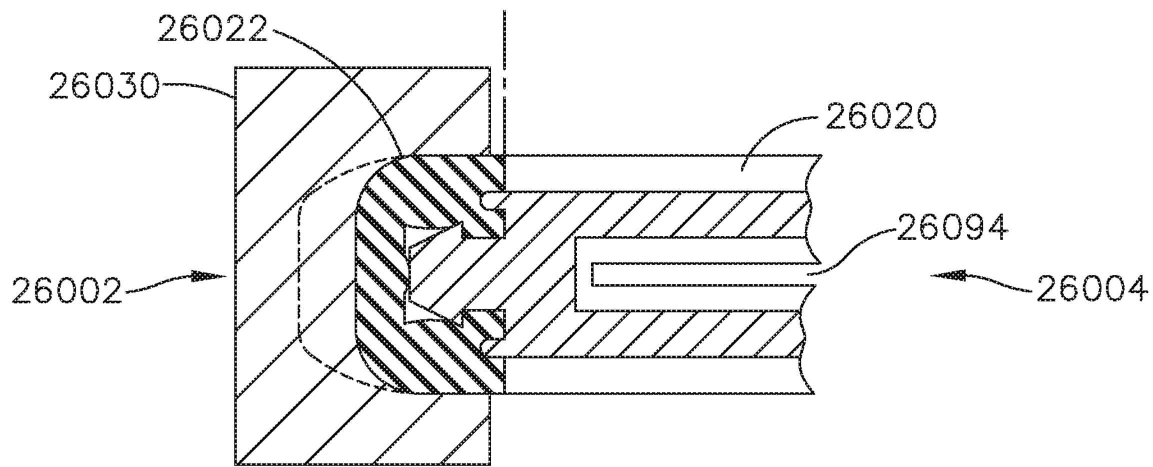
FIG. 99 is a cross-sectional view of the anvil depicted in FIG. 97 taken along line 99-99 in FIG. 97 in an assembled configuration with the temporary holder still attached.

FIGS. 97-99 illustrate another embodiment of a tip attachment arrangement. A distal portion of an anvil 26020 comprises attachment members 26027 configured to retainingly mate with complementary retention channels 26026 defined in the protective tip 26022. In addition, a central retention channel 26028 defined within the protective tip 26022 is configured to receive a central attachment member 26029 of the anvil 26020. FIG. 98 is a cross-sectional view of the anvil 26020 of FIG. 97 taken along the line 98-98 in FIG. 97 in a disassembled configuration showing the alignment of the retention channels 26026, 26028 with their respective attachment members 26027, 26029. FIG. 99 is a cross-sectional view of the anvil 26020 of FIG. 97 taken along the line 99-99 in FIG. 97 in an assembled configuration. The protective tip 26022 is secured to the anvil 26020 using a compression fit. The central attachment member 26029 is press-fit into the central retention channel 26028, remaining in place due to the geometry of the central retention channel 26028. The central attachment member 26029 of the anvil 26020 in FIG. 98 has a trapezoidal shape that is mimicked by the central retention channel 26028. An elongate slot 26094 extends longitudinally from a proximal end 26004 of the anvil 26020 toward the distal end 26002 of the anvil 26020. The elongate slot 26094 is configured to receive a portion of the firing assembly discussed herein.

In addition, or in the alternative, to the above, the protective tip 26022 may be affixed to the anvil 26020 by adhesives such as, for example, cyanoacrylates, light-curable acrylics, polyurethanes, silicones, epoxies, and/or ultraviolet curable adhesives such as HENKEL LOCTITE®, for example. In various embodiments, a combination of attachment members and retention channels may be provided on the anvil 26020 and the protective tip 26022. Still other forms of attachments and attachment arrangements may be used to affix the protective tip 26022 to the anvil 26020. FIGS. 97-99 further illustrate means for assisting a user in attaching the protective tip 26022 to the anvil 26020. FIG. 97 illustrates the protective tip 26022 removably positioned within a temporary holder 26030. In order to releasably affix the protective tip 26022 to the anvil 26020, the user presses the temporary holder 26030 and the anvil 26020 together. The temporary holder 26030 may provide an additional sterilization barrier to the protective tip 26022 while the protective tip 26022 is affixed to the anvil 26020. Furthermore, the temporary holder 26030 provides the user with an object that is more substantial to hold onto while attaching the protective tip 26022 to the anvil 26020, as the protective tip 26022 may be small in size. It is envisioned that the temporary holder 26030 can be used across various embodiments of protective tips, including the other embodiments disclosed herein.

Various protective anvil tips have been described and depicted herein as being used in connection with a linear end effector. Those of ordinary skill in the art will readily appreciate, however, that the protective anvil tips described herein may be used in connection with a variety of different end effector configurations such as curved end effectors and other types of end effectors without departing from the spirit and scope of the present disclosure. Thus, the protective tip described above should not be limited solely to use in connection with linear end effectors and/or staplers.

FIGS. 100-106 illustrate an exemplary practical application of the various end effectors described herein when they are inserted through a trocar seal system prior to being introduced into a surgical site. The trocar seal system 27040 of FIGS. 100-106 comprises a housing 27042 configured to support a floating seal assembly 27050 and a central opening 27044 configured to receive a surgical instrument. The floating seal assembly 27050 comprises a first seal door 27052 and a second seal door 27054 that work together to prohibit gas from escaping from an insufflated cavity in a patient during a surgical procedure. The floating seal assembly 27050 further comprises a centering ring 27058 which is configured to guide a surgical instrument through the central opening 27044 of the trocar seal system 27040. The floating seal assembly 27050 is attached to the housing 27042 of the trocar seal system 27040 through an annular resilient member 27056.

Figures 100, 101:
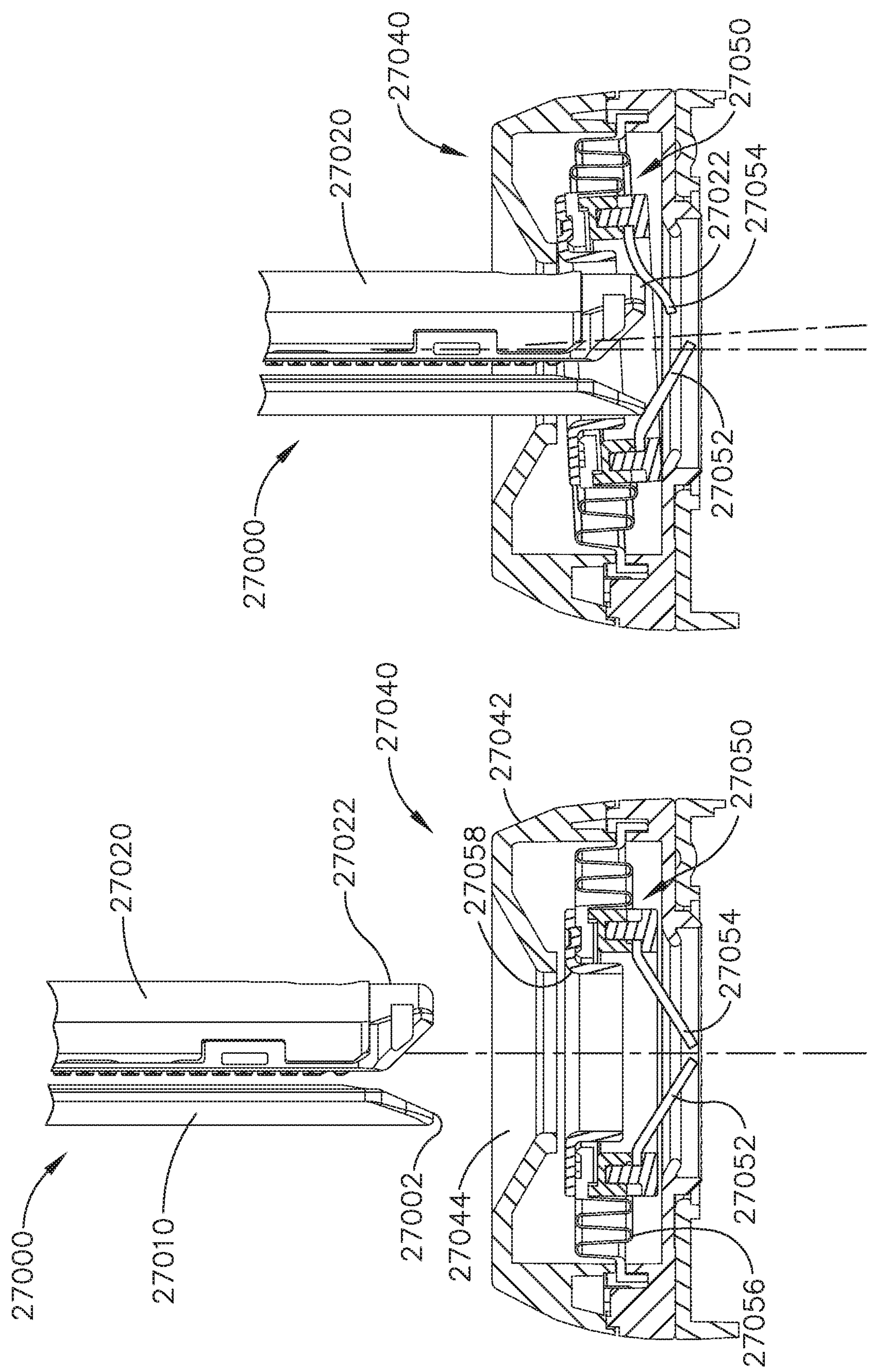

FIG. 100 depicts an end effector 27000 comprising an anvil 27010 and a staple cartridge 27020. The staple cartridge 27020 comprises a blunt, shortened nose 27022, similar to the shortened nose 25250 depicted on the staple cartridge 25200 in FIG. 85. The distal end 27202 of the anvil 27010 is pointed and does not have a protective tip, such as that shown in FIG. 92. As can be seen in FIG. 100, the anvil 27010 is shorter in length than the staple cartridge 27020. In other words, the shortened nose 27022 of the staple cartridge 27020 extends longitudinally beyond the distal end 27002 of the anvil 27010. Prior to inserting the end effector 27000 through the trocar seal system 27040, the first seal door 27052 and the second seal door 27054 extend inwardly to prevent gas from escaping from the surgical site. FIG. 101 depicts the end effector 27000 of FIG. 100 partially inserted into the trocar seal system 27040. The shortened nose 27022 of the staple cartridge 27020 is the first component of the end effector 27000 to come into contact with the first and second seal doors 27052, 27054 of the trocar seal system 27040, tilting the floating seal assembly 27050 to one side. Due to its blunt shape, the shortened nose 27022 does not damage the second seal door 27054 despite exerting a force on it.

Figures 102, 103:
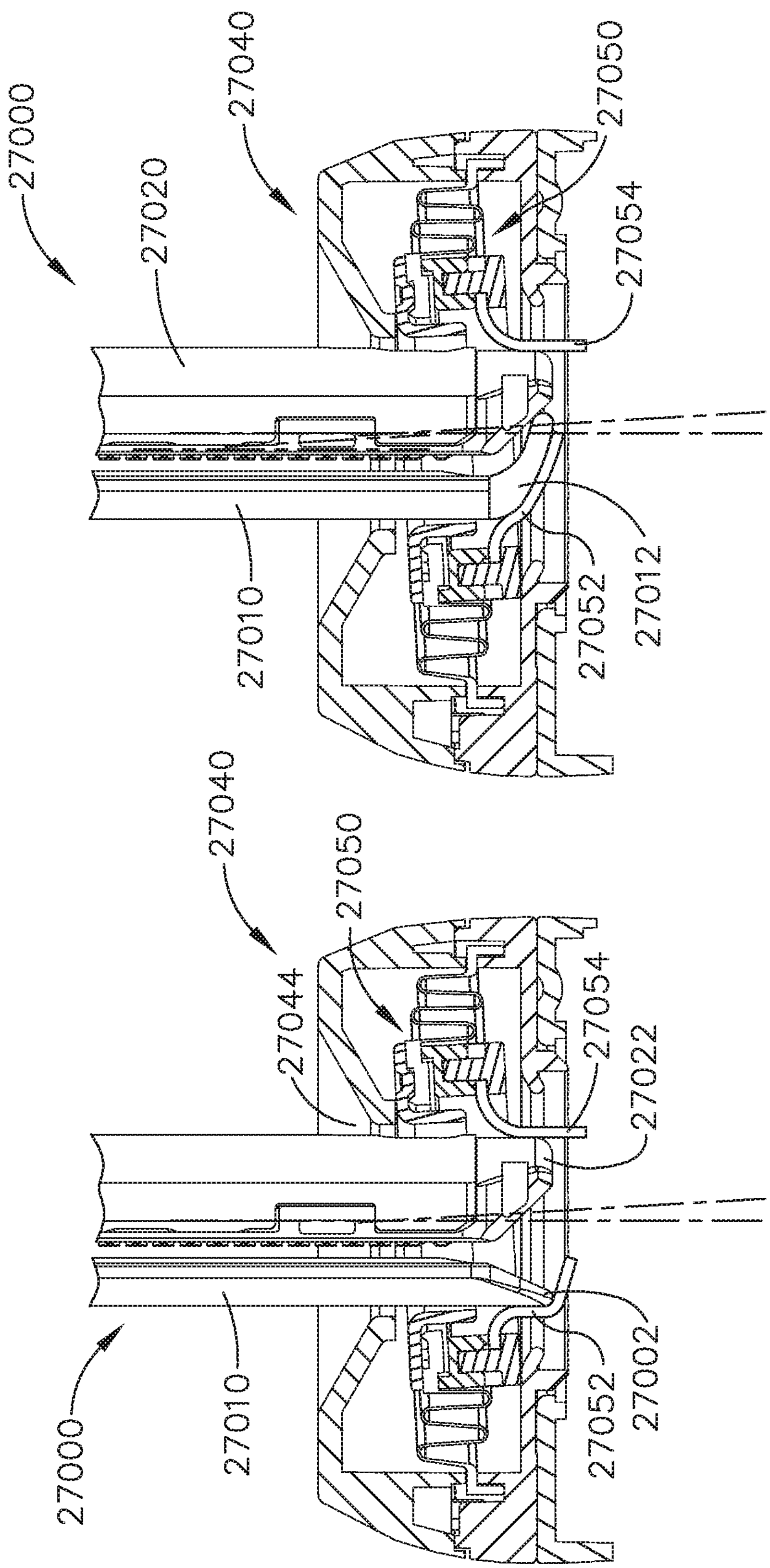

FIG. 102 depicts the end effector 27000 of FIGS. 100 and 101 when the end effector 27000 has been further introduced into the central opening 27044 of the trocar seal system 27040. After the initial contact of the shortened staple cartridge nose 27022 with the trocar seal system 27040, the pointed distal end 27002 of the anvil 27010 contacts the first seal door 27052 of the trocar seal system 27040. In various instances, the pointed distal end 27002 of the anvil 27010 can rupture the first seal door 27052 of the trocar seal system 27040, as the contact between the shortened nose 27022 and the second seal door 27054 has already shifted the position of the floating seal assembly 27050 laterally. As illustrated in FIG. 103, had the distal end 27002 of the anvil 27010 comprised a protective tip 27012 similar to the protective tip 25822 shown in FIG. 92, the risk of rupturing the first seal door 27052 would have been reduced. The risk of rupture decreases with the use of a protective tip 27012 on the anvil 27010, as the first seal door 27052 will smoothly stretch around the protective tip 27012. Moreover, the same length of the cartridge and the anvil reduces, or prevents, the pre-shifting of the floating seal assembly.

Figure 105:
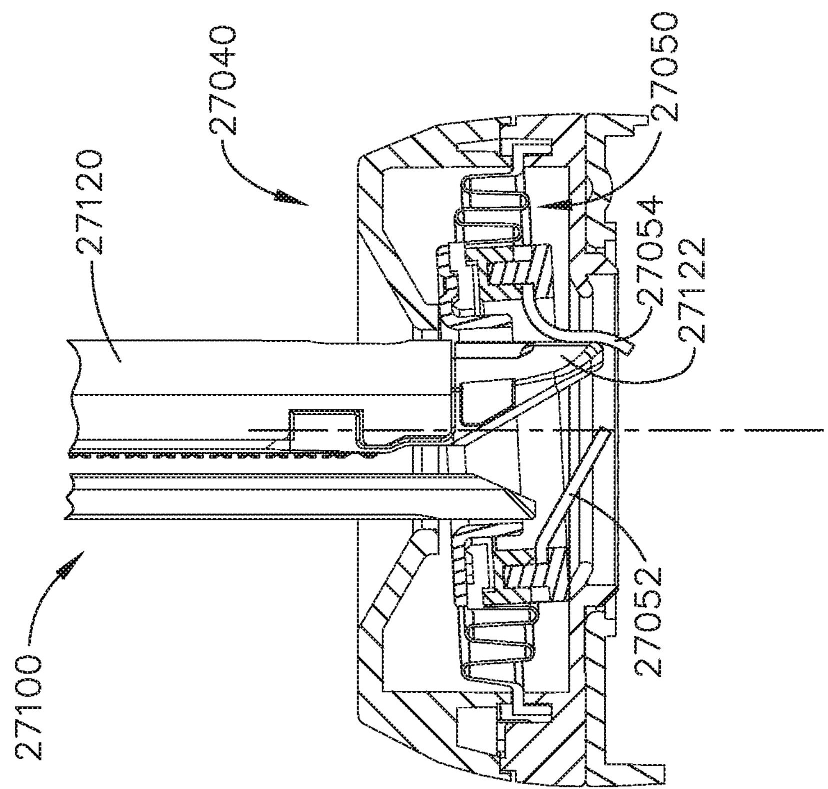
Figure 104:
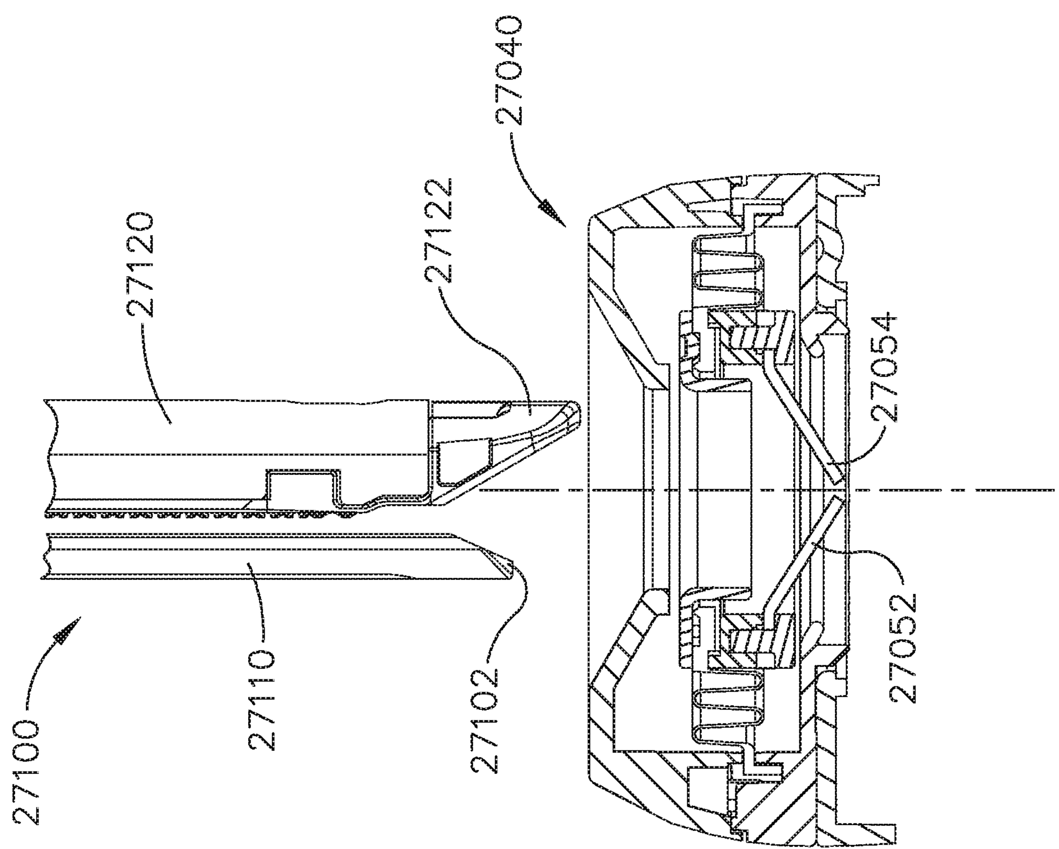

FIG. 104 depicts an end effector 27100 comprising an anvil 27110 and a staple cartridge 27120. The staple cartridge 27120 comprises a pointy, elongate nose 27122, similar to the elongate nose 25150 depicted on the staple cartridge 25100 in FIG. 86. The distal end 27102 of the anvil 27110 is pointed and does not have a protective tip, such as that shown in FIG. 92. The anvil 27110 is shorter in length than the staple cartridge 27120. In other words, the elongate nose 27122 of the staple cartridge 27120 extends longitudinally beyond the distal end 27102 of the anvil 27110. Prior to the insertion the end effector 27100 through the trocar seal system 27040, the first seal door 27052 and the second seal door 27054 of the trocar seal system 27040 extend inwardly to prevent gas from escaping the surgical site. FIG. 105 depicts the end effector 27100 of FIG. 104 when the end effector 27100 is initially inserted into the trocar seal system 27040. The elongate nose 27122 of the staple cartridge 27120 is the first component of the end effector 27100 to come into contact with the first and second seal doors 27052, 27054 of the trocar seal system 27040, tilting, or pre-shifting, the floating seal assembly 27050 to one side as discussed above.

Figure 106:
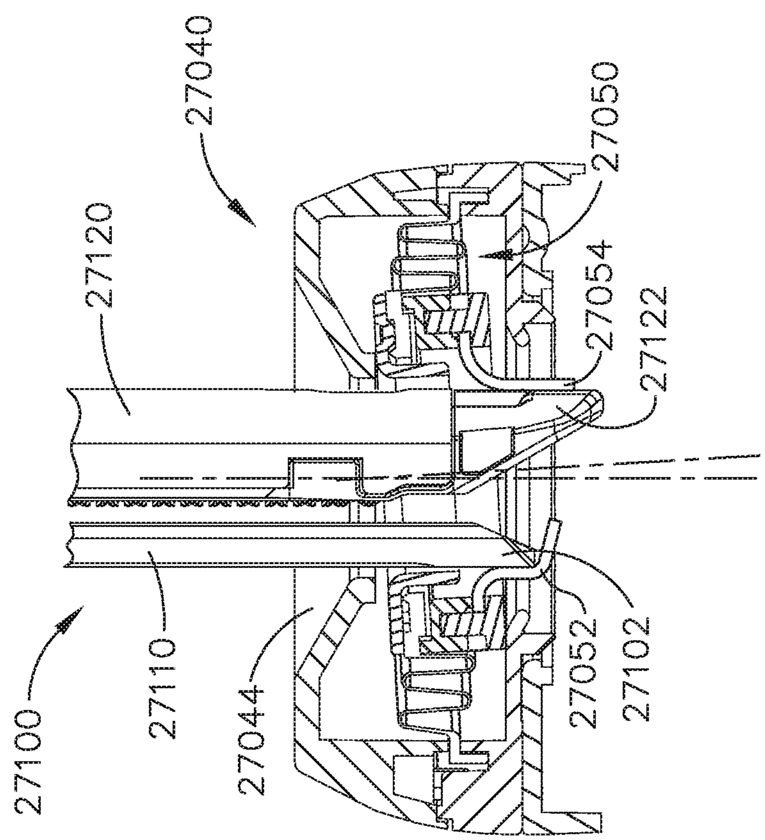

FIG. 106 depicts the end effector 27100 of FIGS. 104 and 105 when the end effector 27100 has been further introduced into the central opening 27044 of the trocar seal system 27040. After the initial contact of the elongate nose 27122 of the staple cartridge 27120, the pointed distal end 27102 of the anvil 27110 contacts the first seal door 27052 of the trocar seal system 27040. In various instances, the pointed distal end 27102 of the anvil 27110 may rupture the first seal door 27052 of the trocar seal system 27040, as the contact between the elongate nose 27122 and the second seal door 27054 displaced the position of the floating seal assembly 27050.

As discussed herein, a first staple cartridge can comprise a first cartridge length and a second staple cartridge can comprise a second cartridge length which is different than the first cartridge length. In various instances, an end effector of a surgical stapling instrument can comprise a cartridge jaw configured to receive the first staple cartridge and, in the alternative, the second staple cartridge. Stated another way, the cartridge jaw is configured to receive the first staple cartridge and the second staple cartridge, but not at the same time. The first staple cartridge and the second staple cartridge each comprise a proximal end which is aligned with a proximal cartridge jaw datum when it is positioned in the cartridge jaw. When the first cartridge length is longer than the second cartridge length, for instance, the distal end of the first staple cartridge would be positioned further away from the proximal cartridge jaw datum than the distal end of the second staple cartridge. The reader should understand that the second cartridge length can be longer than the first cartridge length in other instances.

Further to the above, the end effector comprises an anvil jaw movable relative to the cartridge jaw between an open, or unclamped, position, and a closed, or clamped, position. In alternative embodiments, the cartridge jaw is movable relative to the anvil jaw. In either event, the anvil jaw comprises a distal anvil end which is supported by the first staple cartridge and the second staple cartridge, depending on which staple cartridge is positioned in the cartridge jaw. The distal anvil end is supported at a first location on the first cartridge jaw and at a second location on the second cartridge jaw. In various instances, the first location and the second location may not be the same distance from the proximal cartridge jaw datum. In some instances, however, they can be the same distance from the proximal cartridge jaw datum. Moreover, in various instances, the first location is located a first distance away from the distal end of the first staple cartridge while the second location is located a second, or different, distance away from the distal end of the second staple cartridge. In use, the tissue of a patient will be positioned between the anvil jaw and the cartridge jaw but, nonetheless, the support locations of the staple cartridges will still support the anvil jaw, or the clamping load applied by the anvil jaw.

In various instances, further to the above, the distal anvil end can extend distally beyond the distal end of the first staple cartridge when the end effector is in a clamped configuration and the first staple cartridge is positioned in the cartridge jaw and, similarly, the distal anvil end can extend distally beyond the distal end of the second staple cartridge when the end effector is in a clamped configuration and the second staple cartridge is positioned in the cartridge jaw. However, when the first cartridge length is longer than the second cartridge length, in various instances, the distal anvil tip can extend distally beyond the distal end of the second staple cartridge but not extend distally beyond the distal end of the first staple cartridge. In such instances, the anvil jaw can be longer than the second staple cartridge when the second staple cartridge is positioned in the cartridge jaw but shorter than the first staple cartridge when the first staple cartridge is positioned in the cartridge jaw. In some instances, the anvil jaw is the same length as the first staple cartridge or the second staple cartridge.

Further to the above, the anvil jaw will deflect when it is moved into its clamped position. Owing to the different cartridge lengths of the staple cartridges, the deflection of the anvil jaw may be different depending on which staple cartridge is positioned in the cartridge jaw. As a result, the staple forming gap between the anvil jaw and the staple drivers of the first cartridge jaw can be different than the staple forming gap between the anvil jaw and the staple drivers of the second cartridge jaw. In some instances, the difference in staple forming gap is negligible, and the staples ejected from the first staple cartridge and the second staple cartridge will be formed to the same, or at least suitable, heights and sufficiently staple the tissue captured between the anvil jaw and the cartridge jaw. In such instances, the unformed height of the staples in the first staple cartridge can be the same as the unformed height of the staples in the second staple cartridge. In other instances, the unformed height of the staples in the first staple cartridge is different than the unformed height of the staples in the second staple cartridge. In such instances, taller staples can be used in the first staple cartridge and shorter staples can be used in the second staple cartridge, for example, depending on the anticipated deflection and/or orientation of the anvil jaw when clamped against the first and second staple cartridges. In at least one such instance, each of the staples in the first staple cartridge has an unformed height in a first unformed height range and each of the staples in the second staple cartridge has an unformed height in a second unformed height range. In some instances, the first unformed height range is completely different than the second unformed height range while, in other instances, the first unformed height range partially overlaps the second unformed height range.

As discussed above, the first staple cartridge and the second staple cartridge are selectively positioned in the cartridge jaw of the end effector and, further to the above, the cartridge jaw further comprises a bottom support or surface configured to support the staple cartridges when they are seated in the cartridge jaw. Such a support can comprise a vertical datum. In various instances, the first support location on the first staple cartridge and the second support location on the second staple cartridge, discussed above, are the same vertical distance from the vertical datum of the cartridge jaw. The vertical distance is measured orthogonally from the vertical datum, but can be measured in any suitable manner. In other instances, the first support location on the first staple cartridge has a different vertical height than the second support location on the second staple cartridge. In such instances, the orientation and/or deflection of the anvil jaw when the anvil jaw is in its clamped position can be different as a result of the first support location and the second support location having different vertical heights. Such different vertical heights can occur when the distal end, or nose, of the first staple cartridge is different than the distal end of the second staple cartridge, among other reasons.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, for example, discloses several examples of a robotic surgical instrument system in greater detail.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

EXAMPLES

Example 1

A surgical instrument that comprises an end effector. The end effector comprises a cartridge jaw and an anvil jaw, wherein one of the cartridge jaw and the anvil jaw is rotatable relative to the other about a closure axis. The surgical instrument further comprises a shaft that comprises a frame defining a longitudinal shaft axis and a closure actuator, wherein the closure actuator is translatable relative to the frame. The closure actuator comprises a proximal portion, a distal portion, and a link. The link is rotatably connected to the proximal portion about a proximal link axis and to the distal portion about a distal link axis. The proximal link axis and the distal link axis define a longitudinal link axis therebetween. The surgical instrument further comprises an articulation joint, wherein the end effector is rotatably connected to the shaft about an articulation axis defined by the articulation joint. The end effector is articulatable within an articulation plane between an unarticulated position and an articulated position, wherein the articulation axis is offset from the longitudinal shaft axis. The longitudinal link axis is not collinear with the longitudinal shaft axis when the end effector is in either the unarticulated position or the articulated position.

Example 2

The surgical instrument of Example 1, wherein the proximal link axis is positioned along the longitudinal shaft axis.

Example 3

The surgical instrument of Example 1 or 2, wherein the cartridge jaw comprises a staple cartridge including staples removably stored therein.

Example 4

The surgical instrument of Example 3, wherein the staple cartridge is replaceable.

Example 5

The surgical instrument of Example 3 or 4, further comprising a firing actuator which is separate and distinct from the closure actuator, wherein the firing actuator is actuatable to eject the staples from the staple cartridge.

Example 6

The surgical instrument of Example 3, 4 or 5, wherein the longitudinal link axis is not parallel to the longitudinal shaft axis when the end effector is in either the unarticulated position or the articulated position.

Example 7

The surgical instrument of Example 3, 4 or 5, wherein the end effector further comprises a longitudinal end effector axis. The longitudinal end effector axis is collinear with the longitudinal shaft axis when the end effector is in the unarticulated position. The end effector further comprises a distal end positioned along the longitudinal end effector axis, wherein the distal link axis is offset with respect to an axis extending between the distal end and the proximal link axis when the end effector is in either of the unarticulated position and the articulated position.

Example 8

A surgical instrument that comprises an end effector. The end effector comprises a longitudinal end effector axis, a distal end positioned along the end effector axis, a cartridge jaw, and an anvil jaw, wherein one of the cartridge jaw and the anvil jaw is rotatable relative to the other about a closure axis. The surgical instrument further comprises a shaft that comprises a frame defining a longitudinal shaft axis and a closure actuator translatable relative to the frame. The closure actuator comprises a proximal portion, a distal portion, and a link. The link is rotatably connected to the proximal portion about a proximal link axis and to the distal portion about a distal link axis. The surgical instrument further comprises an articulation joint, wherein the end effector is rotatably connected to the shaft about an articulation axis defined by the articulation joint. The end effector is articulatable within an articulation plane between an unarticulated position and an articulated position, wherein the articulation axis is offset from the longitudinal shaft axis. The longitudinal end effector axis is aligned with the longitudinal shaft axis when the end effector is in the unarticulated position. The distal link axis is offset with respect to an axis extending between the distal end of the end effector and the proximal link axis when the end effector is in either of the unarticulated position and the articulated position.

Example 9

The surgical instrument of Example 8, wherein the proximal link axis and the distal link axis define a longitudinal link axis. The longitudinal link axis is not collinear with the longitudinal shaft axis when the end effector is in either of the unarticulated position and the articulated position.

Example 10

The surgical instrument of Example 9, wherein the longitudinal link axis is not parallel to the longitudinal shaft axis when the end effector is in either of the unarticulated position and the articulated position.

Example 11

The surgical instrument of Example 8, 9 or 10, wherein the proximal link axis is positioned along the longitudinal shaft axis.

Example 12

The surgical instrument of Example 8, 9, 10 or 11, wherein the cartridge jaw comprises a staple cartridge including staples removably stored therein.

Example 13

The surgical instrument of Example 12, wherein the staple cartridge is replaceable.

Example 14

The surgical instrument of Example 12 or 13, further comprising a firing actuator which is separate and distinct from the closure actuator, wherein the firing actuator is actuatable to eject the staples from the staple cartridge.

Example 15

A surgical instrument that comprises an end effector. The end effector comprises a longitudinal end effector axis, a distal end positioned along the end effector axis, a first jaw, and a second jaw, wherein one of the first jaw and the second jaw is rotatable relative to the other between an open position and a closed position. The surgical instrument further comprises a shaft that comprises a frame defining a longitudinal shaft axis and a closure actuator translatable relative to the frame. The closure actuator comprises a proximal portion, a distal portion, and a link. The link is rotatably connected to the proximal portion about a proximal link axis and to the distal portion about a distal link axis. The surgical instrument further comprises an articulation joint, wherein the end effector is rotatably connected to the shaft about an articulation axis defined by the articulation joint. The end effector is articulatable between an unarticulated position and an articulated position, wherein the articulation axis is positioned laterally with respect to the longitudinal shaft axis. The longitudinal end effector axis is aligned with the longitudinal shaft axis when the end effector is in the unarticulated position. The distal link axis is positioned laterally with respect to an axis extending between the distal end of the end effector and the proximal link axis when the first jaw is in the open position, the closed position, and any position between the open position and the closed position.

Example 16

The surgical instrument of Example 15, wherein the proximal link axis and the distal link axis define a longitudinal link axis. The longitudinal link axis is not aligned with the longitudinal shaft axis when the first jaw is in the closed position regardless of whether the end effector is in the unarticulated position or the articulated position.

Example 17

The surgical instrument of Example 15 or 16, wherein the longitudinal link axis is not parallel to the longitudinal shaft axis when the first jaw is in the closed position regardless of whether the end effector is in the unarticulated position or the articulated position.

Example 18

The surgical instrument of Example 15, 16 or 17, wherein the proximal link axis is positioned along the longitudinal shaft axis.

Example 19

The surgical instrument of Example 15, 16, 17 or 18, wherein the first jaw comprises a staple cartridge including staples removably stored therein.

Example 20

The surgical instrument of Example 19, wherein the staple cartridge is replaceable.

Example 21

The surgical instrument of Example 19 or 20, further comprising a firing actuator which is separate and distinct from the closure actuator, wherein the firing actuator is actuatable to eject the staples from the staple cartridge.

Example 22

A surgical instrument comprising a shaft that comprises a proximal end, a distal end, and a longitudinal axis extending between the proximal end and the distal end. The surgical instrument further comprises an end effector that comprises an end effector frame rotatably coupled to the shaft about an articulation pivot, wherein the articulation pivot defines a fixed articulation axis, and wherein the fixed articulation axis is positioned laterally offset with respect to the longitudinal axis. The surgical instrument further comprises an articulation driver coupled to the end effector frame at an attachment location, wherein the articulation driver is movable into a proximal position to rotate the end effector into a first fully-articulated position and a distal position to rotate the end effector into a second fully-articulated position. The proximal position and the distal position define an articulation stroke of the articulation driver, wherein the articulation stroke has an articulation stroke length. A lateral moment arm is defined between the attachment location and the fixed articulation axis, wherein the lateral moment arm is orthogonal to the longitudinal axis. The surgical instrument is configured such that a ratio of the lateral moment arm to the articulation stroke length is maximized.

Example 23

The surgical instrument of Example 22, wherein the end effector is positionable in an unarticulated position which is aligned with the longitudinal axis. The end effector is swept through a first arc length when the end effector is moved from the unarticulated position to the first fully-articulated position. The end effector is swept through a second arc length when the end effector is moved from the unarticulated position to the second fully-articulated position.

Example 24

The surgical instrument of Example 23, wherein the first arc length is equal to the second arc length.

Example 25

The surgical instrument of Example 23, wherein the first arc length and the second arc length are different.

Example 26

The surgical instrument of Example 22, 23, 24 or 25, wherein the ratio is between 1.1 and 1.4.

Example 27

The surgical instrument of Example 22, 23, 24, 25 or 26, wherein the attachment location is swept through an articulation arc length when the end effector is moved between the first fully-articulated position and the second fully-articulated position.

Example 28

The surgical instrument of Example 27, wherein the surgical instrument is configured such that an articulation ratio comprising the articulation arc length to the articulation stroke length is maximized.

Example 29

The surgical instrument of Example 28, wherein the articulation ratio is between 1.2 and 1.7.

Example 30

The surgical instrument of Example 27, 28 or 29, wherein the surgical instrument is configured such that a ratio comprising the product of the articulation arc length and the lateral moment arm to the articulation stroke length is maximized.

Example 31

The surgical instrument of Example 30, wherein the ratio is between 1 and 3.

Example 32

The surgical instrument of Example 22, 23, 24, 25, 26, 27, 28, 29, 30, or 31, wherein the end effector further comprises a staple cartridge comprising staples removably stored therein.

Example 33

The surgical instrument of Example 32, wherein the staple cartridge is replaceable.

Example 34

A surgical instrument comprising a shaft that comprises a proximal end, a distal end, and a longitudinal axis extending between the proximal end and the distal end. The surgical instrument further comprises an end effector that comprises an end effector frame rotatably coupled to the shaft about an articulation pivot, wherein the articulation pivot defines a fixed articulation axis, and wherein the fixed articulation axis is positioned laterally offset with respect to the longitudinal axis. The surgical instrument further comprises an articulation driver coupled to the end effector frame at an attachment location. The articulation driver is movable into a proximal position to rotate the end effector into a first fully-articulated position and a distal position to rotate the end effector into a second fully-articulated position. The proximal position and the distal position define an articulation stroke of the articulation driver. The articulation stroke has an articulation stroke length, wherein a lateral moment arm is defined between the attachment location and the fixed articulation axis. The lateral moment arm is orthogonal to the longitudinal axis. The surgical instrument is configured such that a ratio of the lateral moment arm to the articulation stroke length is larger than 1.

Example 35

The surgical instrument of Example 34, wherein the ratio is between 1.1 and 1.4.

Example 36

The surgical instrument of Example 34 or 35, wherein the attachment location is swept through an articulation arc length when the end effector is moved between the first fully-articulated position and the second fully-articulated position.

Example 37

The surgical instrument of Example 36, wherein the surgical instrument is configured such that an articulation ratio comprising the articulation arc length to the articulation stroke length is maximized.

Example 38

The surgical instrument of Example 37, wherein the articulation ratio is between 1.2 and 1.7.

Example 39

The surgical instrument of Example 36, wherein the surgical instrument is configured such that a ratio comprising the product of the articulation arc length and the lateral moment arm to the articulation stroke length is maximized.

Example 40

The surgical instrument of Example 39, wherein the articulation ratio is between 1 and 3.

Example 41

The surgical instrument of Example 34, 35, 36, 37, 38, 39 or 40, wherein the end effector further comprises a staple cartridge comprising staples removably stored therein.

Example 42

The surgical instrument of Example 41, wherein the staple cartridge is replaceable.

Example 43

A surgical instrument comprising a shaft that comprises a proximal end, a distal end, and a longitudinal axis extending between the proximal end and the distal end. The surgical instrument further comprises an end effector that comprises an end effector frame rotatably coupled to the shaft about an articulation pivot, wherein the articulation pivot defines a fixed articulation axis, and wherein the fixed articulation axis is positioned laterally offset with respect to the longitudinal axis. The surgical instrument further comprises an articulation driver coupled to the end effector frame at an attachment location, wherein the articulation driver is movable into a proximal position to rotate the end effector into a first fully-articulated position and a distal position to rotate the end effector into a second fully-articulated position. The proximal position and the distal position define an articulation stroke of the articulation driver, wherein the articulation stroke has an articulation stroke length. The attachment location is swept through an articulation arc length when the end effector is moved between the first fully-articulated position and the second fully-articulated position. A lateral moment arm is defined between the attachment location and the fixed articulation axis, wherein the lateral moment arm is orthogonal to the longitudinal axis. The surgical instrument is configured such that a ratio of the product of the lateral moment arm and the articulation arc length to the articulation stroke length is larger than 1.

Example 44

A surgical instrument comprising a shaft that comprises a proximal end, a distal end, and a longitudinal axis extending between the proximal end and the distal end. The surgical instrument further comprises an end effector comprising an end effector frame rotatably coupled to the shaft about an articulation pivot, wherein the articulation pivot defines a fixed articulation axis, and wherein the fixed articulation axis is positioned laterally offset with respect to the longitudinal axis. The surgical instrument further comprises an articulation driver coupled to the end effector frame at an attachment location, wherein the articulation driver is movable into a proximal position to rotate the end effector into a first fully-articulated position and a distal position to rotate the end effector into a second fully-articulated position. The proximal position and the distal position define an articulation stroke of the articulation driver, wherein the articulation stroke has an articulation stroke length. A lateral moment arm is defined between the attachment location and the fixed articulation axis. The surgical instrument further comprises means for increasing the lateral moment arm while limiting the articulation stroke.

Example 45

A surgical instrument comprising a shaft that comprises a proximal end, a distal end, a longitudinal axis extending between the proximal end and the distal end, and an outer housing that comprises a shaft radius defined with respect to the longitudinal axis. The surgical instrument further comprises an end effector that comprises an end effector frame rotatably coupled to the shaft about an articulation pivot, wherein the articulation pivot defines a fixed articulation axis, and wherein the fixed articulation axis is positioned laterally offset with respect to the longitudinal axis. The surgical instrument further comprises an articulation driver coupled to the end effector frame at an attachment location, wherein the articulation driver is movable proximally to rotate the end effector in a first direction, wherein the articulation driver is movable distally to rotate the end effector in a second direction which is opposite the first direction. A lateral moment arm is defined between the attachment location and the fixed articulation axis. The lateral moment arm is orthogonal to the longitudinal axis, wherein a ratio of the shaft radius to the lateral moment arm is less than 1.4.

Example 46

The surgical instrument of Example 45, wherein the ratio is less than 1.3.

Example 47

The surgical instrument of Example 45, wherein the ratio is less than 1.2.

Example 48

The surgical instrument of Example 45, wherein the ratio is less than 1.1.

Example 49

The surgical instrument of Example 45, 46, 47 or 48, wherein the end effector is rotatable a first distance in the first direction and a second distance in the second direction, and wherein the first distance and the second distance are equal.

Example 50

The surgical instrument of Example 45, 46, 47 or 48, wherein the end effector is rotatable through a first range in the first direction and a second range in the second direction, and wherein the first range and the second range are not equal.

Example 51

The surgical instrument of Example 45, 46, 47, 48, 49 or 50, further comprising a staple cartridge including staples removably stored therein.

Example 52

The surgical instrument of Example 51, wherein the staple cartridge is replaceable.

Example 53

The surgical instrument of Example 45, 46, 47, 48, 49, 50, 51 or 52, wherein the outer housing defines an inner aperture, and wherein the shaft radius is defined by the inner aperture.

Example 54

The surgical instrument of Example 53, wherein the shaft comprises a shaft frame extending through the inner aperture, and wherein the end effector frame is rotatably coupled to the shaft frame.

Example 55

The surgical instrument of Example 45, 46, 47, 48, 49, 50, 51, 52, 53 or 54, wherein the shaft comprises a first longitudinal portion and a second longitudinal portion, wherein the shaft radius of the outer housing comprises a first shaft radius in the first longitudinal portion and a second shaft radius in the second longitudinal portion, and wherein the first shaft radius is different than the second shaft radius.

Example 56

A shaft assembly comprising a shaft that comprises a proximal end, a distal end, a longitudinal axis extending between the proximal end and the distal end, and an outer housing comprising a shaft radius defined with respect to the longitudinal axis. The shaft assembly further comprises an end effector that comprises an end effector frame rotatably coupled to the shaft about an articulation pivot, wherein the articulation pivot defines a fixed articulation axis, and wherein the fixed articulation axis is positioned laterally offset with respect to the longitudinal axis. The shaft assembly further comprises an articulation driver coupled to the end effector frame at an attachment location. The articulation driver is movable proximally to rotate the end effector in a first direction, wherein the articulation driver is movable distally to rotate the end effector in a second direction which is opposite the first direction. A lateral moment arm is defined between the attachment location and the fixed articulation axis. The lateral moment arm is orthogonal to the longitudinal axis, wherein the shaft assembly is configured such that a ratio of the shaft radius to the lateral moment arm is minimized.

Example 57

The shaft assembly of Example 56, wherein the ratio is less than 1.4.

Example 58

The shaft assembly of Example 56, wherein the ratio is less than 1.1

Example 59

The shaft assembly of Example 56, 57 or 58, further comprising a staple cartridge including staples removably stored therein.

Example 60

The shaft assembly of Example 59, wherein the staple cartridge is replaceable.

Example 61

The shaft assembly of Example 56, 57, 58, 59 or 60, wherein the outer housing defines an inner aperture, and wherein the shaft radius is defined by the inner aperture.

Example 62

The shaft assembly of Example 56, 57, 58, 59, 60 or 61, wherein the shaft comprises a first longitudinal portion and a second longitudinal portion. The shaft radius of the outer housing comprises a first shaft radius in the first longitudinal portion and a second shaft radius in the second longitudinal portion. The first shaft radius is different than the second shaft radius.

Example 63

A surgical instrument that comprises a shaft that comprises an outer housing that comprises a shaft radius. The surgical instrument further comprises an end effector that comprises an end effector frame rotatably coupled to the shaft about an articulation pivot, wherein the articulation pivot defines an articulation axis, and wherein the articulation axis is positioned laterally offset with respect to a centerline of the shaft. The surgical instrument further comprises an articulation driver coupled to the end effector frame at an attachment location. The articulation driver is movable proximally to rotate the end effector in a first direction into a first fully-articulated position, wherein the articulation driver is movable distally to rotate the end effector in a second direction into a second fully-articulated position. A lateral moment arm is defined between the attachment location and the articulation axis. The lateral moment arm is orthogonal to the centerline of the shaft, and wherein a ratio of the shaft radius to the lateral moment arm is between 1 and 1.4.

Example 64

A surgical instrument that comprises a shaft and an end effector. The end effector comprises a proximal end, a distal end, a first jaw, and a second jaw. The first jaw is movable relative to the second jaw between an open position and a closed position, wherein one of the first jaw and the second jaw comprises a staple cartridge including staples removably stored therein. The surgical instrument further comprises an articulation joint, wherein the end effector is rotatably connected to the shaft about the articulation joint. The surgical instrument further comprises an articulation rod operably connected to the end effector. The articulation rod is movable distally to rotate the end effector in a first direction, wherein the articulation rod is movably proximally to rotate the end effector in a second direction. The surgical instrument further comprises a closure tube configured to engage the first jaw and move the first jaw toward the closed position during a closure stroke, wherein the closure tube is slidable over the articulation joint during the closure stroke. The surgical instrument further comprises a staple firing assembly. The staple firing assembly comprises a cutting member movable through the end effector during a staple firing stroke, a firing bar attached to the cutting member, wherein the firing bar comprises a plurality of flexible layers, and wherein the firing bar extends through the articulation joint. The staple firing assembly further comprises a support positioned within the flexible layers, wherein the support is positioned proximally to the articulation joint. The staple firing system further comprises a plurality of control elements, wherein each the control element comprises an aperture defined therein. The firing bar extends through the apertures. The control elements are configured to hold the flexible layers together.

Example 65

The surgical instrument of Example 64, wherein the control elements are positioned within the articulation joint.

Example 66

The surgical instrument of Example 64 or 65, wherein the first jaw comprises the staple cartridge.

Example 67

The surgical instrument of Example 64 or 65, wherein the second jaw comprises the staple cartridge.

Example 68

The surgical instrument of Example 64, 65, 66 or 67, wherein the cutting member is welded to the firing bar.

Example 69

The surgical instrument of Example 64, 65, 66, 67 or 68, wherein the control elements are connected to one another.

Example 70

The surgical instrument of Example 64, 65, 66, 67 or 68, wherein the control elements are unconnected to one another.

Example 71

The surgical instrument of Example 64, 65, 66, 67, 68, 69 or 70, wherein the control elements are unconnected to one another.

Example 72

The surgical instrument of Example 64, 65, 66, 67, 68, 69, 70 or 71, wherein the articulation joint defines a fixed axis of rotation about which the end effector is rotated.

Example 73

A surgical instrument that comprises a shaft defining a longitudinal axis and an end effector. The end effector comprises a proximal end, a distal end, a first jaw, and a second jaw. The first jaw is movable relative to the second jaw between an unclamped position and a clamped position. The surgical instrument further comprises an articulation joint, wherein the end effector is rotatably connected to the shaft about the articulation joint. The surgical instrument further comprises an articulation linkage operably connected to the end effector, wherein the articulation linkage is movable distally to rotate the end effector in a first direction, and wherein the articulation linkage is movably proximally to rotate the end effector in a second direction. The surgical instrument further comprises a clamping member configured to engage the first jaw and move the first jaw toward the clamped position during a clamping stroke, wherein the clamping member is slidable relative to the articulation joint during the clamping stroke. The surgical instrument further comprises a staple firing assembly. The staple firing assembly comprises a cutting member movable through the end effector during a staple firing stroke and a firing member. The firing member comprises a plurality of flexible layers attached to the cutting member, wherein the flexible layers are configured to slide longitudinally relative to one another. The firing member extends through the articulation joint. The surgical instrument further comprises control elements, wherein each the control element comprises an aperture defined therein. The firing bar extends through the apertures, wherein the control elements are configured to hold the flexible layers together.

Example 74

The surgical instrument of Example 73, wherein the control elements are positioned within the articulation joint.

Example 75

The surgical instrument of Example 73 or 74, wherein the first jaw comprises a staple cartridge.

Example 76

The surgical instrument of Example 73 or 74, wherein the second jaw comprises a staple cartridge.

Example 77

The surgical instrument of Example 73, 74, 75, or 76, wherein the cutting member is welded to the firing bar.

Example 78

The surgical instrument of Example 73, 74, 75, 76 or 77, wherein the control elements are connected to one another.

Example 79

The surgical instrument of Example 73, 74, 75, 76 or 77, wherein the control elements are connected to one another.

Example 80

The surgical instrument of Example 73, 74, 75, 76, 77, 78 or 79, wherein the shaft comprises a shaft frame, and wherein the support is mounted to the shaft frame.

Example 81

A surgical instrument that comprises a shaft defining a longitudinal axis and an end effector. The end effector comprises a proximal end, a distal end, a first jaw, and a second jaw. The first jaw is movable relative to the second jaw between an unclamped position and a clamped position. The surgical instrument further comprises an articulation joint, wherein the end effector is rotatably connected to the shaft about the articulation joint. The surgical instrument further comprises an articulation linkage operably connected to the end effector. The articulation linkage is movable distally to rotate the end effector in a first direction, wherein the articulation linkage is movably proximally to rotate the end effector in a second direction. The surgical instrument further comprises a clamping member configured to engage the first jaw and move the first jaw toward the clamped position during a clamping stroke. The clamping member is slidable relative to the articulation joint during the clamping stroke. The surgical instrument further comprises a staple firing assembly. The staple firing assembly comprises a cutting member and a firing member. The cutting member is movable through the end effector during a staple firing stroke. The firing member comprises a plurality of flexible layers attached to the cutting member, wherein the flexible layers are configured to slide longitudinally relative to one another. The firing member extends through the articulation joint. The staple firing assembly further comprises a support positioned between two of the flexible layers. The staple firing assembly further comprises means for limiting lateral displacement between the flexible layers.

Example 82

The surgical instrument of Example 81, wherein the first jaw comprises a staple cartridge.

Example 83

The surgical instrument of Example 81, wherein the second jaw comprises a staple cartridge.

Example 84

A surgical instrument that comprises a shaft and an end effector. The end effector comprises a proximal end, a distal end, a longitudinal axis extending between the proximal end and the distal end, a first jaw, and a second jaw. The first jaw is movable relative to the second jaw between an unclamped position and a clamped position. The surgical instrument further comprises an articulation joint, wherein the end effector is rotatably connected to the shaft about the articulation joint. The surgical instrument further comprises a staple firing assembly. The staple firing assembly comprises a cutting member movable through the end effector during a staple firing stroke, wherein the cutting member comprises a first portion configured to engage the first jaw and a second portion configured to engage the second jaw. The staple firing assembly further comprises a firing member comprising a plurality of flexible layers welded to the cutting member along a weld line. The weld line comprises a longitudinal portion and a transverse portion which extends orthogonally to the longitudinal portion.

Example 85

The surgical instrument of Example 84, wherein the first jaw comprises a staple cartridge.

Example 86

The surgical instrument of Example 84, wherein the second jaw comprises a staple cartridge.

Example 87

The surgical instrument of Example 84, 85 or 86, wherein the second jaw comprises a staple cartridge.

Example 88

The surgical instrument of Example 84, 85, 86 or 87, wherein the firing member comprises a first lateral side and a second lateral side, and wherein the weld line is present on the first lateral side and the second lateral side.

Example 89

A surgical instrument that comprises a shaft comprising a shaft frame and an end effector. The end effector comprises a proximal frame, a distal end, a first jaw, and a second jaw. The first jaw is movable relative to the second jaw between an unclamped position and a clamped position. The surgical instrument further comprises an articulation joint, wherein the end effector is rotatably connected to the shaft about the articulation joint. The surgical instrument further comprises a staple firing assembly that comprises a cutting member movable through the end effector during a staple firing stroke. The staple firing assembly further comprises a firing member, wherein the firing member comprises a plurality of flexible layers attached to the cutting member, and wherein the firing member extends through the articulation joint. The surgical instrument further comprises a lateral spring support positioned adjacent the firing member. The lateral spring support comprises a distal end mounted to the proximal frame of the end effector. The lateral spring support further comprises a proximal end configured to slide relative to the shaft frame Example 90

The surgical instrument of Example 89, wherein the first jaw comprises a staple cartridge.

Example 91

The surgical instrument of Example 89, wherein the second jaw comprises a staple cartridge.

Example 92

The surgical instrument of Example 89, 90 or 91, wherein the lateral spring support comprises a first lateral spring support positioned alongside a first lateral side of the firing member. The surgical instrument further comprises a second lateral spring support positioned alongside a second lateral side of the firing member.

Example 93

A surgical instrument that comprises a shaft and an end effector. The end effector comprises a proximal end, a distal end, a first jaw, and a second jaw. The first jaw is movable relative to the second jaw between an open position and a closed position, wherein one of the first jaw and the second jaw comprises a staple cartridge including staples removably stored therein. The surgical instrument further comprises an articulation joint, wherein the end effector is rotatably connected to the shaft about the articulation joint. The surgical instrument further comprises an articulation rod operably connected to the end effector, wherein the articulation rod is movable distally to rotate the end effector in a first direction, and wherein the articulation rod is movably proximally to rotate the end effector in a second direction. The surgical instrument further comprises a firing bar comprising a plurality of flexible layers, wherein the firing bar is movable through the articulation joint during a staple firing stroke. The surgical instrument further comprises a first flexible support positioned on a first side of the firing bar, a second flexible support positioned on a second side of the firing bar, and a plurality of control elements, wherein each the control element comprises an aperture defined therein. The firing bar extends through the apertures, wherein the first flexible support, the second flexible support, and the control elements are configured to hold the flexible layers together.

Example 94

The surgical instrument of Example 93, wherein the first flexible support and the second flexible support extend through at least some of the control element apertures.

Example 95

A surgical instrument that comprises an end effector that comprises a proximal end and a distal end. The surgical instrument further comprises a shaft. The shaft comprises a frame, a lock plate moveable relative to the frame wherein the lock plate comprises a first longitudinal rack of lock teeth. The shaft further comprises an articulation joint, wherein the end effector is rotatably connected to the shaft by the articulation joint. The shaft further comprises an articulation actuator operably connected to the end effector, wherein the articulation actuator is movable distally to rotate the end effector in a first direction and proximally to rotate the end effector in a second direction. The articulation actuator comprises a second longitudinal rack of lock teeth. The shaft further comprises an articulation lock comprising a third longitudinal rack of lock teeth. The articulation lock is positionable in an unlocked position in which the articulation actuator can move relative to the frame and a locked position in which the third longitudinal rack of lock teeth is engaged with the first longitudinal rack of lock teeth and the second longitudinal rack of lock teeth to prevent the proximal and distal movement of the articulation actuator.

Example 96

The surgical instrument of Example 95, wherein the first longitudinal rack of lock teeth is defined in a first plane and the second longitudinal rack of lock teeth is defined in a second plane. The first plane and the second plane are different.

Example 97

The surgical instrument of Example 95 or 96, wherein the lock plate is slidable relative to the frame.

Example 98

The surgical instrument of Example 95, 96, or 97, wherein the frame comprises a recess and the lock plate is positioned within the recess. The recess comprises a proximal end wall configured to limit the proximal movement of the lock plate within the recess. The recess further comprises a distal end wall configured to limit the distal movement of the lock plate within the recess.

Example 99

The surgical instrument of Example 98, further comprising a biasing member positioned between the proximal end wall and the lock plate.

Example 100

The surgical instrument of Example 98, further comprising a biasing member positioned between the distal end wall and the lock plate.

Example 101

The surgical instrument of Example 95, 96, 97, 98, 99 or 100, wherein the end effector comprises a first jaw and a second jaw, wherein the first jaw is movable relative to the second jaw between an open position and a closed position. The surgical instrument further comprises a closure member configured to move the first jaw toward the closed position during a closure stroke. The closure member is configured to engage the articulation lock during the closure stroke and hold the articulation lock in the locked position.

Example 102

The surgical instrument of Example 101, wherein the shaft defines a longitudinal axis. The frame comprises a flexible portion, wherein the closure member is configured to push the lock plate against the flexible portion and deflect the flexible portion laterally with respect to the longitudinal axis.

Example 103

The surgical instrument of Example 102, wherein the flexible portion comprises a lateral sidewall and a cavity defined behind the lateral sidewall. The lateral sidewall is configured to flex into the cavity.

Example 104

The surgical instrument of Example 95, 96, 97, 98, 99, 100, 101, 102 or 103, wherein the articulation lock is biased into engagement with the lock plate and the articulation actuator.

Example 105

The surgical instrument of Example 95, 96, 97, 98, 99, 100, 101, 102, 103 or 104, wherein the end effector further comprises a staple cartridge comprising staples removably stored therein.

Example 106

The surgical instrument of Example 105, wherein the staple cartridge is replaceable.

Example 107

The surgical instrument of Example 105 or 106, wherein the end effector comprises a first jaw and a second jaw. The first jaw is movable relative to the second jaw between an open position and a closed position. The first jaw comprises the staple cartridge.

Example 108

The surgical instrument of Example 105 or 106, wherein the end effector comprises a first jaw and a second jaw. The first jaw is movable relative to the second jaw between an open position and a closed position. The second jaw comprises the staple cartridge.

Example 109

The surgical instrument of Example 95, 96, 97, 98, 99, 100, 101, 102, 103, 104, 105, 106, 107 or 108, wherein the first longitudinal rack of lock teeth comprises teeth spaced at a first pitch. The second longitudinal rack of lock teeth comprises teeth spaced at a second pitch, wherein the second pitch is different than the first pitch. The third longitudinal rack of lock teeth comprises teeth spaced at a third pitch, wherein the third pitch is different than the first pitch and the second pitch.

Example 110

A surgical instrument that comprises an end effector and a shaft. The end effector comprises a proximal end and a distal end. The shaft comprises a frame that comprises a first longitudinal rack of lock teeth. The shaft further comprises an articulation joint, wherein the end effector is rotatably connected to the shaft by the articulation joint. The shaft further comprises an articulation actuator operably connected to the end effector. The articulation actuator is movable distally to rotate the end effector in a first direction and the articulation actuator is movable proximally to rotate the end effector in a second direction. The articulation actuator comprises a second longitudinal rack of lock teeth. The shaft further comprises an articulation lock that comprises a third longitudinal rack of lock teeth. The articulation lock is positionable in an unlocked position in which the articulation actuator can move relative to the frame and a locked position in which the third longitudinal rack of lock teeth are engaged with the first longitudinal rack of lock teeth of the frame and the second longitudinal rack of lock teeth of the articulation actuator to inhibit the proximal and distal movement of the articulation actuator.

Example 111

The surgical instrument of Example 110, wherein the frame comprises a slidable lock plate, and wherein the first longitudinal rack of lock teeth are defined on the lock plate.

Example 112

The surgical instrument of Example 110 or 111, wherein the end effector comprises a staple cartridge including staples removably stored therein.

Example 113

A surgical instrument that comprises an end effector and a shaft. The shaft comprises a frame and an articulation joint, wherein the end effector is rotatably connected to the shaft by the articulation joint. The shaft further comprises an articulation actuator operably connected to the end effector. The articulation actuator is movable in a first direction to rotate the end effector in one direction and the articulation actuator is movable in a second direction to rotate the end effector in another direction. The shaft further comprises an articulation lock positionable in a first position in which the articulation actuator can move relative to the frame and a second position in which the articulation lock is engaged with the frame and the articulation actuator to limit the movement of the articulation actuator in the first direction and the second direction.

Example 114

The surgical instrument of Example 113, wherein the end effector comprises a staple cartridge including staples removably stored therein.

Example 115

A surgical instrument that comprises an end effector head configurable in an unclamped configuration and a clamped configuration. The surgical instrument further comprises a shaft. The shaft comprises a frame comprising a longitudinal axis and an articulation joint, wherein the end effector head is rotatably connected to the shaft by the articulation joint. The shaft further comprises an articulation actuator operably connected to the end effector head. The articulation actuator is movable in a first direction to rotate the end effector head in one direction and the articulation actuator is movable in a second direction to rotate the end effector head in another direction. The articulation actuator comprises at least one lock projection extending laterally relative to the longitudinal axis. The shaft further comprises an articulation lock that comprises at least two projections extending laterally relative to the longitudinal axis. The articulation lock is configured to flex laterally relative to the longitudinal axis to allow for articulation motion of the end effector head. The shaft further comprises a closure member configured to move the end effector head from the unclamped configuration into the clamped configuration during a closure stroke, wherein the closure member prevents the articulation lock from flexing laterally after the closure stroke thereby restraining the end effector head from articulating.

Example 116

A surgical instrument that comprises an end effector that comprises a proximal end, a distal end, a first jaw, and a second jaw. The first jaw is movable relative to the second jaw between an open position and a closed position. The surgical instrument further comprises a shaft that comprises a frame, wherein the frame comprises a first longitudinal rack of lock teeth. The shaft further comprises an articulation joint, wherein the end effector is rotatably connected to the shaft by the articulation joint. The shaft further comprises an articulation actuator operably connected to the end effector, wherein the articulation actuator is movable distally to rotate the end effector in a first direction and proximally to rotate the end effector in a second direction. The articulation actuator comprises a second longitudinal rack of lock teeth. The shaft further comprises an articulation lock comprising a third group of lock teeth. The articulation lock is positionable in a disengaged position in which the third group of lock teeth is not engaged with the frame and the articulation actuator and an engaged position in which the third group of lock teeth is engaged with the first longitudinal rack of lock teeth and the second longitudinal rack of lock teeth to prevent the proximal and distal movement of the articulation actuator. The shaft further comprises a closure member configured to move the first jaw toward the closed position during a closure stroke. The closure member is configured to engage the articulation lock during the closure stroke and move the articulation lock from the disengaged position into the engaged position.

Example 117

The surgical instrument of Example 116, wherein the first longitudinal rack of lock teeth is defined in a first plane. The second longitudinal rack of lock teeth is defined in a second plane. The first plane and the second plane are different.

Example 118

The surgical instrument of Example 116 or 117, wherein the end effector further comprises a staple cartridge comprising staples removably stored therein.

Example 119

The surgical instrument of Example 118, wherein the staple catridge is replaceable.

Example 120

The surgical instrument of Example 118 or 119, wherein the end effector comprises a first jaw and a second jaw. The first jaw is movable relative to the second jaw between an open position and a closed position. The first jaw comprises the staple cartridge.

Example 121

The surgical instrument of Example 118 or 119, wherein the end effector comprises a first jaw and a second jaw. The first jaw is movable relative to the second jaw between an open position and a closed position. The second jaw comprises the staple cartridge.

Example 122

The surgical instrument of Example 116, 117, 118, 119, 120 or 121, wherein the first longitudinal rack of lock teeth comprises teeth spaced at a first pitch. The second longitudinal rack of lock teeth comprises teeth spaced at a second pitch, wherein the second pitch is different than the first pitch. The third group of lock teeth comprises teeth spaced at a third pitch, wherein the third pitch is different than the first pitch and the second pitch.

Example 123

The surgical instrument of Example 116, 117, 118, 119, 120, 121 or 122, wherein the shaft defines a longitudinal axis. The articulation lock comprises a lock plate slidable laterally relative to the longitudinal axis between the disengaged position and the engaged position. The frame comprises a proximal guide post and a distal guide post. The lock plate comprises a proximal lateral slot and a distal lateral slot, wherein the proximal guide post extends into the proximal lateral slot and the distal guide post extends into the distal lateral slot. The proximal guide post and the distal guide post co-operate to define the lateral path of the lock plate.

Example 124

The surgical instrument of Example 123, wherein the lock plate comprises a lock slot including sidewalls defined therein. The closure member comprises a lock driver extending into the lock slot. The lock driver is configured to engage a sidewall to shift the lock plate from the disengaged position to the engaged position during the closure stroke.

Example 125

The surgical instrument of Example 124, wherein the closure member is movable through a retraction stroke to allow the first jaw to be moved into the open position. The lock driver is configured to engage one of the sidewalls of the lock slot to shift the lock plate from the engaged position to the disengaged position during the retraction stroke.

Example 126

The surgical instrument of Example 124, wherein the closure member is movable through an opening stroke to move the first jaw into the open position. The lock driver is configured to engage one of the sidewalls of the lock slot to shift the lock plate from the engaged position to the disengaged position during the opening stroke.

Example 127

The surgical instrument of Example 116, 117, 118, 119, 120, 121, 122, 123, 124, 125 or 126, wherein the articulation lock comprises a lock arm deflectable into the engaged position by the closure member.

Example 128

The surgical instrument of Example 116, 117, 118, 119, 120, 121, 122, 123, 124, 125 or 126, wherein the articulation lock comprises a first lock arm and a the second lock arm. The closure member comprises a wedge positionable between the first lock arm and the second lock arm during the closure stroke to deflect the articulation lock into the engaged position.

Example 129

The surgical instrument of Example 128, wherein the third group of lock teeth are present on the first lock arm and the second lock arm.

Example 130

The surgical instrument of Example 128 or 129, wherein the first lock arm is configured to engage the first longitudinal rack of lock teeth and the second lock arm is configured to engage the second longitudinal rack of lock teeth.

Example 131

A surgical instrument that comprises an end effector that comprises a first jaw and a second jaw. The first jaw is movable relative to the second jaw between an open position and a closed position. The surgical instrument further comprises a shaft. The shaft comprises a frame and a lock plate movable relative to the frame, wherein the lock plate comprises a first group of lock teeth. The shaft further comprises an articulation joint, wherein the end effector is rotatably connected to the shaft by the articulation joint. The shaft further comprises an articulation actuator operably connected to the end effector, wherein the articulation actuator is configured to rotate the end effector in a first direction and a second direction. The articulation actuator comprises a second group of lock teeth. The shaft further comprises an articulation lock that comprises a third group of lock teeth. The articulation lock is positionable in a disengaged position in which the third group of lock teeth is not engaged with the lock plate, the frame, and the articulation actuator and an engaged position in which the third group of lock teeth is engaged with the first group of lock teeth and the second group of lock teeth to inhibit the articulation of the end effector. The shaft further comprises a closure member configured to move the first jaw toward the closed position during a closure stroke. The closure member is configured to engage the articulation lock during the closure stroke and move the articulation lock from the disengaged position into the engaged position.

Example 132

The surgical instrument of Example 131, wherein the end effector further comprises a staple cartridge including staples removably stored therein.

Example 133

A surgical instrument that comprises an end effector that comprises a first jaw and a second jaw. The first jaw is movable relative to the second jaw between an open position and a closed position. The surgical instrument further comprises a shaft. The shaft comprises a frame, wherein the frame comprises a first group of lock teeth. The shaft further comprises an articulation joint, wherein the end effector is rotatably connected to the shaft by the articulation joint. The shaft further comprises an articulation actuator operably connected to the end effector, wherein the articulation actuator is configured to rotate the end effector in a first direction and a second direction. The shaft further comprises an articulation lock comprising a gear including a second group of teeth meshingly engaged with the first group of teeth, wherein the gear is rotatably mounted to the frame. The shaft further comprises a closure member configured to move the first jaw toward the closed position during a closure stroke. The closure member is configured to engage the gear during the closure stroke to inhibit the end effector from being articulated.

Example 134

The surgical instrument of Example 133, wherein the end effector further comprises a staple cartridge including staples removably stored therein.

Example 135

A surgical instrument that comprises an end effector that comprises a first jaw and a second jaw. The first jaw is movable relative to the second jaw between an open position and a closed position. The surgical instrument further comprises a shaft. The shaft comprises a frame and a lock plate movable relative to the frame, wherein the lock plate comprises a first group of coupling features. The shaft further comprises an articulation joint, wherein the end effector is rotatably connected to the shaft by the articulation joint. The shaft further comprises an articulation actuator operably connected to the end effector, wherein the articulation actuator is configured to rotate the end effector in a first direction and a second direction. The articulation actuator comprises a second group of coupling features. The shaft further comprises an articulation lock comprising a third group of coupling features, wherein the articulation lock is positionable in a disengaged position in which the third group of coupling features is not engaged with the lock plate and the articulation actuator and an engaged position in which the third group of coupling features is engaged with the first group of coupling features and the second group of coupling features to inhibit the articulation of the end effector. The shaft further comprises a closure member configured to move the first jaw toward the closed position during a closure stroke. The closure member is configured to engage the articulation lock during the closure stroke and move the articulation lock from the disengaged position into the engaged position.

Example 136

A surgical instrument that comprises an end effector that comprises a first jaw and a second jaw. The first jaw is movable relative to the second jaw between an open position and a closed position. The surgical instrument further comprises a shaft. The shaft comprises a frame, a grounding member movable relative to the frame, and an articulation joint, wherein the end effector is rotatably connected to the shaft by the articulation joint. The shaft further comprises an articulation actuator operably connected to the end effector, wherein the articulation actuator is configured to rotate the end effector in a first direction and a second direction. The shaft further comprises an articulation lock positionable in a disengaged position in which the articulation lock is not engaged with the grounding member and the articulation actuator and an engaged position in which the articulation lock is engaged with the grounding member and the articulation actuator to inhibit the articulation of the end effector. The shaft further comprises a closure member configured to move the first jaw toward the closed position during a closure stroke. The closure member is configured to engage the articulation lock during the closure stroke and move the articulation lock from the disengaged position into the engaged position.

Example 137

A surgical instrument insertable through a trocar. The surgical instrument comprises a handle and a shaft extending from the handle. The shaft comprises a frame, a proximal portion connected to the handle, a distal portion that comprises an end effector, and an articulation joint, wherein the end effector is rotatable about the articulation joint. The shaft further comprises an articulation actuator operably coupled to the end effector, wherein the articulation actuator is selectively movable to rotate the end effector in a first direction and a second direction. The shaft further comprises an outer housing slidable relative to the frame. The outer housing comprises a distal non-round housing portion adjacent the articulation joint and a longitudinal round housing portion extending between the proximal portion and the distal non-round housing portion. The longitudinal round housing portion comprises a first diameter. The distal non-round housing portion comprises a second diameter. The first diameter is less than the second diameter. The distal non-round housing portion and the longitudinal round housing portion are sized and configured to be inserted through the trocar into a surgical site. The shaft further comprises an articulation lock configured to engage the articulation actuator and prevent the rotation of the end effector, wherein the articulation lock is positioned within the distal non-round housing portion.

Example 138

The surgical instrument of Example 137, wherein the end effector comprises a staple cartridge including staples removably stored therein.

Example 139

The surgical instrument of Example 138, wherein the end effector further comprises an anvil configured to deform the staples. The anvil is rotatable relative to the staple cartridge.

Example 140

The surgical instrument of Example 138, wherein the end effector further comprises an anvil configured to deform the staples, and wherein the staple cartridge is rotatable relative to the anvil.

Example 141

The surgical instrument of Example 137, 138, 139 or 140, wherein the staple cartridge is replaceable.

Example 142

The surgical instrument of Example 137, 138, 139, 140 or 141, wherein the end effector is replaceable.

Example 143

The surgical instrument of Example 137, 138, 139, 140, 141 or 142, wherein the longitudinal round housing portion defines a longitudinal axis. The distal non-round housing portion is eccentrically offset with respect to the longitudinal axis.

Example 144

The surgical instrument of Example 137, 138, 139, 140, 141, 142 or 143, wherein the proximal portion of the shaft comprises a connector including a latch configured to releasably hold the shaft to the handle.

Example 145

The surgical instrument of Example 137, 138, 139, 140, 141, 142, 143 or 144, wherein the articulation lock is entirely positioned in the distal non-round housing portion.

Example 146

The surgical instrument of Example 137, 138, 139, 140, 141, 142, 143 or 144, wherein the articulation lock comprises a fixed portion mounted to the frame and a lock portion movable within the distal non-round housing portion.

Example 147

The surgical instrument of Example 146, wherein the articulation lock comprises a fixed portion mounted to the frame and a lock portion movable within the distal non-round housing portion.

Example 148

A surgical instrument insertable through a trocar. The surgical instrument comprises a handle and a shaft extending from the handle. The shaft comprises a frame, a proximal portion attachable to the handle, a distal portion comprising an end effector, and an articulation joint, wherein the end effector is rotatable about the articulation joint. The shaft further comprises an articulation actuator operably coupled to the end effector, wherein the articulation actuator is movable to rotate the end effector in a first direction and a second direction. The shaft further comprises an outer housing slidable relative to the frame. The outer housing comprises a distal housing portion adjacent the articulation joint, wherein the distal housing portion comprises a non-round perimeter comprising a width. The outer housing further comprises a longitudinal housing portion extending between the proximal portion and the distal housing portion. The longitudinal housing portion comprises a substantially round perimeter comprising a diameter, wherein the diameter is smaller than the width. The distal housing portion and the longitudinal housing portion are sized and configured to be inserted through the trocar into a surgical site. The shaft further comprises an articulation lock configured to engage the articulation actuator and prevent the rotation of the end effector, wherein the articulation lock is positioned within the distal housing portion.

Example 149

The surgical instrument of Example 148, wherein the end effector comprises a staple cartridge including staples removably stored therein.

Example 150

The surgical instrument of Example 148 or 149, wherein the staple cartridge is replaceable.

Example 151

The surgical instrument of Example 148, 149 or 150, wherein the end effector is replaceable.

Example 152

The surgical instrument of Example 148, 149, 150 or 151, wherein the articulation lock is entirely positioned in the distal housing portion.

Example 153

The surgical instrument of Example 148, 149, 150 or 151, wherein the articulation lock comprises a fixed portion mounted to the frame and a lock portion movable within the distal housing portion.

Example 154

The surgical instrument of Example 153, wherein the fixed portion is in the longitudinal housing portion.

Example 155

A surgical instrument that comprises a handle, a detachable shaft extending from the handle. The detachable shaft comprises a frame, a proximal latch attachable to the handle, a distal portion comprising an end effector, and an articulation joint, wherein the end effector is rotatable about the articulation joint. The detachable shaft further comprises an articulation actuator configured to articulate the end effector in a first direction and a second direction. The detachable shaft further comprises an outer tube translatable relative to the frame. The outer tube comprises a distal tube portion adjacent the articulation joint, wherein the distal tube portion comprises a non-round perimeter comprising a width. The outer tube further comprises a longitudinal tube portion. The longitudinal tube portion comprises a substantially round perimeter comprising a diameter, wherein the diameter is smaller than the width. The distal tube portion and the longitudinal tube portion are sized and configured to be inserted through the trocar into a surgical site. The detachable shaft further comprises an articulation lock configured to engage the articulation actuator and prevent the rotation of the end effector, wherein the articulation lock is positioned within the distal tube portion.

Example 156

A surgical stapling instrument system that comprises a handle, a nozzle, and an elongate shaft. The an elongate shaft comprises a proximal end, a distal end, a proximal region that comprises a first diameter, a central region that comprises a second diameter, wherein the central region defines a longitudinal axis, and a distal region that comprises a third diameter. The first diameter is different than the second diameter and the distal region is offset laterally with respect to the longitudinal axis. The surgical stapling instrument system further comprises an end effector that comprises a first jaw. The first jaw comprises an elongate channel and a staple cartridge that comprises a plurality of staples, wherein the staple cartridge is operably supported in the elongate channel. The end effector further comprises a second jaw, wherein the second jaw is movable relative to the first jaw. The surgical stapling instrument system further comprises an articulation joint rotatably connecting the end effector to the elongate shaft, a firing member configured to move within the end effector, and a firing system configured to apply a firing motion to the firing member.

Example 157

The surgical stapling instrument system of Example 156, wherein the first diameter is larger than the second diameter.

Example 158

The surgical stapling instrument system of Example 156 or 157, wherein the second diameter is smaller than the third diameter.

Example 159

The surgical stapling instrument system of Example 156, 157 or 158, wherein the third diameter is smaller than the first diameter and larger than the second diameter.

Example 160

The surgical stapling instrument system of Example 156, 157, 158 or 159, wherein the second jaw comprises an anvil configured to deform the staples.

Example 161

The surgical stapling instrument system of Example 156, 157, 158, 159 or 160, wherein the distal region of the elongate shaft comprises at least one flat side.

Example 162

The surgical stapling instrument system of Example 156, 157, 158, 159, 160 or 161, wherein the distal region is not entirely cylindrical.

Example 163

A surgical stapling instrument that comprises an elongate shaft. The elongate shaft comprises a proximal end, a distal end, and a first width at the proximal end, wherein the first width of the elongate shaft transitions to a second width in the center of the elongate shaft, and wherein the second width of the elongate shaft transitions to a third width at the distal end of the elongate shaft. The distal end of the elongate shaft is not cylindrical, wherein the distal end comprises an enlargement extending laterally with respect to the second width, and wherein the first, second, and third widths are different. The surgical stapling instrument further comprises an end effector configured to be attached to the distal end of the elongate shaft. The end effector comprises a first jaw and a second jaw, wherein the first jaw is movable relative to the second jaw. The surgical stapling instrument further comprises an articulation assembly configured to apply articulation motions to the end effector, a firing member, and a firing system configured to apply a firing motion to the firing member.

Example 164

The surgical stapling instrument of Example 163, wherein the first width is larger than the second width.

Example 165

The surgical stapling instrument of Example 163 or 164, wherein the second width is smaller than the third width.

Example 166

The surgical stapling instrument of Example 163, 164 or 165, wherein the third width is smaller than the first width and larger than the second width.

Example 167

The surgical stapling instrument of Example 163, 164, 165 or 166, wherein the distal end of the elongate shaft is configured to fit through a 12 mm cannula passageway.

Example 168

The surgical stapling instrument of Example 163, 164, 165, 166 or 167, wherein the center of the elongate shaft comprises a width which is less than 10 mm.

Example 169

A surgical fastening instrument that comprises an elongate shaft. The elongate shaft comprises a proximal end, a distal end, a proximal region that comprises a first circumference, a central region that comprises a second circumference, wherein the central region defines a central longitudinal axis, and a distal region comprising a third circumference. The first circumference is different than the second circumference, wherein the third circumference is offset with respect to the second circumference. The surgical fastening instrument further comprises an end effector configured to be attached to the distal end of the elongate shaft. The end effector comprises a fastener cartridge jaw and an anvil. The surgical fastening instrument further comprises an articulation system configured to apply articulation motions to the end effector, a firing member, wherein the firing member is configured to travel through the end effector, and a firing system configured to apply firing and retraction motions to the firing member.

Example 170

The surgical fastening instrument of Example 169, wherein the first circumference is larger than the second circumference.

Example 171

The surgical fastening instrument of Example 169 or 170, wherein the second circumference is smaller than the third circumference.

Example 172

The surgical fastening instrument of Example 169, 170 or 171, wherein the third circumference is smaller than the first circumference and larger than the second circumference.

Example 173

The surgical fastening instrument of Example 169, 170, 171 or 172, wherein the proximal region comprises a stepped down configuration.

Example 174

The surgical fastening instrument of Example 169, 170, 171, 172 or 173, wherein the distal region of the elongate shaft comprises at least one flat side.

Example 175

The surgical fastening instrument of Example 169, 170, 171, 172, 173 or 174, wherein the central region comprises a stepped up region at the distal end.

Example 176

A surgical instrument that comprises a housing and a shaft extending from the housing that comprises an outer tube portion. The outer tube portion includes a proximal tube portion, wherein the proximal tube portion defines a longitudinal axis, and an elongate intermediate tube portion extending distally from the proximal tube portion, wherein the intermediate tube portion is centered along the longitudinal axis. The outer tube portion further includes a distal tube portion extending distally from the intermediate tube portion, wherein the distal tube portion is laterally offset with respect to the longitudinal axis, and wherein the distal tube portion comprises an enlargement extending to a side of the longitudinal axis. The outer tube portion further includes a tapered neckdown defined between the intermediate tube portion and the distal tube portion.

Example 177

The surgical instrument of Example 176, further comprising an end effector and an articulation joint rotatably connecting the end effector to the distal tube portion.

Example 178

The surgical instrument of Example 177, wherein the end effector comprises a staple cartridge including staples removably stored therein.

Example 179

A surgical instrument that comprises a housing comprising an electric motor. The surgical instrument further comprises a shaft extending from the housing, wherein the shaft comprises a frame, and an end effector. The end effector comprises a first jaw, a second jaw, wherein the first jaw is rotatable relative to the second jaw, a staple cartridge comprising staples removably stored therein, and an anvil configured to deform the staples. The surgical instrument further comprises a closure system configured to move the first jaw toward the second jaw during a closure stroke, an articulation joint rotatably connecting the end effector to the shaft, an articulation system configured to articulate the end effector relative to the shaft, and a firing system operably engaged with the electric motor. The firing system is configured to eject the staples from the staple cartridge during a staple firing stroke. The surgical instrument further comprises a first rotatable member configured to selectively transmit motion from the firing system to the articulation system and a second rotatable member rotatably mounted to the frame, wherein the second rotatable member is operably engaged with the articulation system. The closure system is configured to engage the second rotatable member during the closure stroke to lock the articulation system in place and prevent the articulation of the end effector.

Example 180

The surgical instrument of Example 179, wherein the closure system comprises a closure tube surrounding the frame. The closure system further comprises a wedge configured to engage the second rotatable member and lock the second rotatable in position during the closure stroke.

Example 181

The surgical instrument of Example 179 or 180, wherein the first rotatable member is rotatably mounted within the frame.

Example 182

The surgical instrument of Example 179, 180 or 181, wherein the second rotatable member comprises a gear intermeshed with a rack of teeth defined on the articulation system.

Example 183

The surgical instrument of Example 179, 180, 181 or 182, wherein the first jaw comprises the staple cartridge and the second jaw comprises the anvil.

Example 184

The surgical instrument of Example 179, 180, 181 or 182, wherein the first jaw comprises the anvil and the second jaw comprises the staple cartridge.

Example 185

The surgical instrument of Example 179, 180, 181, 182, 183 or 184, wherein the housing comprises a handle.

Example 186

The surgical instrument of Example 179, 180, 181, 182, 183, 184 or 185, wherein the housing is attachable to a robotic surgical system.

Example 187

The surgical instrument of Example 179, 180, 181, 182, 183, 184, 185 or 186, wherein the first rotatable member is configured to operably decouple the articulation system from the firing system during the closure stroke.

Example 188

The surgical instrument of Example 179, 180, 181, 182, 183, 184, 185, 186 or 187, wherein the articulation system is operably decoupled from the firing system during the staple firing stroke.

Example 189

The surgical instrument of Example 179, 180, 181, 182, 183, 184, 185, 186, 187 or 188, wherein the closure system is retractable after the closure stroke to open the first jaw and to unlock the articulation system.

Example 190

The surgical instrument of Example 179, 180, 181, 182, 183, 184, 185, 186, 187, 188 or 189, wherein the second rotatable member is rotatable about a post extending from the frame. The post comprises a first brake arm and a second brake arm, wherein the closure system is configured to engage the first and second brake arms during the closure stroke and prevent the rotation of the second rotatable member.

Example 191

The surgical instrument of Example 179, 180, 181, 182, 183, 184, 185, 186, 187, 188, 189 or 190, wherein the second rotatable member comprises an annular array of teeth, and wherein the closure system is configured to engage the annular array of teeth during the closure stroke and prevent the rotation of the second rotatable member.

Example 192

A surgical instrument that comprises a housing comprising a rotatable input, a shaft extending from the housing, wherein the shaft comprises a frame, and an end effector. The end effector comprises a first jaw and a second jaw, wherein the first jaw is rotatable relative to the second jaw. The surgical instrument further comprises a closure system configured to close the first jaw during a closure stroke, an articulation joint rotatably connecting the end effector to the shaft, an articulation system configured to articulate the end effector relative to the shaft, and a firing system operably engaged with the rotatable input. The firing system is configured to move through the end effector during a firing stroke. The surgical instrument further comprises a first rotatable member configured to selectively synchronize the firing system and the articulation system and a second rotatable member rotatably mounted to the frame. The second rotatable member is operably engaged with the articulation system, wherein the closure system is configured to engage the second rotatable member during the closure stroke to lock the articulation system in place and prevent the articulation of the end effector.

Example 193

The surgical instrument of Example 192, further comprising a staple cartridge including staples removably stored therein.

Example 194

A surgical instrument that comprises a housing comprising a rotatable input, a shaft extending from the housing, wherein the shaft comprises a frame, and an end effector. The end effector comprises a first jaw and a second jaw, wherein the first jaw is rotatable relative to the second jaw. The surgical instrument further comprises a closure system configured to close the first jaw during a closure stroke, an articulation joint rotatably connecting the end effector to the shaft, an articulation system configured to articulate the end effector relative to the shaft, and a firing system operably engaged with the rotatable input. The firing system is configured to move through the end effector during a firing stroke. The surgical instrument further comprises a first rotatable member configured to selectively synchronize the motion of the firing system with the motion of the articulation system and a second rotatable member operably engageable with the articulation system. The closure system is configured to stop the rotation of the second rotatable member during the closure stroke to lock the articulation system in place and prevent the articulation of the end effector.

Example 195

The surgical instrument of Example 194, further comprising a staple cartridge including staples removably stored therein.

Example 196

A staple cartridge assembly that comprises a proximal end, a distal end, a cartridge body comprising a blunt nose at the distal end, a plurality of staple cavities defined within the cartridge body, wherein the plurality of staple cavities extends longitudinally from the proximal end to the distal end, a plurality of staples removably stored within the plurality of staple cavities, a driver configured to support at least one of the plurality of staples, and a sled movable toward the distal end during a firing stroke. The sled comprises a first ramp and a second ramp, wherein the first ramp is laterally offset from the second ramp. The first ramp and the second ramp are configured to lift the driver, wherein the blunt nose of the cartridge body comprises a first recess formed within the distal end configured to receive the first ramp of the sled after the completion of the firing stroke and a second recess formed within the distal end configured to receive the second ramp of the sled after the firing stroke has been completed.

Example 197

The staple cartridge assembly of Example 196, wherein the first ramp and the second ramp are exposed at the distal end upon the completion of the firing stroke.

Example 198

The staple cartridge assembly of Example 196 or 197, wherein the driver comprises a first driver portion configured to support a first staple, a second driver portion configured to support a second staple, and a third driver portion configured to support a third staple.

Example 199

The staple cartridge assembly of Example 198, wherein the driver further comprises a central base member which connects the first driver portion, the second driver portion, and the third driver portion.

Example 200

The staple cartridge assembly of Example 199, wherein the first driver portion comprises a first forward support column comprising a proximal end and the second driver portion comprises a second forward support column comprising a distal end. The central base member extends longitudinally between the proximal end of the first forward support column and the distal end of the second forward support column.

Example 201

The staple cartridge assembly of Example 196, 197, 198, 199 or 200, wherein the central base member comprises a rearwardly-angled wall configured to be engaged by the sled.

Example 202

The staple cartridge assembly of Example 196, 197, 198, 199, 200 or 201, wherein the sled is configured to drive the driver toward an anvil positioned opposite the staple cartridge assembly.

Example 203

A staple cartridge assembly that comprises a proximal end, a distal end, a cartridge body comprising a shortened nose at the distal end, and a row of staples removably stored in the cartridge body. The row of staples extends longitudinally from the proximal end to the distal end. The row of staples comprises a distal-most staple and a proximal-most staple. The staple cartridge assembly further comprises drivers, wherein each the driver is configured to support at least one of the staples, and a sled movable toward the distal end. The sled comprises a ramp configured to lift the drivers and the staples toward an anvil positioned opposite the staple cartridge assembly during a firing stroke. The sled further comprises a base, wherein a length of the shortened nose extends from the distal-most staple to the distal end, and wherein the length of the shortened nose is shorter than the base of the sled.

Example 204

The staple cartridge assembly of Example 203, further comprising the anvil, wherein the anvil comprises a protective tip on the distal end.

Example 205

The staple cartridge assembly of Example 203 or 304, further comprising the anvil, wherein the distal end of the shortened nose extends beyond the distal end of the anvil.

Example 206

The staple cartridge assembly of Example 203, 204 or 205, wherein the ramp of the sled is exposed at the distal end upon the completion of the firing stroke.

Example 207

An end effector for a surgical stapling instrument. The end effector comprises a staple cartridge assembly. The staple cartridge assembly comprises a proximal end, a distal end, a cartridge body comprising a shortened nose at the distal end, staples removably stored in the cartridge body, a driver configured to support at least one of the staples, and a sled movable toward the distal end. The sled comprises a ramp configured to lift the driver and at least one staple. The sled further comprises a base, wherein the shortened nose of the cartridge body is shorter than the base of the sled. The end effector further comprises an anvil. The anvil comprises a staple forming surface comprising a plurality of staple forming pockets. The anvil further comprises a blunt distal nose extending downward toward the staple cartridge assembly.

Example 208

The end effector of Example 207, wherein the blunt distal nose is removably attached to the anvil.

Example 209

The end effector of Example 207 or 208, wherein the anvil further comprises a frame comprising an attachment feature configured to facilitate the attachment of the blunt distal nose to the frame.

Example 210

The end effector of Example 207, 208 or 209, wherein the anvil comprises a distal end, and wherein the distal end of the staple cartridge assembly extends beyond the distal end of the anvil.

Example 211

A staple cartridge assembly that comprises a cartridge body, a proximal end, a distal end, a slot configured to receive a cutting member, and a first row of staples removably stored in the cartridge body, wherein the first row of staples extends between the proximal end and the distal end alongside a first side of the slot. The staple cartridge assembly further comprises a second row of staples removably stored in the cartridge body, wherein the second row of staples extends between the proximal end and the distal end alongside the first row of staples on the first side of the slot. The staple cartridge assembly further comprises a third row of staples removably stored in the cartridge body, wherein the third row of staples extends between the proximal end and the distal end alongside the second row of staples on the first side of the slot. The staple cartridge assembly further comprises a driver configured to support a first staple from the first row of staples, a second staple from the second row of staples, and a third staple from the third row of staples, wherein the second staple is closer to the proximal end than the first staple and the third staple.

Example 212

The staple cartridge assembly of Example 211, wherein the first staple, the second staple, and the third staple form a reverse arrow configuration.

Example 213

The staple cartridge assembly of Example 211 or 212, further comprising a sled configured to lift the driver toward an anvil positioned opposite the staple cartridge assembly.

Example 214

The staple cartridge assembly of Example 211, 212 or 213, further comprising an anvil, wherein the anvil comprises a distal end.

Example 215

The staple cartridge assembly of Example 214, wherein the distal end of the staple cartridge extends distally with respect to the distal end of the anvil.

Example 216

A staple cartridge system that comprises an end effector configurable in an unclamped configuration and a clamped configuration. The end effector comprises an anvil jaw and a cartridge jaw. The cartridge jaw is configured to receive a staple cartridge. The cartridge jaw comprises a cartridge support datum. The staple cartridge system further comprises a first staple cartridge. The first staple cartridge comprises a first deck configured to support the tissue of a patient, first staple cavities defined in the first deck, first staples removably stored in the first staple cavities, and a first proximal end. The first proximal end is aligned with a datum of the cartridge jaw when the first staple cartridge is positioned in the cartridge jaw. The first staple cartridge further comprises a first distal end, wherein a first cartridge length is defined between the first proximal end and the first distal end. The staple cartridge system further comprises a second staple cartridge. The second staple cartridge comprises a second deck configured to support the tissue of a patient, second staple cavities defined in the second deck, second staples removably stored in the second staple cavities, and a second proximal end. The second proximal end is aligned with the datum of the cartridge jaw when the second staple cartridge is positioned in the cartridge jaw. The second staple cartridge further comprises a second distal end, wherein a second cartridge length is defined between the second proximal end and the second distal end, wherein the anvil is supported by a first location on the first staple cartridge when the end effector is in the clamped configuration and the first staple cartridge is positioned in the cartridge jaw. The anvil is supported by a second location on the second staple cartridge when the end effector is in the clamped configuration and the second staple cartridge is positioned in the cartridge jaw. The first location is a first orthogonal distance away from the cartridge support datum when the first staple cartridge is positioned in the cartridge jaw and the second location is a second orthogonal distance away from the cartridge support datum when the second staple cartridge is positioned in the cartridge jaw. The first orthogonal distance is different than the second orthogonal distance. The anvil jaw deflects differently in response to whether the first staple cartridge or the second staple cartridge is positioned in the cartridge jaw.

Example 217

The staple cartridge system of Example 216, wherein the second cartridge length is different than the first cartridge length.

Example 218

The staple cartridge system of Example 216 or 217, wherein the second cartridge length is shorter than the first cartridge length.

Example 219

The staple cartridge system of Example 216, 217 or 218, wherein the second orthogonal distance is shorter than the first orthogonal distance.

Example 220

The staple cartridge system of Example 216, 217 or 218, wherein the second orthogonal distance is taller than the first orthogonal distance.

Example 221

The staple cartridge system of Example 216, 217, 219 or 220, wherein the second cartridge length is longer than the first cartridge length.

Example 222

The staple cartridge system of Example 216, 217, 218 or 221, wherein the second orthogonal distance is shorter than the first orthogonal distance.

Example 223

The staple cartridge system of Example 216, 217, 218 or 221, wherein the second orthogonal distance is taller than the first orthogonal distance.

Example 224

The staple cartridge system of Example 216, 217, 218, 219, 220, 221, 222 or 223, wherein the second location is closer to the second distal end than the first location to the first distal end.

Example 225

The staple cartridge system of Example 216, 217, 218, 219, 220, 221, 222 or 223, wherein the second location is positioned further from the second distal end than the first location from the first distal end.

Example 226

The staple cartridge system of Example 216, 217, 218, 219, 220, 221, 222, 223, 224 or 225, wherein the anvil jaw comprises a distal anvil tip. The first cartridge length is set such that the distal anvil tip extends beyond the first distal end, wherein the second cartridge length is set such that the distal anvil tip does not extend beyond the second distal end.

Example 227

The staple cartridge system of Example 216, 217, 218, 219, 220, 221, 222, 223, 224, 225 or 226, wherein the anvil jaw experiences a first deflection when the end effector is in the clamped configuration and the first staple cartridge is positioned in the cartridge jaw. The anvil jaw experiences a second deflection when the end effector is in the clamped configuration and the second staple cartridge is positioned in the cartridge jaw. The second deflection is larger than the first deflection.

Example 228

The staple cartridge system of Example 216, 217, 218, 219, 220, 221, 222, 223, 224, 225, 226 or 227, wherein each first staple comprises an unformed height within a first unformed height range, wherein each second staple comprises an unformed height within a second unformed height range, and wherein the second unformed height range comprises heights which are taller than the heights in the first unformed height range.

Example 229

The staple cartridge system of Example 216, 217, 218, 219, 220, 221, 222, 223, 224, 225, 226 or 227, wherein each first staple comprises an unformed height within a first unformed height range, wherein each second staple comprises an unformed height within a second unformed height range, and wherein the second unformed height range comprises heights which are shorter than the heights in the first unformed height range.

Example 230

The staple cartridge system of Example 216, 217, 218, 219, 220, 221, 222, 223, 224, 225, 226, 227, 228 or 229, wherein each first staple comprises an unformed height within a first unformed height range, wherein each second staple comprises an unformed height within a second unformed height range, and wherein the second unformed height range is different than the first unformed height range but partially overlaps with the first unformed height range.

Example 231

The staple cartridge system of Example 216, 217, 218, 219, 220, 221, 222, 223, 224, 225, 226, 227, 228, 229 or 230, wherein the anvil jaw comprises a distal anvil tip, wherein the first cartridge length is set such that the distal anvil tip extends beyond the first distal end, and wherein the second cartridge length is set such that the distal anvil tip is shorter than the second distal end.

Example 232

The staple cartridge system of Example 216, 217, 218, 219, 220, 221, 222, 223, 224, 225, 226, 227, 228, 229, 230 or 231, wherein the anvil jaw is rotatable relative to the cartridge jaw.

Example 233

The staple cartridge system of Example 216, 217, 218, 219, 220, 221, 222, 223, 224, 225, 226, 227, 228, 229, 230 or 231, wherein the cartridge jaw is rotatable relative to the anvil jaw.

Example 234

The staple cartridge system of Example 216, 217, 218, 219, 220, 221, 222, 223, 224, 225, 226, 227, 228, 229, 230, 231, 232 or 233, wherein the first distal end comprises a first cartridge nose and the second distal end comprises a second cartridge nose. The second cartridge nose is blunter than the first cartridge nose.

Example 235

The staple cartridge system of Example 216, 217, 218, 219, 220, 221, 222, 223, 224, 225, 226, 227, 228, 229, 230, 231, 232, 233 or 234, wherein the first distal end comprises a first cartridge nose and the second distal end comprises a second cartridge nose. The second cartridge nose is shorter than the first cartridge nose.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:

an end effector comprising a proximal end and a distal end, wherein said end effector is configurable in an unclamped configuration and a clamped configuration; and a shaft, comprising:

a frame;

a lock plate moveable relative to said frame, wherein said lock plate comprises a first longitudinal rack of lock teeth;

an articulation joint, wherein said end effector is rotatably connected to said shaft by said articulation joint;

an articulation actuator operably connected to said end effector, wherein said articulation actuator is movable distally to rotate said end effector in a first direction and proximally to rotate said end effector in a second direction, and wherein said articulation actuator comprises a second longitudinal rack of lock teeth; and an articulation lock comprising a third longitudinal rack of lock teeth, wherein said articulation lock is positionable in an unlocked position in which said articulation actuator can move relative to said frame and a locked position in which said third longitudinal rack of lock teeth is concurrently and directly engaged with said first longitudinal rack of lock teeth and said second longitudinal rack of lock teeth to prevent said proximal and distal movement of said articulation actuator.

2. The surgical instrument of claim 1, wherein said first longitudinal rack of lock teeth is defined in a first plane, wherein said second longitudinal rack of lock teeth is defined in a second plane, and wherein said first plane and said second plane are different.

3. The surgical instrument of claim 1, wherein said lock plate is slidable relative to said frame.

4. The surgical instrument of claim 3, wherein said frame comprises a recess, wherein said lock plate is positioned within said recess, wherein said recess comprises a proximal end wall configured to limit the proximal movement of said lock plate within said recess, and wherein said recess comprises a distal end wall configured to limit the distal movement of said lock plate within said recess.

5. The surgical instrument of claim 4, further comprising a biasing member positioned between said proximal end wall and said lock plate.

6. The surgical instrument of claim 4, further comprising a biasing member positioned between said distal end wall and said lock plate.

7. The surgical instrument of claim 1, wherein said end effector comprises a first jaw and a second jaw, wherein said first jaw is movable relative to said second jaw between an open position and a closed position, wherein said surgical instrument further comprises a closure member configured to move said first jaw toward said closed position during a closure stroke, and wherein said closure member is configured to engage said articulation lock during said closure stroke and hold said articulation lock in said locked position.

8. The surgical instrument of claim 7, wherein said shaft defines a longitudinal axis, wherein said frame comprises a flexible portion, wherein said closure member is configured to push said lock plate against said flexible portion and deflect said flexible portion laterally with respect to said longitudinal axis.

9. The surgical instrument of claim 8, wherein said flexible portion comprises a lateral sidewall and a cavity defined behind said lateral sidewall, and wherein said lateral sidewall is configured to flex into said cavity.

10. The surgical instrument of claim 1, wherein said articulation lock is biased into engagement with said lock plate and said articulation actuator.

11. The surgical instrument of claim 1, wherein said end effector further comprises a staple cartridge comprising staples removably stored therein.

12. The surgical instrument of claim 11, wherein said staple cartridge is replaceable.

13. The surgical instrument of claim 11, wherein said end effector comprises a first jaw and a second jaw, wherein said first jaw is movable relative to said second jaw between an open position and a closed position, and wherein said first jaw comprises said staple cartridge.

14. The surgical instrument of claim 11, wherein said end effector comprises a first jaw and a second jaw, wherein said first jaw is movable relative to said second jaw between an open position and a closed position, and wherein said second jaw comprises said staple cartridge.

15. The surgical instrument of claim 1, wherein said first longitudinal rack of lock teeth comprises teeth spaced at a first pitch, wherein said second longitudinal rack of lock teeth comprises teeth spaced at a second pitch, wherein said second pitch is different than said first pitch, wherein said third longitudinal rack of lock teeth comprises teeth spaced at a third pitch, and wherein said third pitch is different than said first pitch and said second pitch.

16. A surgical instrument, comprising:
- an end effector comprising a proximal end and a distal end, wherein said end effector is configurable in an unclamped configuration and a clamped configuration; and
- a shaft, comprising:
  - a frame comprising a first longitudinal rack of lock teeth;
  - an articulation joint, wherein said end effector is rotatably connected to said shaft by said articulation joint;
  - an articulation actuator operably connected to said end effector, wherein said articulation actuator is movable distally to rotate said end effector in a first direction, wherein said articulation actuator is movable proximally to rotate said end effector in a second direction, and wherein said articulation actuator comprises a second longitudinal rack of lock teeth; and
  - an articulation lock comprising a third longitudinal rack of lock teeth, wherein said articulation lock is positionable in an unlocked position in which said articulation actuator can move relative to said frame and a locked position in which said third longitudinal rack of lock teeth are concurrently and directly engaged with said first longitudinal rack of lock teeth of said frame and said second longitudinal rack of lock teeth of said articulation actuator to inhibit said proximal and distal movement of said articulation actuator.

17. The surgical instrument of claim 16, wherein said frame comprises a slidable lock plate, and wherein said first longitudinal rack of lock teeth are defined on said lock plate.

18. The surgical instrument of claim 16, wherein said end effector comprises a staple cartridge including staples removably stored therein.

19. A surgical instrument, comprising:
- an end effector; and
- a shaft, comprising:
  - a frame;
  - an articulation joint, wherein said end effector is rotatably connected to said shaft by said articulation joint;
  - an articulation actuator operably connected to said end effector, wherein said articulation actuator is movable in a first direction to rotate said end effector in one direction, and wherein said articulation actuator is movable in a second direction to rotate said end effector in another direction; and
  - an articulation lock positionable in a first position in which said articulation actuator can move relative to said frame and a second position in which said articulation lock is directly engaged with said frame and said articulation actuator simultaneously to limit the movement of said articulation actuator in said first direction and said second direction.

20. The surgical instrument of claim 19, wherein said end effector comprises a staple cartridge including staples removably stored therein.

* * * * *